United States Patent
Chen et al.

(10) Patent No.: US 9,526,897 B2
(45) Date of Patent: Dec. 27, 2016

(54) NEUROSTIMULATOR CONFIGURED TO SENSE EVOKED POTENTIALS IN PERIPHERAL NERVES

(71) Applicant: Greatbatch Ltd., Clarence, NY (US)

(72) Inventors: Joey Chen, Valencia, CA (US); Kerry Bradley, Glendale, CA (US); Leslie Halberg, Valencia, CA (US)

(73) Assignee: GREATBACH LTD., Clarence, NY (US)

(*) Notice: Subject to any disclaimer, the term of this patent is extended or adjusted under 35 U.S.C. 154(b) by 0 days.

(21) Appl. No.: 15/001,327

(22) Filed: Jan. 20, 2016

(65) Prior Publication Data

US 2016/0144188 A1    May 26, 2016

Related U.S. Application Data

(63) Continuation of application No. 14/322,716, filed on Jul. 2, 2014, now Pat. No. 9,248,279.
(Continued)

(51) Int. Cl.
*A61N 1/36* (2006.01)
*A61N 1/05* (2006.01)
(Continued)

(52) U.S. Cl.
CPC .......... *A61N 1/36139* (2013.01); *A61B 5/064* (2013.01); *A61B 8/0841* (2013.01); *A61N 1/05* (2013.01);
(Continued)

(58) Field of Classification Search
CPC ..... A61B 5/4824; A61B 5/061; A61B 5/1116; G06F 19/3406; G06F 19/345; A61N 1/36071; A61N 1/36132; A61N 1/36135
See application file for complete search history.

(56) References Cited

U.S. PATENT DOCUMENTS 5,284,154 A    2/1994    Raymond et al.
5,417,719 A    5/1995    Hull et al.
(Continued)

FOREIGN PATENT DOCUMENTS

CN    101325985    12/2008
FR    2339894    8/1977
(Continued)

OTHER PUBLICATIONS

Gordon M. Greenblatt, M.D. et al. "Needle Nerve Stimulator-Locator: Nerve Blocks with a New Instrument for Locating Nerves" Anesthesia and Analgesia, vol. 41, No. 5, Sep.-Oct. 1962, pp. 599-602.
(Continued)

*Primary Examiner* — Robert N Wieland
(74) *Attorney, Agent, or Firm* — Haynes and Boone, LLP; Eric Li

(57) ABSTRACT

A patient is detected to be in a first posture state. In response to the patient being detected to be in the first posture state, a first electrical stimulation therapy is applied to a body region of the patient by a pulse generator implanted in the patient. The patient is detected to be in a second posture state. In response to the patient being detected to be in the second posture state that is different from the first posture state, a second electrical stimulation therapy is applied to the body region of the patient by the pulse generator. The second electrical stimulation therapy is different from the first electrical stimulation therapy.

20 Claims, 56 Drawing Sheets

Related U.S. Application Data

(60) Provisional application No. 61/841,965, filed on Jul. 2, 2013.

(51) Int. Cl.
*A61B 5/06* (2006.01)
*A61B 8/08* (2006.01)
*A61N 1/372* (2006.01)

(52) U.S. Cl.
CPC ........... *A61N 1/0551* (2013.01); *A61N 1/0553* (2013.01); *A61N 1/36017* (2013.01); *A61N 1/36071* (2013.01); *A61N 1/36125* (2013.01); *A61N 1/36146* (2013.01); *A61N 1/36153* (2013.01); *A61N 1/37223* (2013.01); *A61N 1/37235* (2013.01); *A61N 1/37252* (2013.01)

(56) References Cited

U.S. PATENT DOCUMENTS

| | | | |
|---|---|---|---|
| 5,702,429 A | 12/1997 | King | |
| 5,775,331 A | 7/1998 | Raymond et al. | |
| 5,941,906 A | 8/1999 | Barreras, Sr. et al. | |
| 6,236,892 B1 | 5/2001 | Feler | |
| 6,366,814 B1 | 4/2002 | Boveja et al. | |
| 6,687,538 B1 | 2/2004 | Hrdlicka et al. | |
| 6,725,096 B2 | 4/2004 | Chinn et al. | |
| 7,009,313 B1 | 3/2006 | Parramon et al. | |
| 7,104,965 B1 | 9/2006 | Jiang et al. | |
| 7,174,215 B2 | 2/2007 | Bradley | |
| 7,221,981 B2 | 5/2007 | Gliner | |
| 7,444,184 B2 | 10/2008 | Boveja et al. | |
| 7,450,992 B1 | 11/2008 | Cameron | |
| 7,680,540 B2 | 3/2010 | Jensen et al. | |
| 7,697,985 B2 | 4/2010 | Kaiser et al. | |
| 7,697,995 B2 | 4/2010 | Cross, Jr. et al. | |
| 7,751,884 B2 | 7/2010 | Ternes et al. | |
| 7,801,615 B2 | 9/2010 | Meadows et al. | |
| 7,806,862 B2 | 10/2010 | Molnar | |
| 8,195,304 B2 | 6/2012 | Strother et al. | |
| 8,219,206 B2 | 7/2012 | Skelton et al. | |
| 8,233,984 B2 | 7/2012 | Forsberg et al. | |
| 8,335,569 B2 | 12/2012 | Aghassian | |
| 8,380,314 B2 | 2/2013 | Panken et al. | |
| 8,457,756 B2 | 6/2013 | Rahman | |
| 8,504,160 B2 | 8/2013 | Lee et al. | |
| 8,538,548 B2 | 9/2013 | Shi et al. | |
| 8,588,927 B2 | 11/2013 | Roy et al. | |
| 8,600,505 B2 | 12/2013 | Libbus et al. | |
| 8,606,362 B2 | 12/2013 | He et al. | |
| 8,612,002 B2 | 12/2013 | Faltys et al. | |
| 8,628,475 B2 | 1/2014 | Wang | |
| 8,634,893 B2 | 1/2014 | Skubitz et al. | |
| 8,634,927 B2 | 1/2014 | Olson et al. | |
| 8,644,947 B2 | 2/2014 | Zhu et al. | |
| 8,700,178 B2 | 4/2014 | Anderson | |
| 8,712,539 B2 | 4/2014 | Goetz et al. | |
| 2006/0195159 A1 | 8/2006 | Bradley et al. | |
| 2006/0253182 A1 | 11/2006 | King | |
| 2008/0103559 A1 | 5/2008 | Thacker et al. | |
| 2009/0312817 A1 | 12/2009 | Hogle et al. | |
| 2010/0198308 A1 | 8/2010 | Zhou et al. | |
| 2011/0172564 A1* | 7/2011 | Drew | A61B 5/061 600/587 |
| 2011/0208265 A1 | 8/2011 | Erickson et al. | |
| 2012/0004709 A1 | 1/2012 | Chen et al. | |
| 2012/0123502 A1 | 5/2012 | Aghassian et al. | |
| 2012/0239108 A1 | 9/2012 | Foutz et al. | |
| 2013/0079635 A1 | 3/2013 | Patrick et al. | |
| 2013/0110201 A1 | 5/2013 | Bonde et al. | |
| 2013/0245715 A1 | 9/2013 | Peterson | |
| 2013/0310897 A1 | 11/2013 | Marnfeldt et al. | |
| 2013/0310909 A1 | 11/2013 | Simon et al. | |
| 2013/0338732 A1 | 12/2013 | Foutz et al. | |
| 2014/0039578 A1 | 2/2014 | Whitehurst et al. | |
| 2014/0046407 A1 | 2/2014 | Ben-Ezra et al. | |
| 2014/0046423 A1 | 2/2014 | Rajguru et al. | |
| 2014/0058189 A1 | 2/2014 | Stubbeman | |
| 2014/0058495 A1 | 2/2014 | Sakai et al. | |
| 2014/0073926 A1 | 3/2014 | Rajendran et al. | |
| 2014/0136585 A1 | 5/2014 | Brockway | |
| 2014/0236257 A1 | 8/2014 | Parker et al. | |
| 2014/0243926 A1* | 8/2014 | Carcieri | A61N 1/36071 607/46 |

FOREIGN PATENT DOCUMENTS

| | | |
|---|---|---|
| WO | WO 93/25271 | 12/1993 |
| WO | WO 02/09808 | 2/2002 |
| WO | WO 2013/165628 | 11/2013 |
| WO | WO 2014/036184 | 3/2014 |

OTHER PUBLICATIONS

Stephen A. Raymond, Ph.D. et al. "The NerveSeeker: A System for Automated Nerve Localization" Regional Anesthesia & Pain Medicine, May/Jun. 1992, 1 page Abstract.

* cited by examiner

| Fig. 8A | Fig. 8B | Fig. 8C | Fig. 8D | Fig. 8E | Fig. 8F |
|---|---|---|---|---|---|
| Fig. 8G | Fig. 8H | Fig. 8I | Fig. 8J | Fig. 8K | Fig. 8L |

Fig. 8

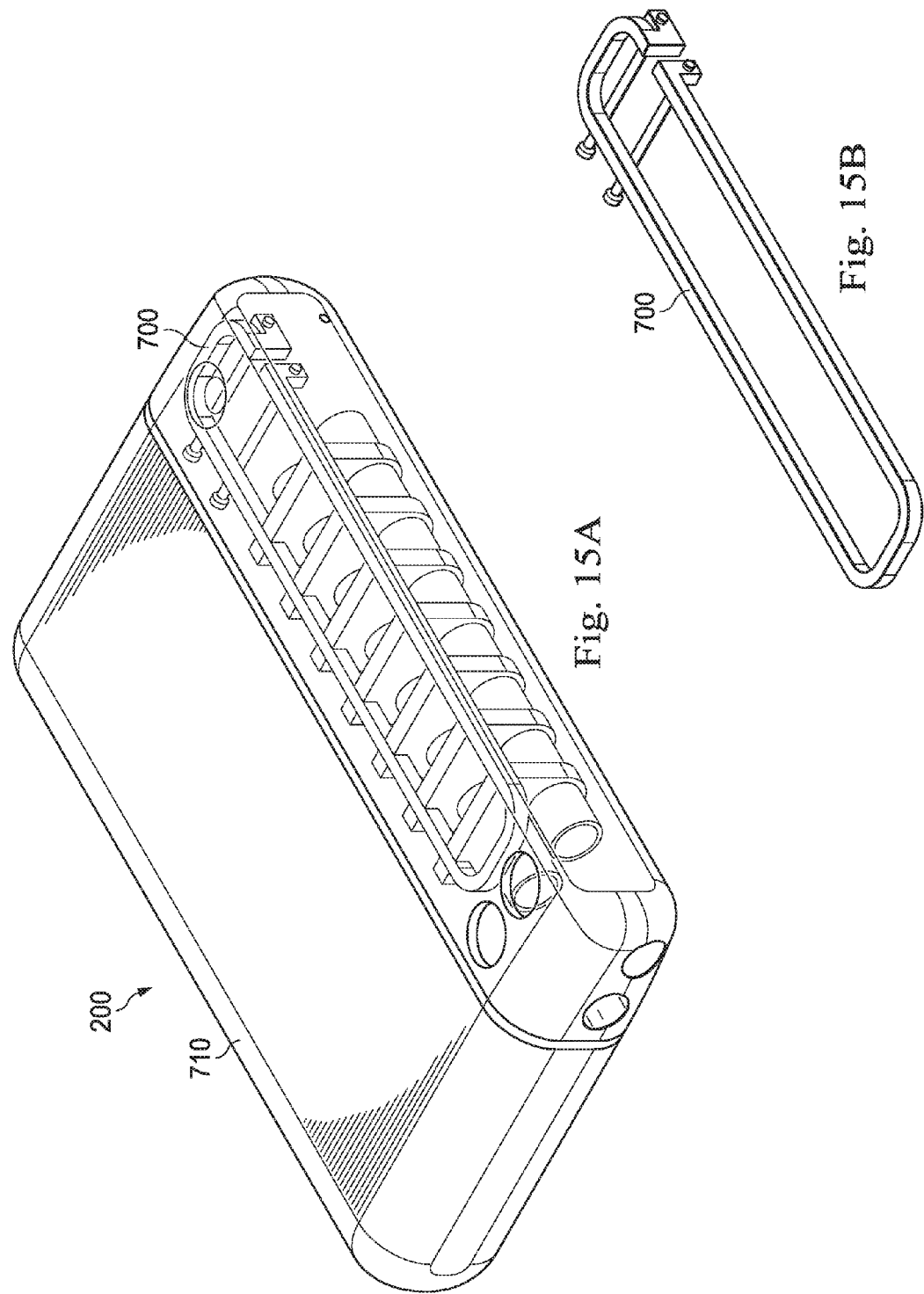

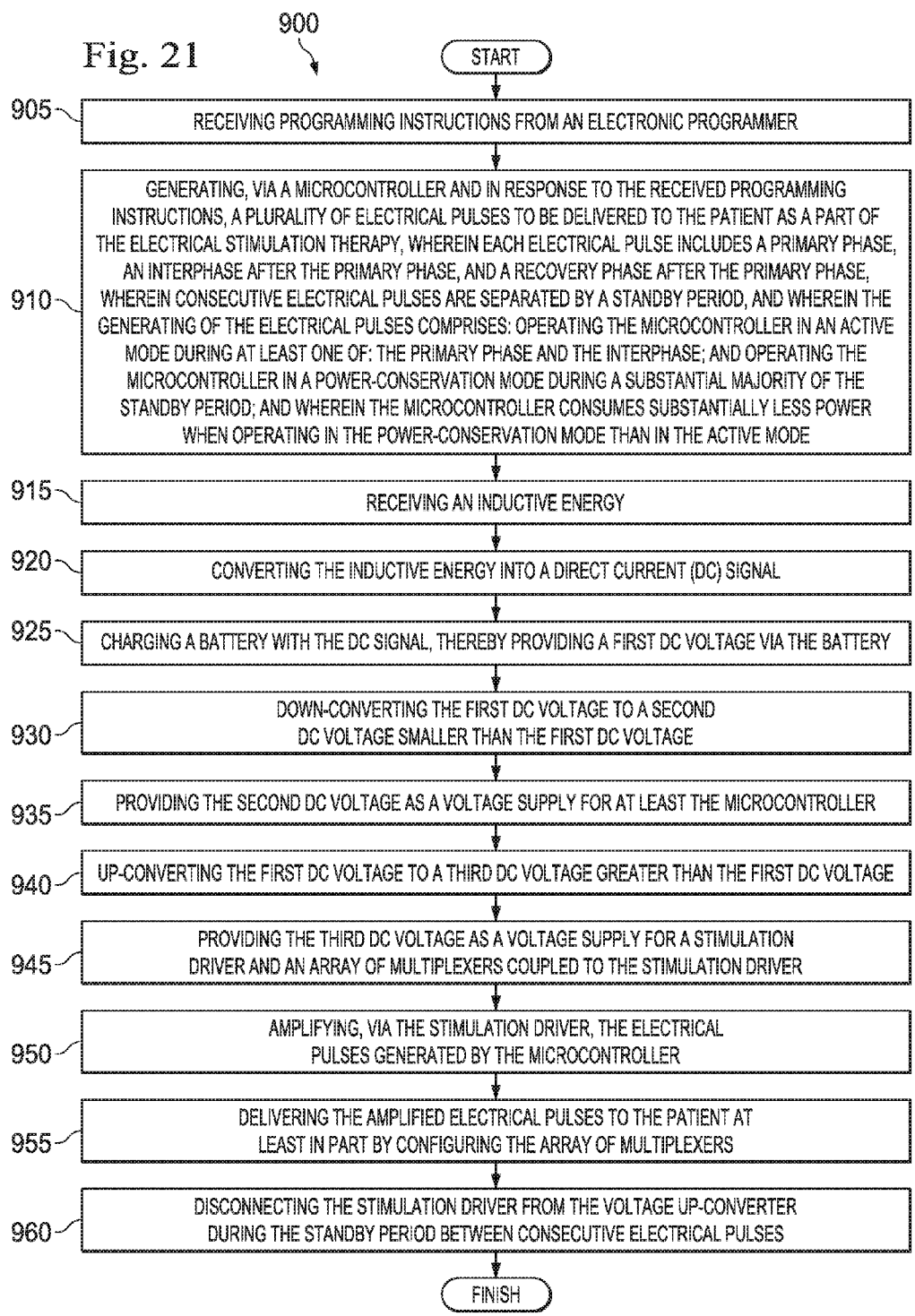

NEUROSTIMULATOR CONFIGURED TO SENSE EVOKED POTENTIALS IN PERIPHERAL NERVES

PRIORITY DATA

The present application is a utility application of provisional U.S. Patent Application No. 61/841,965, filed on Jul. 2, 2013, entitled "Stimulation Apparatuses, Devices, Systems, and Methods," the disclosure of which is hereby incorporated by reference in its entirety.

FIELD

Various embodiments described herein relate to the field of implantable medical devices, and methods of communicating therewith.

BACKGROUND

As medical device technologies continue to evolve, neurostimulator devices have gained much popularity in the medical field. Neurostimulator devices are typically battery-powered devices that are designed to deliver electrical stimulation to a patient. Through proper electrical stimulation, the neurostimulator devices can provide pain relief for patients. In effect, the electrical signals sent by the neurostimulator devices "mask" or modify the pain signals before the pain signals reach the patient's brain. As a result, the patient may feel only a tingling sensation (known as "Paresthesia) in the area that is stimulated instead of pain. For example, peripheral nerve stimulation has been used to treat chronic pain emanating from a patient's extremity, such as in the patient's arm and/or leg. A typical peripheral neurostimulator (PNS) device may include one or more integrated circuit chips containing the control circuitry and neurostimulation circuitry. The PNS device may also include a plurality of electrodes that are in contact with different areas of a patient's body. The PNS device typically includes a battery, either permanent or rechargeable, that is utilized to power the stimulation circuitry and the external communications. Controlled by the control circuitry within the neurostimulator, the electrodes are each capable of delivering electrical stimulation to their respective target contact areas. Thus, the patient can use the PNS device to stimulate areas in a localized manner.

In spite of recent advances, conventional PNS devices still have various shortcomings. As an example, the nerves in a spinal cord are typically arranged more orderly and run along a linear path, whereas the nerves to be stimulated in peripheral nerve stimulation usually wind tortuously along a neurovascular bundle. Therefore, a typical paddle lead for a conventional PNS device or for spinal cord stimulation does not offer the flexibility and versatility needed to stimulate the target nerve fibers for peripheral nerve stimulation, as they are not configured to allow electrical stimulation energy to follow the tortuous peripheral nerve targets selectively. As another example, conventional PNS devices typically require an antenna to receive telemetry signals and a separate charging coil to receive charging signals. As a result, PNS design is more complex and more expensive. As yet another example, conventional PNS devices typically do not employ sophisticated power maximization techniques to reduce power consumption. Consequently, conventional PNS devices tend to have battery life that does not last as long as desired. The short battery life may lead to user dissatisfaction. As yet another example, it may be difficult to determine a target nerve site for applying stimulation. As a further example, conventional PNS devices may not be able to provide a constant paresthesia intensity to account for patient movements. As yet a further example, conventional methods and systems may not be able to quickly devise a stimulation protocol that effectively treats the patient.

As a result, although existing systems and methods of peripheral neurostimulation have been generally adequate for their intended purposes, they have not been entirely satisfactory in every aspect.

SUMMARY

One aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The plurality of electrodes is arranged into at least three columns that each include a respective subset of the electrodes. The plurality of electrodes each includes a unique centerline, wherein the centerlines extend in directions transverse to the columns.

Another aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The plurality of electrodes each have a respective first centerline extending along a first direction and a respective centerline extending along a second direction different from the first axis. A substantial majority of the first centerlines are not aligned in the first direction with any of the other first centerlines. A substantial majority of the second centerlines are not aligned in the second direction with any of the other second centerlines.

Yet another aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The electrodes collective define a stimulation region on the paddle. A substantial majority of linear paths across the stimulation region intersect with at least one of the electrodes.

Another aspect of the present disclosure involves a medical device for providing an electrical stimulation therapy for a patient. The medical device includes a coil configured to receive both inductive charging signals and telemetry signals. The inductive charging signals are in a first frequency band. The telemetry signals are in a second frequency band that is substantially higher than the first frequency band. The medical device includes inductive charging circuitry configured to provide electrical power to the medical device via the inductive charging signals. The medical device includes telemetry circuitry configured to conduct telecommunications with external device via the telemetry signals. The medical device includes a first component that is electrically coupled between the coil and the inductive charging circuitry. The first component is configured to allow the inductive charging signals to pass through. The medical device includes a second component that is electrically coupled between the coil and the telemetry circuitry. The second component is configured to substantially block the inductive charging signals while allowing the telemetry signals to pass through.

Another aspect of the present disclosure involves a medical system for providing an electrical stimulation therapy for a patient. The medical system includes an electronic programmer configured to generate first telemetry signals that contain stimulation programming instructions for an implantable pulse generator (IPG) and second telemetry signals for waking up the IPG. The medical system includes the IPG configured to generate electrical pulses in response to the stimulation programming instructions. The IPG contains an antenna configured to receive the first telemetry signals, the second telemetry signals, and inductive charging signals. The inductive charging signals are in a first frequency band, the first telemetry signals are in a second frequency band that is substantially higher than the first frequency band, and the second telemetry signals are in a third frequency band that is substantially higher than the second frequency band. The IPG contains an inductive charging circuitry configured to provide electrical power to the medical device via the inductive charging signals. The IPG contains telemetry circuitry configured to conduct telecommunications with external device via the telemetry signals. The IPG contains a first circuit that is electrically coupled between the antenna and the inductive charging circuitry. The first circuit contains one or more electronic components that create a resonant frequency centered around the first frequency band. The IPG contains a second circuit that is electrically coupled between the antenna and the telemetry circuitry. The second circuit is configured to substantially reject the inductive charging signals and the second telemetry signals while allowing the first telemetry signals to pass through. The IPG contains a third circuit that is electrically coupled between the antenna and the telemetry circuitry and in parallel with the second circuit. The third circuit is configured to reject the inductive charging signals and the first telemetry signals while allowing the second telemetry signals to pass through.

Another aspect of the present disclosure involves a method of providing discrimination for a plurality of types of input signals received from a single antenna. The method includes receiving, via the single antenna, inductive charging signals and first telemetry signals. The inductive charging signals are in a first frequency band, the first telemetry signals are in a second frequency band that is substantially higher than the first frequency band. The method includes generating, via a first circuit coupled to the single antenna, a resonant frequency substantially near the first frequency band such that the first circuit allows the inductive charging signals to pass through while attenuating the first telemetry signals. The method includes rejecting, via a second circuit coupled to the single antenna, the inductive charging signals while allowing the first telemetry signals to pass through.

Another aspect of the present disclosure involves a medical device for providing an electrical stimulation therapy for a patient. The medical device includes telemetry circuitry configured to receive programming instructions via telecommunications conducted with an electronic programmer. The medical device includes stimulation circuitry configured to provide, in response to the received programming instructions, a plurality of electrical pulses to be delivered to the patient as a part of the electrical stimulation therapy. The stimulation circuitry contains a microcontroller configured to generate the electrical pulses. Each electrical pulse includes a primary phase, an interphase after the primary phase, and a recovery phase after the primary phase. Consecutive electrical pulses are separated by a standby period. The medical device includes power supply circuitry configured to provide electrical power to the telemetry circuitry and the stimulation circuitry. The microcontroller is configured to operate in an active mode during at least one of: the primary phase and the interphase, and the microcontroller is configured to operate in a power-conservation mode during a substantial majority of the standby period. The microcontroller consumes substantially less power when operating in the power-conservation mode than in the active mode.

Another aspect of the present disclosure involves a medical system for providing an electrical stimulation therapy for a patient. The medical system includes an electronic programmer configured to generate stimulation programming instructions for an implantable pulse generator (IPG). The medical system includes the IPG. The IPG comprises telemetry circuitry configured to receive the programming instructions via telecommunications conducted with the electronic programmer. The IPG comprises stimulation circuitry configured to provide, in response to the received programming instructions, a plurality of electrical pulses to be delivered to the patient as a part of the electrical stimulation therapy. The stimulation circuitry contains a microcontroller configured to generate the electrical pulse. Each electrical pulse includes a primary phase, an interphase after the primary phase, and a recovery phase after the primary phase. Consecutive electrical pulses are separated by a standby period. The IPG comprises power supply circuitry configured to provide electrical power to the telemetry circuitry and the stimulation circuitry. The microcontroller is configured to operate in an active mode during at least one of: the primary phase and the interphase, and the microcontroller is configured to operate in a power-conservation mode during a substantial majority of the standby period. The microcontroller consumes substantially less power when operating in the power-conservation mode than in the active mode.

Another aspect of the present disclosure involves a method of providing an electrical stimulation therapy for a patient. The method includes receiving programming instructions from an electronic programmer. The method includes generating, via a microcontroller and in response to the received programming instructions, a plurality of electrical pulses to be delivered to the patient as a part of the electrical stimulation therapy. Each electrical pulse includes a primary phase, an interphase after the primary phase, and a recovery phase after the primary phase. Consecutive electrical pulses are separated by a standby period. The generating of the electrical pulses comprises: operating the microcontroller in an active mode during at least one of: the primary phase and the interphase, and operating the microcontroller in a power-conservation mode during a substantial majority of the standby period. The microcontroller consumes substantially less power when operating in the power-conservation mode than in the active mode.

Yet another aspect of the present disclosure involves a medical device for providing an electrical stimulation therapy for a patient. The medical device includes a microcontroller configured to generate a plurality of electrical pulses and a control signal. The medical device includes a stimulation driver coupled to the microcontroller. The stimulation driver is configured to amplify the electrical pulses into amplified electrical pulses to be delivered to the patient as a part of the electrical stimulation therapy. The medical device includes a battery configured to supply a first voltage. The medical device includes a voltage up-converter coupled between the battery and the stimulation driver. The voltage up-converter is configured to convert, in response to the control signal from the microcontroller, the first voltage to a compliance voltage for the stimulation driver. The compliance voltage is a fraction of the first voltage, and the fraction is greater than 1.

Yet another aspect of the present disclosure involves a medical system for providing an electrical stimulation therapy for a patient. The medical system includes an electronic programmer configured to generate stimulation programming instructions for an implantable pulse generator (IPG). The medical system includes the IPG configured to provide, in response to the stimulation programming instructions, stimulation pulses to be delivered to the patient as a part of the electrical stimulation therapy. The IPG contains a microcontroller configured to generate a plurality of electrical pulses and a control signal. The IPG contains a stimulation driver coupled to the microcontroller, the stimulation driver being configured to amplify the electrical pulses into the stimulation pulses. The IPG contains a battery configured to supply a first voltage. The IPG contains a voltage up-converter coupled between the battery and the stimulation driver. The voltage up-converter is configured to convert, in response to the control signal from the microcontroller, the first voltage to a compliance voltage for the stimulation driver. The compliance voltage is a fraction of the first voltage, the fraction is greater than 1.

Yet another aspect of the present disclosure involves a method of providing an electrical stimulation therapy for a patient. A plurality of electrical pulses and a control signal are generated via a microcontroller. A first voltage is supplied via a battery. In response to the control signal, the first voltage is converted via the voltage up-converter to a compliance voltage. The compliance voltage is a fraction of the first voltage, and the fraction is greater than 1. The compliance voltage is provided to a stimulation driver. The plurality of electrical pulses is amplified via the stimulation driver into amplified electrical pulses to be delivered to the patient as a part of the electrical stimulation therapy.

Yet another aspect of the present disclosure involves a method of identifying a location for applying a stimulation therapy to treat a patient. A first body region of the patient is stimulated transcutaneously via a stimulus generator. The body region contains a first portion of a nerve that has an elongate shape. In response to the stimulating, action potentials received from a second portion of the nerve are monitored over a period of time. The second portion of the nerve is in a second body region of the patient that is located remotely from the first body region. Based on the monitoring, an optimized location of the second portion of the nerve is determined for applying the stimulation therapy to treat the first body region.

Yet another aspect of the present disclosure involves a method of identifying a location for applying a stimulation therapy to treat a patient. A first body region of the patient is stimulated transcutaneously via an external pulse generator (EPG). The body region contains a first portion of a nerve that has an elongate shape. A trigger signal is sent to a measurement instrument. The trigger signal defines a time window for making a measurement. A plurality of different action potentials is measured via the measurement instrument. The measuring is performed in response to a plurality of engagements with different fascicles of a second portion of the nerve while the first body region is stimulated. The second portion of the nerve is in a second body region of the patient that is located remotely from the first body region. The measuring is performed within the time window defined by the trigger signal. In some embodiments, the steps of the method are performed while the patient is sedated.

Yet another aspect of the present disclosure involves a medical system. The medical system includes a stimulus generator configured to apply stimulation to a first body region of the patient transcutaneously. The body region contains a first portion of an elongate nerve. The medical system includes a tool configured to engage with a second portion of the nerve that is in a second body region of the patient that is located remotely from the first body region. The tool is configured to receive action potentials from the second portion of the nerve in response to the stimulation at the first body region of the patient. The tool includes one of: a seeking needle or a paddle lead. The medical system also includes a measurement instrument electrically coupled to the tool and configured to measure and analyze the action potentials received by the tool.

Yet another aspect of the present disclosure involves a method of providing a stimulation therapy to a patient. A first calibration process is performed in a first patient posture state. The first calibration process associates a sensation experienced by a patient, in the first patient posture state, with a first amount of an evoked potential and a first value of a stimulation parameter for the stimulation therapy to achieve the first amount of evoked potential. A second calibration process is performed in a second patient posture state. The second calibration process associates the sensation experienced by a patient, in the second patient posture state, with a second amount of the evoked potential and a second value of the stimulation parameter for the stimulation therapy to achieve the second amount of evoked potential. After the first and second calibration processes have been performed, a current patient posture state is detected. If the current patient posture state is detected as the first patient posture state, the stimulation therapy is applied to the patient using the first value of the stimulation parameter as an initial value. If the current patient posture state is detected as the second patient posture state, the stimulation therapy is applied to the patient using the second value of the stimulation parameter as the initial value.

Yet another aspect of the present disclosure involves a medical system for stimulating a patient. The medical system includes an electronic storage configured to store: an association of a sensation experienced by the patient in a first patient posture state with a first amount of an evoked potential and a first value of a stimulation parameter for a stimulation therapy to cause the first amount of evoked potential; and an association of a sensation experienced by the patient in a second patient posture state with a second amount of the evoked potential and a second value of the stimulation parameter for the stimulation therapy to cause the second amount of evoked potential. The medical system includes one or more sensors configured to detect a present patient posture state. The medical system includes a microcontroller coupled to the one or more sensors and the electronic storage. The medical system includes stimulation circuitry configured to generate, in response to instructions from the microcontroller: a first stimulation therapy using the first value as an initial value of the stimulation parameter in response to a detection of the patient being in the first patient posture state; and a second stimulation therapy using the second value as the initial value of the stimulation parameter in response to a detection of the patient being in the second patient posture state.

Yet another aspect of the present disclosure involves a medical device for providing a stimulation therapy to a patient. The medical device includes an electronic storage storing respective results of a first calibration process and a second calibration process. The result of the first calibration process associates a sensation experienced by the patient, in a first patient posture state, with a first amount of an evoked potential and a first value of a stimulation parameter for the stimulation therapy to achieve the first amount of evoked potential. The result of the second calibration process associates the sensation experienced by the patient, in a second patient posture state, with a second amount of the evoked potential and a second value of the stimulation parameter for the stimulation therapy to achieve the second amount of evoked potential. The medical device includes one or more sensors configured to detect a current patient posture state. The medical device includes a microcontroller coupled to the electronic storage and to the one or more sensors. The medical device includes stimulation circuitry configured to generate the stimulation therapy to be delivered to a nerve site of the patient in response to instructions from the microcontroller in a manner such that: the stimulation therapy is generated using the first value as an initial value of the stimulation parameter in response to the first patient posture state being detected as the current patient posture state; and the stimulation therapy is generated using the second value as the initial value of the stimulation parameter in response to the second patient posture state being detected as the current patient posture state.

Yet another aspect of the present disclosure involves a method of establishing a stimulation treatment protocol for a patient. The method includes delivering electrical stimulation to a nerve site of the patient. The electrical stimulation is delivered using a stimulation configuration with respect to one or more of the following: activation of a subset of a plurality of electrodes on a lead, electrode polarity for the activated electrodes, stimulation pulse width, and stimulation pulse amplitude. An action potential evoked from the nerve site in response to the electrical stimulation is measured. The action potential includes a sensory fiber contribution and a motor fiber contribution. Both the sensory fiber contribution and the motor fiber contribution are measured. The delivering and the measuring are repeated for a plurality of cycles. Each cycle is performed using a different stimulation configuration. The stimulation configuration that offers a greatest sensory fiber contribution relative to the motor fiber contribution is recommended as a candidate for optimized stimulation configuration.

Yet another aspect of the present disclosure involves a medical system for establishing a stimulation treatment protocol for a patient. The medical system includes a stimulation component configured to deliver electrical stimulation to a nerve site of the patient. The electrical stimulation is delivered using a stimulation configuration with respect to one or more of the following: activation of a subset of a plurality of electrodes on a lead, electrode polarity for the activated electrodes, stimulation pulse width, and stimulation pulse amplitude. The medical system includes a measurement component configured to measure an action potential evoked from the nerve site in response to the electrical stimulation. The action potential includes a sensory fiber contribution and a motor fiber contribution. The measurement component is configured to measure both the sensory fiber contribution and the motor fiber contribution. The medical system includes a processor component. The processor component is configured to instruct the stimulation component and the measurement component to repeat the delivering of the electrical stimulation and the measurement of the action potential for a plurality of cycles. Each cycle is performed using a different stimulation configuration. The processor component is configured to thereafter recommend, as a candidate for optimized stimulation configuration, the stimulation configuration that offers a greatest sensory fiber contribution relative to the motor fiber contribution.

Yet another aspect of the present disclosure involves a medical device for establishing a stimulation treatment protocol for a patient. The medical device includes stimulation circuitry configured to deliver electrical stimulation to a nerve site of the patient. The electrical stimulation is delivered using a stimulation configuration with respect to one or more of the following: activation of a subset of a plurality of electrodes on a lead, electrode polarity for the activated electrodes, stimulation pulse width, and stimulation pulse amplitude. The medical device includes measurement circuitry configured to measure an action potential evoked from the nerve site in response to the electrical stimulation. The action potential includes a sensory fiber contribution and a motor fiber contribution. The measurement circuitry is configured to measure both the sensory fiber contribution and the motor fiber contribution. The medical device includes controller circuitry. The controller circuitry is configured to instruct the stimulation circuitry and the measurement circuitry to repeat the delivering of the electrical stimulation and the measurement of the action potential for a plurality of cycles. Each cycle is performed using a different stimulation configuration. The controller circuitry is configured to thereafter recommend, as a candidate for optimized stimulation configuration, the stimulation configuration that offers a greatest sensory fiber contribution relative to the motor fiber contribution.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 8 is a legend showing how the FIGS. 8A-8L are arranged together.

FIGS. 15A-15C illustrate a conductive element used by a peripheral neurostimulator according to various embodiments of the present disclosure.

FIG. 21 is a simplified flowchart illustrating a method of reducing power consumption for a peripheral neurostimulator according to an embodiment of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn to different scales for simplicity and clarity.

Figure 1:
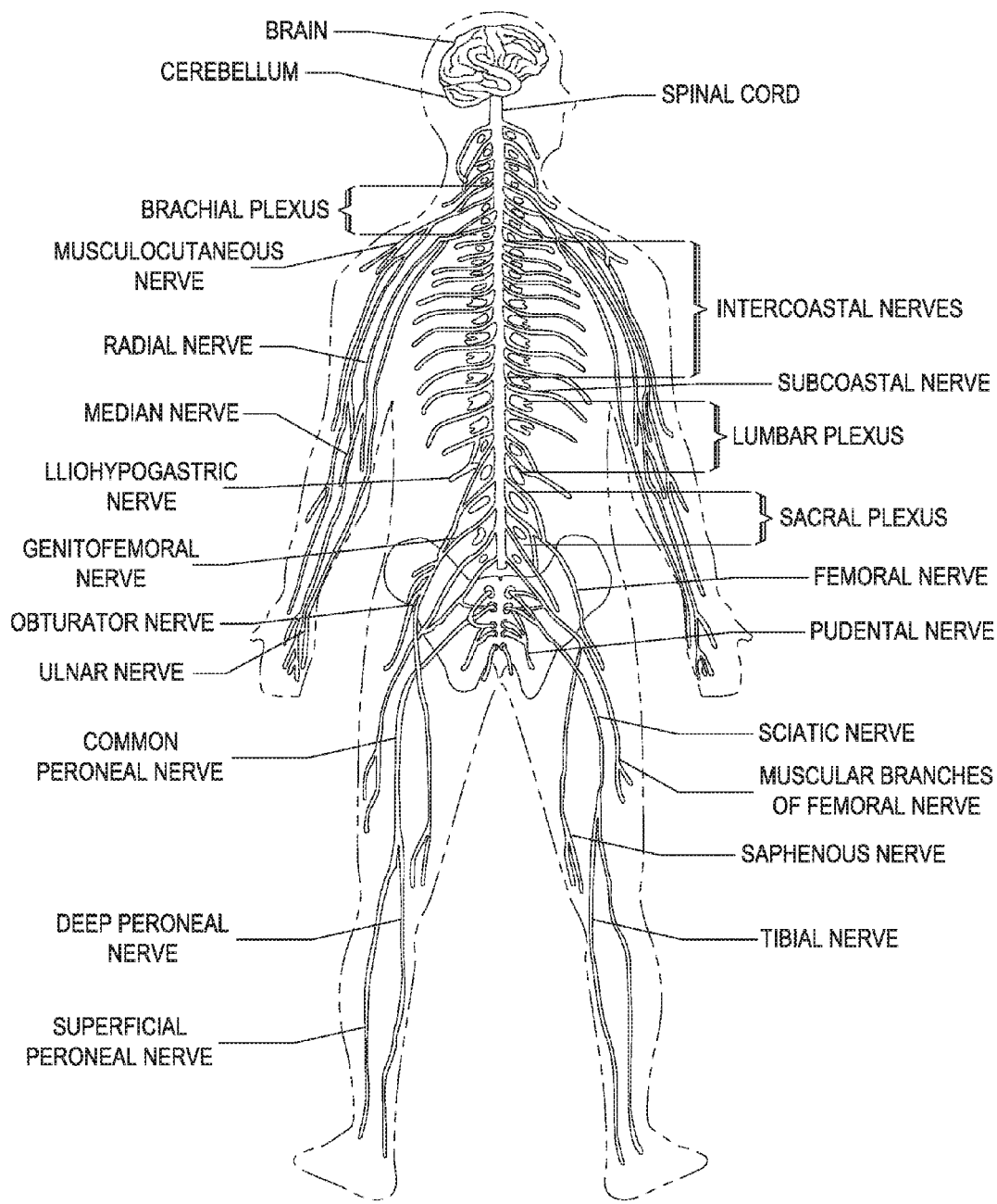
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are particularly well suited to stimulation of limb peripheral nerves, including those identified in FIG. 1.

Figure 2:
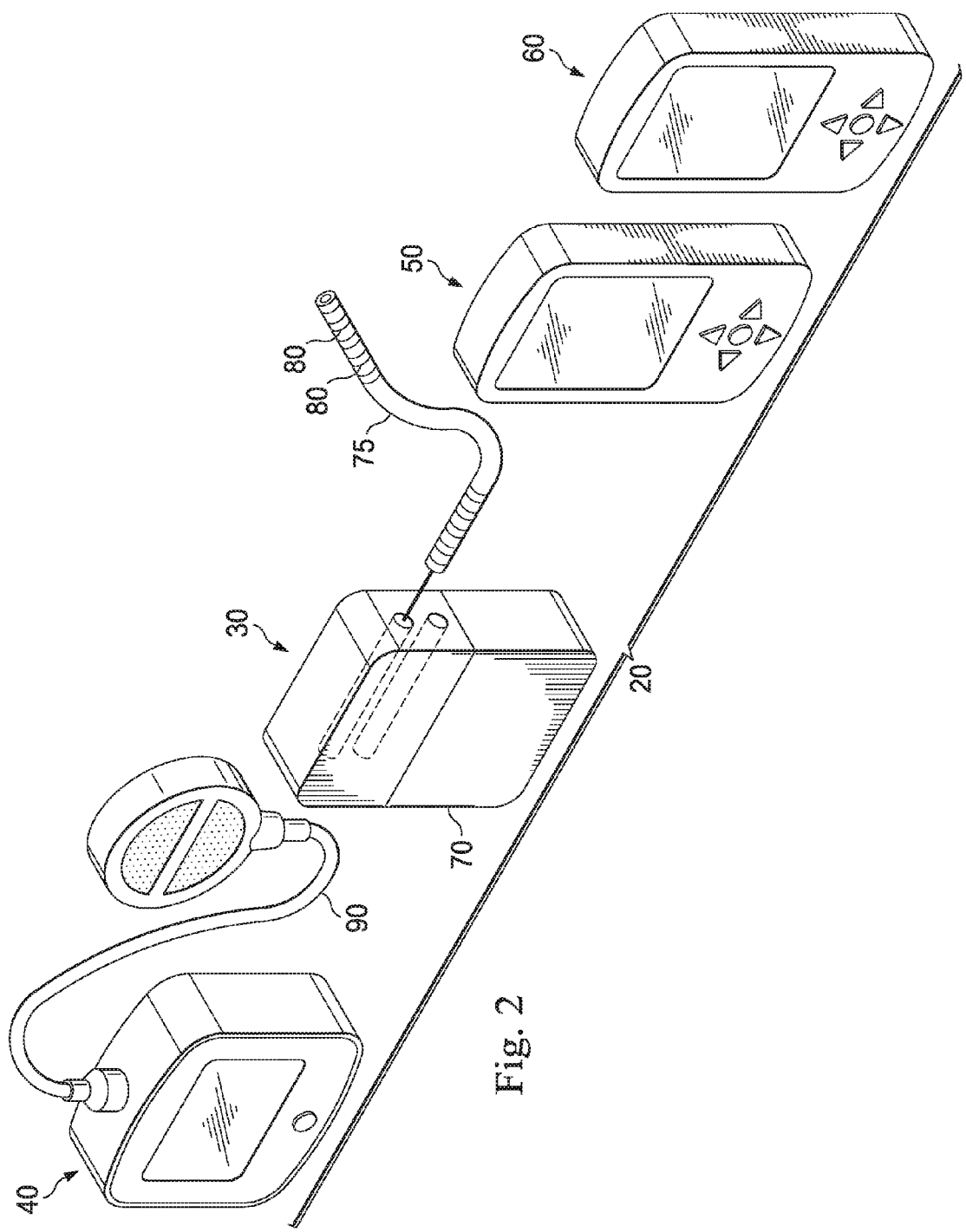
FIG. 2 is a simplified block diagram of an example medical system according to various embodiments of the present disclosure.

FIG. 2 illustrates a simplified block diagram of a medical system 20 to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. The implantable medical device 30 may include an implantable pulse generator (IPG) 70. In some embodiments, the IPG 70 is a peripheral neurostimulator (PNS) device. The IPG 70 is coupled to one end of an implantable lead 75. The other end of the implantable lead 75 includes multiple electrode surfaces 80 through which electrical current is applied to a desired part of a body tissue of a patient. The implantable lead 75 incorporates electrical conductors to provide a path for that current to travel to the body tissue from the IPG 70. Although only one implanted lead 75 is shown in FIG. 1, it is understood that a plurality of implanted leads may be attached to the IPG 70. Furthermore, the type of implanted lead that may be used in the medical system 20 is not limited to the embodiment shown in FIG. 1. For example, a paddle lead may be implemented in certain embodiments.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, or longer, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters. It is also understood that although FIG. 2 illustrates the patient programmer 50 and the clinician programmer 60 as two separate devices, they may be integrated into a single programmer in some embodiments.

Figure 3A:
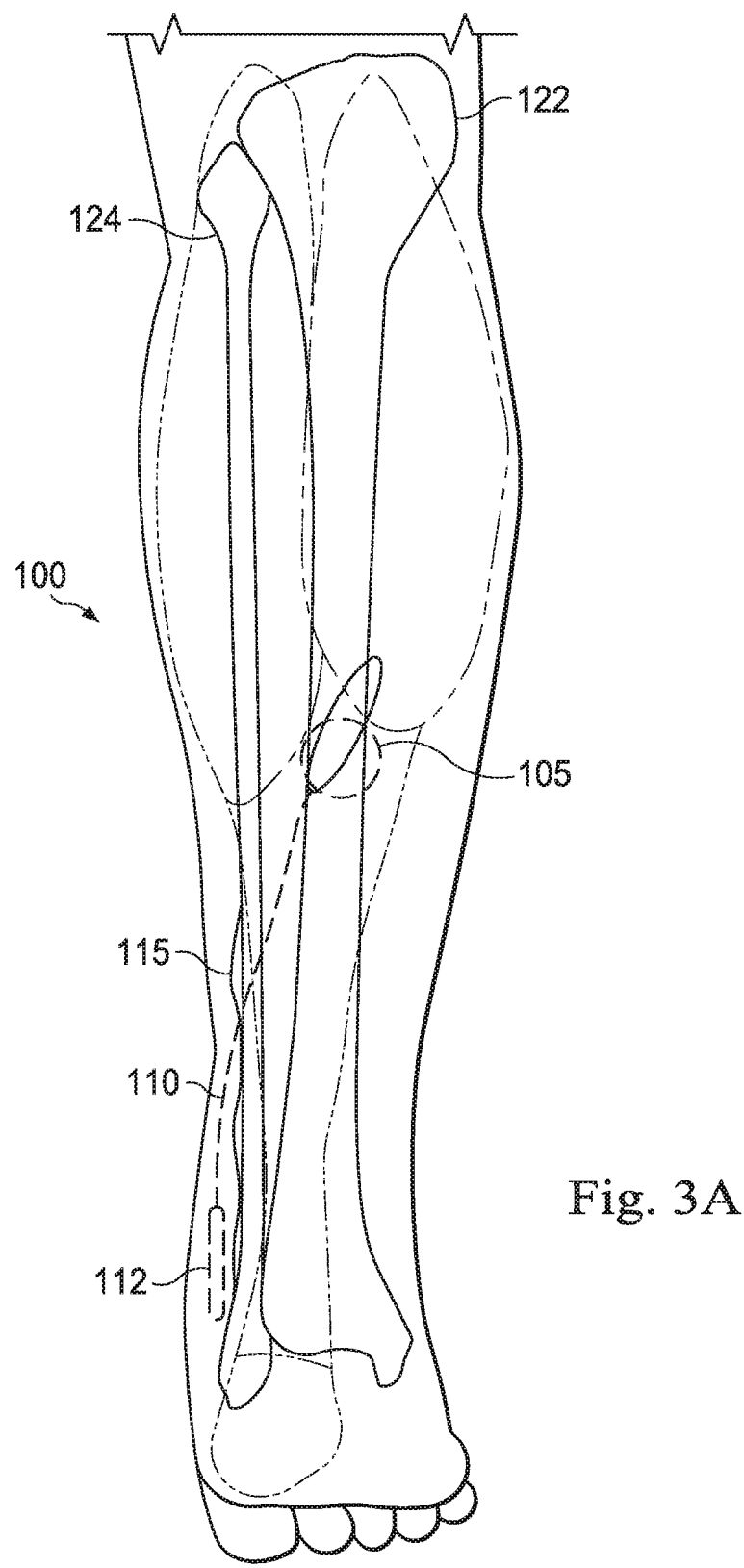
FIGS. 3A-3B illustrate stylized views of various portions of the human body with example peripheral neurostimulators implanted according to embodiments of the present disclosure.
Figure 3B:
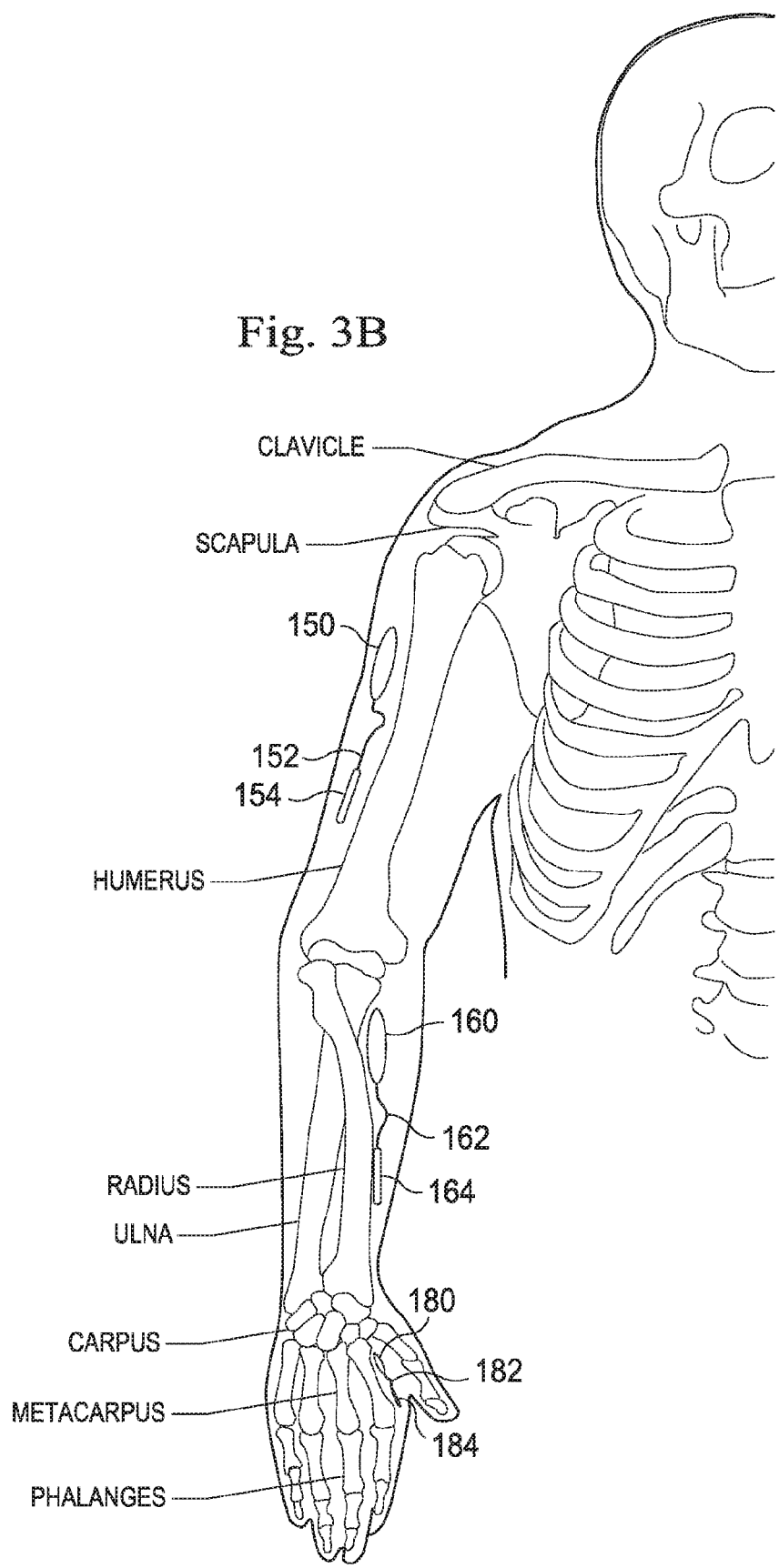

FIGS. 3A-3B illustrate various example regions of the human body within which a peripheral PNS device may be implanted. For example, referring to FIG. 3A, a lower leg 100 of a patient is illustrated. As an embodiment of the implantable medical device 30 discussed above with reference to FIG. 2, a PNS device 105 is implanted in the lower leg 100, for example, near the calf muscles. Through an elongate lead body 110, the PNS device 105 is electrically coupled to implanted electrodes 112. The electrodes are positioned for stimulation of the posterior tibial nerve 115. In the illustrated embodiment, the PNS device 105, the lead body 110, and the implanted electrodes 112 all reside below the knee and are contained within the length of the tibia 122 and the fibula 124. In other words, the lead body 110 does not traverse a joint as it extends between the PNS device 105 and the implanted electrode 112. In the illustrated embodiment, the PNS device 105, the lead body 110, and the implanted electrodes 112 are positioned between a knee joint and an ankle joint.

Referring now to FIG. 3B, another example PNS device 150 is implanted along the humerous bone. The PNS device 150 is coupled to implanted electrodes 154 through a lead body 152. The PNS device, the lead body 152, and the implanted electrodes 154 are positioned along the humerous bone without extending into or across the adjacent joints in the shoulder or elbow. Similarly, another example PNS device 160 may be implanted along and within the length of the radius and ulna bones. The PNS device 160 is coupled to implanted electrodes 164 through a lead body 162. The PNS device 160, the lead body 162, and the implanted electrodes 164 are implanted under the skin of the forearm but without any of the components extending into the adjacent joints of the elbow and the wrist. As yet another example, a PNS device 180 may be implanted along a metacarpus bone in the hand. The PNS device 180 is coupled to implanted electrodes 184 through a lead body 182. The implantation of the PNS device 180, the lead body 182, and the implanted electrodes 184 is configured such that none of them extends across an adjacent joint in the wrist or the fingers.

It is understood that FIGS. 3A-3B merely illustrate several example sites of the body in which a PNS device may be implanted to stimulate one or more target nerves (such as the posterior tibial nerve in FIG. 3A). A PNS device may also be implanted in a number of other different peripheral nerves locations shown in FIG. 1. For instance, a PNS device may be implanted in a patient's arms to stimulate one or more of the median, ulnar, radial, and brachial plexus nerves, as well as in a patient's legs to stimulate one or more of the tibial, saphenous, sciatic, and femoral nerves. For reasons of simplicity, these configurations are not specifically illustrated herein.

Figure 4:
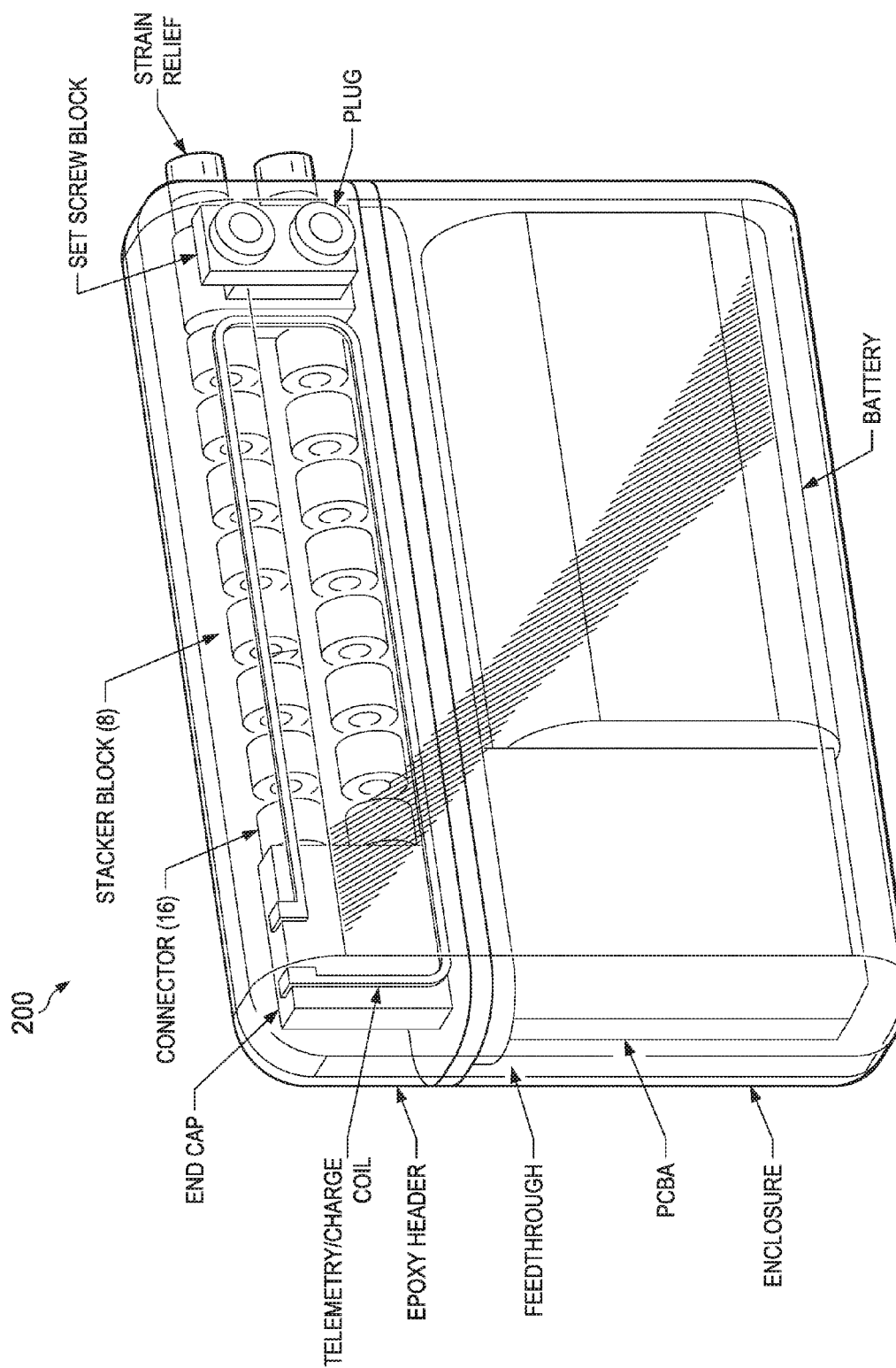
FIGS. 4-5 illustrate an example peripheral neurostimulator according to an embodiment of the present disclosure.
Figure 5:
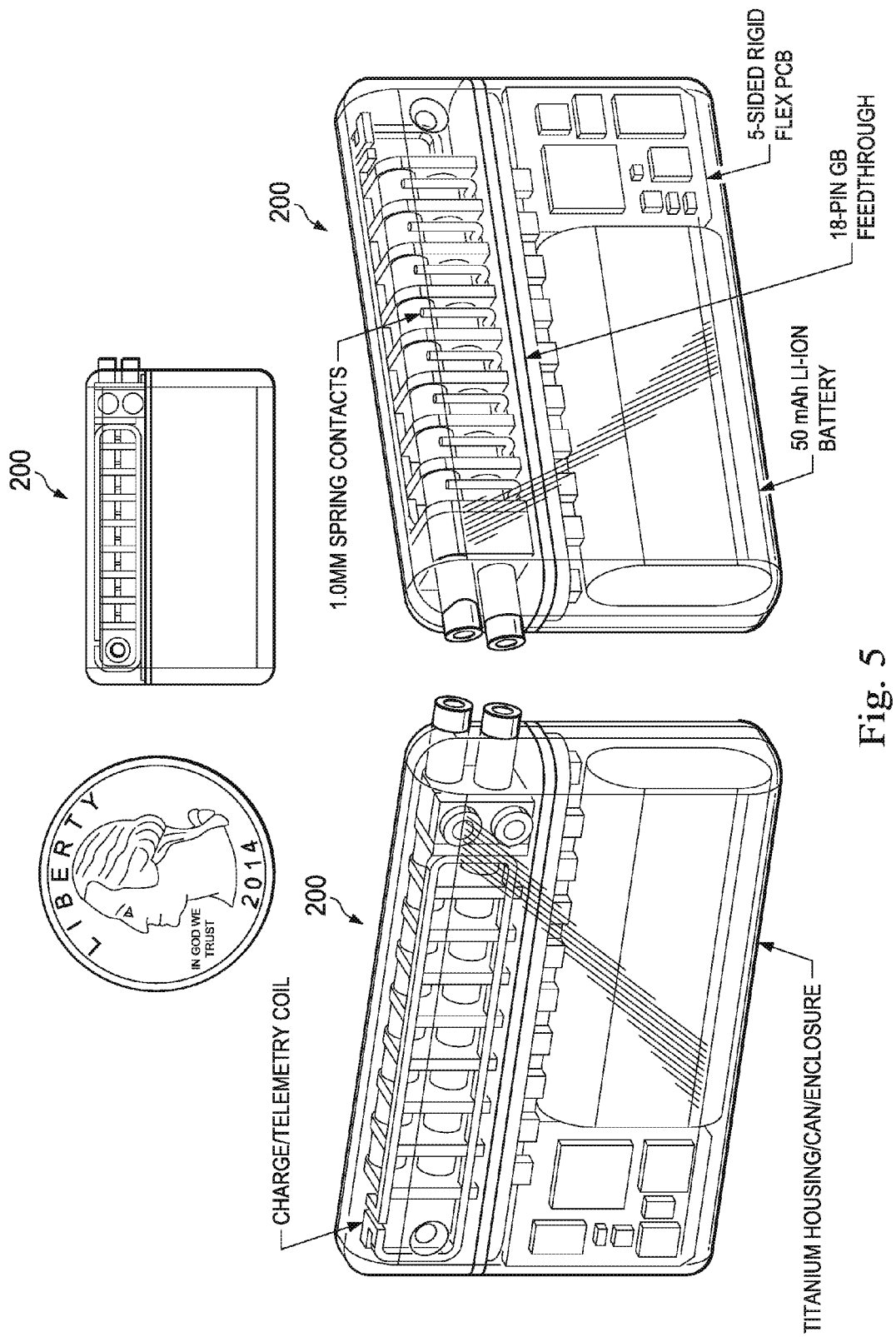

Referring now to FIGS. 4-5, a PNS device 200 is illustrated according to an embodiment of the present disclosure. In general, peripheral nerve stimulation is a technique configured to provide medical therapy for different diseases and/or to treat different types of pain. Depending upon the therapeutic application, peripheral nerve stimulation systems generally seek to activate only motor nerves (e.g., for functional purposes, such as dorsiflexion for a dropped foot, or a grasp for upper extremity hemiplegia) or only sensory nerves (e.g., for neuropathic pain management).

In treating pain, stimulation of innocuous sensory fibers in the periphery ostensibly affects pain transmission to the brain via the Gate Control Theory. Clinically, stimulation of these fibers usually results in a comfortable, moderate 'buzzing' sensation in the area of pain, termed paresthesia.

In general, peripheral nerve stimulation can utilize relatively simple stimulation techniques to provide excellent therapy. However, PNS therapy today is generally delivered by equipment designed for spinal cord stimulation (SCS). Spinal cord stimulation equipment utilizes large and overpowered implantable pulse generators (IPGs) designed not for stimulating peripheral nerves, but is designed to deliver electrical pulses to the spinal column. IPGs designed for SCS is also placed in large pockets in the lower back/upper buttock, rather than being implanted near the targeted peripheral nerve for electrical stimulation. These poorly adapted technologies for peripheral nerve therapy can cause significant tissue morbidity in the need to route the wires between the targeted peripheral nerve and the distantly located IPG unit. This, in turn, can result in frequent device failure (and thus therapy failure) due largely to lead migration and breakage. In many cases where SCS equipment was used for PNS, a large percentage of patients needed revision surgeries to address issues with the SCS IPG and leads. Additionally, while some peripheral nerve pain can be addressed by stimulating the nerve root through SCS of the spinal column, it can be difficult to achieve effective pain relief with respect to a targeted nerve and anatomy without affecting nearby, undesired areas.

To overcome the limitations associated with using SCS equipment to perform PNS, the present disclosure provides a small, flexible PNS system—an example embodiment of which includes the PNS device 200 shown in FIGS. 4-5—that can be made simple and small enough to be deployed in a minimally invasive surgical procedure, locally to the region of the targeted nerves, thereby avoiding tunneling through tissue to remote regions of the anatomy.

In some embodiments, the PNS system is characterized by a low parts count, low cost-of-goods, ease of manufacturability, a high energy density long lasting rechargeable battery, use of known biocompatible materials, compatibility with industry preferred electrode/lead systems, and a hermetic implantable device geometry that is well suited for most preferred anatomical locations. In some embodiments, the system, although simplified, is still flexible enough to handle a wide range of unilateral and bilateral applications, has high stimulation power output capability, covers accepted ranges of therapeutic waveform frequency and duration, can drive multiple leads of eight or more contacts each, and utilizes custom software applications reconfigurable for the different clinical applications (e.g., pain, incontinence, depression, epilepsy, etc.).

In some embodiments, the PNS system of the present disclosure includes the PNS device 200 in the form of a hermetically-sealed implantable pulse generator. The PNS device 200 has a miniature form factor. For example, the PNS device 200 may have a total volume of less than 5 cubic centimeters and a thickness less than 5 millimeters. To illustrate the small dimensions of the PNS device 200, FIG. 5 shows the PNS device 200 next to a quarter. As can be seen in FIG. 5, the PNS device 200 is shorter than the quarter and not much longer either. Such small package size of the PNS device 200 enables comfortable and cosmetically attractive placement of the PNS device 200 on the limbs of the patient.

Furthermore, the PNS device 200 offers one or more of the following features:
- Active can/enclosure technology that allows for broader stimulation fields;
- Deep drawn small but shallow rectangular form factor for the can that allows for ease of manufacture and low cost;
- Connects to proximal ends of "industry standard" electrodes, which have become preferred for ease of handling characteristics;
- Single piece high reliability connector stack;
- High density pin-less hermetic feedthrough connection system;
- Two reversibly connectible header ports enable connection of two leads for multi-region stimulation targeting, nominally distal from implanted package;
- High number of contacts per lead to allow for a wide range of lead designs (for instance, 8 tightly spaced contacts per lead) and different therapeutic applications (for instance, chronic intractable pain).

In addition to the PNS device 200, the PNS system of the present disclosure may also include an external stimulator used for trial therapy periods, one or more leads with corresponding electrodes, an extension for a lead/electrode, accessories such as lead anchors and surgical procedure tools, a remote control and pulse generator charger that may be combined into one device, and/or a remote controller for physician or patient programming use.

Figure 6A:
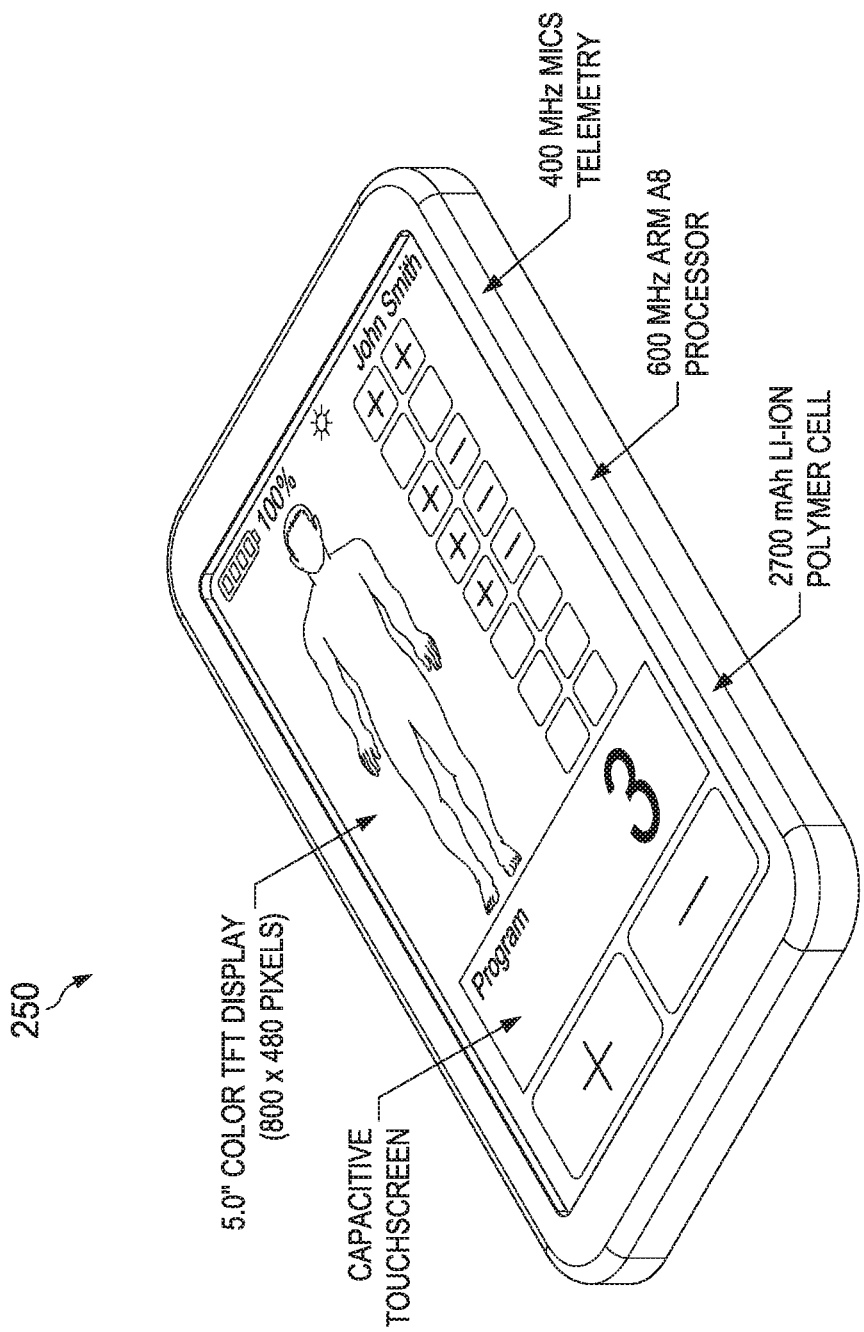
FIGS. 6A-6C illustrate an example programmer for a neurostimulator according to an embodiment of the present disclosure.
Figure 6B:
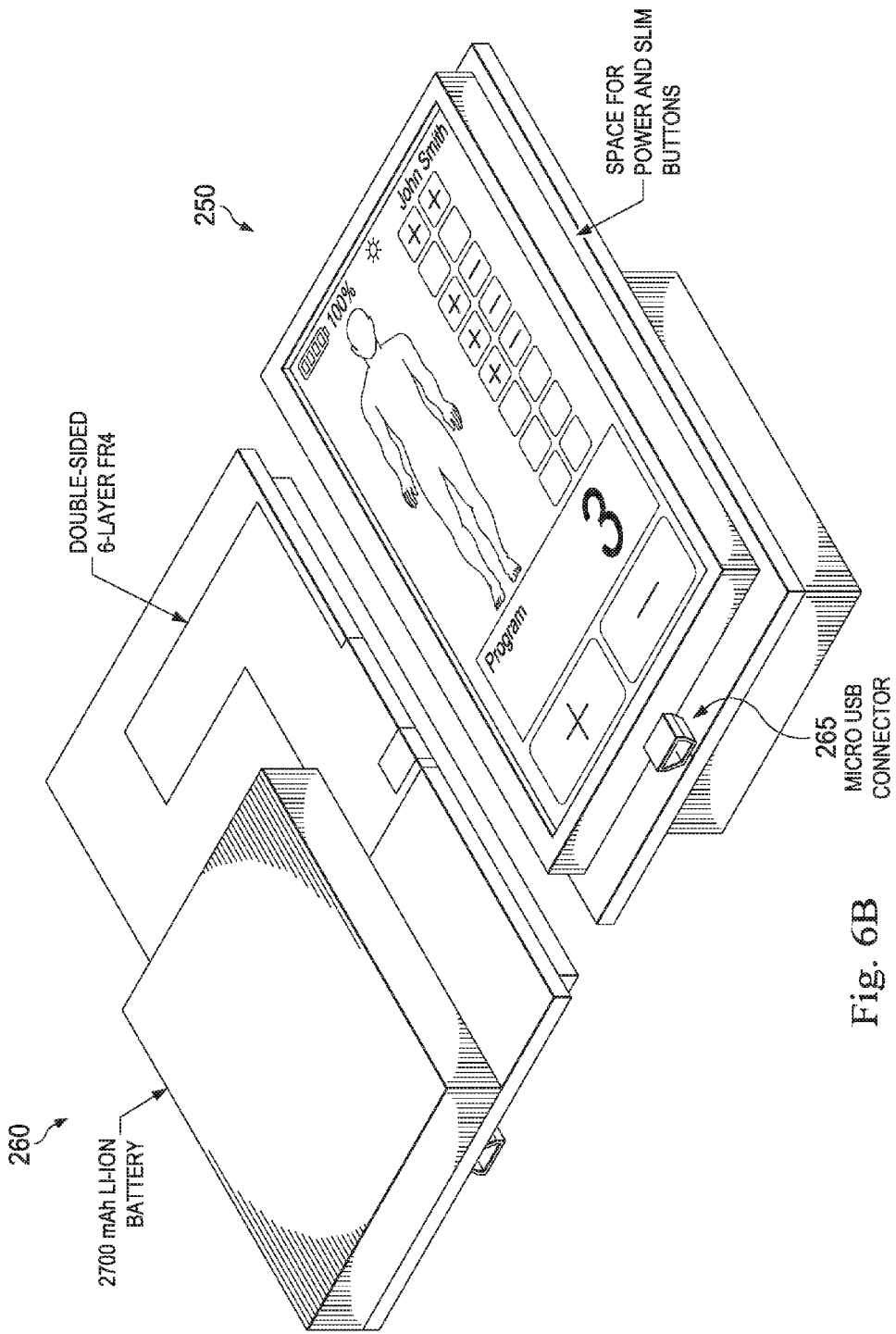
Figure 6C:
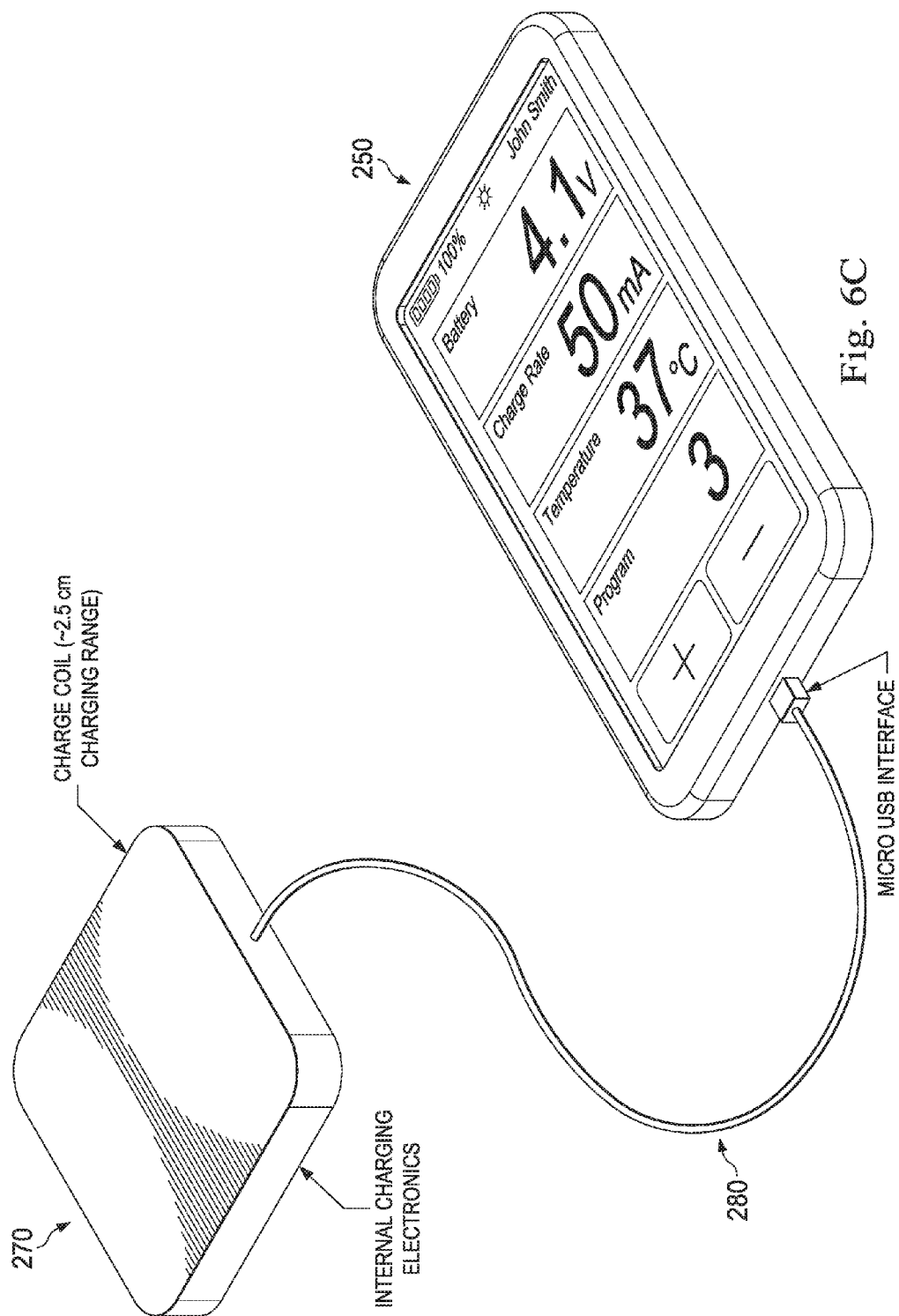

For example, FIGS. 6A-6C illustrate an example electronic programmer 250 configured to send programming instructions to the PNS device 200. The PNS device 200 generates a corresponding electrical stimulation therapy (e.g., a series of electrical stimulation pulses) in response to the received programming instructions. In certain embodiment, the electronic programmer 250 is configured to be used by either the patient or a healthcare professional. As such, the electronic programmer 250 may be viewed as an embodiment of the patient programmer 50 and the clinician programmer 60 integrated together as a single device.

As is shown in FIG. 6A, the electronic programmer 250 has a "smartphone-like" industrial design. For example, the electronic programmer 250 has a touchscreen (e.g., a capacitive touchscreen) graphical user interface with virtual buttons and input/output fields. The electronic programmer 250 may also have tactile buttons that provide an immediate control input to the programmer 250 for quick and simple core system functions. Such "smartphone-like" design reduces the stigma of using a medical device. The "smartphone-like" design of the electronic programmer also makes it easier for the user of the electronic programmer to learn how to use it quickly, since smartphones have become very popular, and most people are comfortable interacting with a smartphone-like user interface.

Aside from its elegant and intuitive industrial design, the electronic programmer 250 also offers flexible functionalities. For example, the electronic programmer 250 may be configurable from patient to patient, according to the patient's level of technical competence and/or comfort. The electronic programmer 250 may also be reconfigurable via firmware for different therapeutic applications (for instance, chronic intractable pain). Furthermore, the electronic programmer 250 may have multiple user modes: e.g., patient programming and patient charging mode (both configurable by a clinician), clinician mode, engineering mode, diagnostic mode, etc.

Referring to FIG. 6B, the electronic programmer 250 also includes an onboard battery 260. In the illustrated embodiment, the battery 260 is sealed within the housing of the electronic programmer 250 and is non-removable. In alternative embodiments, however, the battery 260 may be user-removable. The battery 260 is a rechargeable battery. In various embodiments, the battery 260 has a capacity ranging from about 400 milli-amp hours (mAh) to about 4000 mAh, for example with a capacity around 2700 mAh. The rechargeable nature of the battery 260 allows it to have a reduced size and mass.

The electronic programmer 250 also has a USB port 265, which allows the electronic interchange (e.g., telemetry or power) between the electronic programmer 250 and external devices. For example, referring to FIG. 6C, a charger 270 is coupled to the USB port 265 of the electronic programmer 250 through a USB cable 280. The battery 260 may provide power to the charger 270, which contains internal charging electronics and a charge coil for inductively charging the PNS device 200 discussed above. This type of power/charging configuration shown in FIGS. 6B-6C greatly simplifies patient tasks with respect to charging the PNS device 200, as patients only has a few things to manage. In addition, charging can be done at any time as needed and while the patient is ambulatory/mobile.

The electronic programmer 250 and the charger 270 are also both implemented in small and lightweight packages. For example, they may each have a thickness less than about 10 millimeters (mm). The small size of the electronic programmer 250 and the charger 270 enables comfortable, convenient, and cosmetically attractive wearing of the electronic programmer 250 and/or the charger 270 on a patient's limb, for example with a detachable belt or band. In some embodiments, the relative simplicity and versatility of the electronic programmer 250 discussed above reduce or eliminate the need for a cumbersome separate clinician programmer.

The various sections and components of the PNS device 200 will now be discussed in more detail below.

Figure 7:
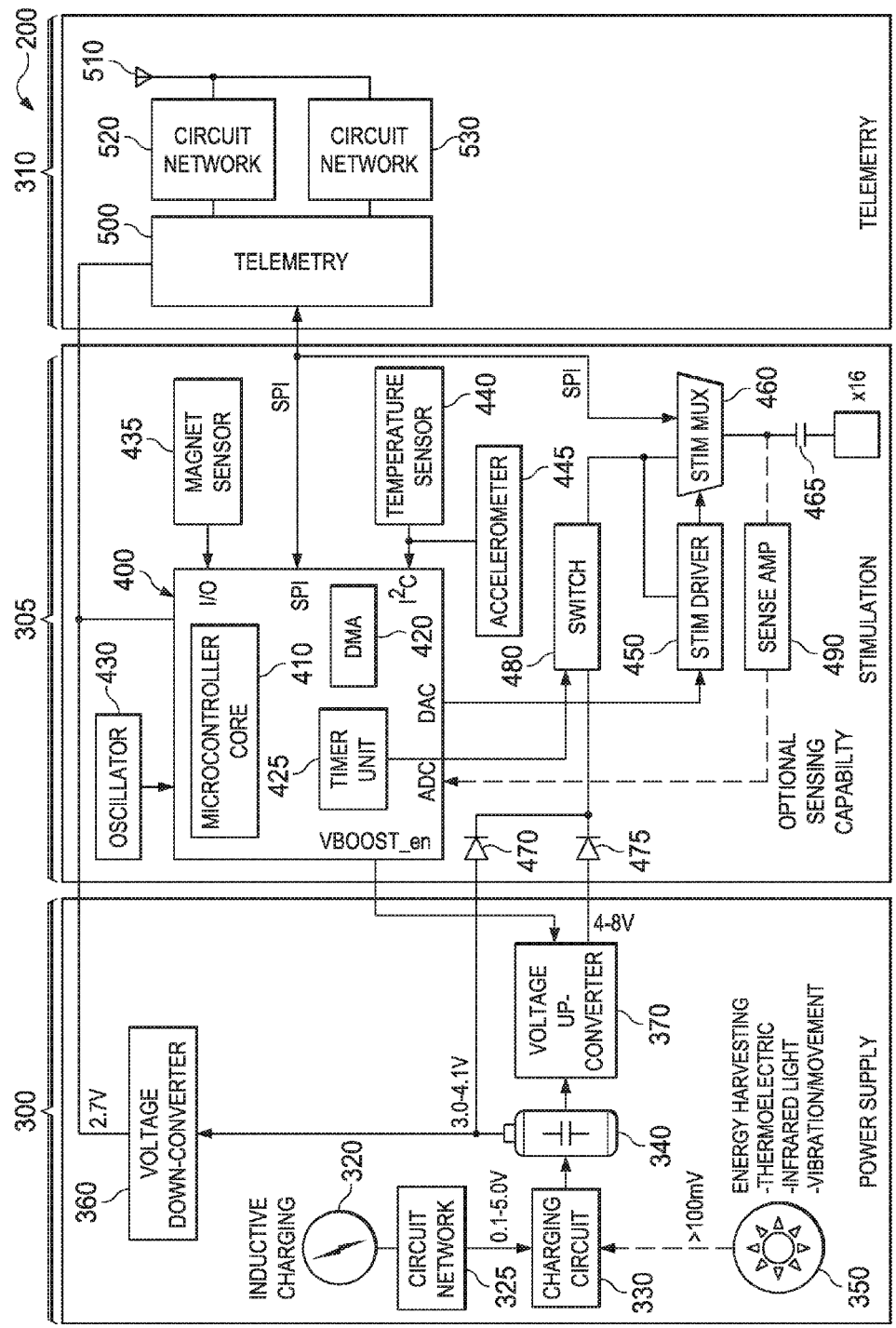
FIG. 7 illustrates a simplified block diagram of an example peripheral neurostimulator according to an embodiment of the present disclosure.
Figure 8A:
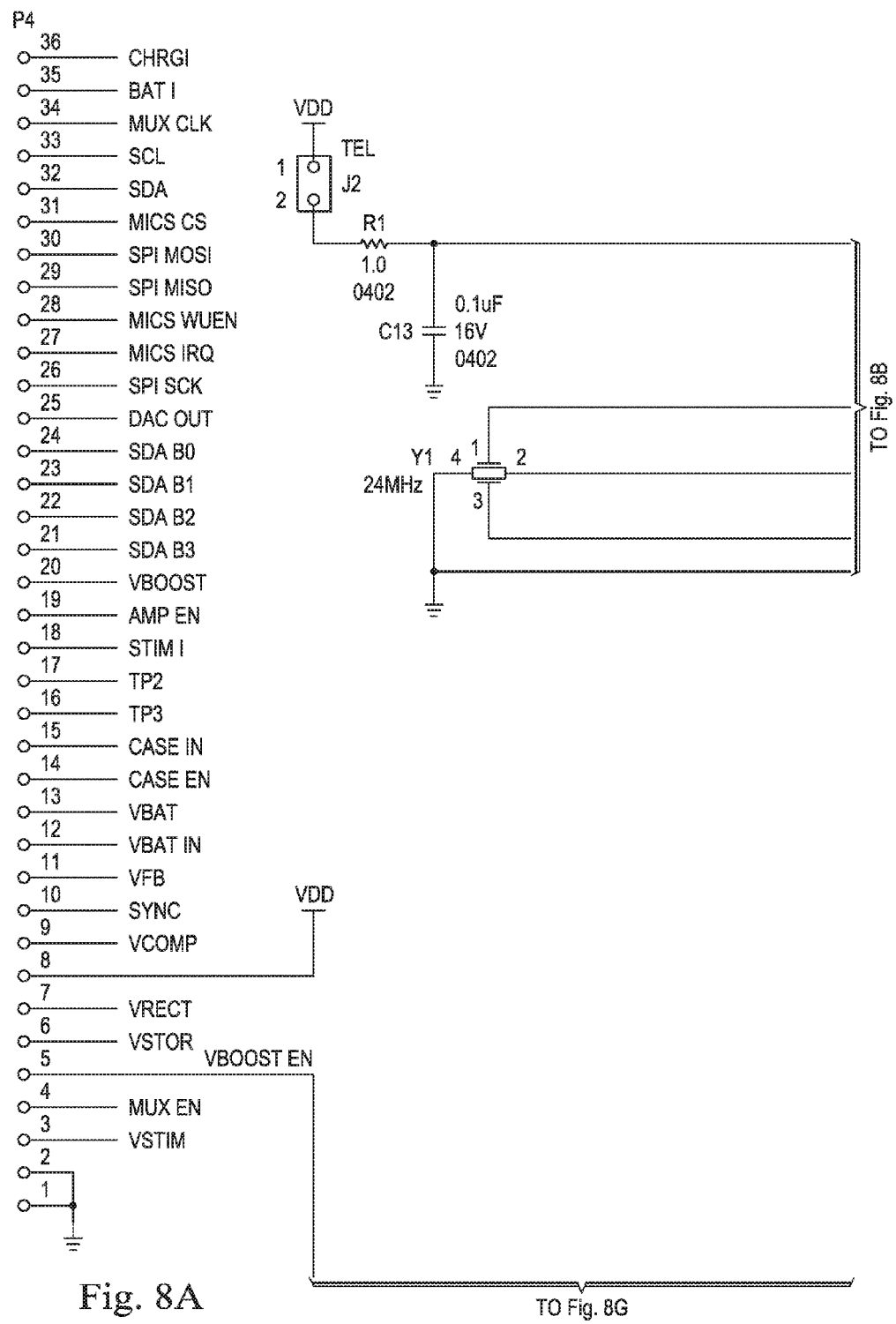
FIGS. 8A-8L illustrates a circuit schematic of the peripheral neurostimulator of FIG. 7 according to an embodiment of the present disclosure.
Figure 8B:
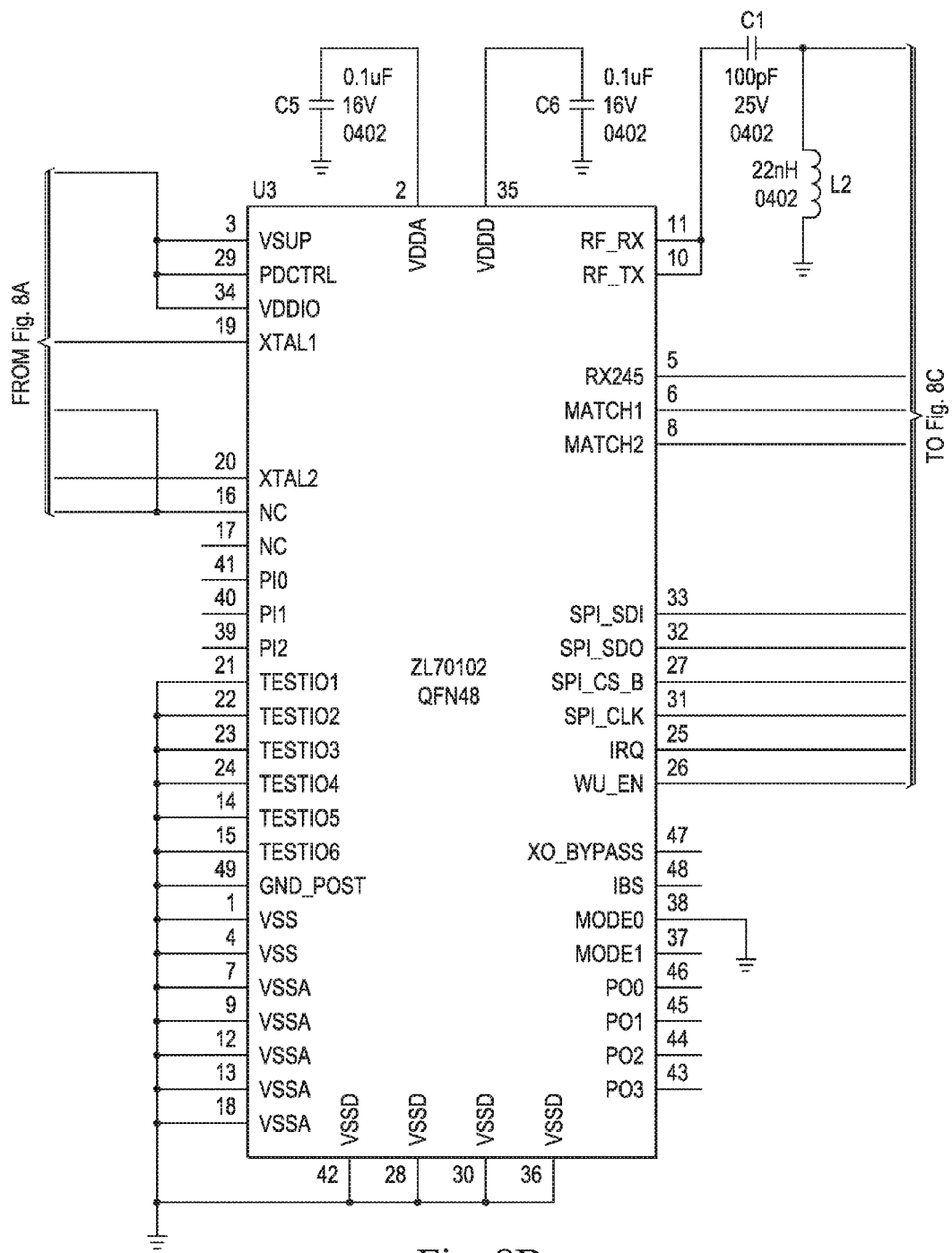
Figure 8C:
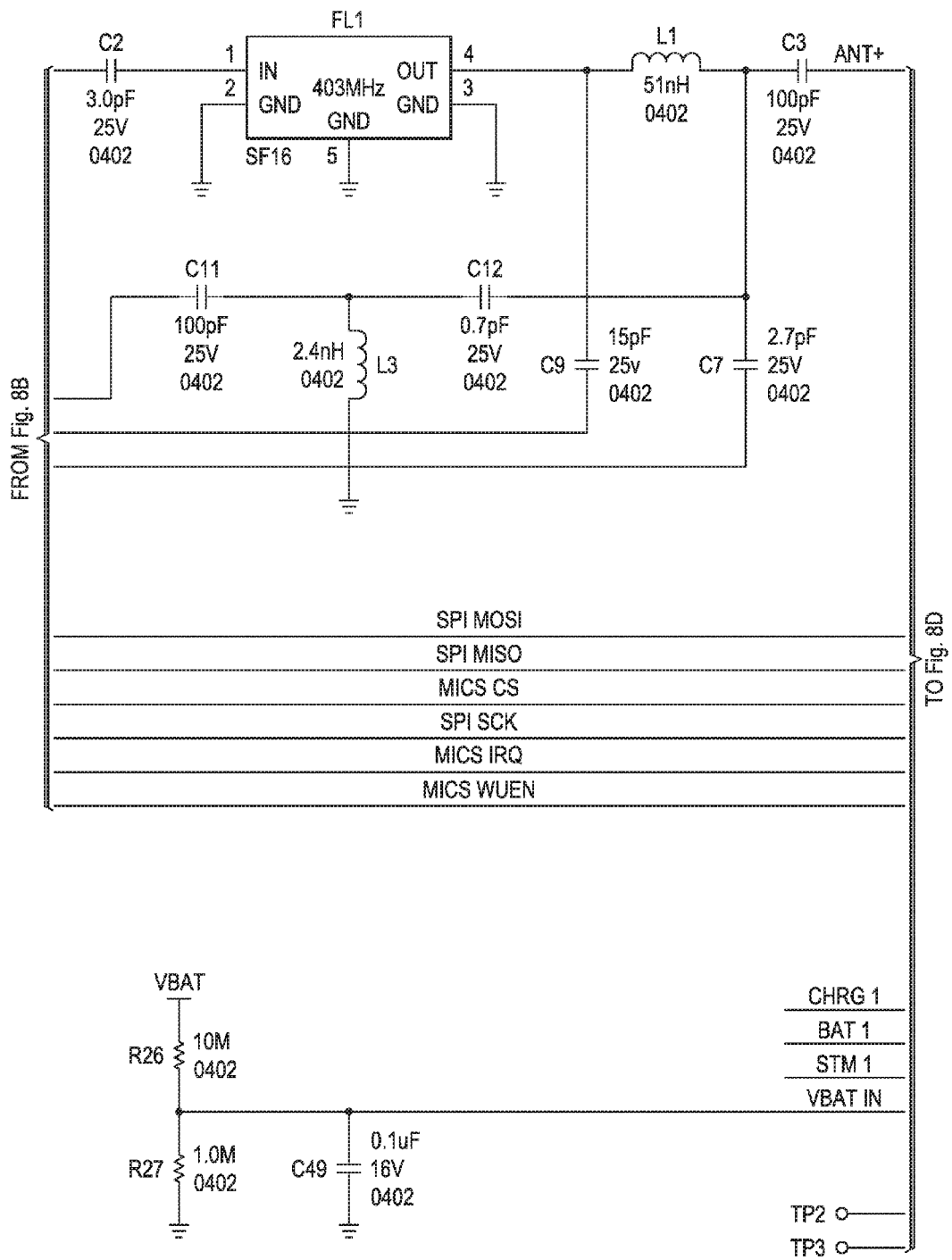
Figure 8D:
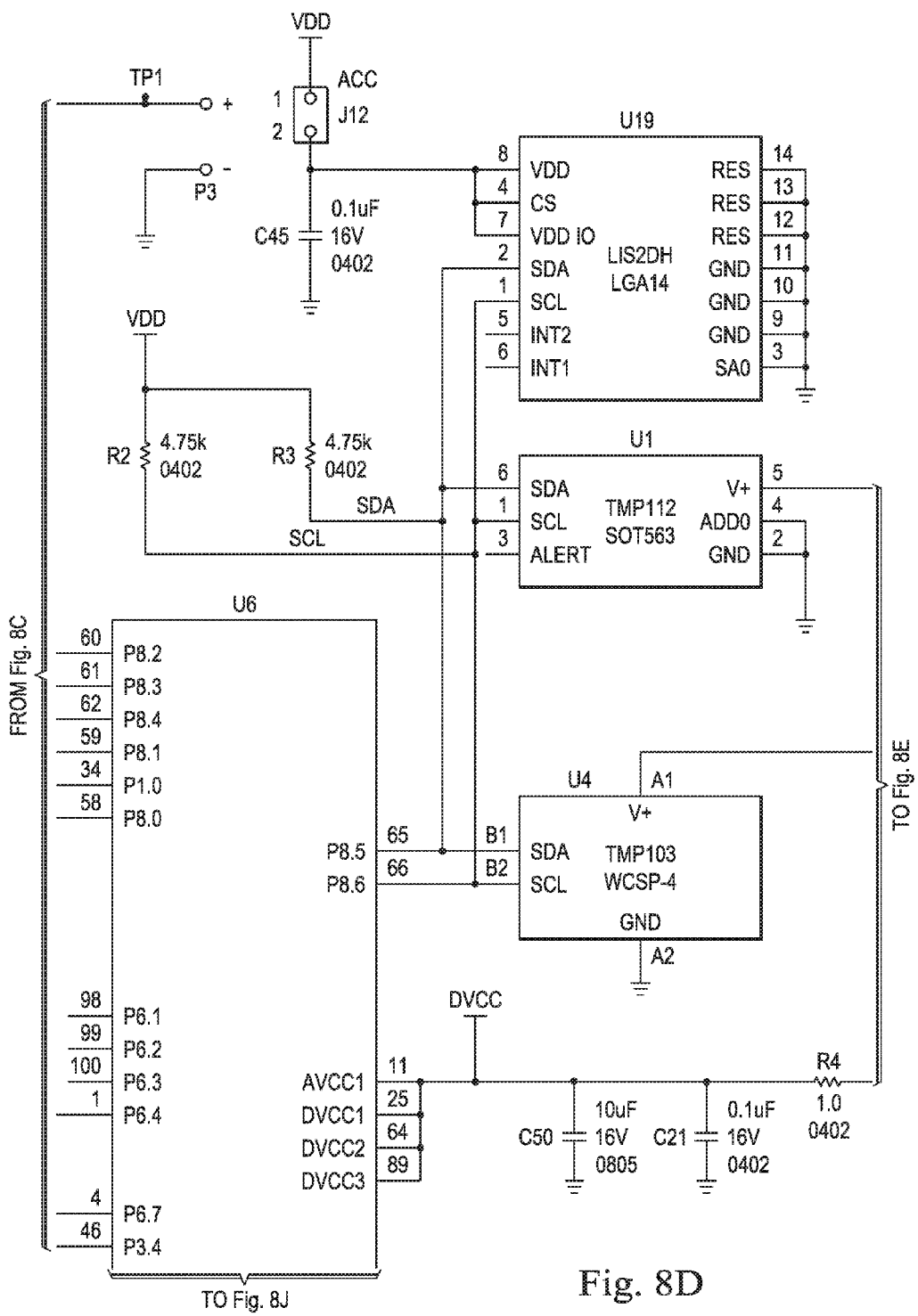
Figure 8E:
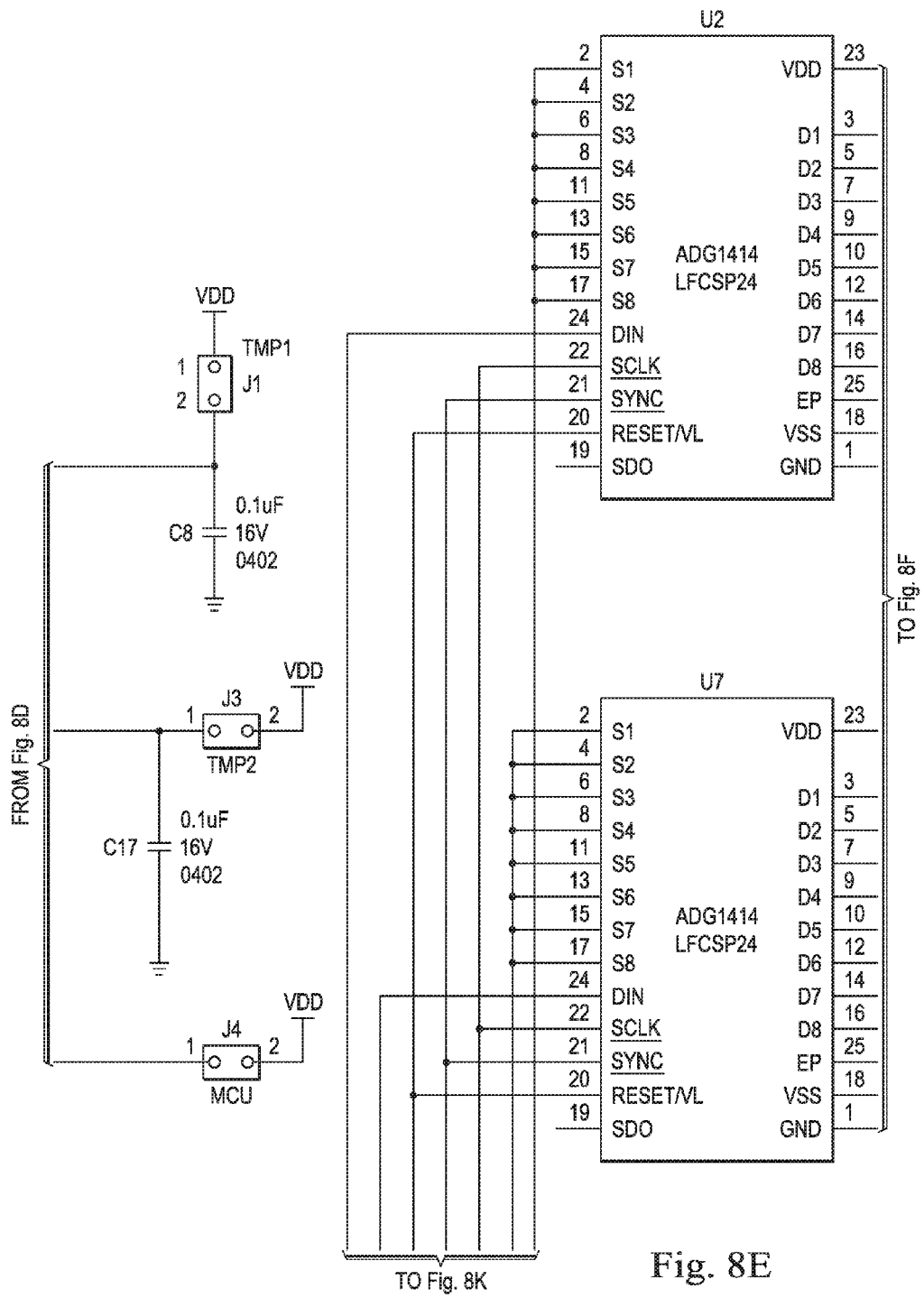
Figure 8F:
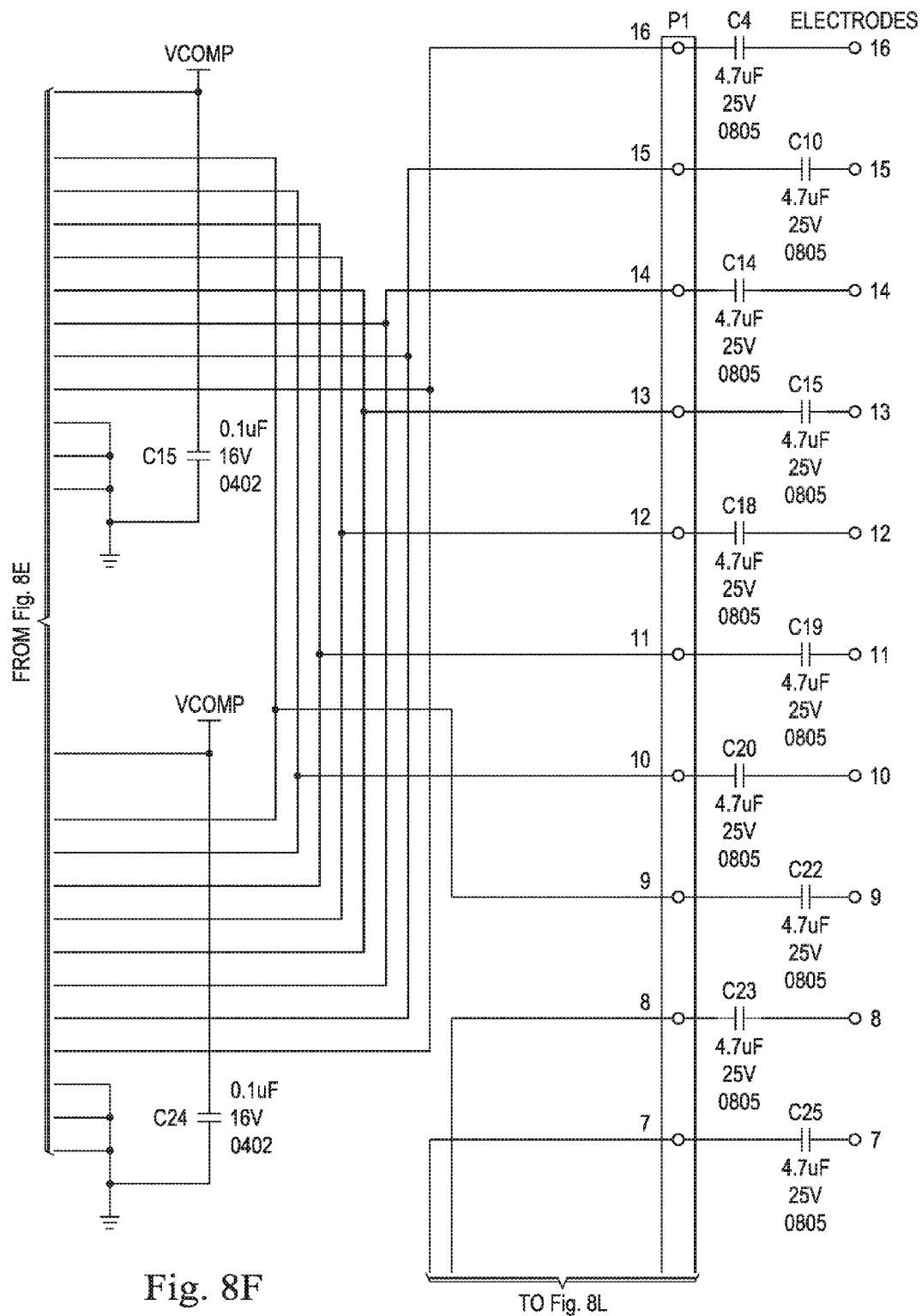
Figure 8G:
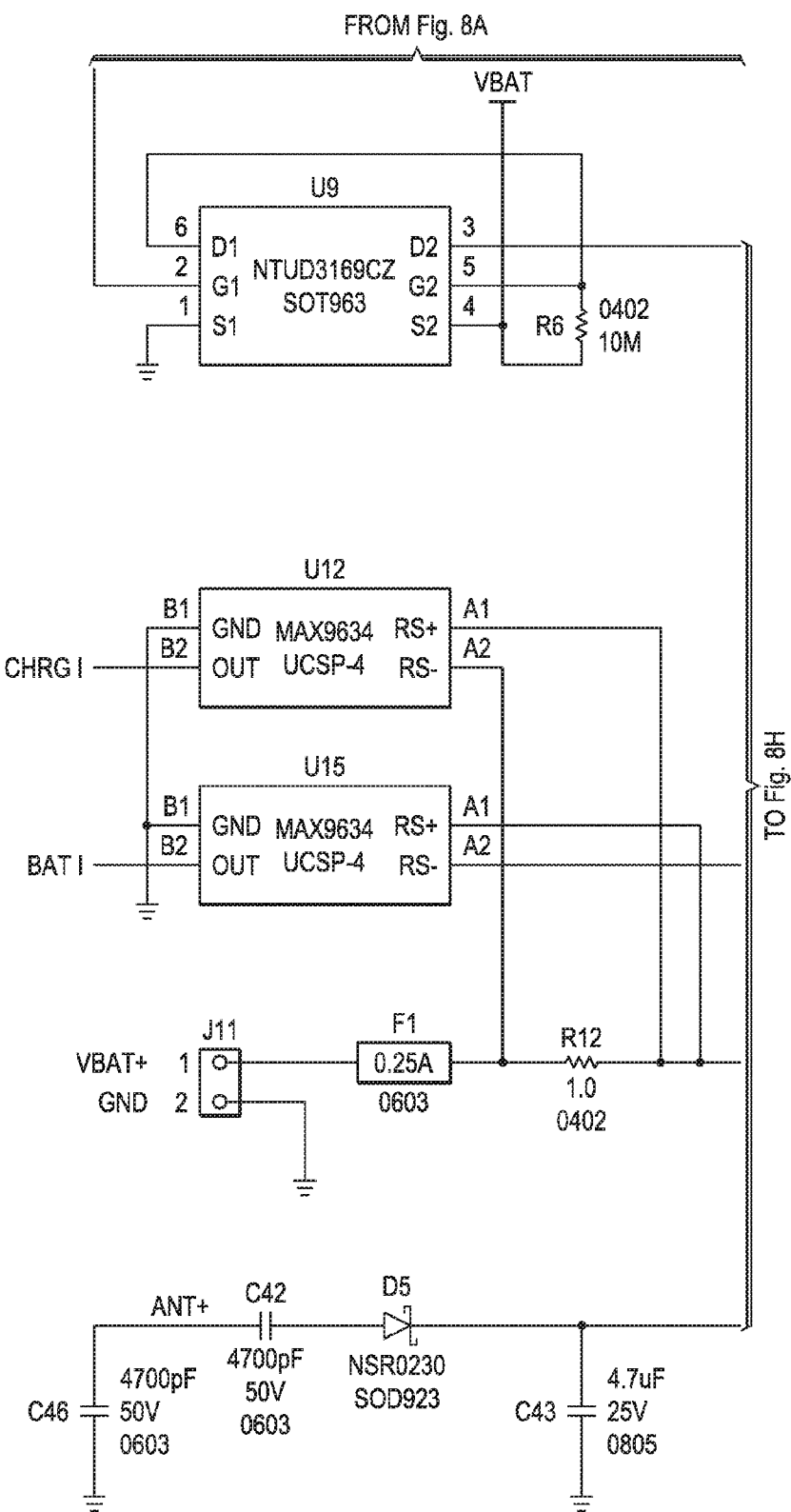
Figure 8H:
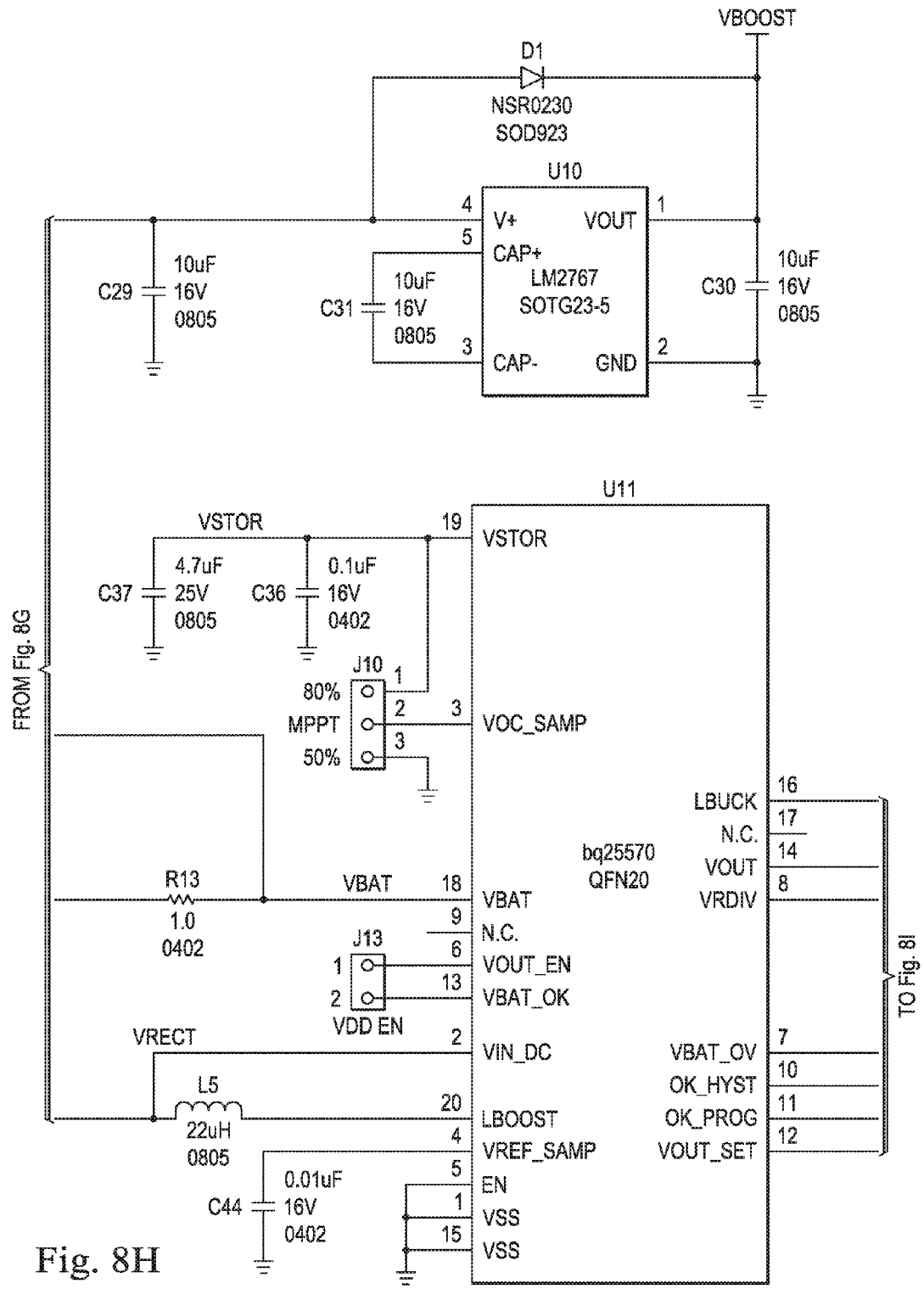
Figure 8I:
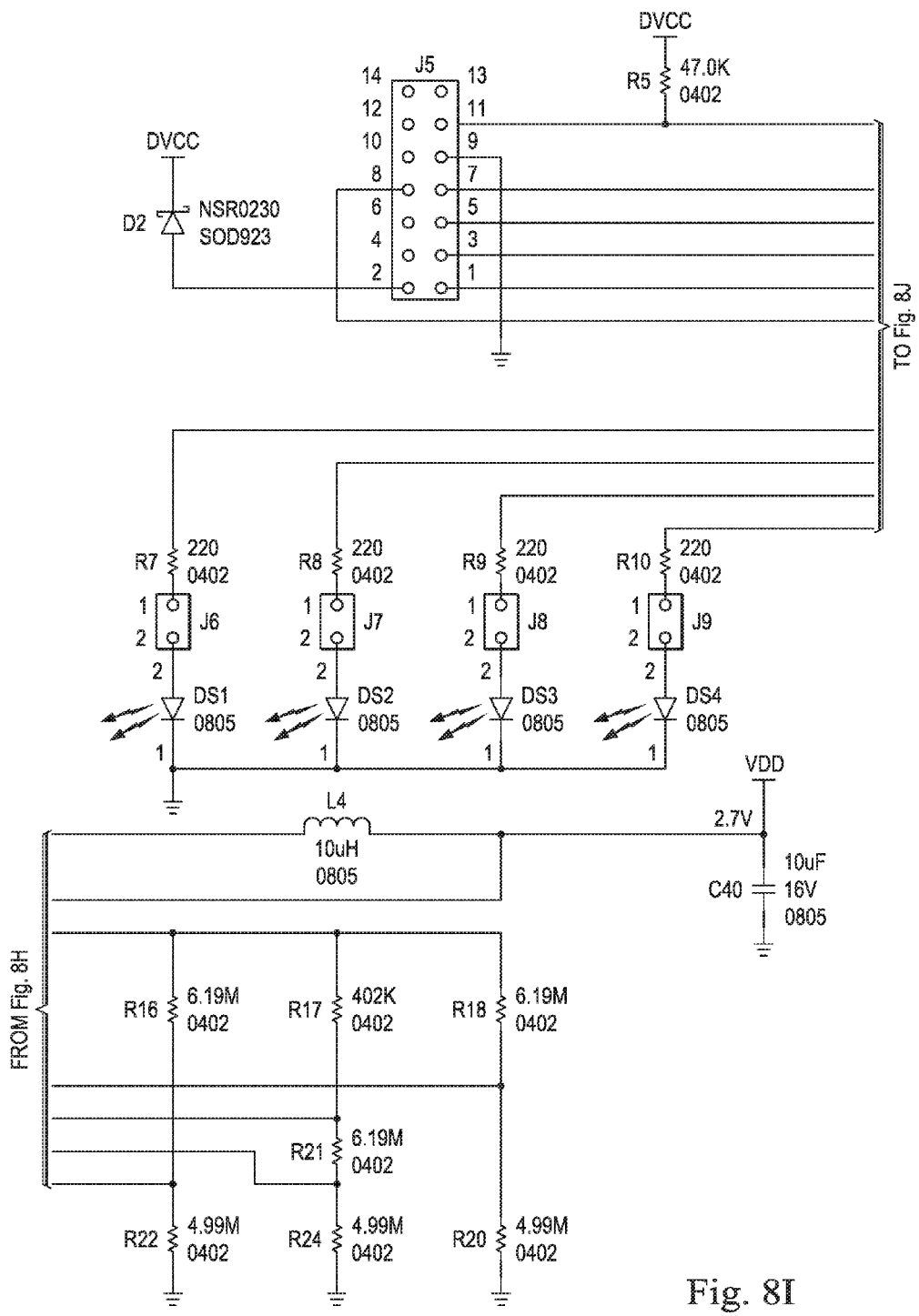
Figure 8J:
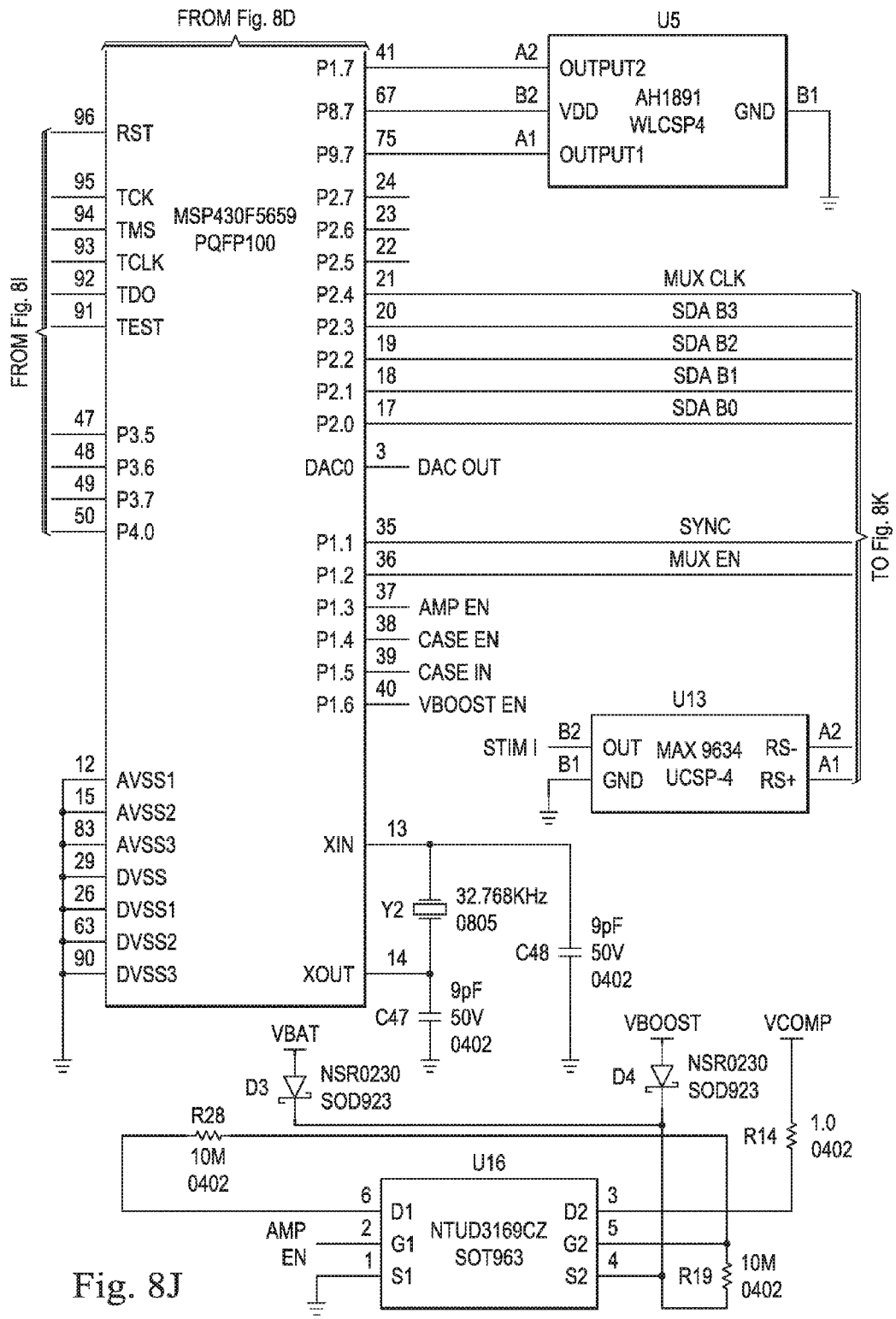
Figure 8K:
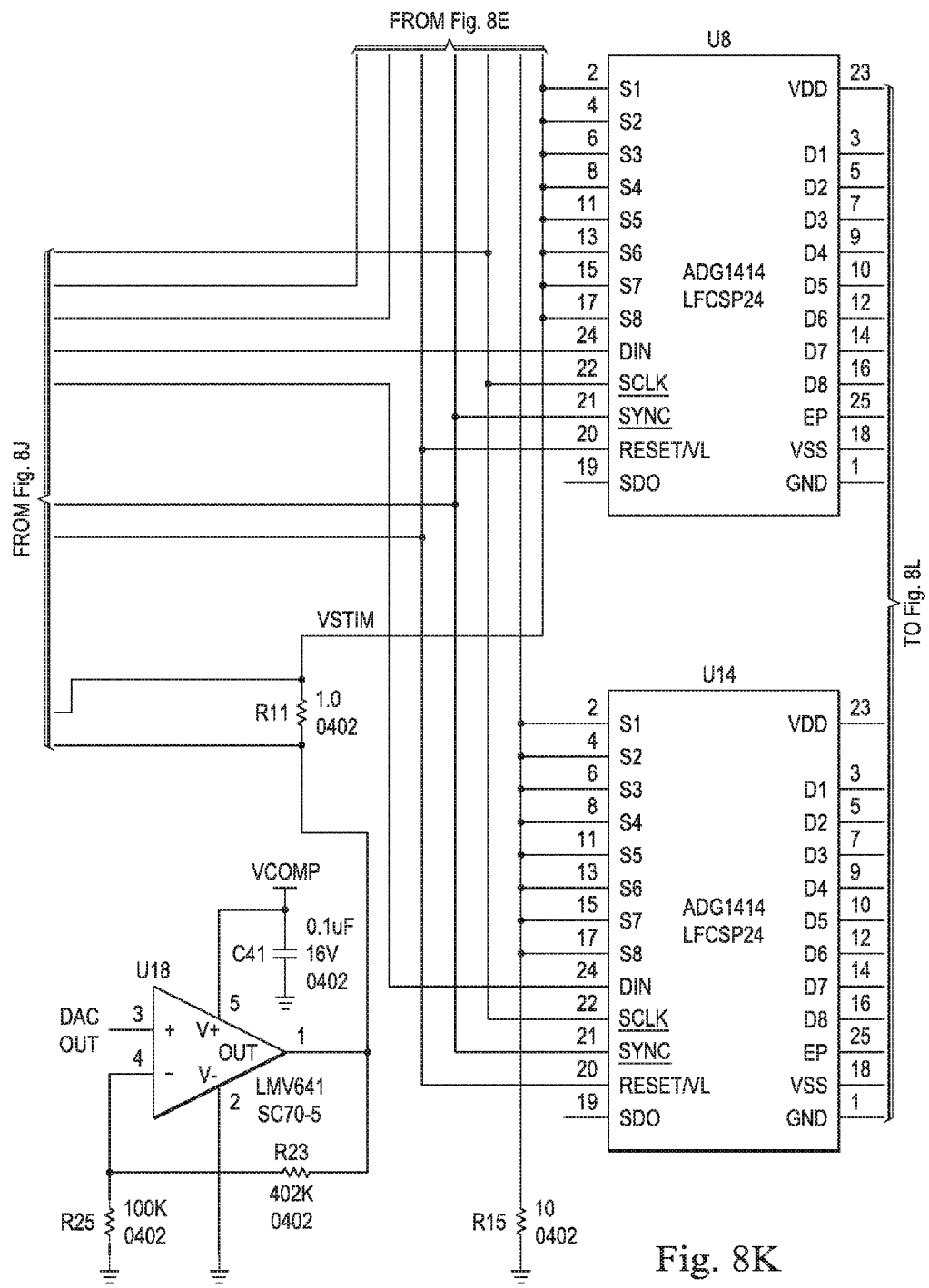
Figure 8L:
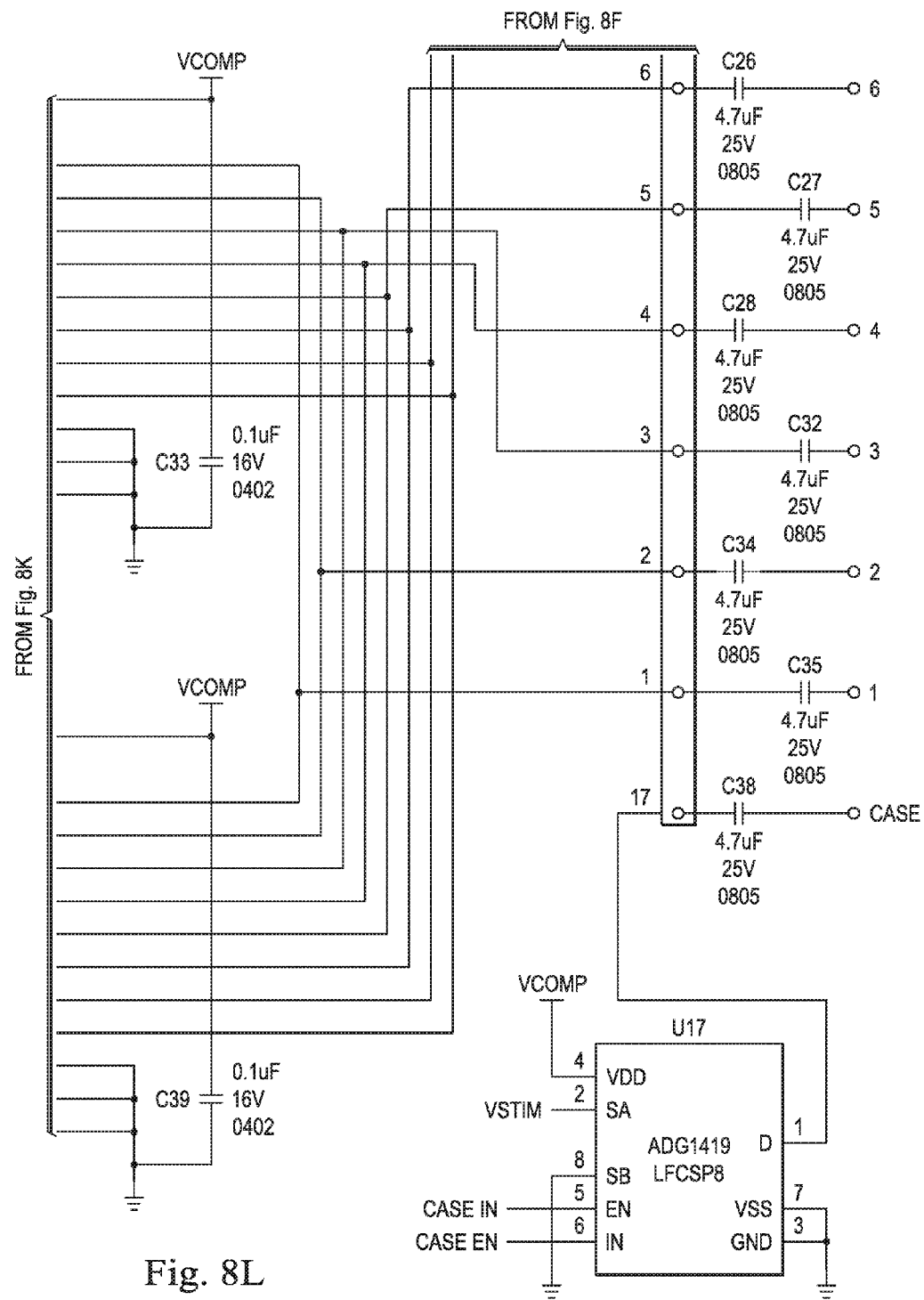

Referring to FIG. 7, a simplified block diagram of the PNS device 200 is illustrated. The PNS device 200 includes a power supply circuitry section 300, a stimulation circuitry section 305, and a telemetry circuitry section 310. The power supply circuitry section 300 includes an inductive charging component 320. In some embodiments, the charging component 320 includes a coil for receiving power/energy inductively from an external charger, for example from the charger 270 discussed above with reference to FIG. 6C. In some embodiments, the inductive energy (i.e., the charging signal) received from the inductive charging component 320 ranges from about 0.1 volts to about 5 volts in amplitude, and it has a frequency range that is within one of the Industrial, Scientific, and Medical (ISM) radio bands. For example, in some embodiments, the inductive energy is in a 13.56 Mhz band, that is, it ranges from 13.553 Mhz to 13.567 Mhz with a center frequency at 13.56 Mhz. In other embodiments, the inductive energy may be in alternative ISM radio bands.

The power supply circuitry section 300 further includes a circuit network 325. The circuit network includes microelectronic components that provide a resonant frequency at or near the center frequency of the ISM radio band associated with the inductive energy received by the charging component 320. Thus, in the embodiments where the inductive energy is in the 13.56 Mhz ISM radio band, the microelectronic components of the circuit network 325 provide a resonant frequency at or near 13.56 Mhz. This resonant frequency allows the inductive energy to pass through, but effectively rejects signals from outside the selected ISM radio band. For example, telemetry signals that have much higher (or lower) frequencies than the selected ISM radio band will be blocked by the circuit network 325. In this manner, the circuit network 325 may function similar to a filter. The various aspects of the circuit network 325 will be discussed in greater detail below.

The power supply circuitry section 300 also includes a charging circuit 330 that is electrically coupled to the inductive charging component 320. The charging circuit 330 includes various electronic components that convert the inductive energy received from the inductive charging component 320 into a direct current (DC) voltage. In some embodiments, the charging circuit 330 may include a voltage booster that can convert a lower input voltage to a higher output voltage, so as to adequately charge a battery 340 coupled thereto. In some embodiments, the battery 340 is configured to output a DC output voltage ranging from about 3.5 volts to about 4 volts. Thus, the charging circuit 330 can boost an input voltage (e.g., received from the inductive charging component 320) to meet or exceed the requisite DC output voltage of the battery 340.

The power supply circuitry section 300 further includes an energy harvesting component 350 that is configured to supply power to the battery 340. As is illustrated, the output of the energy harvesting component 350 is electrically coupled to the charging circuit 330, which boosts the energy harvested by the energy harvesting component to a level that can be used to charge the battery 340. In some embodiments, the energy harvesting component 350 includes a thermoelectric generator (TEG) that converts the body heat of the patient (inside whom the PNS device 200 is implanted) to electrical energy. The converted electrical energy may then be used to charge the battery 340 (after being boosted up by the charging circuit 330). In some other embodiments, the energy harvesting component 350 may also include circuitry to convert infrared light and/or vibration and movement of the patient into electrical energy. In various embodiments, the electrical energy harvested by the energy harvesting component 350 may exceed about 100 millivolts (mV).

The power supply circuitry section 300 also includes a voltage down-converter 360 coupled to the battery 340. The voltage down-converter 360 converts the nominal DC output voltage of the battery 340 to a lower level suitable for powering some of the electronic circuitry of the PNS device 200, such as a microcontroller, amplifiers, and telemetry circuitry (discussed below in more detail). For example, in embodiments where the DC voltage output of the battery 340 is about 4 volts, the down-converter 360 reduces it to about 2.7 volts. In the illustrated embodiment, 2.7 volts is a sufficient voltage to power electronic components such as the microcontroller, amplifiers, or the telemetry circuitry, and thus there is no need to waste the higher voltage output (e.g., 4 V) produced by the battery 340. In other words, the voltage down-converter 360 saves energy by down-converting the DC voltage output of the battery 340. In some embodiments, the voltage down-converter 360 includes a buck regulator or a low-dropout (LDO) linear regulator.

The power supply circuitry section 300 further includes a voltage up-converter 370 coupled to the battery 340. The voltage up-converter 370, when turned on, converts the nominal DC output voltage of the battery 340 to a higher level to enable high output voltage compliance for electrical stimulation. In more detail, the electrical stimulation pulses for the stimulation therapy may require higher voltages (e.g., as high as 12 volts) than the nominal DC voltage output of the battery 340. In these cases, the voltage up-converter 370 may be activated to boost the DC output voltage of the battery 340, for example from 4 volts to 8 volts or 12 volts, or at a fractional value in between. In the illustrated embodiment, the voltage up-converter 370 supplies power to stimulation circuitry (e.g., stimulation driver) that will be discussed below in more detail. To accomplish the voltage boost, the voltage up-converter 370 includes a charge pump in the present embodiment, but it is understood that it may include alternative types of voltage up-converters in alternative embodiments.

It is understood that the specific voltage values here are provided merely as an example and are not intended to be limiting. For example, the voltage down-converter 360 may down-convert a 4 volt DC output of the battery 340 to a 2.3 volt DC voltage that will then be supplied to certain electronic circuitry of the PNS device 200. As another example, the voltage up-converter 370 may up-convert a 4 volt DC output of the battery 340 to a number that is a fraction (greater than 1) of the 4 volt DC voltage.

The stimulation circuitry section 305 includes a microprocessor or microcontroller 400 (referred to as a microcontroller hereinafter) that is powered by the output of the voltage down-converter 360. The microcontroller 400 controls various operations of the PNS device 200. For example, the microcontroller 400 is configured to generate electrical stimulation pulses in response to programming instructions received from a programmer, such as from the electronic programmer 250 discussed above with reference to FIGS. 6A-6C. In various embodiments, the microcontroller 400 may include a microcontroller chip (e.g., an applications processor) with internal instruction and data caches, multimedia capabilities, external memory interfacing, and interfacing flexibility.

The microcontroller 400 may also include memory such as FLASH memory, a read-only memory ("ROM"), a random access memory ("RAM"), an electrically erasable programmable read-only memory ("EEPROM"), a hard disk, an optical disk, or another suitable magnetic, optical, physical, or electronic memory device. In some embodiments, the microcontroller 400 includes a double data rate (DDR2) synchronous dynamic random access memory (SDRAM) for storing data relating to and captured during the operation of the portable electronic device 90. Of course, other types of data storage devices may be used in place of the data storage devices discussed herein. It is understood that the different types of memory discussed above may be integrated into the microcontroller chip discussed above or may be separately implemented from the microcontroller chip. Software code, firmware code, or other types of program modules and applications may be stored on the memory and may be executed to perform certain tasks, such as generating the stimulation pulses.

According to some embodiments, the microcontroller 400 is configured to perform one or more of the following tasks:
  Generate stimulation waveforms with internal 12-bit DAC, contact combinations, and manages compliance voltage
  Manage bidirectional telemetry & external communications
  Manage sensing for impedance, battery voltage, and physiological signals Store data for diagnostics and device use tracking Store Code, bootloader, and other suitable data in onboard FLASH and RAM Enter various power-conservation consumptions modes to reduce power consumption Manages emergency ON/OFF states from a magnetic switch Reconfigure system with a new firmware download As is shown in FIG. 7, the microcontroller 400 includes a microcontroller core 410. Most of the functions of the microcontroller 400 discussed above may be performed by, or at least in part by, the microcontroller core 410. As such, the microcontroller core 410 is a power-hungry device and consumes significantly more power than the rest of the components of the microcontroller 400. In order to save power, the microcontroller 400 also includes a direct memory access (DMA) unit 420. In some embodiments, the DMA unit 420 is a task handler that can operate independently from the microcontroller core 410. For example, the DMA unit 420 may be capable of sending instructions to peripherals (discussed in more detail below) within the microcontroller 400, without having to go through the microcontroller core 410. One benefit of using the DMA unit 420 is that it consumes substantially less power than the microcontroller core 410. For example, in some embodiments, the DMA unit 420 consumes less than 10% of the power of the microcontroller core 410. Therefore, according to various aspects of the present disclosure, the DMA unit 420 may be utilized to execute certain simple tasks while the microcontroller core 410 is turned off in order to reduce power consumption.

The microcontroller 400 further includes a plurality of peripherals, channels, or buses. For example, the microcontroller 400 may include a digital-to-analog converter (DAC) to generate the waveforms for the electrical stimulation pulses. The microcontroller 400 may also include an analog-to-digital converter (ADC) to convert an analog feedback signal to digital numbers. The microcontroller 400 may also include a VBOOST_EN line that is electrically coupled to the voltage up-converter 370. When the VBOOST_EN line is enabled, the voltage up-converter 370 is activated and doubles or triples the DC output voltage from the battery 340, or scales up the DC output voltage from the battery 340 by a fractional number greater than 1. In some embodiments, the VBOOST_EN line is only enabled to turn on the voltage up-converter 370 during the stimulation pulse. Between consecutive stimulation pulses, the VBOOST_EN line is disabled to turn off the voltage up-converter 370. In this manner, power consumption is reduced, since the voltage up-converter is not running all the time. The microcontroller 400 further includes an Input/Output (I/O) bus, a Serial-Peripheral-Interface (SPI) communication bus, and an Inter-Integrated-Circuit (I²C) communication bus, which allow the microcontroller 400 to communicate with peripherals or external devices.

Another peripheral-like device of the microcontroller 400 is a timer unit 425. The timer unit 425 includes hardware and firmware/software that control the timing for turning on and off the microcontroller core 410 and/or enabling/disabling the peripherals or other components of the PNS device 200. Although not illustrated herein for reasons of simplicity, the microcontroller 400 may also include one or more internal clocks. These internal clocks serve as timing sources for the timer unit 425.

In addition, a crystal oscillator 430 is external to the microcontroller 400 and is coupled to the microcontroller 400. In some embodiments, the crystal oscillator 430 generates a 32.678 Khz clock that may be used when the microcontroller 400 enters a power-conservation operating mode (also referred to as a low-power mode or a sleep mode) to reduce power consumption. The crystal oscillator 430 may also serve as a timing source for the timer unit 425.

In addition to the microcontroller 400, the stimulation circuitry 305 further includes a plurality of sensors that are electrically or communicatively coupled to the microcontroller 400. In the illustrated embodiment shown in FIG. 7, a magnetic sensor 435 is coupled to the microcontroller 400 through the I/O bus, and a temperature sensor 440 and an accelerometer 445 are each coupled to the microcontroller 400 through the I²C communication bus. In some embodiments, the magnetic sensor 435 may be used to turn on or off the PNS device 200, the temperature sensor 440 may be used to facilitate the energy harvested by the energy harvesting component 350, and the accelerometer 445 may be used to detect a posture of the patient, which may then be used to perform posture-dependent calibration. It is understood that these sensors 435-445 are merely examples, and that additional sensors such as pressure sensors, humidity sensors, vibration sensors, proximity sensors, light sensors, strain/stress sensors, transducers, gyroscopes, or compasses may be implemented in the PNS device 200 in various embodiments.

The stimulation circuitry section 305 further includes a stimulation driver 450 coupled to the DAC output of the microcontroller 400. The stimulation driver 450 includes amplification circuitry (e.g., op-amps) that is capable of amplifying an amplitude of the stimulation pulses generated by the DAC of the microcontroller 400. For example, in some embodiments, the stimulation driver 450 can amplify the amplitude of the stimulation pulses by a factor of 5. The amplification (or scaling up) of the variation stimulation waveforms (i.e., the stimulation pulses outputted by the DAC) obviates the need for a custom DAC.

The stimulation circuitry section 305 also includes stimulation multiplexers 460 that are coupled to the stimulation driver 450. The multiplexed stimulation outputs allow for configured stimulation contact combinations. In more detail, the stimulation multiplexers 460 serve as an array (e.g., 16 for anodes and 16 for cathodes) of switches that coupled to a plurality of stimulation channels through DC-blocking capacitors 465, respectively. The switches are coupled in parallel to one another. Through the turning on and off of these switches, electrical stimulation pulses can be delivered to the desired stimulation channel(s).

To help conserve energy, the stimulation driver 450 and the stimulation multiplexers are powered by either the battery 340 directly, or by the voltage output produced by the voltage up-converter 370, but not both. For example, when the stimulation pulse amplitude is less than what the battery 340 is capable of providing (e.g., stimulation voltage is at 3 volts, and the battery 340 outputs 4 volts), the voltage up-converter 370 need not be turned on, because the voltage up-converter 370 would consume power when it is turned on. The voltage up-converter 370 is turned on when the stimulation pulse demands a greater amplitude than the battery 340 is capable of providing. In this manner, the voltage up-converter 370 is selectively turned on or off to minimize power consumption. Thus, the output of the voltage up-converter 370 serves as the power supply for the stimulation driver 450 and the stimulation multiplexers 460 when needed, and the battery 340 serves as the power supply the rest of the time.

To ensure such operation, the present disclosure implements a diode 470 coupled between the output of the battery 340 and the inputs of the stimulation driver 450 and the stimulation multiplexers 460. Another diode 475 is also implemented between the output of the voltage up-converter 370 and the inputs of the stimulation driver 450 and the stimulation multiplexer 460. These two diodes 470 and 475 are coupled in parallel with each other and serve as switches such that only one path is created between the power source (either the battery 340 or the voltage up-converter 370) and the stimulation driver 450 and the stimulation multiplexer 460. When the voltage up-converter 370 is turned on, the diode 475 is forward-biased to create a charging path from the voltage up-converter 370 and the stimulation driver 450 and the stimulation multiplexers 460, while the diode 470 is reverse-biased to block the path from the battery 340 to the stimulation driver 450 and the stimulation multiplexers 460. This also ensures that the voltage up-converter 370 will not inadvertently charge the battery 340. When the voltage up-converter 370 is turned off, the diode 470 is forward-biased to create a charging path from the battery 340 and the stimulation driver 450 and the stimulation multiplexers 460, while the diode 475 is reverse-biased to block the path from the voltage up-converter 370 to the stimulation driver 450 and the stimulation multiplexers 460.

The stimulation circuitry section 305 further includes a switch 480 that is coupled between the output of the voltage up-converter 370 and the inputs of the stimulation driver 450 and the stimulation multiplexers 460. The switch 480 is also coupled to the microcontroller 400. In response to instructions from the microcontroller 400, this switch 480 may disconnect any load (e.g., the stimulation driver 450 and the stimulation multiplexers 460) from the voltage up-converter 370 between consecutive stimulation pulses, thereby preserving energy stored in the voltage up-converter 370 for the next stimulation pulse.

The stimulation circuitry section 305 may also include a sense amplifier 490 coupled between the output of the stimulation multiplexers and the microcontroller 400. In certain embodiments, the sense amplifier 490 is configured to sense action potentials of a target nerve. The sensed action potentials are fed back to the microcontroller for further processing and analysis. In some embodiments, the sense amplifier 490 can also measure impedance values.

The telemetry circuitry section 310 includes a telemetry block 500. The telemetry block 500 is powered by the voltage down-converter 360. The telemetry block 500 is also electrically and communicatively coupled to the microcontroller 400. The telemetry block 500 includes one or more transmitters, receivers, and/or transceiver. For example, the telemetry block 500 may include one or more of the following: a Medical Implant Communication Services (MICS) transceiver, an Industrial, Scientific and Medical (ISM) transceiver, a Wi-Fi transceiver, a Bluetooth transceiver, DLNA, or any of the 3G or 4G cellular networking transceivers. Through the telemetry block 500, the PNS device 200 may conduct bidirectional telecommunications with external devices, for example turning on/off the PNS device 200, receiving commands or programming instructions from the electronic programmer 250 discussed above, or transfer diagnostic data or unique patient information to the electronic programmer 250 or to a remote server.

The telemetry circuitry section 310 further includes an antenna 510 for transmitting and receiving telemetry signals. In some embodiments, the antenna 510 and the inductive charging component 320 may be the same component. In other words, a single conductive component such as a loop coil or wire may be used to charge the PNS device 200 and to conduct telecommunications with the PNS device 200.

For example, the antenna 510 may receive telemetry signals that are in different radio bands, such as signals in a MICS band (between 402 Mhz and 405 Mhz, which may hereinafter be referred to as a 400 Mhz MICS band) and signals in a 2.45 Ghz ISM band (between 2.4 Ghz and 2.5 Ghz). The telemetry signals in the 2.45 Ghz band may be used to "wake up" the PNS device 200, which is normally in a deep "sleep" mode, where little power is being consumed. After the PNS device 200 is "woken up," the telemetry signals in the MICS band are used to conduct telecommunications between the PNS device 200 and external devices such as the electronic programmer 250. Since the PNS device 200 employs a single antenna 510 to receive multiple types of telemetry signals, these different types of telemetry signals need to be properly discriminated, otherwise one type of telemetry signals may cause interference or create noise for the other type of telemetry signals.

According to the various aspects of the present disclosure, the telemetry circuitry section 310 includes a plurality of circuits or circuit networks to discriminate different types of input signals received from the antenna 510. In the illustrated embodiment, circuit networks 520 and 530 are implemented in the telemetry circuitry section 310. The circuit network 520 includes microelectronic components that will allow the telemetry signals in the MICS radio band to pass through but will reject signals outside the MICS radio band, including the telemetry signals in other bands (e.g., telemetry signals in the 2.45 Ghz band) and charging signals (e.g., charging signals in the 13.56 Mhz ISM band). The circuit network 530 includes microelectronic components that will allow the telemetry signals in the 2.45 Ghz radio band to pass through but will reject signals outside the 2.45 Ghz radio band, including the telemetry signals in other bands (e.g., telemetry signals in the 400 Mhz MICS band) and charging signals (e.g., charging signals in the 13.56 Mhz ISM band). In this manner, the circuit networks 520 and 530 provide discrimination for the input signals.

It is understood that although the circuit network 325 is not a part of the telemetry circuitry section 310, it also helps provide discrimination of the input signals. As discussed above, the antenna 510 and the inductive charging component 320 may be the same conductive component, for example, a single turn wire or coil. In other words, the same wire or coil may be used to receive both charging signals (e.g., inductive energy in the 13.56 Mhz ISM band) and telemetry signals in the 400 Mhz MICS band and telemetry signals in the 2.45 Ghz band. Thus, the circuit network 530 includes microelectronic components that will allow the charging signals in the 13.56 Mhz ISM band to pass through but will reject signals outside the 13.56 Mhz ISM band, including the telemetry signals in the 400 Mhz MICS band and in the 2.45 Ghz ISM band.

The circuit networks 520 and 530 may also each include passive components such as inductors and capacitors for impedance matching Impedance matching may maximize power transfer or may reduce signal reflection (for example, reflection from a load). In the illustrated embodiment, the circuit networks 520 may include passive circuit elements collectively arranged to match the impedances of the telemetry block 500 and the antenna 510 in the 400 Mhz MICS band. In some embodiments, the circuit network 530 may also include passive circuit elements collectively arranged to match the impedances of the telemetry block 500 and the antenna 510 in the 2.45 Ghz frequency band.

FIGS. 8A-8L are detailed circuit schematics of the PNS device 200 according to an embodiment of the present disclosure. However, it is understood that the PNS device 200 may be implemented differently in alternative embodiments and is not limited to the specific implementation shown in FIGS. 8A-8L.

Paddle Lead Maximizing Lateral Target Points Across a Peripheral Nerve

Figure 9:
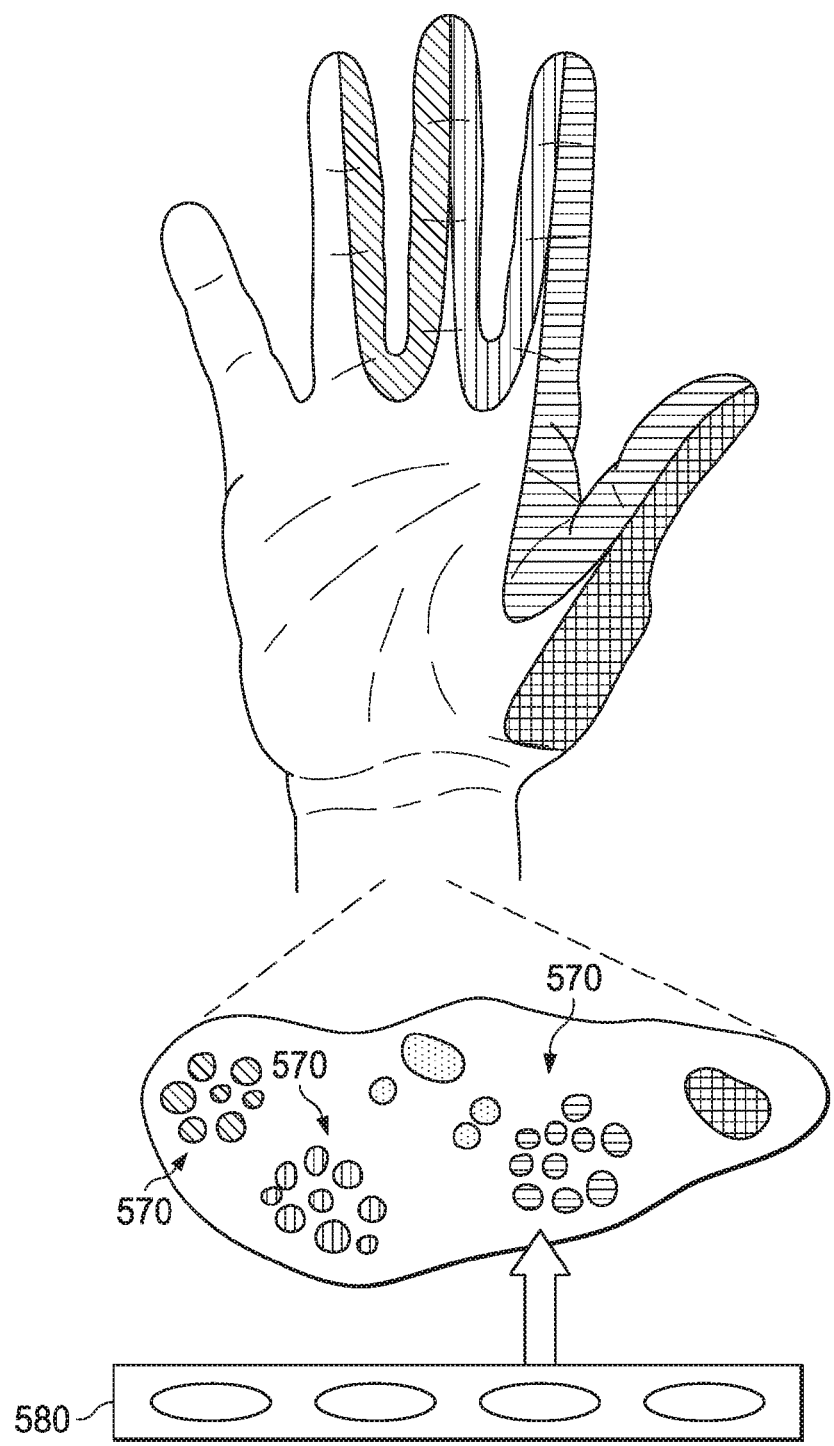
FIG. 9 illustrates example peripheral nerve bundles being stimulated by a paddle lead according to an embodiment of the present disclosure.

As discussed above, unlike spinal cord stimulation devices, the PNS device 200 is specifically configured to deliver electrical stimulation for peripheral nerves. Referring to FIG. 9, peripheral nerves comprise 'bundles' (e.g., bundles 570) of groupings of axons called fascicles. Typically, a fascicle innervates a particular area or region of the body. Additionally, some fascicles carry a predominance of efferent motor fibers while others carry mostly afferent sensory fibers.

Depending upon the therapeutic application at hand, peripheral nerve stimulation systems typically seek to activate only motor nerves (e.g., for functional purposes, such as dorsiflexion for a dropped foot, or a grasp for upper extremity hemiplegia), or only sensory nerves (e.g., for neuropathic pain management). In any particular application, neural selectivity is usually achieved by maximally activating the targeted fascicles while avoiding activation of those fascicles that may lead to side effects (e.g., in pain management, stimulation of motor nerves can limit the efficacy of the therapy that is to be provided).

One method of peripheral nerve stimulation uses paddle leads, a simplified example of which is shown as a lead 580 in FIG. 9. Concerted effort is required to place paddles at least near or over the targeted fascicles, but this can usually be achieved intraoperatively in a nominal amount of time.

One challenge with paddle leads in peripheral nerve stimulation is the need to provide contacts or electrodes in the paddle lead that are of a certain size or surface area so that charge density concerns can be managed, which include avoiding the creation of toxic electrochemical products generated by stimulation currents at the contact or electrode location, or associated with contact corrosion. Typical paddle electrodes or contacts are rectangular with a nominal surface area. The contact width necessary to maintain current flow below charge density limits is such that the ability to provide fine fascicular targeting becomes limited, in part because contacts can only be placed on a paddle lead such that they do not electrically short together during manufacture or implantation. What is needed includes a paddle lead configured to maximize transverse fascicular targeting or selectivity in a peripheral nerve, or a paddle lead that permits fine separation of fascicles in a targeted nerve.

Figure 10:
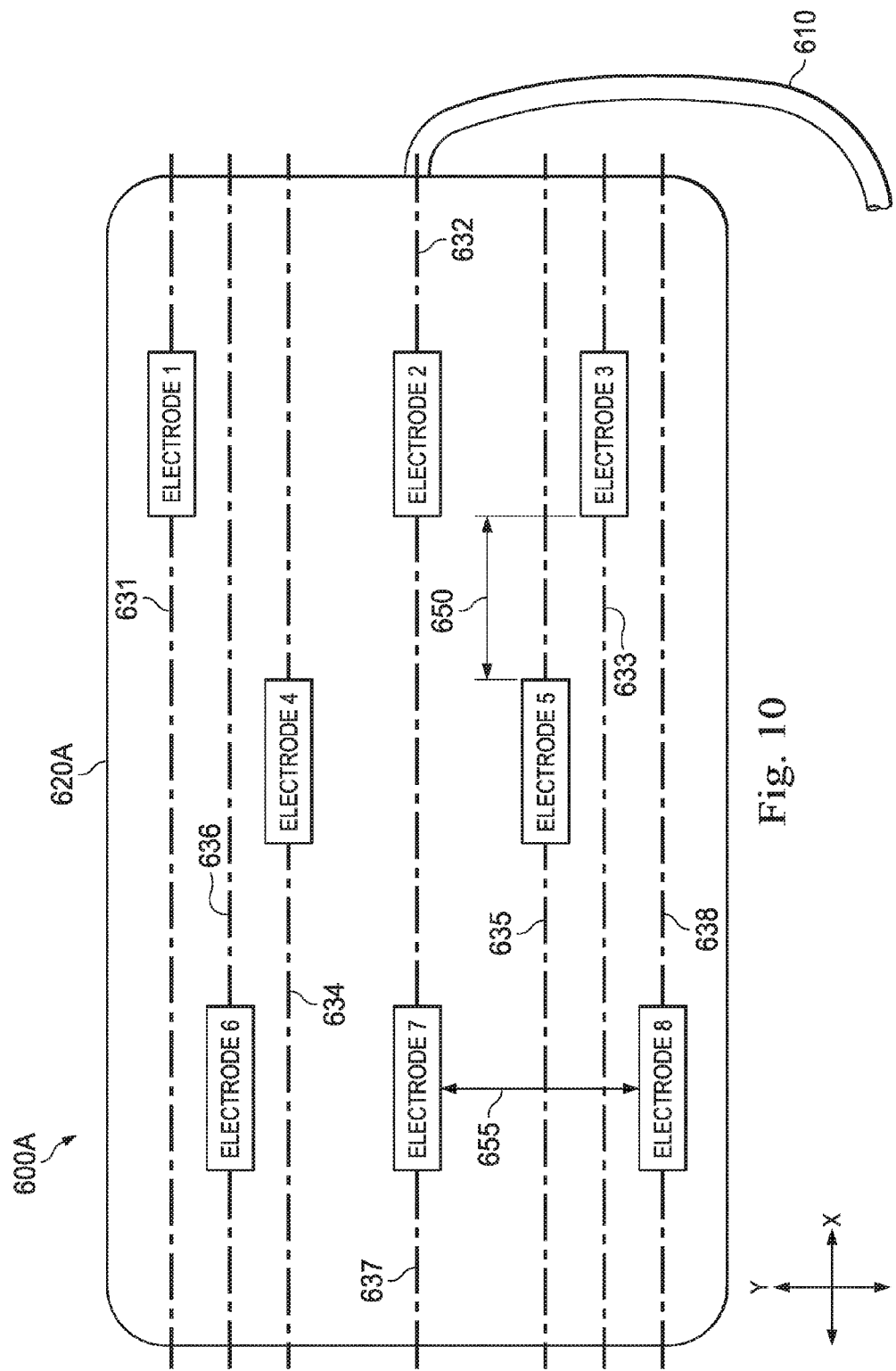
FIGS. 10-14 illustrate example paddle leads for delivering electrical stimulation to peripheral nerve according to various embodiments of the present disclosure.

Referring now to FIG. 10, a simplified diagrammatic view of an example implantable lead 600A of the present disclosure is illustrated according to an embodiment. The implantable lead is configured to be coupled or attached to the PNS device 200 discussed above. The implantable lead 600A delivers electrical stimulation pulses generated by the stimulation circuitry 305 of the PNS device 200 to target peripheral nerves. The implantable lead 600A includes an elongate flexible/bendable lead body 610 that includes a coupling assembly (not specifically illustrated herein), which is configured to be coupled to the PNS device 200. The implantable lead 600A also includes a paddle 620A that includes a plurality of electrodes (also referred to as contacts), for example electrodes 1-8 as shown in FIG. 10. Electrical stimulation pulses are delivered to the target peripheral nerve through these electrodes.

According to various aspects of the present disclosure, the electrodes 1-8 are collectively arranged in a manner such that they provide a plurality of unique centerlines 631-638. For example, the paddle lead 600A includes a plurality of rows of electrodes oriented along its length such that the respective centerline of the electrode(s) on each row is mostly or completely different from those on other rows. In the illustrated embodiment, the centerlines 631-638 extend in an X-direction or along an X-axis, whereas the fascicles of the target peripheral nerve typically extend in a Y-direction or along a Y-axis (perpendicular to the X-axis). In general, it is desired to try to keep the centerlines of the electrodes in the middle of the targeted nerves, as it offers redundancy and flexibility to recover/restore stimulation in spite of slight movements of the nerve or electrode.

Most conventional paddle leads typically employ a grid approach for its electrodes, where the electrodes are neatly arranged into rows and columns, and where all the electrodes in the same row are aligned with one another (e.g., aligned along the X-axis), and all the electrodes in the same column are aligned with one another (e.g., aligned along the Y-axis). Consequently, conventional paddle leads can only offer a very limited number of unique centerlines. For example, a conventional paddle lead with 9 electrodes with a 3×3 configuration can only offer 3 unique centerlines. As discussed above, the centerlines are correlated with the associated electrode's ability to provide target stimulation. Thus, having a limited number of centerlines may prevent the PNS device from providing flexible stimulation therapies.

In comparison, the paddle 620A has a 3-2-3, 8-contact or electrode configuration in the embodiment illustrated in FIG. 10. As is shown in FIG. 10, the 8 electrodes are arranged to achieve 7 unique centerlines (electrodes 2 and 7 have substantially the same centerline) transversely disposed across the nerve over which it is placed. In other words, a substantial majority (7 out of 8) of the electrodes on the paddle 620A have their own respective unique centerlines. Alternatively stated, the electrodes 1-8 on the paddle 620 are "staggered." Such staggered 3-2-3 electrode arrangement of the paddle lead 600A permits fine separations of fascicles (or allows for greater fascicular selectivity) in a nerve to be targeted, because individual electrodes can be activated as cathodes on different rows to 'sweep' the stimulation field across the nerve to find the location that maximizes the desired therapeutic effect while minimizing side effects. In some embodiments, the electrodes 631-638 of the paddle lead 600A are configured to take into account the tendency of fascicles in peripheral nerves to run in a relatively fixed longitudinal course along the length of the nerve that is to be stimulated.

In addition, since the paddle lead 600A is configured for peripheral neural stimulation, the spacing between adjacent electrodes may be small too. In some embodiments, a distance 650 separating adjacent electrodes in the X-direction is in a range from about 1 millimeters (mm) to about 5 mm, and a distance 655 separating adjacent electrodes in the Y-direction is in a range from about 2 millimeters (mm) to about 5 mm. The distance 650 may also be referred to as a horizontal spacing, and the distance 655 may also be referred to as a vertical spacing.

These distances 650-655 are significantly smaller than the distances separating adjacent electrodes on a paddle lead configured to deliver spinal cord stimulation. This is because in the context of spinal cord stimulation, the paddle would be implanted near the spinal cord, which may span a great distance. Thus, the paddle lead for spinal cord stimulation is typically configured to have electrodes that are spaced farther apart, so that they can span a relatively long distance that may be required to reach the target stimulation site. It is not as important to achieve such fine resolution in the spinal cord stimulation context.

In comparison, peripheral nerve stimulation is typically focused in a relatively small area. In addition, as discussed above, peripheral nerve stimulators need to achieve high neural selectivity in the target nerve such that only the desired nerve fibers (for example, only the efferent fibers or only the afferent fibers) are activated but not the other. As such, peripheral nerve stimulators need to have smaller distances separating adjacent electrodes to allow for the high neural selectivity.

It is understood that the electrodes 631-638 may be substantially evenly or uniformly spaced apart in either the X-direction or the Y-direction (or both) in some embodiments, or they may be unevenly spaced apart in the X or Y-directions in other embodiments.

Figure 11:
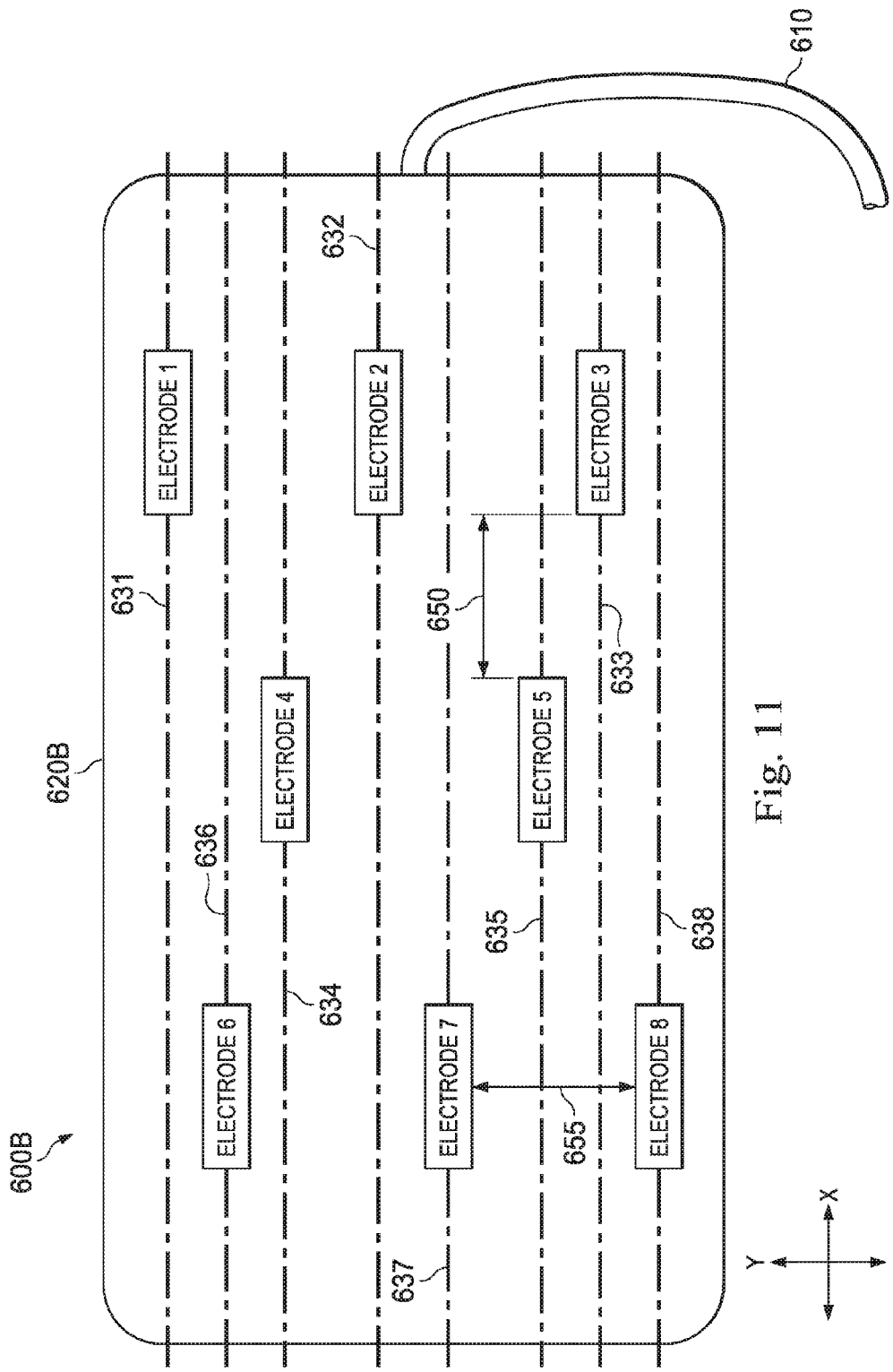

FIG. 11 illustrates a simplified diagrammatic view of an implantable lead 600B according to another embodiment of the present disclosure. The implantable 600B has a paddle 620B that is similar to the paddle 620A shown in FIG. 10. However, the electrodes 1-8 of the paddle 620B are arranged such that every electrode has a unique respective centerline that extends in the X-direction. In other words, the paddle 620B achieves a total of 8 unique centerlines with 8 electrodes, compared to the 7 centerlines achieved by the paddle 620A in FIG. 10.

In some embodiments, electrodes are not arranged in a grid per se, but are offset from one row to the next. In some embodiments, none of the electrodes in a single row on the paddle are arranged in a single column. For example, referring now to FIG. 12, a simplified diagrammatic view of an implantable lead 600C is illustrated according to another embodiment of the present disclosure. The implantable 600C has a paddle 620C that contains electrodes 1-9. The electrodes 1-9 are arranged in a staggered manner in both the X-direction and the Y-direction. In more detail, the electrodes 1-9 are roughly arranged into 3 "columns" 660, 661, and 662, and 3 "rows" 665, 666, and 667. The column 660 includes electrodes 1-3, the column 661 includes electrodes 4-6, and the column 662 includes electrodes 7-9. The row 665 includes electrodes 1, 4, and 7, the row 666 includes electrodes 2, 5, and 8, and the row 667 includes electrodes 3, 6, and 9.

However, the electrodes in each column are not aligned in the Y-direction, and the electrodes in each row are not aligned in the X-direction. Rather, the electrodes in each column are still offset from one another, as are the electrodes in each row. For example, the columns 660-662 may each extend in a direction 668 that is somewhat "vertical" but is not parallel to the X-axis or the Y-axis. In other words, the direction 668 has a greater Y-component than an X-component. The rows 665-667 may each extend in a direction 669 that is somewhat "horizontal" but is also not parallel to the X-axis or the Y-axis. In other words, the direction 669 has a greater X-component than a Y-component.

Since the directions in which the columns and rows extend are not parallel with the X or Y axes, the electrodes 1-9 offer unique vertical and horizontal centerlines. According to the embodiment of the paddle 620C shown in FIG. 12, the electrodes 1-9 have horizontal centerlines (i.e., centerlines spanning in the X-direction) 631-639, and the electrodes 1-9 have vertical centerlines (i.e., centerlines spanning in the Y-direction) 671-679. The electrodes 1-9 are staggered horizontally and vertically such that they collectively offer 9 unique horizontal centerlines 631-639, as well as 9 unique vertical centerlines 671-679.

As discussed above, having the plurality of unique horizontal and vertical centerlines 631-639 and 671-679 affords the paddle 620C the flexibility and versatility to selectively stimulate one or more target nerve fibers but not the undesired nerve fibers, even if the desired and undesired nerve fibers are closely located to one another. In other words, the staggered electrode arrangement discussed herein can achieve high neural selectivity, and the PNS system with the implantable lead 600C permits very precise spatial targeting of different portions of a nerve.

Figure 12:
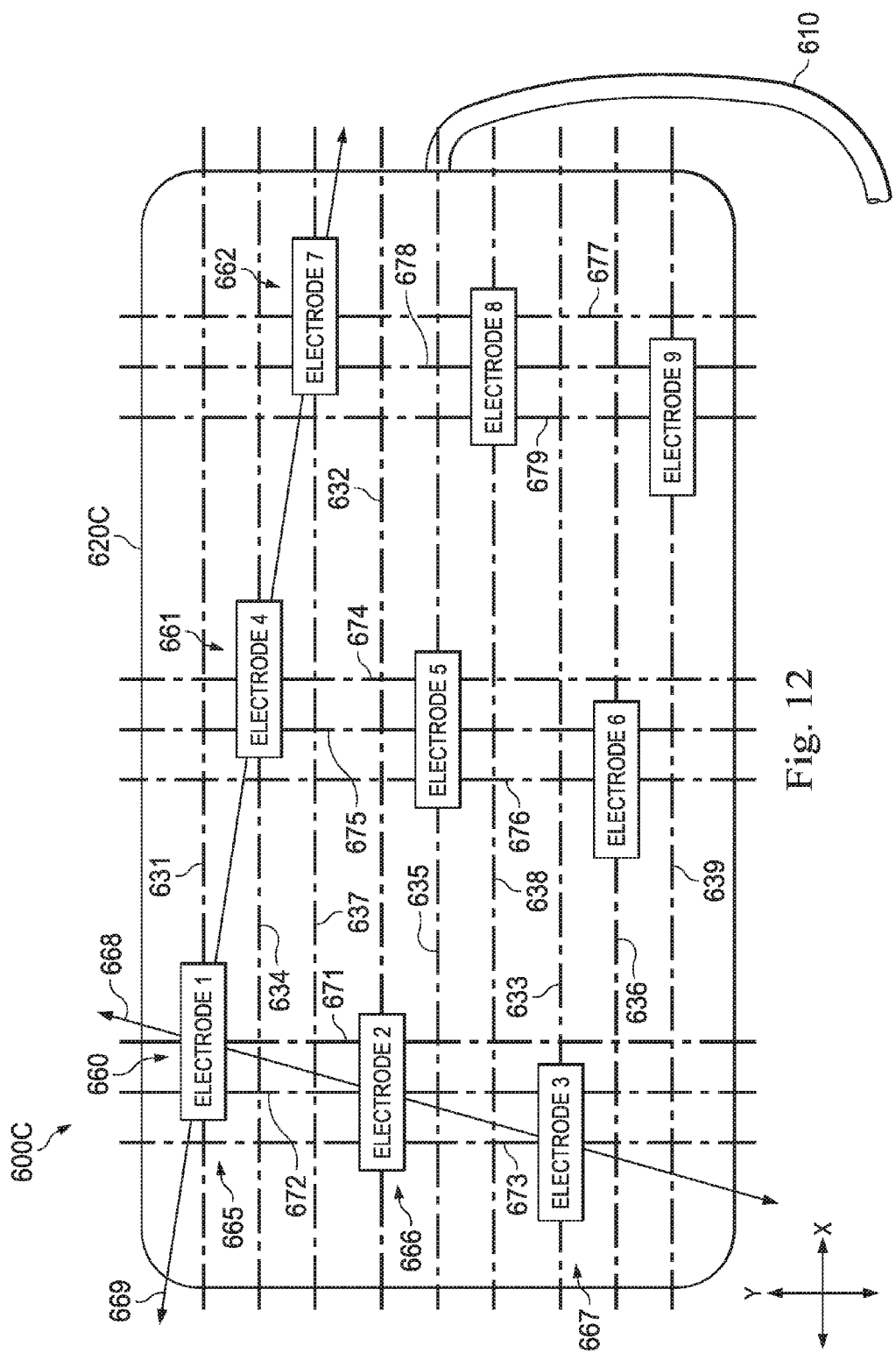
Figure 13:
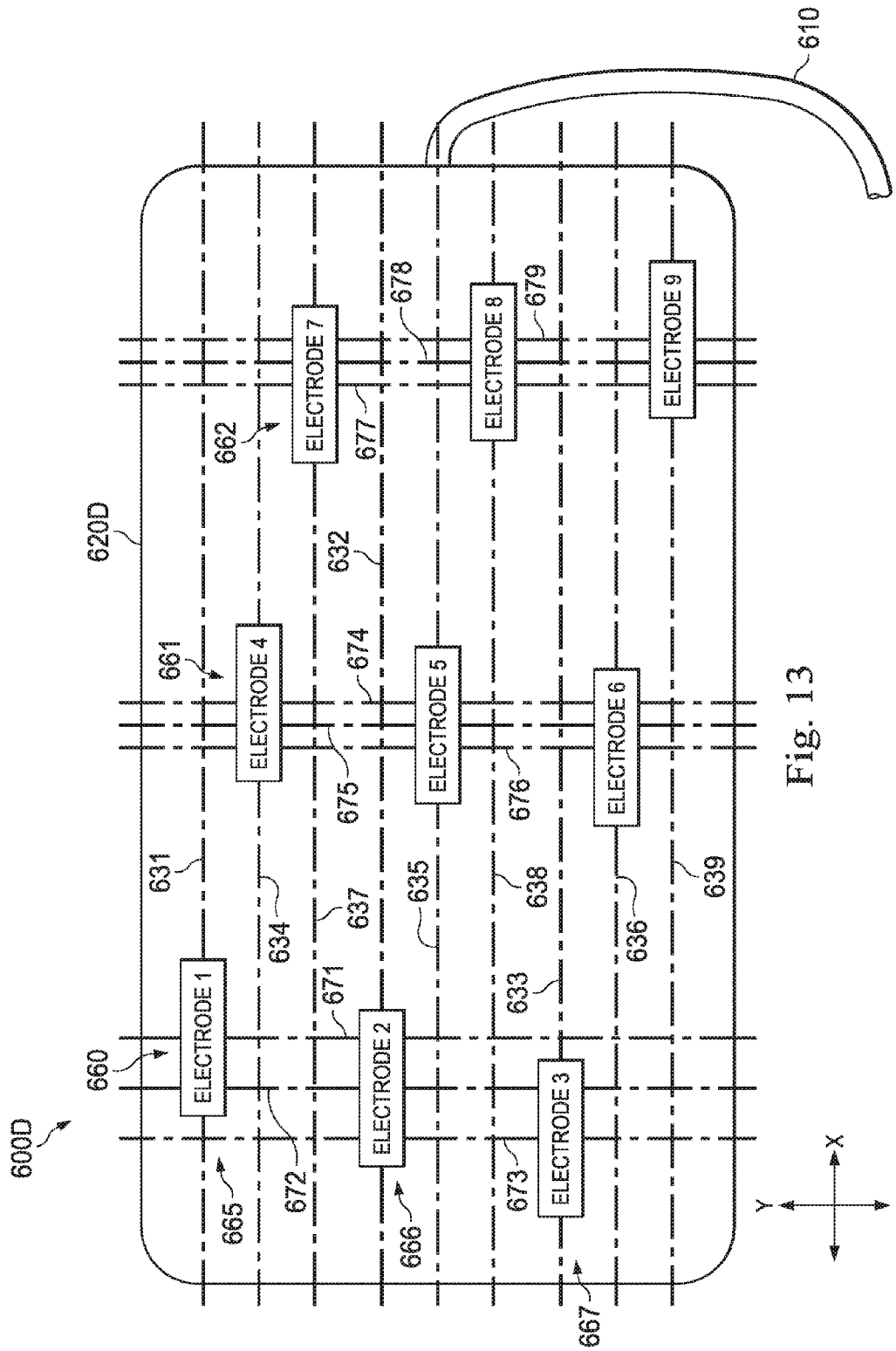

FIG. 13 illustrates a simplified diagrammatic view of an implantable lead 600D according to yet another embodiment of the present disclosure. The implantable lead 600D is similar to the implantable lead 600C shown in FIG. 12 in that it also offers an electrode arrangement that is both horizontally staggered and vertically staggered. However, the electrodes 1-9 on the paddle 620D are even more staggered. For example, the horizontal and vertical distances separating adjacent electrodes may be uneven or non-uniform. As another example, there may not be any linear direction in which any of the "columns" 660-662 or the "rows" 665-667 extend, let alone a direction that is parallel to either the X-axis or the Y-axis. In some embodiments, even if some of the "columns" or "rows" extend along a particular linear direction, such linear direction would not be parallel with any linear direction of any other "column" or "row." Stated differently, none of the "columns" 660-662 is parallel with any other of the columns on the paddle 620D, and none of the "rows" 665-667 is parallel with any other of the rows on the paddle 620D. The horizontal centerlines 631-639 are still each unique, as are the vertical centerlines 670-679. Again, such staggered electrode arrangement may permit good neural selectivity.

Figure 14:
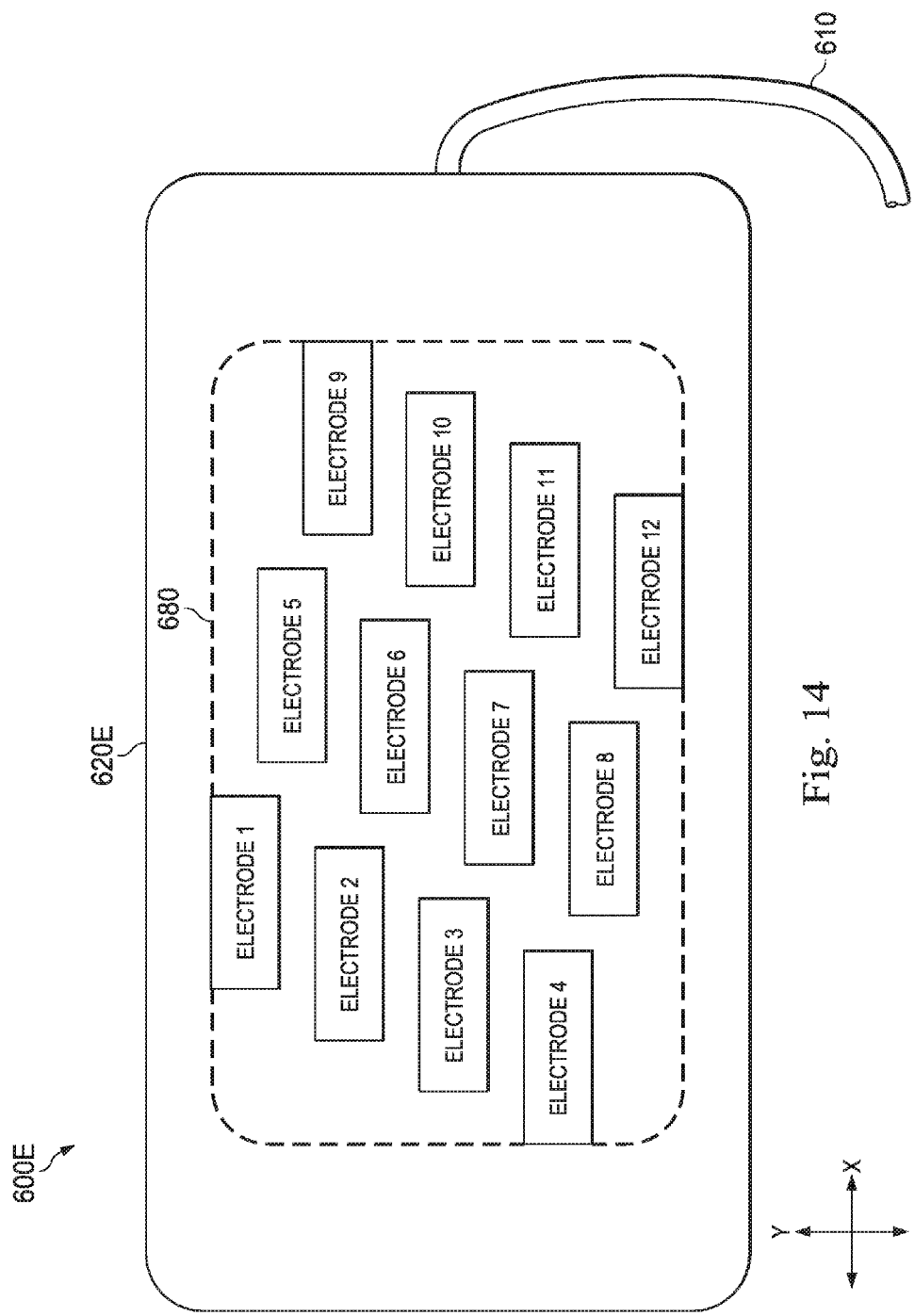

FIG. 14 illustrates a simplified diagrammatic view of an implantable lead 600E according to yet another embodiment of the present disclosure. Here, the implantable lead 600E includes a paddle 620E that has 12 electrodes implemented thereon. The 12 electrodes are collectively arranged in roughly 3 "columns" and 4 "rows" and collectively define a stimulation region 680 on the paddle 620E. The boundaries or outlines of stimulation region 680 may be defined by a topmost edge of a topmost electrode (electrode 1 in this case), a bottommost edge of a bottommost electrode (electrode 12 in this case), a leftmost edge of a leftmost electrode (electrode 4 in this case), and a rightmost edge of a rightmost electrode (electrode 9 in this case). As such, the stimulation region 680 has approximately a rectangular shape. However, it is understood that the outlines or boundaries of the stimulation region 680 may not be actually visible on the paddle 620E.

The electrodes 1-12 are staggered to the extent such that no horizontal linear paths (or a straight line parallel to the X-axis) or vertical linear paths (or a straight line parallel to the Y-axis) across the stimulation region 680 may exist without intersecting at least one of the electrodes 1-12. Stated differently, within the stimulation region 680, every horizontal linear path and every vertical linear path will intersect at least one of the electrodes 1-12. This is due to the partial overlap in both the X-and-Y-directions among the electrodes 1-12. For example, electrodes 1 and 5 are overlapped in the Y-direction, as are electrodes 5 and 9, as are electrodes 9 and 2, as are electrodes 2 and 6, so on and so forth. Similarly, electrodes 4 and 3 are overlapped in the X-direction, as are electrodes 3 and 2, as are electrodes 2 and 1, as are electrodes 1 and 8, so on and so forth. Therefore, if a horizontal or vertical linear path is to extend across the entire stimulation region 680, one or more of the electrodes 1-12 will necessarily be in its path. It may be said that the staggered electrode arrangement of the paddle 620E completely blocks all horizontal and linear paths across the stimulation region 680. As such, the staggered electrode arrangement of the paddle 680 may theoretically permit electrical stimulation in almost every target nerve site covered by the stimulation region 680, thereby imparting a high degree of adjustability and targetability of delivered electrical stimulus.

It is understood that in some embodiments, such as the embodiment of the paddle 620C shown in FIG. 12, there may be some horizontal or vertical linear paths that may extend across the entire stimulation region 680 without intersecting at least one of the electrodes. However, even in such embodiments, a substantial majority (e.g., greater than 70%, 80%, or 90% in various implementations) of the available horizontal and vertical linear paths may still intersect with at least one electrode, because there is still some amount of horizontal or vertical overlap among the electrodes 1-9 on the paddle 620C. Therefore, it may be said that in these embodiments (e.g., embodiment shown in FIG. 12), the staggered electrode arrangement blocks a substantial majority of the horizontal and linear paths across the stimulation region. Even in these embodiments, however, the amount of overlap (in the X or Y directions) among the electrodes may still offer a high degree of adjustability and targetability of delivered electrical stimulus.

In each of the embodiments of the paddle lead 600 shown in FIGS. 10-14 and discussed above, there are at least 3 "rows" and/or 3 "columns" of electrodes. In other embodiments, any other number of columns or rows greater than 3 may be implemented for the paddle with staggered electrodes. The greater number of rows or columns allows the paddle to be better suited for peripheral nerve stimulation, as the peripheral nerves may have irregular shapes and may span in various directions. In comparison, many conventional paddle leads only have 1 or 2 columns of electrodes. This is adequate for spinal cord stimulation, since the target nerves in the SCS context extend along the spine, which is mostly straight and narrow. However, these SCS paddle leads with 1 or 2 columns of electrodes will not work very well in the peripheral nerve stimulation context, since the 1 or 2 columns of electrodes may not be able to reach all the target stimulation areas, and maintain targeted stimulation over desired regions, due to the geometric differences between the spinal cord and the peripheral nerves, primarily the tortuous winding nature of peripheral nerves within their neurovascular bundles. For these reasons, the various embodiments of the implantable lead 600 discussed herein are specifically configured to have 3 or more columns or rows of electrodes, which are also arranged in a staggered formation, in order to provide better a peripheral stimulation therapy. Further, the staggered electrode arrangements shown in FIGS. 10-14 allow for formations of a plurality of different "stimulation paths" between the various electrodes on the lead. These "stimulation paths" between the electrodes extend in a variety of directions due to the electrodes being staggered, whereas the conventional neatly-arranged rows and columns of electrodes may allow for much fewer "stimulation paths" that extend in different direction. Also due to the staggered electrodes herein, various "stimulation paths" may be created to generate electric fields that can be flexibly shaped. Therefore, the ability of the paddle lead herein to establish these "stimulation paths" allows for more versatile and flexible stimulation zones and steering of stimulation over small and larger target regions, which as discussed above is a unique concern of peripheral stimulation that does not exist in the spinal cord stimulation context.

Circuit for Discriminating Between Battery Charging Signals and RF Telemetry Signals Received by a Single Coil in an Implantable Medical Device As discussed above, another one of the unique aspects of the present disclosure is that it utilizes a single conductive element (e.g., coil) to receive different types of charging and telemetry signals and utilizes various circuit elements to provide discrimination for these different types of signals. This aspect of the present disclosure is now discussed in greater detail below.

Figure 15C:
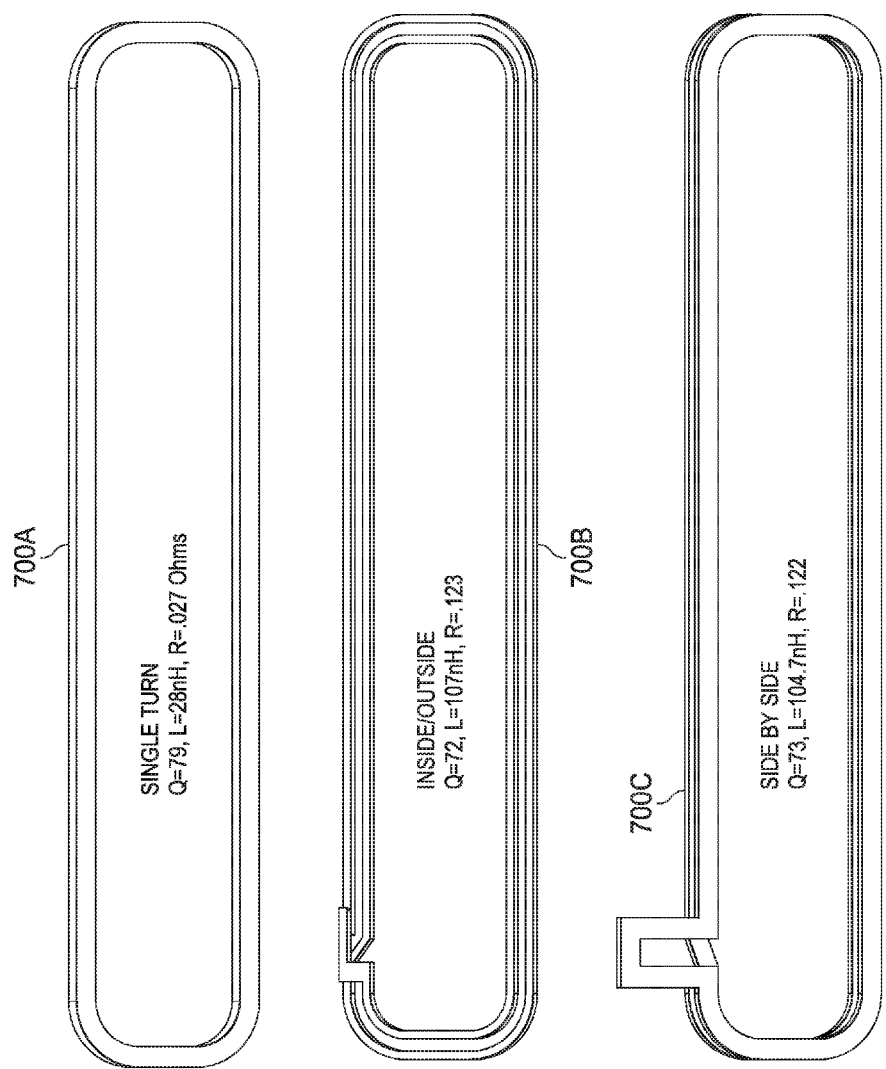

FIGS. 15A-15C provide various illustrations of a coil 700 that is an embodiment of the inductive charging component 320 and the antenna 510 shown in the block diagram of FIG. 7. In other words, the coil 700 can be used to receive both inductive charging signals (e.g., at the 13.56 Mhz ISM band) and telemetry signals (e.g., at the 400 Mhz MICS band and at the 2.45 Ghz ISM band). In more detail, FIG. 15A illustrates the disposition of the coil 700 in an embodiment of the PNS device 200, FIG. 15B illustrates the coil 700 by itself, and FIG. 15C shows top views of a few different embodiments of the coil as coil 700A, 700B, and 700C.

The coil 700 shown in FIGS. 15A and 15B in FIG. 15C are each a single turn piece of wire having an approximately rectangular shape with rounded corners. The embodiment of the coil 700B shown in FIG. 15C includes an inside turn and an outside turn and thus has a slightly different Q factor, inductance, and resistance compared to the single turn embodiment of the coil 700A. The embodiment of the coil 700C shown in FIG. 15C includes two side-by-side turns and thus also has a slightly different Q factor, inductance, and resistance compared to the single turn embodiment of the coil 700A or compared to the inside/outside turn embodiment of the coil 700B. As shown in FIG. 15A, the coil 700 is implemented outside of a hermetically-sealed housing or enclosure (also referred to as a can) 710 of the PNS device 200. Most of the circuitry discussed above with reference to FIG. 7 are implemented within the hermetically-sealed housing 710, including but not limited to, the battery 340, the voltage down-converter 360 and the voltage up-converter 370, the microcontroller 400, the sensors 435-445, the stimulation driver 450, the stimulation multiplexers 460, the telemetry chip 500, the circuit networks 325, 520, 530, etc.

It is understood that in these embodiments, the coil 700 is optimized to receive signals at the 13.56 Mhz band, the 400 Mhz band, and the 2.45 Ghz band, since these bands are employed to carry out the inductive charging and telecommunications of the present embodiment of the PNS device 200. However, in alternative embodiments where the PNS device may utilize different frequency bands to conduct charging and telecommunications, the coil may be optimized differently for those bands as well.

Conventionally, neurostimulators use an antenna to receive telemetry signals and a separate charging coil to receive inductive charging signals. The antenna is typically located outside a hermetically-sealed housing (e.g., made of metal or a metal alloy) for the pulse generator, which contains most of the circuitry such as charging circuitry, stimulation circuitry, and telemetry circuitry. The placement of the antenna outside the housing is for better signal reception. The charging coil is typically located inside the hermetically-sealed housing because traditional charging signals are limited at very low frequencies (e.g., 40 Khz-80

Khz), which can penetrate through metal relatively easily. However, the low charging frequencies are associated with a lower quality factor (Q), which leads to charging inefficiencies. The low charging frequencies also require the charging coil to have many turns (e.g., 50 turns or more), which consumes a lot of space. In other words, the implementation of a signal antenna outside the housing and a separate charging coil inside the housing results in bigger, more cumbersome neurostimulation device that may have inadequate charging performance.

In comparison, a single conductive element such as the coil 700 is used to receive both telemetry signals and charging signals. The coil 700 and the corresponding circuitry inside the PNS device 200 are configured to receive charging signals at a much higher frequency (e.g., 13.56 Mhz) than the low charging frequencies for conventional neurostimulators. As such, the coil 700 can have a much higher Q than the charging coils for conventional neurostimulators. The higher Q results in better charging efficiency and quicker charging time. In addition, since the charging frequency is higher, a single turn is sufficient for the coil 700, and it can be implemented outside the hermetically-sealed housing. Furthermore, the implementation of the coil 700 outside the housing reduces heating effects, and it may allow less expensive materials to be used for the housing. In some embodiments, MRI compatibility can also be enhanced, for instance, by providing no ferrite core. The material used for the single-turn coil 700 may also result in low resistance. The size of the coil 700 (e.g., due to using only a single turn wire) can also be much smaller than the charging coil for conventional neurostimulators.

For these reasons discussed above, the design of using a single coil for both telemetry and charging allows the PNS device 200 to be made small, cheap, and have improved performance over conventional neurostimulators. However, since a single coil 700 is used for both telemetry and charging, the PNS device 200 needs to be able to discriminate the telemetry and charging signals, so that they do not cause interference for one another, as discussed below.

Figure 16:
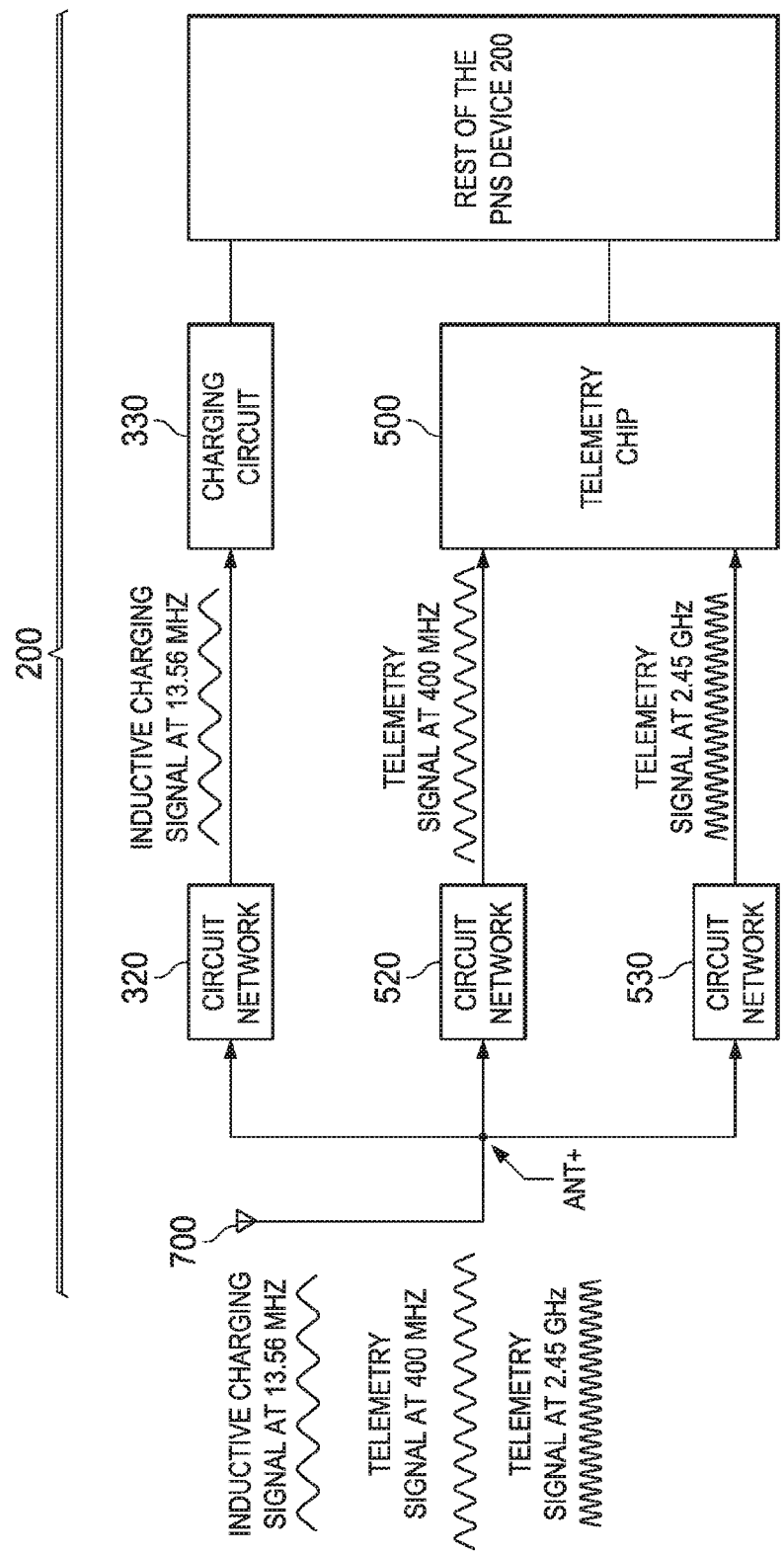
FIG. 16 illustrates a simplified block diagram of components of the peripheral neurostimulator used to provide signal discrimination according to various embodiments of the present disclosure.

FIG. 16 is a simplified block diagram of the various components and devices of the PNS device 200 that provide signal discrimination for the different types of signals received by a single antenna. Again, it is understood that in the illustrated embodiment, the inductive charging component 320 and the antenna 510 shown in the block diagram of FIG. 7 are integrated together as a single coil 700. The coil 700 is electrically coupled to the circuit networks 320, 520, and 530, each of which is discussed above with reference to FIG. 7. It can be seen that the circuit networks 320, 520, and 530 are electrically coupled in parallel. As such, the networks 320, 520, and 530 provide parallel signal paths for different types of signals.

The circuit network 320 is coupled to the charging circuit 330 (also discussed above with reference to FIG. 7) and allows inductive charging signals at the 13.56 Mhz band to pass through to the charging circuit 330 by way of resonant network elements. In some embodiments, the circuit network 320 includes a resonant network that generates a high Q at the resonant frequency, where the resonant frequency is tuned to be substantially equal to the frequency of the charging signal (e.g., at 13.56 Mhz). As such, the reception of signals is maximized at the charging frequency, thereby allowing the charging signal to pass through with minimal attenuation. Meanwhile, although the resonant network is not specifically configured to filter out signals from the 400 Mhz or the 2.45 Ghz bands, the reception of the signals outside the resonant frequency is not maximized due to the resonant frequency being at or substantially near the 13.56 Mhz. Thus, the resonant network of the circuit network 320 may effectively function as a very narrow band-pass filter to "block" signals that are outside of the 13.56 Mhz band. As such, to the extent that the 400 Mhz and the 2.45 Ghz telemetry signals are received by the network 320, they will be substantially attenuated by the time they reach the charging circuit 330.

Meanwhile, the circuit networks 520 and 530 are each coupled to a telemetry chip 500 that is an embodiment of the telemetry block 500 (also discussed above with reference to FIG. 7). Using filters such as a band-pass filter and a high-pass filter, the circuit network 520 allows telemetry signals at the 400 Mhz MICS band to pass through to the telemetry chip 500, but blocks out telemetry signals at other frequency bands (e.g., signals at the 2.45 Ghz ISM band) and inductive charging signals (e.g., signals at the 13.56 Mhz band). Similarly, using filters such as a high-pass filter, the circuit network 530 allows telemetry signals at the 2.45 Ghz ISM band to pass through to the telemetry chip 500, but blocks out telemetry signals at other frequency bands (e.g., signals at the 400 Mhz MICS band) and inductive charging signals (e.g., signals at the 13.56 Mhz band). Additionally, the circuit network 520 and/or the circuit network 530 may include additional passive circuit elements such as inductors and/or capacitors for impedance matching, so as to maximize power transfer or to reduce signal reflection, etc. The filtering out of the undesired signals will minimize the interference that these undesired signals may cause to the desired signals.

Again, it is understood that the frequency bands used herein are merely examples. In other embodiments, the same approach shown in FIG. 16 may be used to provide discrimination of other types of inductive charging signals and telemetry signals that may be collectively received by the same antenna or coil. It is also understood that in a real world implementation, it may not be possible to completely block or filter out signals from an undesired frequency band. Thus, in the context of the present disclosure, "signal blocking", "signal filtering", or other similar phrases may mean that the undesired signals are substantially attenuated to the point where they no longer cause any meaningful interference. In other words, even if some portions of the undesired signals may get through one of the circuit networks 320, 520, and 530 discussed above, they may be negligible because their amplitudes are sufficiently small. In various embodiments, the circuit networks 320, 520, and 530 may provide signal attenuations anywhere from about 10 dB to about 100 dB, for example from about 20 dB to about 60 dB.

Figure 17:
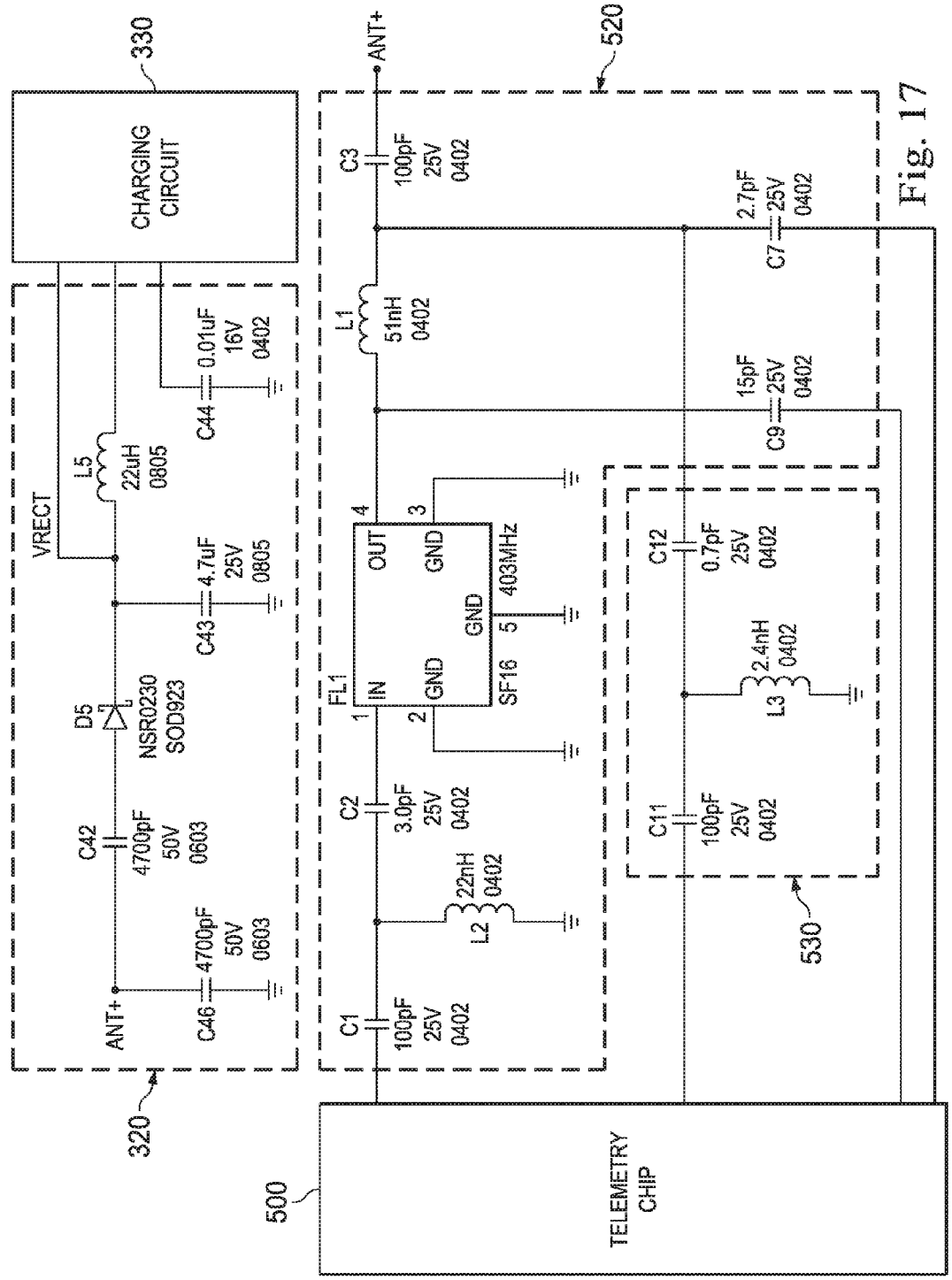
FIG. 17 illustrates circuit schematics of the various components of the peripheral neurostimulator used to provide signal discrimination according to an embodiment.

FIG. 17 includes detailed circuit schematics of an embodiment for each of the circuit networks 320, 520, and 530 discussed above. These circuit schematics are extracted from the circuit schematic of the PNS device 200 shown in FIGS. 8A-8L. In addition, to provide more clarity, simplified block diagrams of the charging circuit 330 and the telemetry chip 500 are appended next to the circuit schematics of the corresponding circuit networks 320, 520, and 530. It is also understood that a circuit node "ANT+" represents the signal line to the single antenna (or the coil 700 shown in FIG. 16)

According to the embodiment shown in FIG. 17, the circuit network 320 includes a series-resonant capacitor C42 and/or a parallel-resonant capacitor 46. These resonant capacitors C42 and C46 are tuned such that they have a narrow resonant frequency at around 13.56 Mhz (since 13.56 Mhz is the band of the inductive charging signals in this case). As discussed above, the resonant capacitors C42 and C46 in effect serve as a narrow band-pass-like filter, where the pass-band is centered around 13.56 Mhz. As such, the inductive charging signals of the 13.56 Mhz ISM band are able to pass through, whereas signals from other frequency bands end up being "rejected" because they are outside the resonant frequency. In some embodiments, the series capacitor C42 may be removed, and only the parallel-resonant capacitor C46 is used to provide a resonant frequency.

The circuit network 320 further includes a diode D5 that is electrically coupled to the capacitor C42. The diode D5 serves as a rectifying element. In other words, the diode D5 converts the AC inductive signal that passes through (13.56 Mhz) into a DC signal. In other embodiments, alternative types of DC rectifiers may be used instead. The circuit network 320 also includes a capacitor C43, which serves as an energy storage element herein. The inductor L5 may serve as an inductor for the booster circuit, and the capacitor C44 may serve as a reference capacitor for the booster circuit.

The circuit network 520 includes a band-pass filter FL1, whose pass-band in this embodiment is centered around the 400 Mhz MICS band. For example, the pass-band of the band-pass filter FL1 may be from approximately 402 Mhz to about 405 Mhz. As such, the desired telemetry signals in the MICS band will pass through the circuit network 520, whereas inductive charging signals and telemetry signals from other bands will be substantially rejected. In order to provide further attenuation for undesired signals, the circuit network 520 also includes a high-pass filter that is formed by an inductor L2 and capacitors C1 and C2. This high-pass filter is specifically targeted at the inductive charging signals, for example signals at the 13.56 Mhz band, since these inductive charging signals may be high in amplitude and thus warrants further attenuation.

In addition, the circuit network 520 also includes passive circuit elements L1, C9, C3, and C7 that are collectively configured to optimize impedance matching between the antenna (coil 700) and the telemetry chip 500. Again, the impedance matching provided by the passive circuit elements L1, C9, C3, and C7 may maximize power transfer (e.g., from the antenna to the telemetry chip 500 or vice versa) and/or reduce signal reflection.

The circuit network 530 includes a high-pass filter formed by an inductor L3 and capacitors C11 and C12. This high-pass filter is configured such that the inductive charging signals in the 13.56 Mhz band and the telemetry signals in the 400 Mhz MICS band will be substantially rejected, but the telemetry signals in the 2.45 Ghz band (e.g., used to wake up the PNS device 200) will be allowed to pass through.

Again, it is understood that the specific implementation of the circuit networks 320, 520, and 530 shown in FIG. 17 is merely an example implementation. In alternative embodiments, the specific values may be changed for the resistors, the inductors, and the capacitors shown in FIG. 17. The circuit networks 320, 520, and 530 may also include additional circuit elements, or some of the circuit elements may be eliminated without departing from the spirit and scope of the present disclosure. Furthermore, in some embodiments, digital-signal-processor (DSP) chips or other chips with advanced firmware/software may be used to replace one or more of the circuit networks 320, 520, and 530 discussed above.

Figure 18:
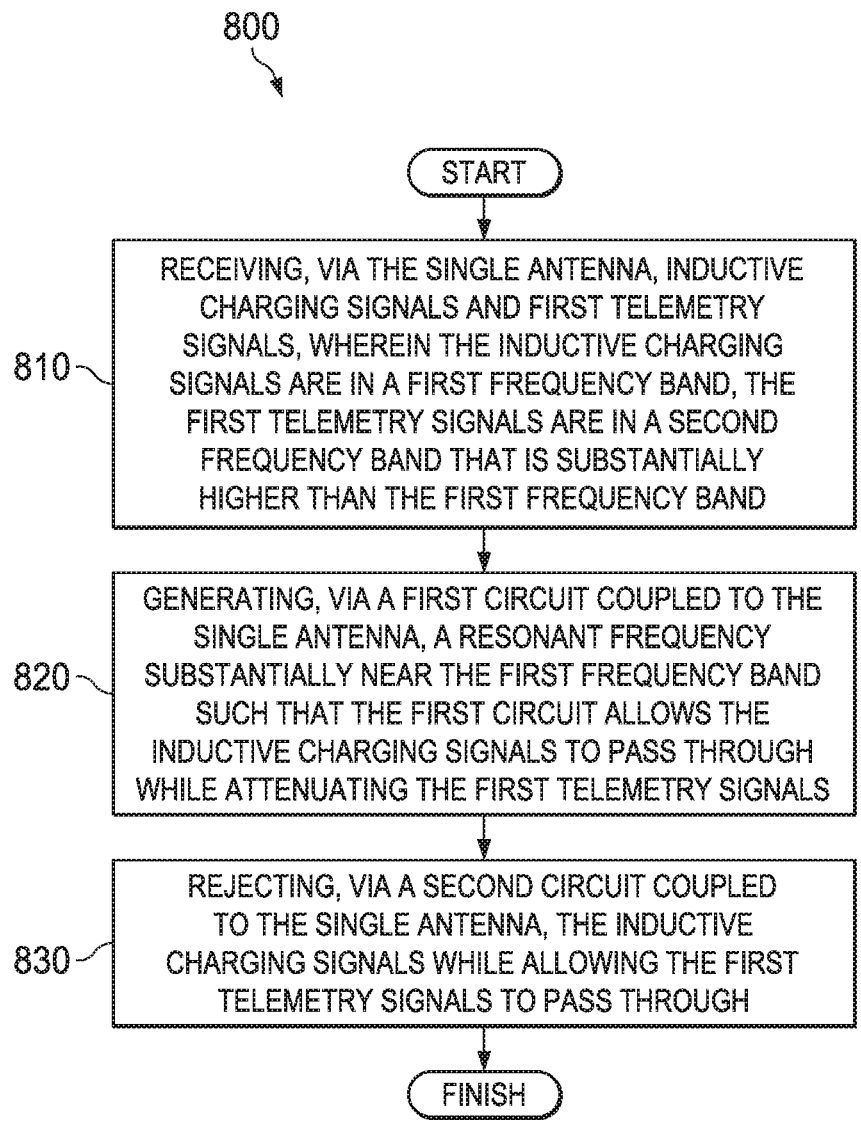
FIG. 18 is a simplified flowchart illustrating a method of providing discrimination for a plurality of types of signals received from a single conductive element according to an embodiment of the present disclosure.

FIG. 18 is a simplified flowchart of a method 800 of providing discrimination for a plurality of types of input signals received from a single antenna according to an embodiment of the present disclosure. The method 800 includes a step 810 of receiving, via the single antenna, inductive charging signals and first telemetry signals. The inductive charging signals are in a first frequency band, the first telemetry signals are in a second frequency band that is substantially higher than the first frequency band.

The method 800 includes a step 820 of generating, via a first circuit coupled to the single antenna, a resonant frequency substantially near the first frequency band such that the first circuit allows the inductive charging signals to pass through while attenuating the first telemetry signals.

The method 800 includes a step 830 of rejecting, via a second circuit coupled to the single antenna, the inductive charging signals while allowing the first telemetry signals to pass through.

In some embodiments, the first and second circuits are integrated within a hermetically-sealed housing of a peripheral nerve stimulation (PNS) device. The single antenna is located outside the hermetically-sealed housing. The method 800 may further include the following steps: receiving, via the single antenna, second telemetry signals in a third frequency band that is substantially higher than the second frequency band; charging a battery of the PNS device in response to the receiving of the inductive charging signals; waking up stimulation circuitry of the PNS device in response to the receiving of the second telemetry signals; and generating, via the stimulation circuitry, a plurality of electrical pulses to be delivered to a patient for an electrical stimulation therapy.

It is understood that additional process steps may be performed before, during, or after the steps 810-830. For example, the method 800 may include a step of rejecting, via a third circuit coupled to the single antenna, the inductive charging signals and the first telemetry signals while allowing the second telemetry signals to pass through. As another example, the method 800 may include a step of matching an impedance of the single antenna with an impedance of a telemetry chip via a plurality of passive circuit elements in the second circuit, wherein the second circuit is coupled between the single antenna and the telemetry chip. For reasons of simplicity, other additional steps are not discussed herein. In addition, the steps 810-830 need not necessarily be performed according to the sequence shown in FIG. 18.

Method and Apparatus of Conserving Power for an Implantable Peripheral Neurostimulator For implantable medical devices such as peripheral neurostimulators, battery life is one of the important considerations. An implantable medical device with poor battery life may require frequent charging, which may diminish the user's satisfaction with the implantable medical device. Many conventional neurostimulators, such as spinal cord stimulators, lack optimized power management. Therefore, in spite of the relatively large size and the accompanying onboard battery with a relatively big capacity, many conventional neurostimulators have poor battery life performance.

In comparison, the PNS device 200 of the present disclosure has a miniature size (especially compared to conventional spinal cord stimulators) and therefore a smaller battery with limited capacity. Therefore, the present disclosure employs various advanced power conservation strategies to maximize the battery life of the PNS device 200, as discussed in more detail below. The advanced power conservation strategies lead to excellent battery performance of the PNS device 200 (e.g., lasting for weeks or months without needing a charge), in spite of its miniature size.

One of the power conservation strategies of the PNS device 200 involves operating the microcontroller 400 (discussed above with reference to FIG. 7) in different power modes depending on the stage of the stimulation pulse. In more detail, the microcontroller 400 offers a plurality of different operating modes, where each operating mode may be used to performance a suitable task(s) and therefore has a different power consumption level.

This is summarized briefly as follows:

Active Mode (AM)

All clocks are active

Low-Power Mode 0 (LPM0)

CPU is disabled

ACLK and SMCLK remain active, MCLK is disabled

FLL loop control remains active

TABLE 1 below includes a brief listing of the different operating modes:

| Mode | AM | LPM0 | LPM1 | LPM2 | LPM3 | LPM4 | LPM3.5 | LPM4.5 | |
|---|---|---|---|---|---|---|---|---|---|
| | Active | Active, FRAM off | CPU Off | CPU Off | Standby | Standby | Off | RTC only | Shutdown with SVS | Shutdown w/o SVS |
| Maximum System Clock | 16 MHz | | 16 MHz | 16 MHz | 50 kHz | 50 kHz | 0 | 50 kHz | | 0 |
| Typical Current Consumption, $T_A = 25°$ C. | 103 µA/MHz | 65 µA/MHz | 70 µA at 1 MHz | 35 µA at 1 MHz | 0.7 µA | 0.4 µA | 0.3 µA | 0.25 µA | 0.2 µA | 0.02 µA |
| Typical Wake-Up Time | | N/A | Instant | 6 µs | 6 µs | 7 µs | 7 µs | 250 µs | 250 µs | 1000 µs |
| Wake-Up Events | | N/A | All | All | LF I/O comp | LF I/O comp | I/O Comp | RTC I/O | | I/O |
| CPU | On | On | Off | Off | Off | Off | Off | Reset | | Reset |
| FRAM | On | Off | Standby (or off) | Off | Off | Off | Off | Off | | Off |
| High-Frequency Peripherals | | Available | Available | Available | Off | Off | Off | Reset | | Reset |
| Low-Frequency Peripherals | | Available | Available | Available | Available | Available | Off | RTC | | Reset |
| Unclocked Pheripherals | | Available | Available | Available | Available | Available | Available | Reset | | Reset |
| MCLK | | On | Off | Off | Off | Off | Off | Off | | Off |
| SMCLK | | Optional | Optional | Optional | Off | Off | Off | Off | | Off |
| ACLK | | On | On | On | On | On | Off | Off | | Off |
| Full Retention | | Yes | Yes | Yes | Yes | Yes | Yes | No | | No |
| SVS | | Always | Always | Always | Optional | Optional | Optional | Optional | On | Off |
| Brownout | | Always | Always | Always | Always | Always | Always | Always | | Always |

In more detail, AM refers to an active mode of operation, where no power conservation approaches are used. LPM0, LPM1, LPM2, LPM3, LPM4, LPM3.5, and LPM4.5 are the various power-conservation modes in which the microcontroller 400 can operate. CPU refers to the microcontroller core 410 (discussed above with reference to FIG. 7). MCLK is the main clock (clocked at 10 Mhz in this embodiment but may have a different clock rate in other embodiments, for example 20 Mhz) of the microcontroller 400, ACLK is an auxiliary clock (clocked at 32.768 Khz in this embodiment but may have a different clock rate in other embodiments) of the microcontroller 400, SMCLK is a sub-main clock of the microcontroller 400, DCOCLK is a digitally-generated clock that is feeding the main clock. In addition, DCO is a digitally-controller oscillator, and FLL is a frequency-locked loop.

As is shown in Table 1, the microcontroller 400 turns on and off the various clocks and/or the peripherals of the microcontroller differently for each of the operating modes.

Low-Power Mode 1 (LPM1)

CPU is disabled

FLL loop control is disabled

ACLK and SMCLK remain active, MCLK is disabled

Low-Power Mode 2 (LPM2)

CPU is disabled

MCLK, FLL loop control, and DCOCLK are disabled

DCO's DC generator remains enabled

ACLK remains active

Low-Power Mode 3 (LPM3)

CPU is disabled

MCLK, FLL loop control, and DCOCLK are disabled

DCO's DC generator is disabled

ACLK remains active

Low-Power Mode 4 (LPM4)

CPU is disabled

ACLK is disabled

MCLK, FLL loop control, and DCOCLK are disabled

DCO's DC generator is disabled

Crystal oscillator is stopped

Complete data retention

As one example, the microcontroller 400 may operate in the LPM4 power-conservation when the PNS device 200 is not in use. The LPM4 mode is also referred to as a "deep sleep" mode, where the microcontroller 400 draws almost no current (i.e., consumes virtually no power). The microcontroller 400 has to be "woken up" from this deep sleep LPM4 mode by an external signal. By doing so, the deep sleep LPM4 mode allows the microcontroller 400 to not waste power in standby.

As another example, the waveforms for the electrical stimulation pulses are generated by the microcontroller 400's internal DAC (digital-to-analog converter) in real-time for each pulse. In between stimulation pulses—referred to as a standby period herein—the microcontroller 400 enters one of the power-conservation modes (also referred to as a low-power mode or sleep mode), for example the LPM3 mode. This reduces power consumption, since many parts of the microcontroller does not need to be turned on during the standby period. It is understood that the microcontroller 400 does not necessarily need to operate in the LPM3 throughout the entirety of the standby period in order to realize the power savings. According to various embodiments of the present disclosure, the microcontroller 400 may operate in the LPM3 power conservation mode in a substantial majority of the standby period, for example >75% of the standby period in some embodiments, or >90% of the standby period in some other embodiments, or >99% of the standby period in yet some other embodiments.

When the microcontroller 400 enters the LPM3 power-conservation mode, the system clock switches from the main system clock (MCLK, which is 10 MHz in this embodiment) to the crystal oscillator 430 (shown in FIG. 7) that is external to the microcontroller 400. The crystal oscillator 430 has a clock frequency that is much lower than the main system clock, for example with a clock frequency of 32.678 kHz in this case, compared to the 10 Mhz clock frequency of the main system clock. Typically, a high clock frequency corresponds with more power consumption. Therefore, switching from a 10 Mhz clock to a 32.678 Khz clock also reduces power consumption.

Figure 19:
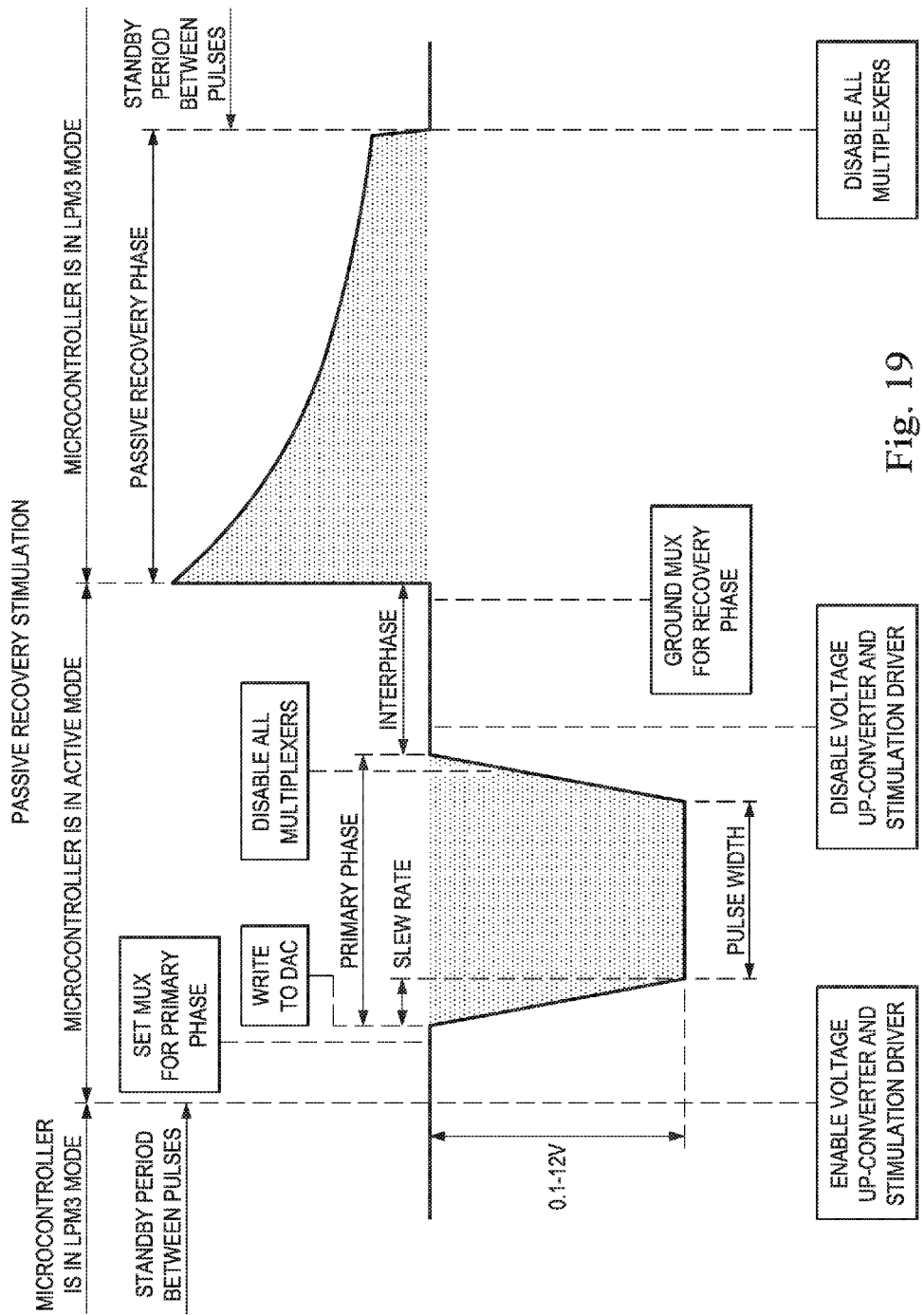
FIG. 19 illustrates the power-reduction approaches employed by a peripheral neurostimulator during a passive recovery stimulation pulse according to an embodiment of the present disclosure.
Figure 20:
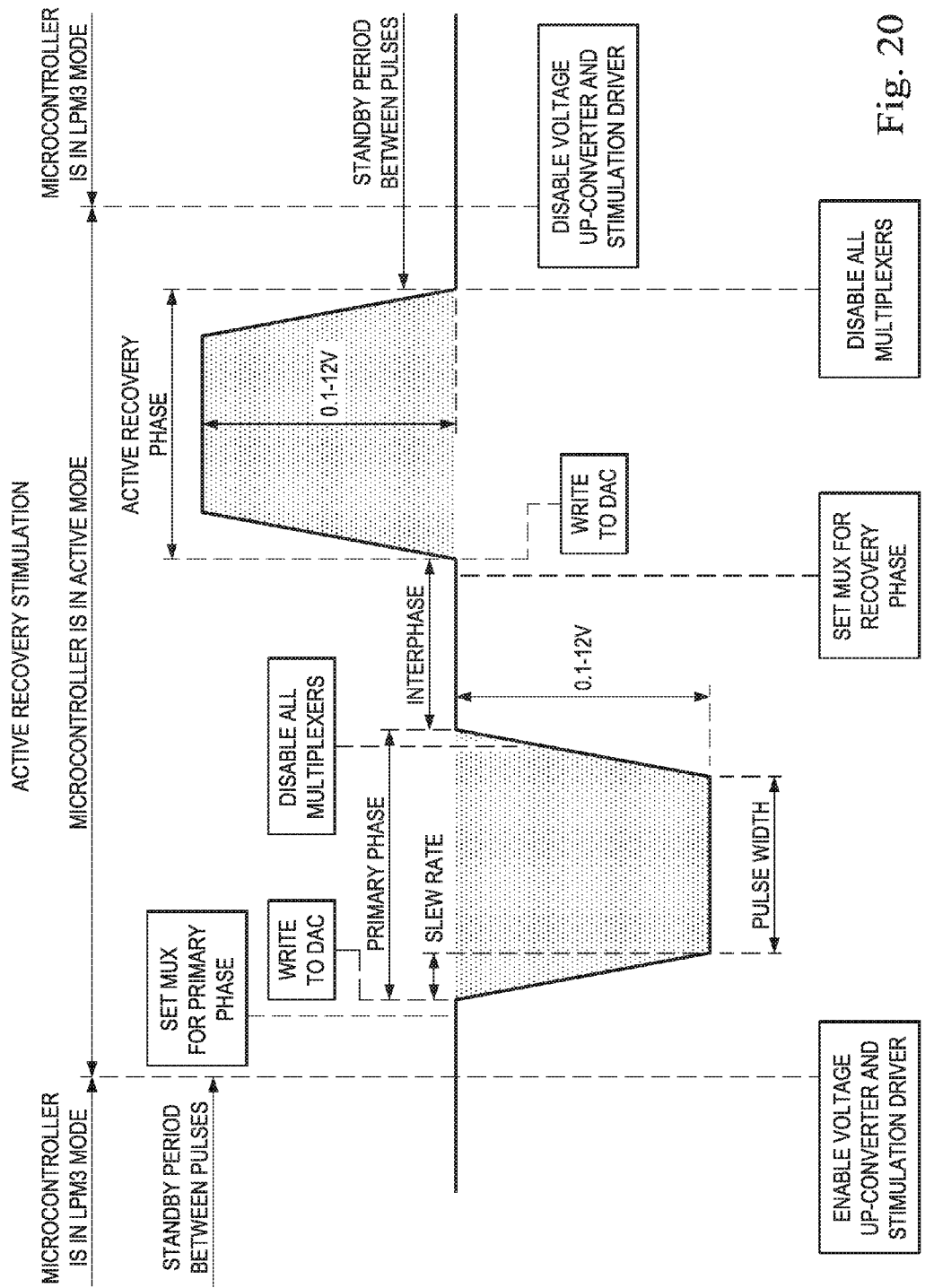
FIG. 20 illustrates the power-reduction approaches employed by a peripheral neurostimulator during an active recovery stimulation pulse according to an embodiment of the present disclosure.

Moreover, the microcontroller core 410 is turned off in the LPM3 mode. Meanwhile, the DMA unit 420 may be kept on (and is driven by the crystal oscillator 430) during the LPM3 mode to send instructions to various peripherals, such as the DAC. For example, the DMA unit 420 may be configured to write the digital waveform data to the DAC. When the writing of the digital waveform data into the DAC is complete, the DAC outputs the analog stimulation waveforms, i.e., the electrical stimulation pulse. Again, this process does not require the microcontroller core 410 to be running. As discussed above, the microcontroller core 410 is the main power-hog in the microcontroller 400 and consumes substantially more power than the DMA unit 420. Consequently, turning off the microcontroller core 410, coupled with the switching from the 10 Mhz main system clock to the 32.678 Khz clock of the crystal oscillator 430, allows the power consumption to be reduced from approximately 3 mA down to approximately 3 uA in some embodiments. In some embodiments, an interrupt signal generated by the timer unit 425 (shown in FIG. 7)—clocked by the 32.768 kHz crystal oscillator 430—may be used to wake the microcontroller 400 up from the LPM3 mode back to the active mode in time to generate the next pulse In addition, depending on the stimulation waveform type (active or passive recovery), additional measures are employed to reduce power consumption. To illustrate, two example waveforms representing two different types of a bi-phasic stimulation pulse are shown in FIGS. 19-20. Specifically, the waveform in FIG. 19 shows a stimulation pulse with a passive recovery, and the waveform in FIG. 20 shows a stimulation pulse with an active recovery. Generally, a bi-phasic stimulation pulse includes a primary phase, an interphase, and a recovery phase. The primary phase is a period of time during which the actual stimulation pulse is generated. The recovery phase is a period of time to allow charges on the electrodes to rebalance. The interphase is a period of time between the primary phase and the recovery phase. For stimulation pulses with a passive recovery phase, the charges are passively rebalanced over time. In comparison, for stimulation pulses with an active recovery phase, a "pulse" that is opposite in polarity (but substantially equal in amplitude) of the actual pulse (e.g., generated in the primary phase) is generated to allow the charges to balance more quickly. Therefore, the trade-off between passive recovery and active recovery is that passive recovery consumes less power but takes longer, and active recovery consumes more power but is quicker, which allows for stimulation at a higher frequency.

Referring now to FIG. 19, the primary phase, interphase, and the passive recovery phase are clearly illustrated for a stimulation pulse with passive recovery. In addition, portions of the standby period that is in between consecutive stimulation pulses are also illustrated. In some embodiments, the standby period may begin at the end of the recovery phase and may last until the beginning of the primary phase for the next pulse. It is understood that the standby period can be much longer than the actual pulse itself. For example, the time duration for an entire pulse—which includes the primary phase, interphase, and recovery phase—may last from about 2 milli-seconds to about 4 milli-seconds according to some embodiments. In comparison, the time duration for the standby period may last between about 1 milli-second to about 1 second. In other words, the standby period may be more than 4 to 10 times longer than the actual pulse in some embodiments.

For most conventional neurostimulators, once a microcontroller is turned on, it remains turned on during the stimulation pulses as well as in between the stimulation pulses. Stated differently, most conventional neurostimulators keep the microcontroller turned on even during the standby period. In comparison, the microcontroller 400 of the PNS device 200 is turned on only when necessary. As FIG. 19 illustrates, the microcontroller operates in the LPM3 power-conservation mode during most of the standby period between consecutive stimulation pulses. As discussed above, the microcontroller core 410 is turned off in the LPM3 mode, which reduces power consumption significantly as the microcontroller core 410 is a power-hungry device. Right before the pulse needs to be generated, the microcontroller 400 "wakes up" from the LPM3 power-conservation mode and begins to operate in the active mode (where the microcontroller core 410 is turned on). The waking of the microcontroller 400 may be done by a timer signal generated by the timer unit 425, for example.

In the embodiment shown in FIG. 19, the microcontroller 400 wakes up from the LPM3 power-conservation mode and begins to operate in the active mode about 100 microseconds before the start of the primary phase. This is done so that the microcontroller 400 can enable the voltage up-converter (e.g., a charge pump) 370 and the stimulation driver 450 discussed above with reference to FIG. 7 in preparation for the pulse generation. At some time after that, but still before the pulse is generated (before the start of the primary phase), the microcontroller 400 sets or configures the multiplexers 460 so that desired stimulation channels can be formed. In the embodiment shown in FIG. 19, the multiplexers 460 are configured about 10 micro-seconds before the start of the primary phase.

Either the DMA unit 420 or the microcontroller core 410 may be used to write the digital data for the stimulation waveform to the DAC. Once the data has been completely written into the DAC, the stimulation pulse is generated by the DAC, thereby defining the start of the primary phase of the pulse. The stimulation pulse coming out of the DAC is amplified by the stimulation driver 450 to achieve the target amplitude needed for the peripheral stimulation therapy. In the illustrated embodiment, the amplified pulse amplitude ranges from about 0.1 V to about 12 V. The stimulation driver 450 may also have a slew rate of about 2.3 V/micro-seconds in the illustrated embodiment.

The pulse width, or the time duration of the primary phase, may be programmably configured. In various embodiments, the pulse width may be in a range from about 20 micro-seconds to about 2000 micro-seconds. Right before (or at) the end of the primary phase and before the start of the interphase, the multiplexers 460 are also disabled in order to further reduce power consumption. In the illustrated embodiment, the multiplexers 460 are disabled about 1 micro-second before the start of the interphase.

In the illustrated embodiment, the interphase may last for about 20 micro-seconds. At the start of the interphase, or shortly after (e.g., a few micro-seconds), the voltage up-converter 370 is disabled to further reduce power consumption. The voltage up-converter 370 (e.g., a charge pump), when activated, supplies power to the stimulation driver 450 and the multiplexers 460 when the stimulation pulse calls for a higher voltage than what the battery 340 can supply. For example, in the present embodiment, when the stimulation pulse needs to have an amplitude higher than about 3.5 V or 4 V, the battery 340 cannot supply this high of voltage. The voltage up-converter 370 is then turned on to ensure that the compliance voltage is sufficiently high. For conventional neurostimulators, such voltage-converter (if it exists) is typically kept turned on to generate a constant high-voltage stimulation compliance voltage, regardless of the phase of the stimulation pulse. This causes power to be wasted needlessly. In comparison, the voltage up-converter 370 of the PNS device 200 can be enabled shortly before (e.g., a few microseconds) the stimulation pulse is generated and disabled just after (e.g., a few microseconds) the stimulation pulse is generated. By doing so, steady-state power consumption of the PNS device 200 is reduced significantly.

Similarly, the stimulation driver 450 can be enabled shortly before (e.g., a few microseconds) the stimulation pulse is generated and disabled shortly after (e.g., a few microseconds) the stimulation pulse is generated. Again, the timely enabling and disabling of the stimulation driver 450 prevents power from being wasted needlessly outside the primary phase of the stimulation pulse.

Shortly before the end of the interphase and before the start of the passive recovery phase, the multiplexers 460 are turned on but grounded. This allows the electrical charge that has been built up on the capacitors 465 to discharge back into the tissue. In the illustrated embodiment, the grounding of the multiplexers 460 occurs about 1 micro-second before the recovery phase. The recovery phase is passive because the built-up charges are just "passively" being discharged to perform charge balancing, so as to achieve zero voltage on the electrodes at the end of the passive recovery phase. In the illustrated embodiment, the passive recovery phase may last for about 2 to 6 milli-seconds.

At the end (or shortly after) of the passive recovery phase, the multiplexers 460 are disabled (e.g., they may go into a high impedance mode) in order to further reduce power consumption. This marks the end of one cycle of the bi-phasic pulse, and the standby period follows the end of the previous pulse (and before the start of the subsequent pulse). To further reduce power consumption, the timer unit 425 instructs the microcontroller 400 to enter or operate in the LPM3 mode again during the standby period. This process discussed above may repeat indefinitely for each passive stimulation pulse cycle until stimulation is shut off.

Referring now to FIG. 20, the operation of the PNS device 200 for active recovery stimulation shares many similarities with the passive recovery stimulation discussed above with reference to FIG. 19, with certain differences. In more detail, up to the point of the interphase, the operation/configuration of the microcontroller 400 and the various other components of the PNS device 200 are substantially identical for passive recovery stimulation and active recovery stimulation. However, whereas the voltage up-converter 370 and the stimulation driver 450 are disabled at or shortly after the start of the interphase for passive recovery stimulation, the voltage up-converter 370 and the stimulation driver 450 remain turned on during the interphase for active recovery stimulation. In addition, whereas the multiplexers 460 are grounded before the start of the recovery phase for passive recovery stimulation, the multiplexers 460 are actually configured before (e.g., about 1 milli-seconds before) the recovery phase for active recovery stimulation. These differences reflect the fact that another pulse needs to be generated during the recovery phase for active recovery stimulation.

For example, the microcontroller core 410 or the DMA unit 420 writes digital waveform data into the DAC during the interphase, and at the completion of this data writing process, the DAC outputs a stimulation pulse that is substantially equal in pulse width but opposite in polarity with the actual stimulation pulse generated in the primary phase. The generation of this "opposite" pulse corresponds to the active recovery phase. The active recovery phase is thus much shorter than the passive recovery phase, which may allow for a higher stimulation frequency.

Since the active recovery phase require pulse generation during the recovery phase, the microcontroller 400 operates in the active mode for the entire 3 phases of the stimulation pulse (i.e., the primary phase, the interphase, and the active recovery phase). Furthermore, the voltage up-converter 370 and the stimulation driver 450 remain turned on during the entire 3 phases of the stimulation pulse to ensure voltage compliance and to amplify the stimulation pulse outputted by the DAC.

At the end of the active recovery phase, or shortly thereafter (e.g., a few micro-seconds thereafter), the multiplexers 460 are disabled, and the voltage up-converter 370 and the stimulation driver 450 are also disabled. The microcontroller 400 also reverts back to the LPM3 power-conservation mode after the end of the active recovery phase. In other words, these power-consuming components are disabled in the standby period (or at least a substantial majority thereof) between consecutive pulses in order to conserve power. This process discussed above may repeat for each active recovery stimulation pulse indefinitely until stimulation is shut off.

It is understood that the active mode and the LPM3 power conservation mode are used as mere examples herein to illustrate certain aspects of the power reduction strategies of the PNS device 200. In other embodiments, any of the other power-conservation modes may also be employed to reduce power consumption. For example, in some embodiments, the microcontroller core 410 may be turned off during one or more of the phases within a pulse, and the DMA unit 420 may be used to perform other tasks instead of the microcontroller core 410, such as writing data to the DAC.

The above discussions pertain to power reduction achieved by selectively operating the microcontroller 400 in a power-conservation mode whenever appropriate, as well as timely disabling and enabling power-consuming components such as the voltage up-converter 370, the stimulation driver 450, and the multiplexers 460 throughout the different phases of the stimulation pulse. In other words, the PNS device 200 micro-manages the various power-consuming components within to ensure that no power is needlessly wasted.

Another example of the micromanagement used to conserve power pertains to disconnecting the voltage up-converter 370 from its load (e.g., the stimulation driver 450 and the multiplexers 460) between consecutive stimulation pulses (i.e., during the standby period). In more detail, the voltage up-converter 370 may employ an output capacitor to store charge. Even if the voltage up-converter 370 is turned off between the stimulation pulses (during the standby period), any load connected to the output capacitor may still drain the charge out of the output capacitor. In other words, the stimulation driver 450 and the multiplexers 460 herein may serve as the load that will cause the output capacitor of the voltage up-converter 370 to discharge. This means that when the voltage up-converter is turned on the next time, it will have to charge up the output capacitor again, thereby wasting power.

According to various embodiments of the present disclosure, the switch 480 (discussed above with reference to FIG. 7) can be used to disconnect the stimulation driver 450 and the multiplexers 460 (i.e., the load of the voltage up-converter 370) from the voltage up-converter during the standby period, even as the voltage up-converter 370, the stimulation driver 450, and the multiplexers 460 are turned off. By timely disconnecting the load from the voltage up-converter 370, energy (i.e., electrical charge) stored in the voltage up-converter 370 may be preserved for the next stimulation pulse.

It is understood that in some embodiments, the timer unit 425 (or the timer signals generated therefrom) may be used to control the timing for the micromanage tasks discussed above, i.e., switching the microcontroller 400 between the active mode and one of the power-conservation modes, enabling/disabling the voltage up-converter 370, the stimulation driver 450, and the multiplexers, disconnecting the load from the voltage up-converter 370, and/or writing to the DAC. The timer unit 425 may be programmed by firmware or software to perform these tasks.

It is also understood that although a typical bi-phasic pulse is used herein as an example of a stimulation pulse, the concepts discussed herein may apply to other types of stimulation pulses as well. For example, certain types of stimulation pulses may have a plurality of pulses in the primary phase before the interphase and the recovery phase. Even for these types of stimulation pulses, the microcontroller 400 may still switch its mode of operation in the standby period, and the other components such as the voltage up-converter and stimulation drive may still be micromanaged appropriately in order to reduce power consumption. Furthermore, although the embodiment shown in FIGS. 19-20 illustrate operating the microcontroller 400 in the active mode during the pulse generation, the microcontroller 400 may also operate in one or more of the other power-conservation modes (e.g., the LPM1 mode) even during the pulse generation in order to further reduce power consumption.

FIG. 21 is a simplified flowchart of a method 900 of providing an electrical stimulation therapy for a patient according to an embodiment of the present disclosure. The method 900 includes a step 905 of receiving programming instructions from an electronic programmer.

The method 900 includes a step 910 of generating, via a microcontroller and in response to the received programming instructions, a plurality of electrical pulses to be delivered to the patient as a part of the electrical stimulation therapy. Each electrical pulse includes a primary phase, an interphase after the primary phase, and a recovery phase after the primary phase. Consecutive electrical pulses are separated by a standby period. The step 910 of generating of the electrical pulses comprises: operating the microcontroller in an active mode during at least one of: the primary phase and the interphase; and operating the microcontroller in a power-conservation mode during a substantial majority of the standby period. The microcontroller consumes substantially less power when operating in the power-conservation mode than in the active mode. In some embodiments, the microcontroller is the microcontroller 400 of FIG. 7.

The method 900 includes a step 915 of receiving an inductive energy. In some embodiments, the inductive energy is received via a coil, for example by the conductive charging mechanism 320 of FIG. 7 (an embodiment of which is illustrated as the coil 700 of FIGS. 15A-15C). The method 900 includes a step 920 of converting the inductive energy into a direct current (DC) signal. In some embodiments, the converting of the inductive energy is performed by the charging circuit 330 of FIG. 7. The method 900 includes a step 925 of charging a battery with the DC signal, thereby providing a first DC voltage via the battery. In some embodiments, the battery is the battery 340 of FIG. 7, and the first voltage is the output voltage of the battery 340. The method 900 includes a step 930 of down-converting the first DC voltage to a second DC voltage smaller than the first DC voltage. In some embodiments, the down-converting is performed by the voltage down-converter 360 of FIG. 7, and the second DC voltage is the output voltage of the voltage down-converter 360. In some embodiments, the voltage down-converter 360 includes a buck converter. The method 900 includes a step 935 of providing the second DC voltage as a voltage supply for at least the microcontroller. The method 900 includes a step 940 of up-converting the first DC voltage to a third DC voltage greater than the first DC voltage. In some embodiments, the up-converting is performed by the voltage up-converter 370 of FIG. 7, and the third DC voltage is the output voltage of the up-converter 370. In some embodiments, the voltage down-converter 370 includes a charge pump.

The method 900 includes a step 945 of providing the third DC voltage as a voltage supply for a stimulation driver and an array of multiplexers coupled to the stimulation driver. In some embodiments, the stimulation driver is the stimulation driver 450 of FIG. 7, and the array of multiplexers includes the multiplexers 460 of FIG. 7. The method 900 includes a step 950 of amplifying, via the stimulation driver, the electrical pulses generated by the microcontroller. The method 900 includes a step 955 of delivering the amplified electrical pulses to the patient at least in part by configuring the array of multiplexers. The method 900 includes a step 960 of disconnecting the stimulation driver from the voltage up-converter during the standby period between consecutive electrical pulses. In some embodiments, the disconnecting is performed at least in part by the switch 480 of FIG. 7.

In some embodiments, the microcontroller of the method 900 contains a microcontroller core (e.g., the microcontroller core 410 of FIG. 7) and a direct memory access (DMA) unit (e.g., the DMA unit 420 of FIG. 7) that is separate from the microcontroller core and consumes substantially less power than the microcontroller core. In these embodiments, the operating of the microcontroller may comprises a step of turning on the microcontroller core in the active mode, turning off the microcontroller core in the power-conservation mode, and keeping the DMA unit turned on in the power-conservation mode. In some embodiments, the microcontroller contains a system clock that is running at a first frequency, and the stimulation circuitry further comprises an oscillator that is external to the microcontroller. The oscillator runs at a second frequency that is substantially lower than the first frequency. In these embodiments, the operating of the microcontroller comprises driving the microcontroller with the system clock in the active mode. The DMA unit is also driven with the oscillator in the power-conservation mode. In addition, the method 900 may include a step of generating an interrupt signal with a timer unit (e.g., the timer unit 425 of FIG. 7) that is clocked by the oscillator, and a step of waking up the microcontroller from the power-conservation mode via the interrupt signal immediately before a subsequent electrical pulse needs to be generated.

It is understood that the steps 905-960 need not necessarily be performed according to the sequence shown in FIG. 21. In fact, some of these steps may be performed concurrently, or even in an order different from what is shown in FIG. 21. It is also understood that additional process steps may be performed before, during, or after the steps 905-960. For example, as each electrical pulse may include either a passive recovery phase or an active recovery phase, different process steps may be performed depending on whether the electrical pulse has a passive recovery phase or an active recovery phase. If the electrical pulse has a passive recovery phase, then the method 900 may include a step of enabling the voltage up-converter and the array of multiplexers before the primary phase, a step of disabling the voltage up-converter and the array of multiplexers during the interphase, and a step of operating the microcontroller in the power-conservation mode during the passive recovery phase. If the electrical pulse as an active recovery phase, then the method 900 may include a step of enabling the voltage up-converter and the array of multiplexers before the primary phase, a step of disabling the voltage up-converter and the array of multiplexers after the active recovery phase, and a step of operating the microcontroller in the active mode during the active recovery phase. For reasons of simplicity, other additional steps are not discussed herein.

Charge Pump System, Devices and Methods for an Implantable Stimulator

As discussed above, the voltage up-converter 370 (shown in FIG. 7) of the PNS device 200 scales up the output voltage of the battery 340 to ensure voltage compliance for the stimulation pulses. In more detail, the amplitude of the stimulation pulses that need to be delivered to the patient (e.g., pulses that are amplified by the stimulation driver 450) may be greater than the voltage produced by the battery 370. In some embodiments, the stimulation pulses may vary from 0 volts to about 12 volts, whereas the battery 340 can only produce up to about 4 volts. If the battery 340 is configured to supply its output directly to the stimulation driver 450, the stimulation driver 450 cannot amplify the stimulation pulses to exceed the output voltage of the battery 340, thereby limiting the stimulation pulse amplitude to the output of the battery 340. Thus, the voltage up-converter 370 is implemented to scale up the output voltage of the battery 340 to be sufficiently high, so that it can serve as the power supply or voltage rail of the stimulation driver 450 without clipping the amplitude of the amplified stimulation pulses.

However, conventional voltage up-converters used for voltage compliance purposes typically produce a scaled-up output voltage approximately only as an integer multiple of the input voltage. For example, if conventional voltage up-converters are used herein, its output voltage would be two times (2×) the output voltage of the battery 340, or three times (3×) the output voltage of the battery 340, etc. As such, if the output voltage of the battery 340 is about 4 volts, then the conventional voltage up-converter may only generate about 8 volts or about 12 volts (or another integer multiple of 4 volts) as the voltage rail for its load (e.g., the stimulation driver 450).

While this approach described above is convenient and may ensure the intended operation of the involved devices, it is not optimized in terms of power consumption. For example, suppose the amplitude of the stimulation pulse only requires a fraction (but greater than 1) of the output voltage of the battery 340, for example 1.25 times of the output voltage of the battery 340. In other words, the output voltage of the battery 340 is about 4 volts, and the amplitude of the stimulation pulse is about 5 volts in this example. If the conventional voltage up-conversion approach is used, then the voltage up-converter will generate at least 2× the output voltage of the battery 340, which will be about 8 volts, since this is the closest integer multiple of the output voltage of the battery 340 5 volts (or 5.1 volts if about 0.1 volts of headroom is desired) for its voltage rail is unnecessary, as it wastes power needlessly. As discussed above, power consumption reduction is important for the PNS device 200 in order to achieve excellent battery life in spite of its miniature size. Therefore, the conventional voltage up-conversion approach is not a good solution for the PNS device 200.

According to various aspects of the present disclosure, the voltage up-converter 370 of the PNS device 200 is capable of producing a scaled-up voltage as a fraction of the input voltage (e.g., input voltage being the battery output voltage). The fraction may be greater than 1 and may vary between 1 and 2, 2 and 3, 3 and 4, etc. In this manner, the voltage up-converter 370 can supply a voltage that is tailored to the voltage rail needed for a particular stimulation pulse. By doing so, power consumption is optimized, which further improves the battery performance of the PNS device 200.

Figure 22A:
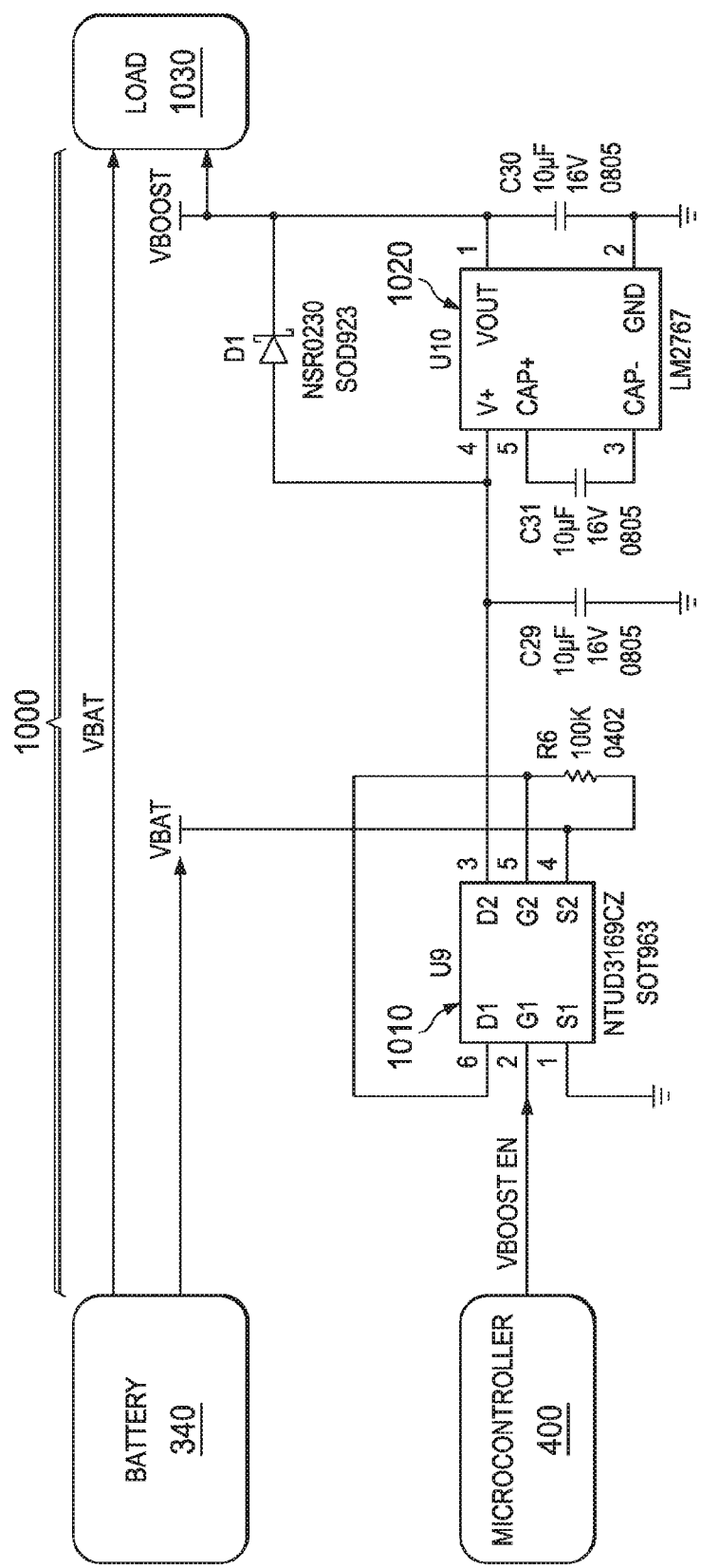
FIGS. 22A-22C illustrate circuit schematics of portions of a voltage up-converter for providing a compliance voltage according to an embodiment of the present disclosure.

FIG. 22A is a simplified block diagram of the voltage up-converter 370 according to an embodiment of the present disclosure. In the illustrated embodiment, the voltage up-converter 370 includes a charge pump 1000. The charge pump includes a level shifter switch 1010 and a charge pump chip 1020 coupled to the level shifter switch 1010. The level shifter switch allows the microcontroller 400 (discussed above with reference to FIGS. 7 and 19-20) to supply the control signal VBOOST_EN (also interchangeably referred to as a VBOOST_EN line) to the charge pump chip 1020. This is because in the illustrated embodiment, the charge pump chip 1020 is configured to accept an input voltage of about 4 volts from the battery 340 (discussed above with reference to FIGS. 7). However, the microcontroller 400 in this embodiment is running at about 2.5 to about 2.7 volts.

Due to the voltage differences (i.e., 4 volts V.S. 2.5-2.7 volts), the microcontroller 400 cannot be tied directly to the charge pump chip 1020. The level shifter switch 1010 is used to "shift up" the 2.5 volts of the microcontroller 400 to the 4 volts of the battery 340, so that the microcontroller 400 can control the enabling and disabling of the charge pump chip 1020 with the VBOOST_EN control signal.

In the illustrated embodiment, the level shifter switch 1010 contains an n-type Field Effect Transistor (nFET), which is represented by D1 (drain), G1 (gate), S1 (source), and a pFET, which is represented by D2 (drain), G2 (gate), and S2 (source). When the nFET is enabled by the VBOOST_EN signal from the microcontroller 400, it turns on the pFET. In other words, the gate of the pFET is pulled down when the level shifter switch 1010 is enabled, which allows the pFET to turn on. When this happens, the output of the battery 340 (the VBAT line) is connected to pin 4 (voltage the input pin) of the charge pump chip 1020.

It is understood that the level shifter switch 1010 is not essential for the charge pump 1000. It is implemented herein merely because the microcontroller 400 and the battery 340 are operating at different voltages, and also because the charge pump chip 1020 does not have a direct enable line. Therefore, the microcontroller 400 cannot directly supply the VBOOST_EN control signal to the charge pump chip 1020. In other embodiments, the charge pump chip 1020 may be implemented to directly accept the VBOOST_EN control signal (or a similar control signal) from the microcontroller 400, in which case the level shifter switch 1010 may be omitted. In other words, the charge pump chip 1020 in alternative embodiments may have an input pin that can be tied directly to the VBAT line (output voltage from the battery 340) and an enable pin that can be tied directly to the VBOOST_EN line. When VBOOST_EN goes high, the charge pump chip 1020 is enabled or turned on, and it may begin to up-convert the VBAT voltage.

Referring back to FIG. 22A, the charge pump 1000 also includes three capacitors C29 (referred to as an input capacitor), C31 (referred to as a flying capacitor), and C30 (referred to as an output capacitor). These capacitors C29, C31, and C30 are used in conjunction with the charge pump chip 1020 to boost the input voltage VBAT to a sufficiently large output voltage that may serve as a compliance voltage for a load 1030. In the embodiment discussed herein, the load 1030 includes the stimulation driver 450 and the multiplexers 460 (shown in FIG. 7). In alternative embodiments, the load 1030 may include other electrical circuits that may draw electrical charge from the output capacitor C30.

Before the charge pump chip 1020 is enabled (e.g., by a control signal such as the VBOOST_EN signal), the charge pump chip 1020 is turned off, and the input capacitor C29 and the flying capacitor C31 are discharged. If the load 1030 is still connected to the charge pump chip 1020, then the output capacitor C30 is being discharged by the load 1020 as well. As discussed above, this is one of the reasons why the switch 480 (FIG. 7) is implemented to disconnect the load 1030 from the charge pump—to preserve charges stored on the output capacitor C30 even when the charge pump is disabled (e.g., between stimulation pulses). If no load is present, then the output capacitor C30 is being very slowly discharged due to leakage current, etc., which may be negligible.

When the charge pump chip 1020 is turned on by the control signal VBOOST_EN, a clock (e.g., a 11 Khz clock in some embodiments or a 50 Khz clock in some other embodiments) inside the charge pump chip 1020 may govern the operation of the charge pump chip 1020. For example, when this clock pulse is high, the charge pump chip 1020 configures its pins so that the input capacitor C29 and the flying capacitor C31 are coupled in parallel. The capacitors C29 and C31 are each charged to the input voltage VBAT under this configuration. Meanwhile, the output capacitor C30 is not being charged at this time. It is understood that, though capacitors typically cannot be charged up instantaneously, the charging speed depends on how much current can be supplied to the capacitors when they are being charged. In this case, the battery 340 provides sufficient amount of current so as to ensure that the capacitors C29 and C31 can be fully charged to VBAT during one half of the clock cycle (i.e., when the clock pulse is high).

When the charge pump chip 1020's clock pulse goes low, the charge pump chip 1020 reconfigures its pins so that the input capacitor C29 and the flying capacitor C31 are now coupled in series, and they are collectively coupled in parallel with the output capacitor C30. This coupling configuration allows the output capacitor C30 to be gradually charged up by the capacitors C29 and C31. In other words, the capacitors C29 and C31 are collective "dumping charge" into the output capacitor C30.

When the clock pulse for the charge pump chip 1020 switches to high again, the charge pump chip 1020 again configures its pins so that the output capacitor C30 is disconnected from the capacitors C29 and C31, and the capacitors C29 and C31 are coupled in parallel again to be charged up to VBAT. At this time, the output capacitor C30 may discharge into a load (such as the load 1030), if a load is present. When the clock pulse for the charge pump chip 1020 switches to low again, the charge pump chip 1020 reconfigures its pins so that the capacitors C29 and C31 are coupled in series and collectively in parallel with the output capacitor C30, and the output capacitor C30 is charged up a little more.

As the above discussions illustrate, the capacitor C30 is not completely charged up to its full capacity in one clock cycle. Instead, the capacitor C30 is charged up a little bit for each clock cycle (when the clock pulse goes low). Therefore, it takes a plurality of clock cycles before the output capacitors C30 is fully charged up. The speed at which the capacitor C30 is charged up is a function of the values for the capacitors C29, C31, and C30. As the values for the capacitors C29 and C31 decrease relative to the capacitor C30, the amount of charge dumped into the output capacitor C30 also decreases, and consequently it takes more clock cycles to fully charge up the output capacitor C30. Since the capacitor C30 is charged up by a smaller amount for each clock cycle, the charge pump 1000 may offer more granularity or a finer resolution for its output, which may be beneficial, as discussed below.

On the other hand, as the values for the capacitors C29 and C31 increase relative to the capacitor C30, the amount of charge dumped into the output capacitor C30 also increases, and consequently it takes fewer clock cycles to fully charge up the output capacitor C30. Since the capacitor C30 is charged up by a greater amount for each clock cycle, the charge pump 1000 may offer less granularity or a lower resolution for its output, but its charging speed is greater. In other words, the charge pump 1000 may be designed and/or configured (e.g., by choosing the values for the capacitors C29, C31, and C30) to find a desired tradeoff balance between output voltage resolution and charging speed. Furthermore, it is understood that the capacitance value for the flying capacitor C31 will dominate the capacitance value C29 in determining the charging speed of the output capacitor C30. Therefore, in some embodiments, the capacitor C29 may be omitted from consideration when doing the output resolution V.S. charging speed tradeoff analysis discussed above.

In any case, when the charge pump chip 1020 is enabled, the voltage at the output capacitor steadily increases for every clock cycle until it reaches its full capacity (2×VBAT in this case). The exact amount of voltage increase at the output capacitor C30 can also be calculated or measured. Since the clock frequency for the charge pump chip 1020 is known (11 Khz in some embodiments or 50 Khz in some other embodiments), the pulse width or the clock period can also be calculated, which means that the voltage increase as a function of time can also be determined. In other words, by controlling the amount of time that the charge pump chip 1020 is enabled, the output voltage of the charge pump chip 1020 (i.e., VBOOST, which is also interchangeably referred to as the output of the charge pump 1000 hereinafter) can be set.

As an example, suppose that it has been calculated or measured that the output voltage VBOOST of the charge pump chip 1020 increases as a rate of 0.5 volts per clock cycle, where the clock cycle is 11 Khz for this example. Thus, if a voltage of 6.5 volts is desired for VBOOST, then 6.5/0.5=13 clock cycles are needed to charge the output capacitor C30 to 6.5 volts. Based on a clock frequency of 11 Khz (which has a clock period of about 91 microseconds), it can be calculated that it would take approximately 1.182 milli-seconds to charge the output capacitor C30 to 6.5 volts. The microcontroller 400 can thus be configured to control the amount of time that the VBOOST_EN line is high to be about 1.182 milli-seconds to achieve 6.5 volts for VBOOST.

It is understood that a load (such as the load 1030) present at the output of the charge pump chip 1020 may slightly affect the calculations discussed above, as the load may drain the charge out of the charge pump chip 1020, thereby decreasing its voltage. In other words, during parts of the clock cycle where the output capacitor C30 is not being charged, it may be discharged by the load 1030 if the load 1030 is connected to the charge pump chip 1020. For example, using the above example, the VBOOST voltage at the output capacitor C30 may increase by 0.5 volts every clock cycle when the clock pulse is low (i.e., the capacitors C29 and C31 are collectively charging up the capacitor C30), but it may also decrease by 0.1 volt every clock cycle when the clock pulse is high (i.e., the capacitor C30 is disconnected from the capacitors C29 and C31, which are charged up to VBAT). Based on this crude approximation, it may take 6.5/(0.5−0.1)=16.25 clock cycles are needed to charge VBOOST to 6.5 volts, which after rounding up is 17 clock cycles. This would correspond to about 1.546 milli-seconds.

Based on the discussions above, it can be seen that the charge pump 1000 of the present disclosure can achieve an output voltage VBOOST that is a fraction (greater than 1) of the input voltage VBAT. The resolution of VBOOST can also be configured in the tradeoff analysis discussed above, i.e., by configuring the capacitor values of one or more of the capacitors C29, C31, and C30. The voltage output versatility and flexibility offered by the charge pump 1000 reduces power consumption waste, because it can be used to generate a customized VBOOST voltage based on the amplitude requirement for a particular stimulation pulse or a stream of stimulation pulses.

The charge pump 1000 further includes a resistor R6 and a diode D1. The resistor R6 serves as a "pull-up" resistor to keep the gate G2 off for the pFET of the level shifter switch 1010. The diode D1 prevents latch-up of internal circuits of the charge pump chip 1020 when it first starts up. It is understood that the resistor R6 and the diode D1 may be omitted in other embodiments that employ a different charge pump chip, for example one that has a direct enable line that may be tied to the VBOOST_EN line directly.

Figure 22B:
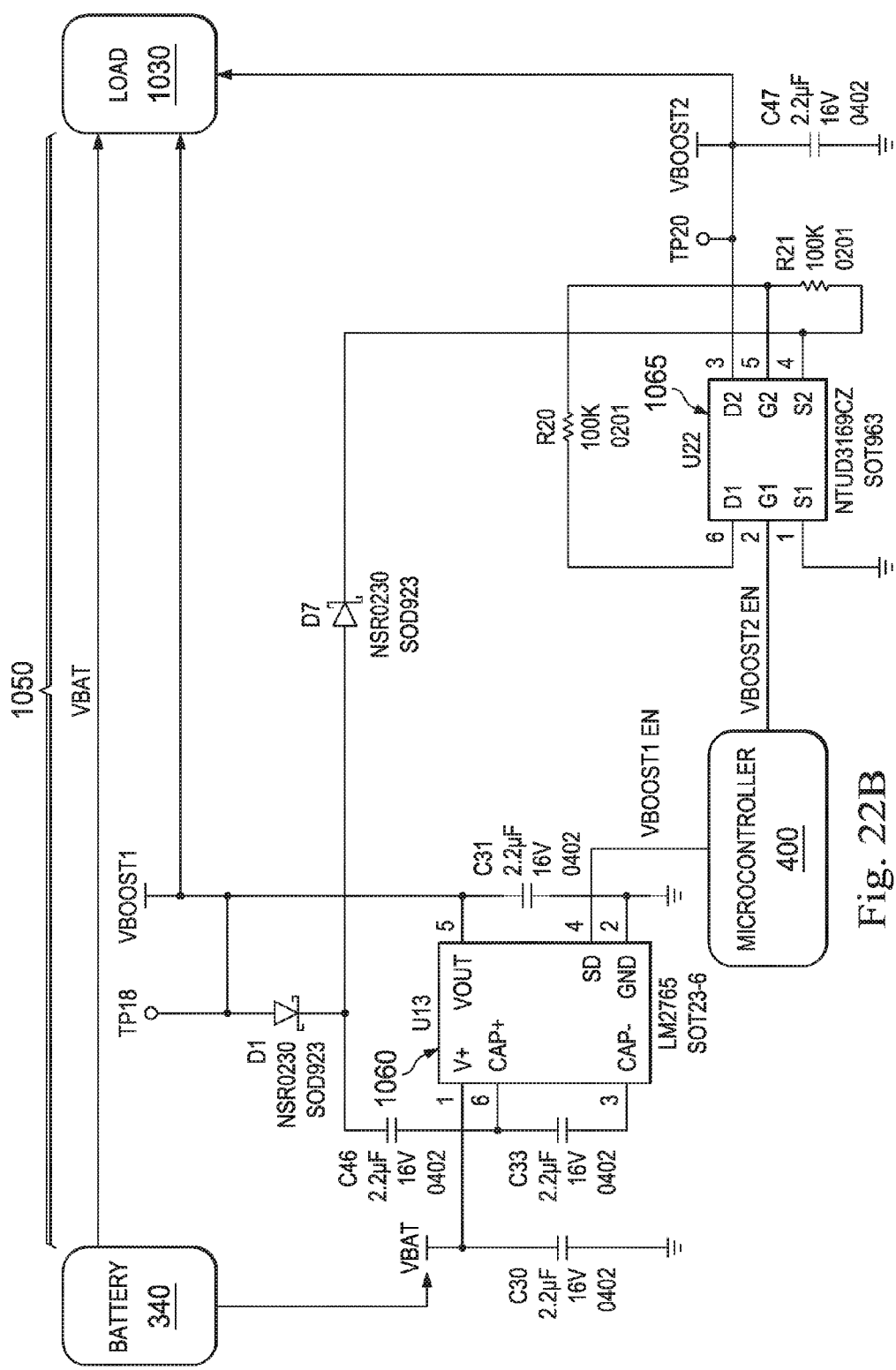

It is understood that the charge pump 1000 of FIG. 22A illustrated herein can effectively achieve an output voltage that is up to twice the battery voltage VBAT. Referring to FIG. 22B, the circuit schematic for an alternative embodiment of the charge pump is illustrated as charge pump 1050, which can provide a voltage up to three times the battery voltage VBAT. In more detail, the charge pump 1050 similar to the charge pump 1000 discussed above with reference to FIG. 22A. However, a different charge pump chip 1060 is used. The charge pump chip 1060 functions similarly to the charge pump 1020 discussed above, except that the charge pump chip 1060 has an enable line (SD) that is directly controlled by a control signal VBOOST1 EN from the microcontroller 400. This allows the charge pump chip 1060 to have its input V+ tied directly to the VBAT input voltage. In this manner, the level shifter 1010 of FIG. 22A is no longer needed.

Based on the operation mechanism similar to those discussed above with reference to the charge pump 1000 in FIG. 22A, the charge pump 1050 can provide an output voltage that is up to three times of its input voltage (i.e., battery voltage VBAT). Specifically, the charge pump 1000 includes a switch 1065, which is also controlled by the microcontroller 400 via a control line VBOOST2 EN. If VBOOST1 EN is active (low) then VBOOST1 outputs approximately 2×VBAT. If both VBOOST1 EN and VBOOST2 EN (high) are active, then VBOOST2 outputs approximately 3×VBAT. Again, by carefully controlling the amount of time that the charge pump chip 1060 is enabled, the charge pump 1050 can also achieve a desired fraction value anywhere from VBAT to 3×VBAT.

As shown in FIG. 22A, either VBAT (output from battery 340) or VBOOST (2×VBAT) may be provided to the load 1030 as a power supply. Similarly, either VBAT, VBOOST1 (2×VBAT), or VBOOST2 (3×VBAT) may be provided to the load 1030 as a power supply. To ensure that the right voltage is selected, a corresponding circuit may be specifically configured to handle the selection of VBAT and VBOOST in the embodiment shown in FIG. 22A, or the selection of VBAT, VBOOST1, and VBOOST2 in the embodiment shown in FIG. 22B, so that the intended voltage output gets to the load 1030. An example embodiment of such circuit is shown in FIG. 22C.

Figure 22C:
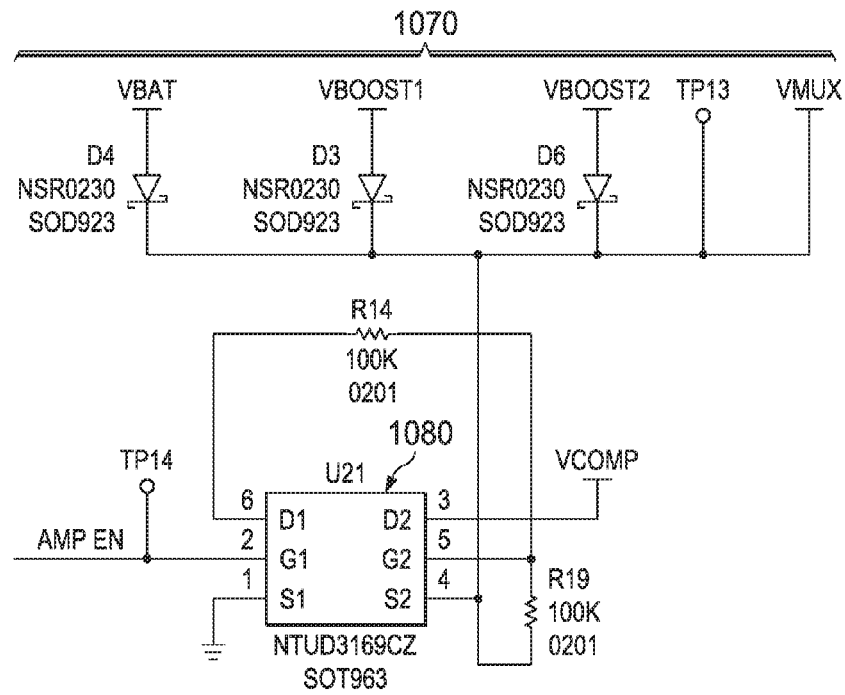

Referring now to FIG. 22C, a circuit 1070 is used to connect VBAT, or VBOOST1, or VBOOST2 to VCOMP (i.e., the compliance voltage or power supply for the load 1030). In more detail, the circuit 1070 includes diodes D4, D3, and D6. These diodes D4, D3 and D6 serve as an analog OR switch, so that the highest of the three signals VBAT, VBOOST1, and VBOOST2 is allowed to transmit through to the VMUX line. As such, if VBOOST1 and VBOOST2 are not enabled, then only VBAT comes through, as VBAT is the smallest voltage of the three. VBAT is used in situations where the stimulation driver only needs to generate a stimulation pulse smaller than about 4 volts (i.e., stimulation pulse<=VBAT). If VBOOST1 is on but VBOOST2 is off, then VBOOST1 gets connected to VMUX. Since VBOOST1 is approximately 2×VBAT, this is used in situations where the stimulation driver needs to generate a stimulation pulse greater than about 4 volts but less than about 8 volts (i.e., VBAT<stimulation pulse<=2×VBAT).

If VBOOST2 is on, then VBOOST2 gets connected to VMUX. Since VBOOST2 is approximately 3×VBAT, this is used in situations where the stimulation driver does not need to generate a stimulation pulse greater than about 8 volts but less than about 12 volts (i.e., 2×VBAT<stimulation pulse<=3×VBAT).

The circuit 1070 also includes a switch 1080. The switch 1080 is controlled by a control signal AMP EN from the microcontroller 400. When AMP EN is high, the switch 1080 connects VMUX to VCOMP, thereby allowing one of the three supply voltages (VBAT, VBOOST1, or VBOOST2) to power the stimulation driver or other components in the load 1030.

It is understood that a circuit similar to the circuit 1070 may be utilized to handle the selection of VBAT and VBOOST if the charge pump 1000 is used. It is also understood that the specific capacitor and resistor values illustrated in FIGS. 22A-22C are mere examples and are not intended to limit the scope of the present disclosure. Other values may be used to implement alternative embodiments.

Figure 23:
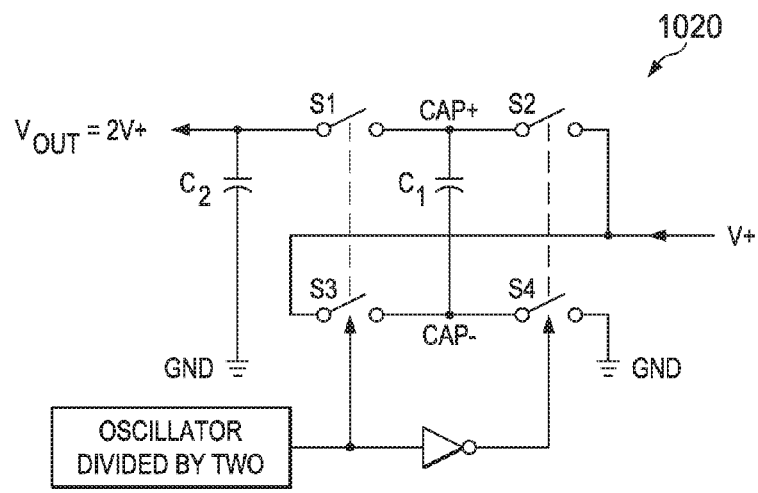
FIG. 23 is a circuit schematic of a charge pump chip according to an embodiment of the present disclosure.

Referring now to FIG. 23, a simplified circuit schematic of the charge pump chip 1020 is illustrated. In the illustrated embodiment, the charge pump chip 1020 is implemented as the LM2767 Switched Capacitor Voltage Converter from Texas Instruments®, the data sheet of which is published at www.ti.com. The content of the data sheet is incorporated herein by reference in its entirety. It is understood that in the embodiment shown in FIG. 22B, the LM2765 chip from Texas Instruments® may be used to implement the charge pump chip 1060. For reasons of simplicity, however, the circuit schematic of the LM2765 chip is not illustrated herein, but its data sheet (published as www.ti.com) is also incorporated by reference herein in its entirety).

As discussed above, conventional charge pumps that are used to scale up input voltages typically scale up the input voltage in integer multiples. If those charge pumps are used herein, the scaled-up voltage (i.e., the compliance voltage) would be 2×VBAT, 3×VBAT, etc, but not in between. This leads to power waste, since compliance voltage is dictated by the amplitude of the stimulation pulse, which could fall within any of the integer multiples of the battery voltage VBAT.

In comparison, the charge pump 1000 (or the charge pump 1050) discussed above allows its output voltage VBOOST (or output voltages VBOOST1 or VBOOST2 in the case of the charge pump 1050) to be dynamically adjusted depending on the amplitude requirements of the stimulation pulse. Therefore, it is theoretically possible to change VBOOST (or VBOOST1 or VBOOST2) from pulse-to-pulse if the pulses themselves have varying amplitudes pulse-to-pulse. In most commercially available neurostimulators, however, the pulse amplitudes may remain constant for at least the same stimulation session. Even for these cases, the charge pump 1000 (or the charge pump 1050) can still provide a VBOOST (or output voltages VBOOST1 or VBOOST2 in the case of the charge pump 1050) that is specifically configured for the amplitude of the stimulation pulses throughout a particular session. As this VBOOST (or VBOOST1 or VBOOST2) may be a fraction of the input voltage VBAT, neurostimulators with conventional charge pump architectures may not be able to achieve the finely-tuned VBOOST (or VBOOST1 or VBOOST2) voltage, thereby wasting power by providing a compliance voltage that may be too high for the stimulation pulses.

To better illustrate the various concepts of the charge pumps discussed above, FIG. 24 illustrates a simplified timing graph 1100 for the waveforms of the various signals associated with the charge pump 1000 discussed above. In more detail, the timing graph 1100 includes the waveforms for the control signal VBOOST_EN, the output voltage of the charge pump 1000 (i.e., the output of the charge pump chip 1020) VBOOST, and the stimulation pulse voltage STIM OUT. To clarify, STIM OUT is the voltage signal that has been amplified by the stimulation driver 450, not the stimulation pulse coming out of the DAC of the microcontroller 400. These signals VBOOST_EN, VBOOST, and STIM OUT are each illustrated as a plot of an Y-axis against and X-axis, where the X-axis corresponds to time, and the Y-axis corresponds to voltage.

The control signal VBOOST_EN is enabled (i.e., goes high) before the start of the stimulation pulse. As discussed above, VBOOST_EN turns on the charge pump chip 1020, and the output capacitor C30 is being charged up a little bit by the capacitors C29 and C31 for each clock cycle (the clock for the charge pump chip 1020 is not illustrated herein for reasons of simplicity). As such, as long as the charge pump chip 1020 is turned on (i.e., for the duration in which VBOOST_EN is high), VBOOST increases steadily until it reaches its maximum capacity (e.g., 2×VBAT or 3×VBAT).

Figure 24:
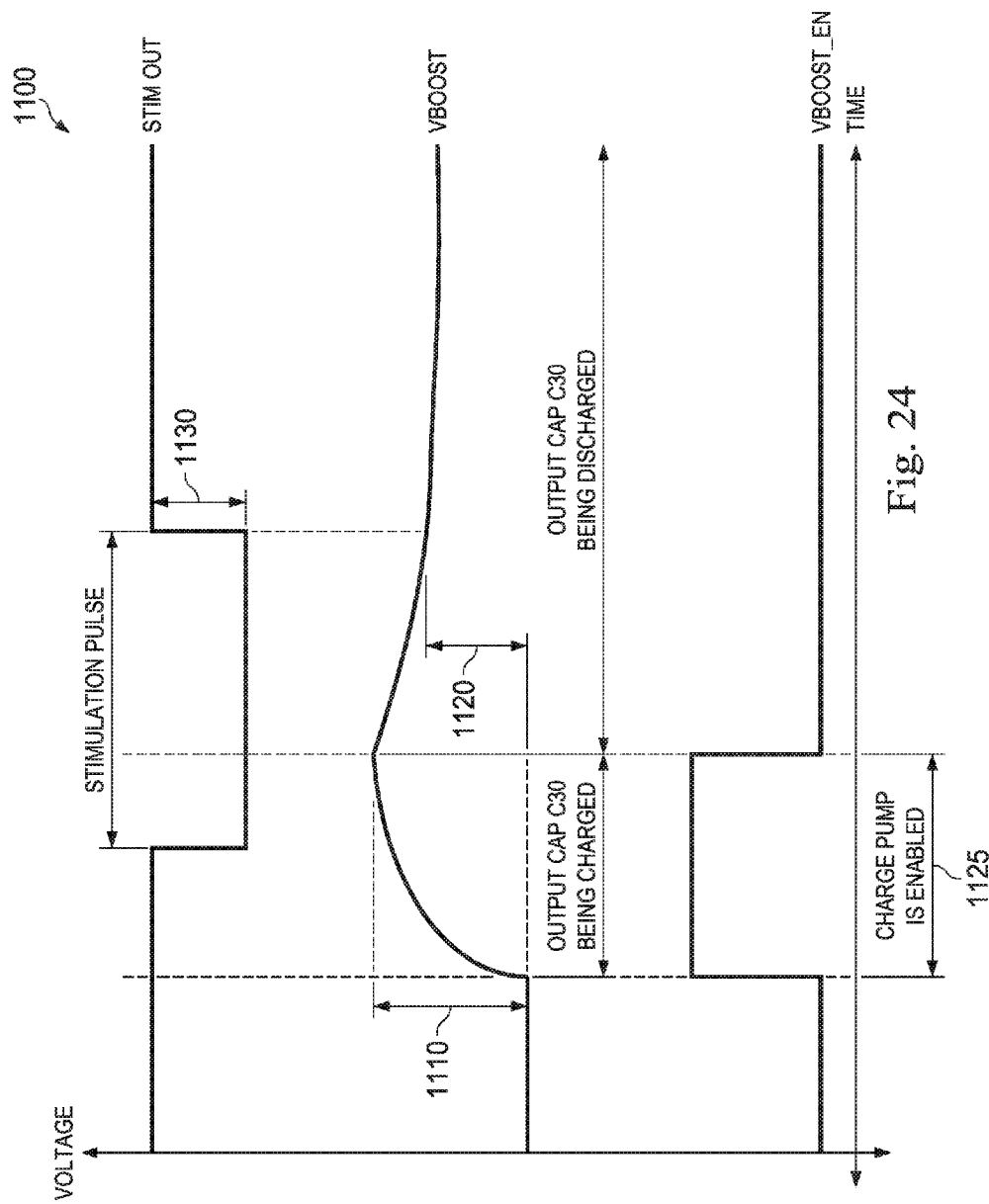
FIGS. 24-26 illustrate various simplified timing graphs for signal waveforms associated with the voltage up-converter of FIGS. 22A-22C according to embodiments of the present disclosure.

In the illustrated embodiment, VBOOST reaches a voltage 1110 when VBOOST_EN is disabled, at which point in time the charge pump chip 1020 is turned off, and VBOOST begins to drop due to the load 1030 being connected to the output of the charge pump 1000. The load 1030 is connected because the stimulation driver 450 (as a part of the load 1030) is amplifying the stimulation pulse outputted by the DAC. During this stimulation pulse (represented by the STIM OUT waveform), the charge pump 1000 has to supply a sufficiently high VBOOST as the voltage rail for the stimulation driver 450. As shown in FIG. 24, VBOOST drops to a voltage 1120 at the end of the stimulation pulse.

This graph 1100 illustrate clearly that the output voltage VBOOST of the charge pump 1000 is a function of the amount of time that it is enabled, for example as a function of the amount of time that the VBOOST_EN signal (coming out of the microcontroller 400) is enabled. One of the unique aspects of the charge pump 1000 of the present disclosure is that, the microcontroller 400 is configured to precisely control the amount of time that VBOOST_EN is enabled in order to produce an output voltage VBOOST for the charge pump 1000 that is tailored to the amplitude of the stimulation pulse.

Using this graph 1100 as an example, suppose that the stimulation pulse STIM OUT is programmed to have a voltage amplitude of 5 volts, as represented by a voltage 1130 in FIG. 24. An optimized compliance voltage in this case may be either at 5 volts or slightly exceeds 5 volts to give it a little bit of head room. The head room may be predetermined, for example it may be about 100 mV in some embodiments, in which case the optimized VBOOST may be about 5.1 volts. As shown in FIG. 24, the optimized voltage for VBOOST is represented by the voltage 1120. This optimized VBOOST provides enough voltage for the circuits (e.g., op-amps) in the stimulation driver 450, and does so without wasting power. In comparison, a conventional voltage doubler (2×VBAT=8 volts) would have wasted about 2.9 volts (8−5.1=2.9) of power.

Knowing that a 5-volt or a 5.1-volt VBOOST is desired and thus needs to be generated by the charge pump 1000, the microcontroller 400 calculates an amount of time 1125 that the charge pump chip 1020 needs to be turned on (or the amount of time that VBOOST_EN needs to remain high). In certain embodiments, the calculation for the amount of time 1125 may also take into account of the voltage drop of VBOOST after the charge pump chip 1020 is disabled. In other words, VBOOST_EN needs to be enabled long enough such that VBOOST reaches voltage 1110 that is adequately high, so that when it discharges over the rest of the stimulation pulse, it will not dip below the voltage 1120, which is the optimized VBOOST voltage.

As an example, suppose that the voltage 1120 is 5.1 volts, and it has been determined that the voltage drop for the rest of the stimulation pulse is about 0.5 volts, then the voltage 1110 is 5.6 volts (5.1+0.5=5.6). Again, conventional charge pumps or voltage doublers cannot produce 5.6 volts in this case, as the input voltage VBAT is 4 volts. 5.6 volts would be a fraction (or a decimal) of the input voltage VBAT (1.4×VBAT in this case). The charge pump 1000 herein can produce this voltage (or very close to it, depending on the resolution of VBOOST), and therefore the charge pump 1000 reduces power waste during the amplification of the stimulation pulses.

It is understood that the charge pump chip 1020 is not simply left turned on for the entire duration of the stimulation pulse STIM OUT, which is evidenced by VBOOST_EN going low before the stimulation pulse STIM OUT is over. The reason is that simply leaving the charge pump chip 1020 turned on during the entire stimulation pulse would likely create an output voltage VBOOST that is too high, since the capacitor C30 will continue to be charged up as a function of time. Again, an unnecessarily high VBOOST will not prevent the stimulation driver 450 from working properly, but it will lead to power waste in a manner similar to conventional neurostimulators. In other words, a compliance voltage that is greater than needed would have been generated if VBOOST_EN is enabled for the duration of the stimulation pulse.

Figure 25:
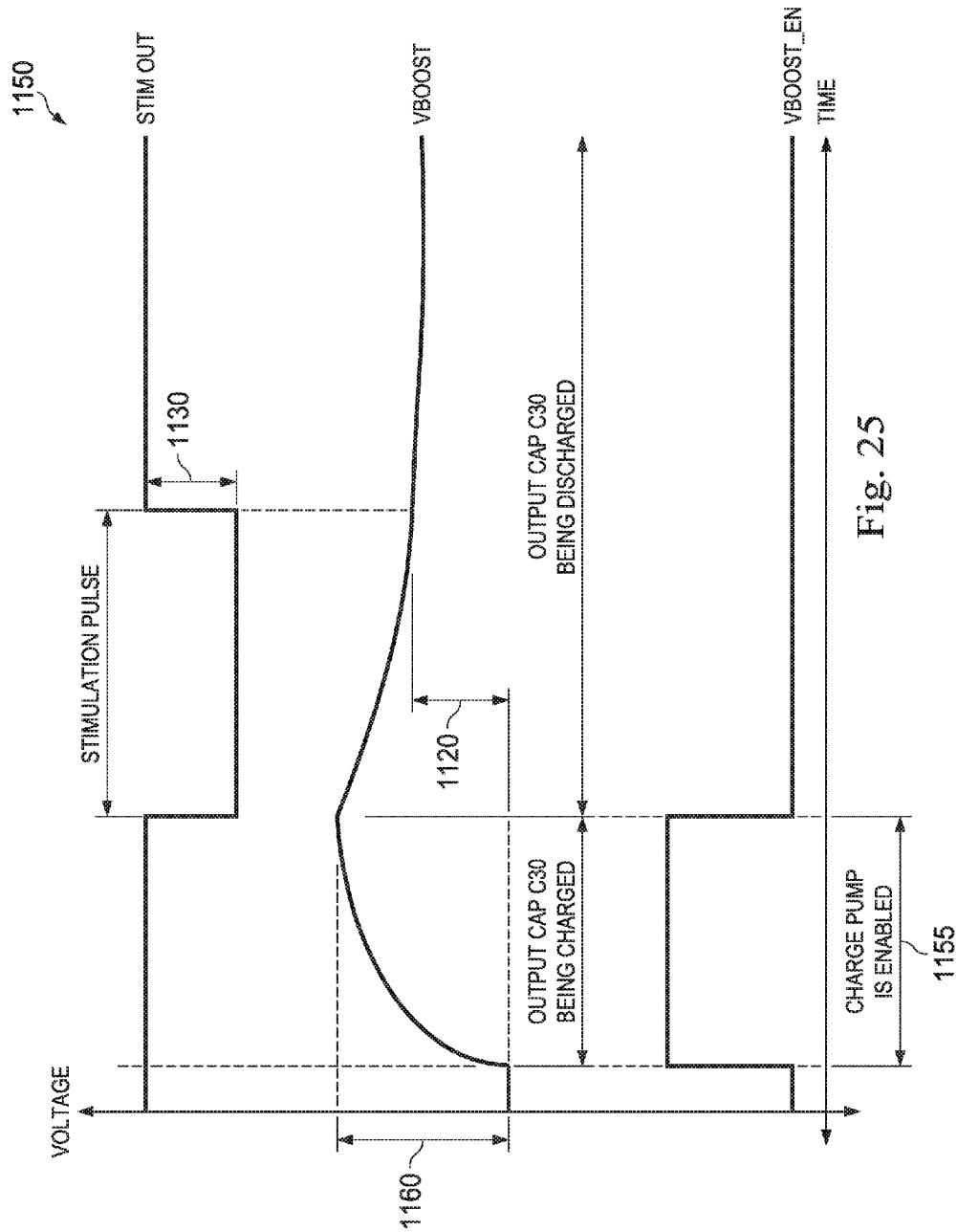

FIG. 25 illustrates a simplified timing graph 1150 for the waveforms of the various signals associated with the charge pump 1000 discussed above according to an alternative embodiment. For reasons of simplicity, the same signals and voltages appearing in both FIGS. 24 and 25 will be labeled the same.

As is shown in FIG. 25, the charge pump chip 1020 is turned on (VBOOST_EN is enabled) to charge up the output voltage VBOOST before the stimulation pulse is generated and turned off at the start of the stimulation pulse. The charge pump chip 1020 remains turned on for an amount of time 1155 that may be longer than the amount of time 1125 shown in FIG. 24. This may be due to the fact that the output voltage VBOOST needs to be charged to a greater voltage 1160 to ensure that it will still remain at or above the voltage 1120 (i.e., the optimized compliance voltage) throughout the stimulation pulse. Stated differently, the fact that the charge pump chip 1020 is turned off at the start of the stimulation pulse leads to a longer discharge period for the output capacitor C30, and therefore VBOOST needs to be charged up to a greater voltage 1160 (greater than the voltage 1110 of FIG. 24) to account for the voltage droop due to the longer discharge period.

Again, the voltage 1160 may still be a fraction (greater than 1) of the input voltage VBAT, and therefore neurostimulators with conventional charge pumps or voltage doublers cannot achieve this voltage. In comparison, the charge pump 1000 of the present disclosure can achieve a voltage close to the voltage 1160 via carefully configuring the amount of time the charge pump chip 1020 is enabled, thereby reducing waste of power in providing the compliance voltage for stimulation pulses.

Figure 26:
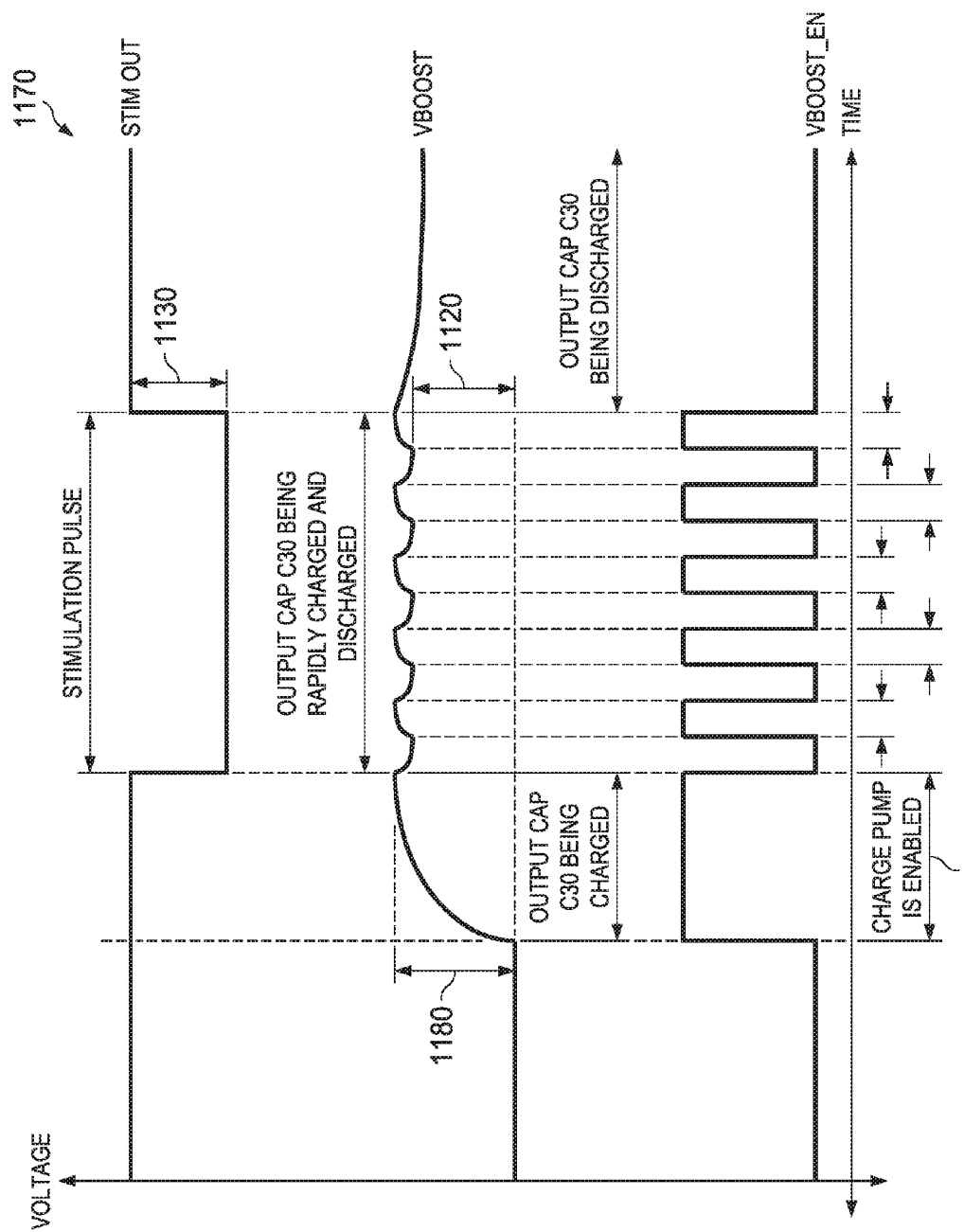

FIG. 26 illustrates a simplified timing graph 1170 for the waveforms of the various signals associated with the charge pump 1000 discussed above according to yet an alternative embodiment. For reasons of simplicity, the same signals and voltages appearing in FIGS. 25-26 will be labeled the same.

As is shown in FIG. 26, the charge pump chip 1020 is turned on (VBOOST_EN is enabled) to charge up the output voltage VBOOST before the stimulation pulse. Throughout the stimulation pulse, the charge pump chip 1020 may be rapidly turned on and off by rapidly enabling and disabling the VBOOST_EN line. When the charge pump chip 1020 is enabled, the output capacitor C30 is charged up a little bit, as evidenced by the output voltage VBOOST going up. When the charge pump chip 1020 is disabled, the output capacitor C30 is discharged by the load 1030 a little bit, as evidenced by the output voltage VBOOST going down. However, the enabling and disabling of the VBOOST_EN line is configured such that the output voltage VBOOST does not dip below the voltage 1120, which as discussed above is the optimized compliance voltage for minimizing power consumption waste.

In addition, it is understood that the output capacitor C30 may be charged up faster than it can be discharged, or vice versa. Thus, the amount of time that the charge pump chip 1020 is turned on does not necessarily have to be equal to the amount of time that the charge pump chip 1020 is turned off. In other words, the VBOOST_EN line may be enabled longer than it is disabled during the stimulation pulse, or vice versa, and FIG. 26 does not intend to portray these amounts of time in scale.

It is also understood that the amount of time 1175 that charge pump chip 1020 is turned on may be shorter than the amount of time 1125 shown in FIG. 24. This is because the output voltage VBOOST in this embodiment only needs to be charged to a voltage 1180 that does not need to be as high as the voltage 1110 to ensure that it will still remain at or above the voltage 1120 (i.e., the optimized compliance voltage) throughout the stimulation pulse. Stated differently, the fact that the charge pump chip 1020 is periodically charged during the stimulation pulse allows it to have a lower initial voltage 1180, which is still greater than the voltage 1120, but not necessarily by much.

Again, the voltage 1180 may still be a fraction (greater than 1) of the input voltage VBAT, and therefore neurostimulators with conventional charge pumps or voltage doublers cannot achieve this voltage. In comparison, the charge pump 1000 of the present disclosure can achieve a voltage close to the voltage 1180 via carefully configuring the amount of time the charge pump chip 1020 is enabled, thereby reducing waste of power in providing the compliance voltage for stimulation pulses.

It is understood that FIGS. 24-26 merely illustrate various example embodiments of controlling the amount of time that the charging pump chip 1020 is enabled in order to produce the desired output voltage as a fraction of the input voltage. However, the concepts of the present disclosure are not limited to the embodiments shown in FIGS. 24-26, and that alternative embodiments may control the timing of the signals such as VBOOST_EN differently without departing from the spirit and scope of the present disclosure.

It is also understood that the graphs or waveforms similar to those shown in FIGS. 24-26 may be produced for the charge pump 1050 as well, to illustrate the capability of the charge pump 1050 to product a voltage that is a fraction of its input voltage. However, for reasons of simplicity, these graphs or waveforms are not specifically illustrated herein.

Figure 27:
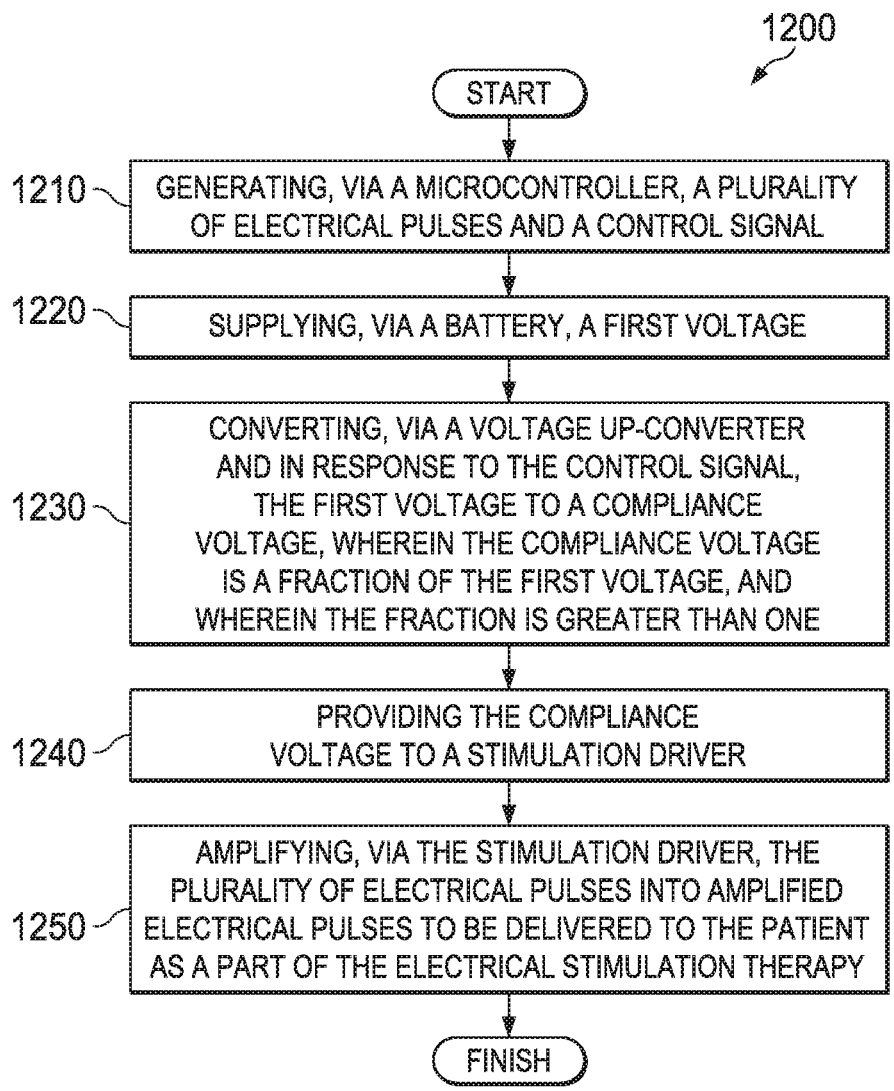
FIG. 27 is a simplified flowchart illustrating a method of providing electrical stimulation therapy for a patient according to an embodiment of the present disclosure.

FIG. 27 is a simplified flowchart of a method 1200 of providing an electrical stimulation therapy for a patient according to an embodiment of the present disclosure. The method 1200 includes a step 1210 of generating, via a microcontroller, a plurality of electrical pulses and a control signal. In some embodiments, the microcontroller is the microcontroller 400 of FIG. 7, the electrical pulses include the analog waveforms outputted by the DAC onboard the microcontroller 400 of FIG. 7, and the control signal includes the VBOOST_EN signal.

The method 1200 includes a step 1220 of supplying, via a battery, a first voltage. In some embodiments, the battery is the battery 340 of FIG. 7, and the first voltage is the output voltage of the battery 340.

The method 1200 includes a step 1230 of converting, via a voltage up-converter and in response to the control signal, the first voltage to a compliance voltage. The compliance voltage is a fraction of the first voltage, and wherein the fraction is greater than 1. In some embodiments, the voltage up-converter is the voltage up-converter 370 of FIG. 7. In some embodiments, the voltage up-converter includes the charge pump 1000 of FIG. 22. In some embodiments, the compliance voltage is the voltage supply or voltage rail for the stimulation driver 450 of FIG. 7. In some embodiments, the converting of step 1230 comprises dynamically adjusting the compliance voltage pulse-to-pulse in response to respective amplitudes of the electrical pulses. In some embodiments, the converting of step 1230 comprises rapidly enabling and disabling the voltage up-converter during the stimulation pulses.

The method 1200 includes a step 1240 of providing the compliance voltage to a stimulation driver. In some embodiments, the stimulation driver is the stimulation driver 450 of FIG. 7. In some embodiments, the step 1240 also comprises providing the compliance voltage to the multiplexers 460 of FIG. 7.

The method 1200 includes a step 1250 of amplifying, via the stimulation driver, the plurality of electrical pulses into amplified electrical pulses to be delivered to the patient as a part of the electrical stimulation therapy.

It is understood that the steps 1210-1250 need not necessarily be performed according to the sequence shown in FIG. 27. In various embodiments, some of these steps may be performed concurrently, or in an order different from what is shown in FIG. 27. It is also understood that additional process steps may be performed before, during, or after the steps 1210-1250. For example, in some embodiments, the method 1200 further includes a step of controlling, via the control signal, an amount of time the voltage up-converter is turned on or off. The fraction is a function of the amount of time that the voltage up-converter is turned on. In some embodiments, the controlling the amount of time the voltage up-converter is turned on such that the compliance voltage exceeds an amplitude of the electrical pulse by at least a predefined headroom voltage. In some embodiments, the controlling the amount of time the voltage up-converter is turned on such that the compliance voltage exceeds an amplitude of the electrical pulse by at least a second voltage, the second voltage being a function of a load of the voltage up-converter. For reasons of simplicity, other additional steps are not discussed herein.

System and Method for Improving Nerve Finding for Peripheral Nerve Stimulation In peripheral nerve stimulation, finding the location of the targeted nerve can be challenging when attempting to implant the therapeutic electrodes. Several techniques are typically employed, including surgical exploration, ultrasonic guidance, fluoroscopic imaging, and electrical nerve mapping. Electrical nerve mapping employs a stimulating needle that is introduced into the tissue while stimulating current or voltage is delivered from the tip of the needle at a low repetition frequency (e.g. 2 Hz). When proximal to the targeted nerve, the stimulation current will activate the motor efferent fibers and some part of the distal tissue will 'twitch' in response, following the stimulation in an expected and observable/detectable manner.

However, electrical nerve mapping is not always simple Many minutes can be spent seeking the nerve without success as the technique can be relatively "blind" as the nerve depth is not often known and anatomic variability from patient to patient can result in nerve locations, and/or specific nerve target sites, that are unexpected to the implanters. Additionally, once the nerve is found, gross motor stimulation may not be predictive of the precise location of the desired fascicles within the nerve which innervate the painful area of the patient. However, it is understood that pain therapy is used herein merely to provide an example and does not limit the concepts of the present disclosure.

According to various embodiments, there are provided systems, devices, and methods that can improve the likelihood and speed of finding a particular nerve and region of the nerve for which therapeutic stimulation will be best targeted for the patient, as discussed in more detail below with reference to FIGS. 28-31.

Figure 28:
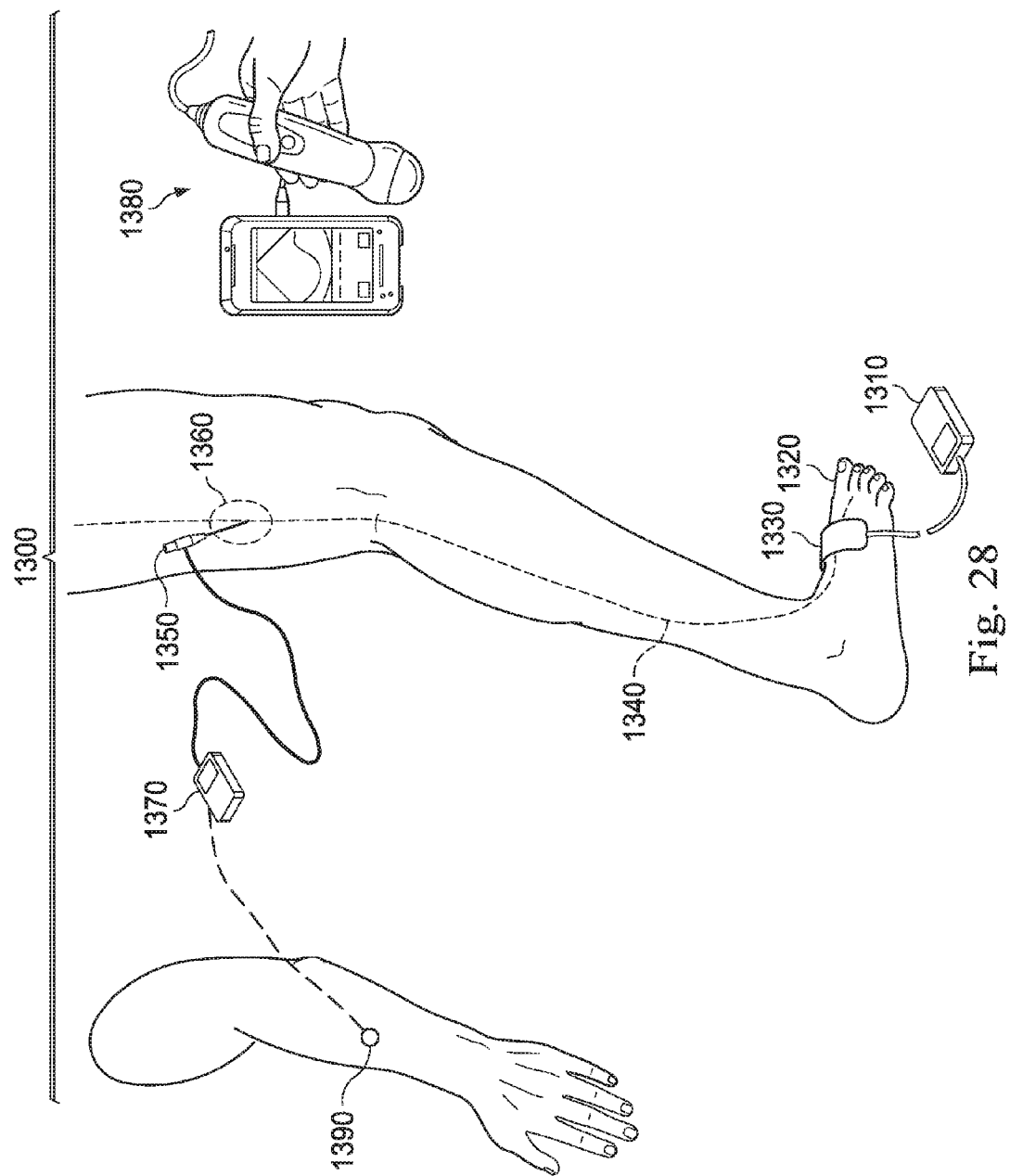
FIGS. 28-30 illustrate a medical system (or parts thereof) for finding a target nerve site for applying stimulation according to embodiments of the present disclosure.

Referring now to FIG. 28, a simplified medical system 1300 is illustrated according to an embodiment of the present disclosure. The medical system 1300 is configured to find the target location (e.g., a particular fascicle) of a peripheral nerve to apply a stimulation therapy such as electrical stimulation therapy to treat pain. The medical system 1300 includes a stimulus generator, such as an external pulse stimulator (EPG) 1310 (hereinafter referred to interchangeably). Similar to the IPG (e.g., the PNS device 200) discussed above, the EPG 1310 may include electrical circuitry configured to generate electrical pulses, which can be applied transcutaneously or percutaneously to a body region of a patient as a part of a stimulation therapy for the patient. In some embodiments, the therapy for the patient may be relief from chronic pain. In some embodiments, the therapy for the patient may be an increase in peripheral blood flow. In yet other embodiments, the therapy for the patient may be neuromuscular rehabilitation, needed for post-stroke rehabilitation. In yet other embodiments, the therapy for the patient may be incontinence associated with pelvic floor disorders.

In the illustrated embodiment, a foot 1320 is used as an example of the body region of the patient that needs the stimulation therapy. Therefore, a transcutaneous electrical nerve stimulating patch 1330 is adhered to the foot 1320, for example near or at the center of the region where the patient therapy is desired (e.g., where the pain is the most intense). The patch 1330 is electrically coupled to the EPG 1310 and delivers the electrical pulses generated by the EPG 1310 to the foot 1320 at a relatively low frequency (e.g., a few Hz or tens of Hz), for example via one or more electrodes on the patch 1330. In some embodiments, a measurement electrode (not illustrated herein for reasons of simplicity) is also positioned within the targeted region of therapy (e.g., the foot 1320), which can be incorporated into the stimulus generator or separately on a skin adhering electrode or subcutaneous electrode.

It is understood that although an electrical-pulse generating EPG 1310 is used herein as an example for providing a stimulus to a body region of the patient as part of a patient therapy, other stimulus generators in alternative embodiments may be implemented differently. For example, in some embodiments, the stimulus may be mechanical, which may be administered using a vibrator positioned within the targeted region of therapy.

Referring back to FIG. 28, the foot 1320 contains a portion of an elongate nerve 1340. The nerve 1340 in this example is the sciatic nerve, which runs distally (after being formed from spinal nerves of the patient's [not illustrated]), through the patient's leg, and segments of which terminate within the patient's foot 1320. The stimulation therapy applied by the EPG 1310 is targeted to the portion of the nerve 1340 that resides within the foot 1320. In response to this stimulation therapy, the electrical signals or impulses are generated and travel up the nerve 1340 back to the spine. In some embodiments, these electrical signals may be measured as action potentials.

A nerve-seeking needle 1350 (also referred to as a sensing needle) is introduced in another body region 1360 that contains a different portion of the nerve 1340. The body region 1360 is a region of the body (thigh in the illustrated embodiment) where implantations of an electrode-containing lead and an IPG are desired. In other words, the body region 1360 is chosen, based on general medical knowledge, as the implantation site for an IPG (such as the PNS device 200) and a lead for delivering the stimulation pulses generated by the IPG to the patient, in order to treat the pain in the foot 1320.

Based on the Gate Control Theory (the primary theoretical basis for the pain-relieving mechanism of electrical nerve stimulation), it is suggested that activation of large-diameter, heavily-myelinated afferents that innervate a particular painful region of the body (e.g., the foot 1320 in the illustrated embodiment) will relieve pain in that body area, because those large afferents increase the activity of inhibitory interneurons in the dorsal horn of the spinal cord segment. That same spinal cord segment is generally believed to be the site where hyperactive, pain-projecting neurons exist (either driven by small diameter fibers from the painful body region, or simply hyperactive due to a prolonged state of central sensitization). Clinically, a key technical requirement for efficacious pain relief from electrical stimulation has been that the stimulation must generate paresthesia in the painful region for the stimulation to be effective. In other words, if the paresthesia doesn't cover the area of pain, it is unlikely to be effective. Therefore, when implanting peripheral nerve stimulation electrodes, it is important to place the electrodes near the large myelinated afferent fibers that innervate the painful regions (e.g., the foot 1320 in the illustrated embodiment).

In this case, the large myelinated afferent fibers on the sciatic nerve 1340 may be accessed by inserting the seeking needle 1350 in the body region 1360 to engage (e.g., measure activity of the nerve due to close proximity) with different fascicles of the portion of the nerve 1340 in the body region 1360. The seeking needle 1350 receives or detects action potentials, such as a compound action potential (CAP), in response to the stimulation delivered to the portion of the nerve 1340 in the foot 1320 by the EPG 1310. A medical professional may operate the seeking needle 1350 to engage different parts of the portion of the nerve 1340 (e.g., different fascicles) located in the body region 1360, and different action potentials may be generated and detected by the seeking needle 1350 as a result. These action potentials may be different from one another in terms of their amplitude, shape, timing relative to the stimulation delivered to the portion of the nerve 1340, etc.

The seeking needle 1350 is electrically coupled to a measurement instrument 1370, for example through a physical wire or through a wireless connection. The seeking needle 1350 receives the action potentials and sends the action potentials to the measurement instrument 1370, which is configured to measure, display, and/or analyze electrical signals, including the action potentials. In some embodiments, the measurement instrument 1370 includes an oscilloscope. Such oscilloscope may be configured to have a predetermined amount of gain and a predetermined bandwidth designed to capture and display the action potentials. In some embodiments, the measurement instrument 1370 includes a dedicated monitor or visual display component. In other embodiments, the measurement instrument 1370 may have a separate monitor or display component. The measurement instrument 1370 may also have a suitable user interface for accepting input from a user and for communicating an output to a user. The user interface may include a touchscreen graphical user interface, a keyboard, a mouse, speakers, etc. In some embodiments, the measurement instrument may include a transducer and a capacitively-coupled amplifier connected to a speaker, so that the action potentials may be transduced and communicated to a user in the form of audio energy. In various embodiments, the measurement instrument 1370 may be one standalone piece of equipment (which may include several components integrated together), or it may include a plurality of pieces of equipment. Via the measurement instrument 1370, the medical professional may obtain a visual or audible representation of the action potentials detected by the needle 1350.

The system 1300 may also include a visual guidance device 1380. The visual guidance device 1380 may include one or more ultrasound devices in some embodiments, or other types of medical imaging devices in other embodiments. Using techniques such as ultrasound imaging, the visual guidance device 1380 provides crude visual guidance for a medical professional who may be inserting the seeking needle 1350 into the body region 1360 to engage with different parts of the nerve 1340 in that region.

The system 1300 may also include an indifferent electrode 1390 that is electrically coupled to the measurement instrument 1370 but is positioned transcutaneously or subcutaneously away from the nerve 1340 and away from the body regions (e.g., the foot and the leg in this example) within which the nerve 1340 is contained. In some embodiments, the indifferent electrode 1390 is placed at least several tens of centimeters away from the target nerve and the body regions containing the target nerve. In the illustrated embodiment, the indifferent electrode 1390 is placed on or inside an arm of the patient. The indifferent electrode 1390 is used as a reference for the measurement of the action potentials. Generally, electrical measurements such as voltages need a reference for which the measurement is made against. In the context of the medical system 1300, the measurement of the action potentials should be made with respect to a reference that is in a region of the volume conductor (i.e., the patient's body) that is relatively quiet, so that it is generally not susceptible to other forms of electrical noise (e.g., noise generated by neural activity), nor does it generate its own noise that may confound the measurement of action potentials herein.

In the embodiment illustrated in FIG. 28, the region that needs pain treatment is in the foot 1320 (e.g., a right foot), and the stimulation electrodes are to be placed on or near the sciatic nerve 1340. Thus, a suitable place for the placement of the indifferent electrode 1390 is in the skin near the patient's left forearm. The placement of the indifferent electrode 1390 in the left forearm allows it to be placed quite far from both the pain and stimulation sites (right foot and right thigh, respectively). In addition, the indifferent electrode 1390 is also placed far away (e.g., at least several tens of centimeters away) from areas of central conduction (spinal cord, brain), which reasonably assures that nearly no nerve-based artifacts will be measured by the indifferent electrode 1390, which would have otherwise induced a common mode measurement and reduced the signal detection at the nerve-seeking needle 1350. Therefore, the use of the indifferent electrode 1390 allows a "cleaner" and more accurate action potential to be measured by the seeking needle 1350.

According to various aspects of the present disclosure, the measurement and monitoring of the action potentials may be used to determine an optimized site on the nerve 1340 for applying stimulation therapy. In other words, the amplitude of any given action potential may be indicative of the effectiveness of the fascicle that gave rise to the action potential in terms of applying stimulation therapy. In more detail, suppose that an engagement of the seeking needle 1350 with a fascicle A produced 50 micro-volts of action potential in response to the stimulation on the foot 1320 applied by the EPG 1310, while an engagement of the seeking needle 1350 with a different fascicle B produced 100 micro-volts of action potential in response to the same stimulation on the foot 1320. In this example, the fascicle B is more sensitive to the stimulation received by the foot (more specifically, by the portion of the nerve 1340 in the foot 1320), and conversely, the portion of the nerve 1340 in the foot 1320 should be more sensitive to stimulation applied through the fascicle B. This means that the fascicle B is a better conduit (i.e., a more optimized nerve site) for applying stimulation to treat the pain at the foot 1320, Therefore, the measurement instrument 1370 measures and monitors a plurality of different action potentials sent thereto by the seeking needle 1350 over a period of time. Since different fascicles of the nerve 1340 are engaged over this period of time while the same stimulation is applied to the foot 1320 by the EPG 1310, the measurement instrument 1370 receives action potentials of different sizes or amplitudes. In some embodiments, the measurement instrument 1370 may be used to record the highest or greatest action potential (which may be updated continuously throughout this measurement and monitoring process). The measurement instrument 1370 may also allow the user (e.g., the medical professional who is engaging the fascicles via the seeking needle 1350) or an assistant to make notes as to which fascicle gave rise to the greatest action potential. In some embodiments, the measurement instrument 1370 may record a number of candidates for the "greatest" action potential and either allows the user to manually pick what he/she thinks is the best one. In other embodiments, the measurement instrument 1370 may use one or more electronic processors to execute an algorithm or perform an analysis of the action potentials and automatically recommend one as the best candidate. In some embodiments, the measurement instrument 1370 may also run a "moving average" of the captured action potentials. This "moving average" provides feedback to the medical professional as to whether each progressive needle positioning is getting closer to the target fascicle, or possibly farther away. In this manner, the maximum action potential signal during the nerve-seeking process may be tracked and identified.

In some embodiments, the fascicle corresponding to the greatest action potential may be deemed as an optimized site or target location for apply a stimulation therapy to the patient. In the context of the illustrated embodiment, it is deemed that if electrodes of a lead (and the corresponding IPG) are implanted on such fascicle in the region 1360, it will achieve the most effective stimulation results for treating the pain in the foot 1320.

In some embodiments, once the user has found a "best site" of named nerve stimulation, the system 1300 can cease the stimulus from being delivered by the EPG 1310, and the nerve-seeking needle 1350 can then be used to deliver test stimulation pulses with the intent of creating measurable action potentials in the region targeted for therapy. The test stimulation pulses may be generated by the measurement instrument 1370 or by another pulse generator. Again, since the system is "connected" to both the named nerve site and the targeted region for therapy, very small signals can be detected electronically that might otherwise elude the visual or palpable capability of the medical professional implanter or operating room staff.

The approach discussed above of finding the optimized location for implantation of the lead is advantageous over conventional nerve seeking methods, though it is understood that not all advantages of the present disclosure are necessarily discussed herein, and different embodiments may offer other advantages, and that no particular advantage is required for all embodiments. According to conventional nerve seeking methods, the medical professional may be generally aware that a particular nerve may be stimulated to treat symptoms such as pain in a different part of the body. Using the example described above, the medical professional may recognize that, if the sciatic nerve is stimulated in the leg region, it may bring forth pain relief in the foot, since the sciatic nerve runs from the leg to the foot. However, the medical professional does not know what part of the sciatic nerve (e.g., which fascicle) is the optimized location for applying the stimulation.

As a result, the medical professionals typically employ a time-consuming trial and error approach to determine the target nerve site for stimulation. In many cases, the patient is first sedated when a cavity wound is created to implant a lead close to a portion of the sciatic nerve in the leg, or a stimulating needle is inserted to access the portion of the sciatic nerve. Stimulation is then applied through the lead or the needle, and the medical profession attempts to observe a response, such as a twitch, from the foot (i.e., the part of the body that needs the stimulation therapy). However, even if a response from the foot is found, the medical professional cannot know with certainty that the current site on the sciatic nerve really offers a sufficient amount of paresthesia for the patient. Consequently, the patient needs to be woken up to provide confirmation as to the effectiveness of the stimulation. However, the patient may be groggy from being sedated and therefore cannot accurately report the paresthesia location in detail, if at all. In cases where the paresthesia is not sufficient or does not cover the right pain area, the medical professional may have to sedate the patient again, reposition the lead or the stimulating needle, and wake up the patient again for confirmation. This process may need to be repeated a number of times, which can be time-consuming Even then, the optimized location on the nerve for applying stimulation may still not be found. If the optimized stimulation site is not found, the stimulation therapy may not be effective, thereby decreasing patient satisfaction with the stimulation therapy.

In comparison, the embodiments of the present disclosure use action potentials to determine the target site for implantation of the lead. Therefore, patient feedback—such as verbal or tactile feedback that require the patient to be at least somewhat conscious and lucid—is not required herein. In some embodiments, the process discussed above may be performed while the patient is sedated or under general anesthesia. The patient may only need to be woken up at the end (after the optimized nerve site for applying stimulation has been found) to confirm that the stimulation therapy is effective. Therefore, the nerve seeking process of the present disclosure may be performed not only more accurately, but much more quickly, as it relies on using electrical signals (rather than patient's verbal or tactile feedback) to determine the right fascicle for applying stimulation.

Although the system 1300 may be used to perform nerve seeking while the patient is sedated (thus requiring no patient feedback), it is also understood that the patient may also be kept awake in the nerve-seeking process in some embodiments. For example, instead of administering general anesthesia to completely sedate the patient, a local anesthetic may be applied just to the body region 1360 where the seeking needle 1350 is introduced, so as to reduce the discomfort experienced by the patient while the needle 1350 is inserted through the skin and body tissue and thereafter moved around to find the best nerve location. No anesthetic needs to be applied to the foot 1320. In these embodiments, once the target site for stimulation has been selected, and test stimulation is being applied thereto, the patient may continuously or periodically offer verbal feedback or tactile feedback as to the efficacy of the stimulation. In some embodiments, the tactile feedback may be offered via a patient feedback tool described in U.S. patent application Ser. No. 13/973,292, filed on Aug. 22, 2013, entitled "Method and System of Bracketing Stimulation Parameters on Clinician Programmers" to Norbert Kaula, et al., the disclosure of which is hereby incorporated by reference in its entirety. The tactile patient feedback tool allows the patient to provide quick feedback to the medical professional, which is important, as the medical professional may only have a short period of time to ascertain that the lead is placed generally in the right location.

Figure 29:
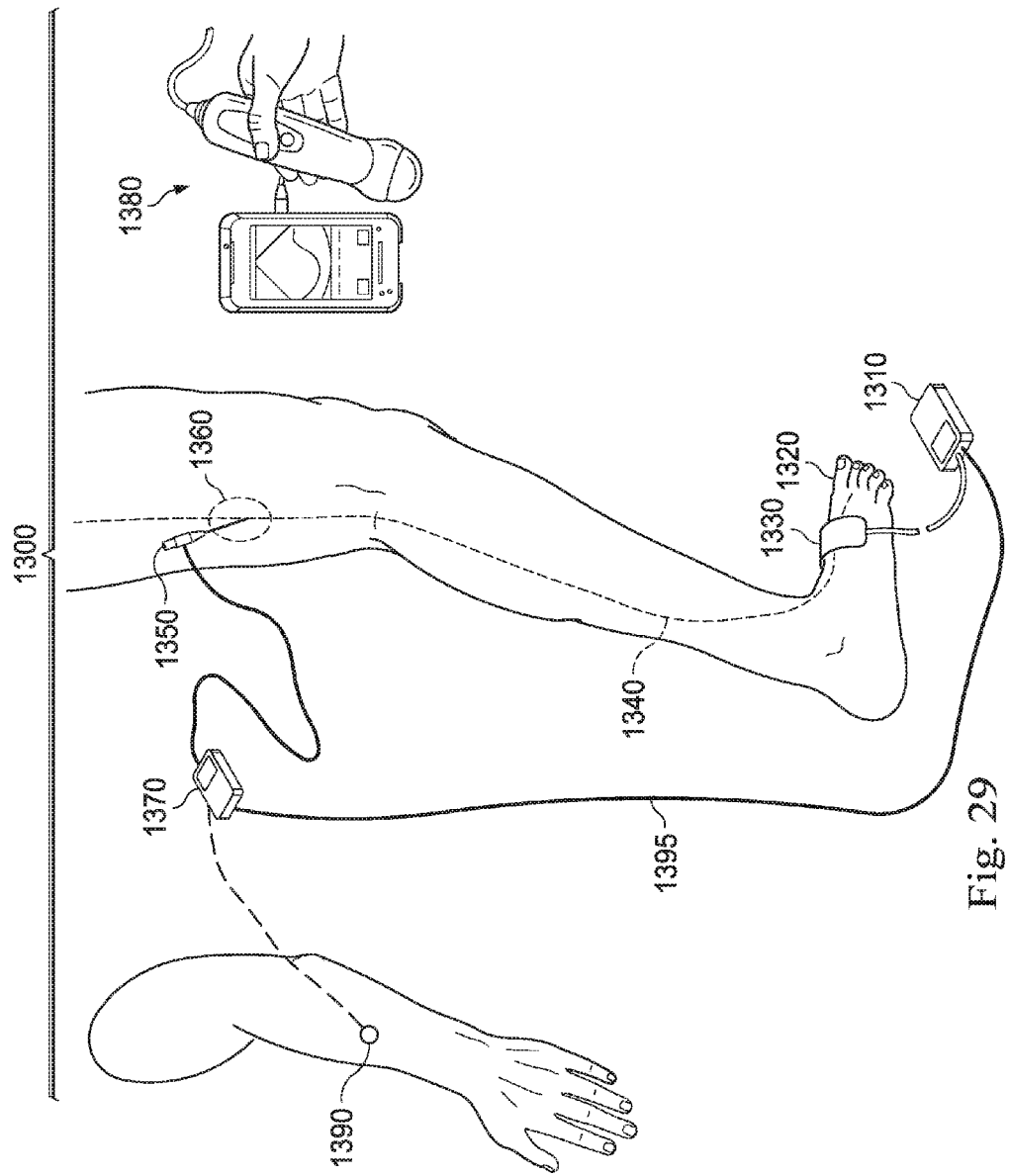
Figure 30:
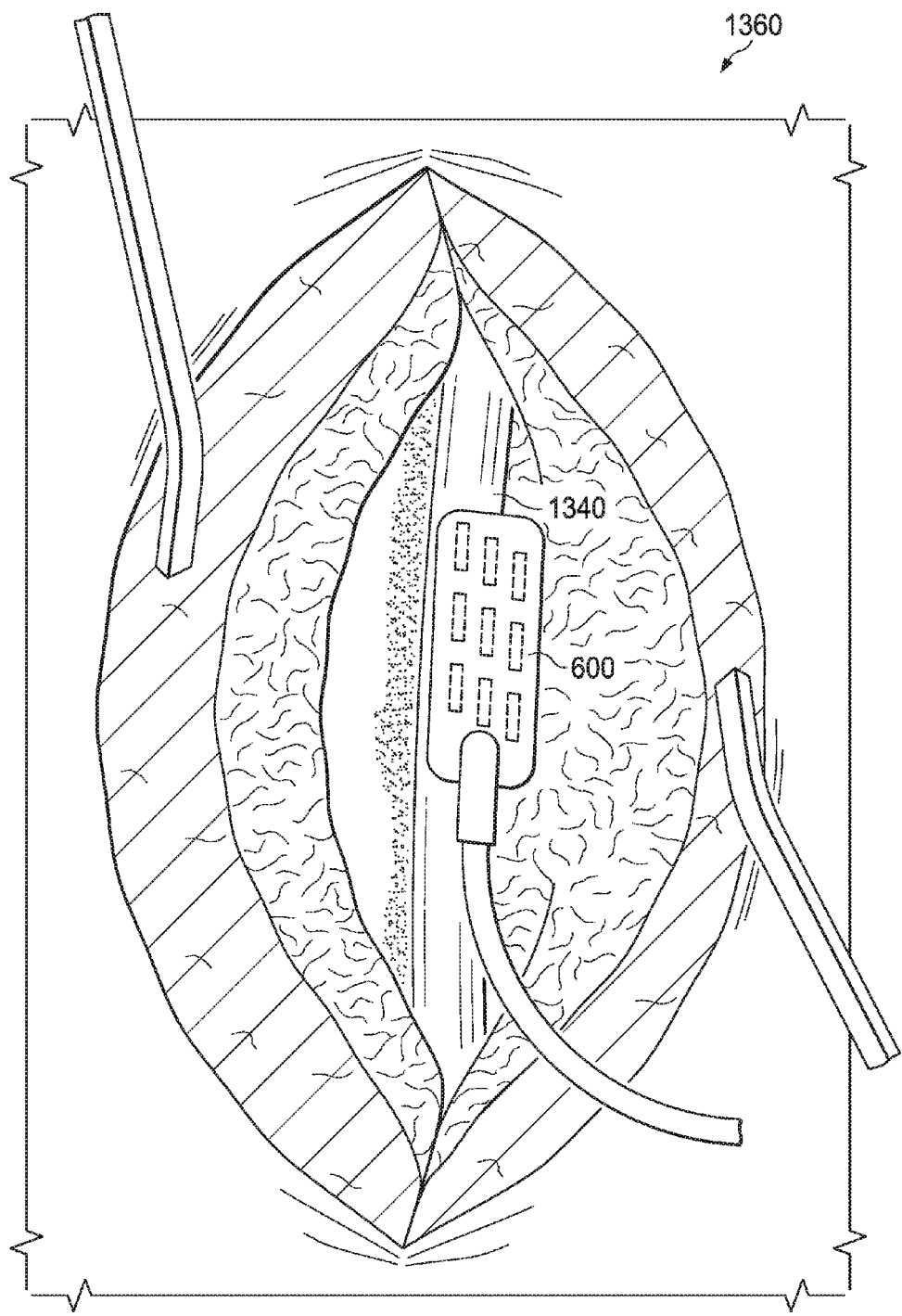

FIG. 29 illustrates an alternative embodiment of the medical system 1300. The alternative embodiment of the medical system 1300 in FIG. 29 is substantially similar to the one illustrated in FIG. 28, with an additional telecommunications link 1395 that is coupled between the EPG 1310 and the measurement instrument 1370. In some embodiments, the telecommunications link 1395 includes a physical wire or another suitable physical connection. In other embodiments, the telecommunications link 1395 may include a wireless connection between the EPG 1310 and the measurement instrument 1370, for example a wireless connection through Wi-Fi, Bluetooth, or MICS, etc.

Communication may be conducted between the EPG 1310 and the measurement instrument 1370 via the telecommunications link 1395. In some embodiments, the EPG 1310 generates a trigger signal and sends the trigger signal to the measurement instrument 1370. The trigger signal may be sent to the measurement instrument 1370 before, or substantially simultaneously with, the application of a pulse to the foot 1320. The trigger signal informs the measurement instrument 1370 that a pulse will be (or is being) applied to the nerve 1340 in the foot 1320, and that the measurement instrument 1370 should be monitoring for a correspondingly generated action potential.

Stated differently, the trigger signal may specify or define a time window inside which the measurement instrument 1370 should look for the action potential. The time window may range from several micro-seconds to several tens of milli-seconds wide. Since the measurement instrument 1370 now "knows" when to "expect" an incoming action potential, it may identify and capture action potential signals with greater accuracy. It may be said that the trigger signal and the stimulus delivered by the EPG 1310 constitute a "correlated activity." Such correlated activity may not otherwise be visually or audibly detectable by the medical professional, but it can be continuously monitored or calculated by the medical system 1300. This improves the medical system 1300's ability to measure and monitor the action potentials.

Regardless of whether the telecommunications link 1395 is used, once a target nerve site (e.g., a particular fascicle) has been identified as the optimized location for applying stimulation therapy, a lead may be implanted on this target nerve site. In some embodiments, once the seeking needle 1350 finds the target nerve site, it remains there. A percutaneous lead with multiple electrode contacts is then threaded through the needle to be placed on the target nerve site. The seeking needle 1350 is then removed without affecting the placement of the percutaneous lead. Thereafter, a pulse generator may be coupled to the percutaneous lead. In the case of a trialing period, an external pulse generator that is located outside the patient's body may be electrically coupled to the percutaneous lead via an extension cable. In the case of a permanent implant, the IPG (e.g., the PNS device 200) may be implanted in the body region 1360 and connected to the percutaneous lead to deliver electrical stimulation to the target nerve site through the electrodes on the percutaneous lead. In embodiments where the percutaneous lead includes a plurality of electrodes, the placement of the percutaneous lead is performed such that a middle electrode or a center electrode on the percutaneous lead is placed right next to the target nerve site. This creates redundancy if the electrodes shift or move in the future.

In some other embodiments, a paddle lead may be used to serve as the nerve seeking tool and as the electrode-containing lead to deliver stimulation once a target nerve site has been confirmed. For example, referring now to FIG. 30, a cavity may be opened up in the body region 1360 to expose the portion of the sciatic nerve 1340 that resides in the body region 1360. A paddle lead may be positioned near or on this portion of the sciatic nerve 1340 to engage with different parts (e.g., different fascicles) of the nerve 1340 while stimulation is applied to the foot 1320 via the EPG 1310. In some embodiments, the paddle lead is implemented as an embodiment of the lead 600 discussed above with reference to FIGS. 10-14, i.e., a paddle lead with staggered electrodes. Through not specifically illustrated herein for reasons of simplicity, it is understood that the paddle lead 600 is also electrically coupled to the measurement instrument 1370 shown in FIG. 28.

Similar to the seeking needle 1350, the paddle lead 600 receives the action potentials as a result of the stimulation applied at the foot 1320 and sends the action potentials to the measurement instrument 1370 for monitoring and analysis. As the paddle lead 600 is moved around to engage with different nerve sites or different fascicles, different action potentials are received and sent to the measurement instrument 1370. Similar to the embodiments in FIGS. 28-29, the measurement instrument 1370 either allows the medical professional to manually choose a best action potential and the corresponding nerve site that gave rise to the action potential, or automatically recommends one to the medical professional. In other words, though a paddle lead 600 is used herein instead of the seeking needle 1350, the target nerve site is determined in a manner that is substantially similar to the embodiments where the seeking needle 1350 is used.

Once the target nerve site is identified, a pulse generator may be coupled to the paddle lead 600 to deliver test stimulation pulses. In some embodiments, the measurement instrument 1370 itself may be configured to supply the test stimulation pulses as well. Again, if the patient was under general anesthesia, he/she may be woken up at this time to confirm the efficacy and coverage of the stimulation therapy applied at this target nerve site. If the patient was only under local anesthesia, he/she does not need to be woken up and may directly provide feedback to the medical professional.

It is understood that the use of a paddle lead as both the nerve-seeking tool and the stimulation-delivering tool does not affect whether or not the telecommunications link 1395 is implemented to send trigger signals to the measurement instrument 1370. In other words, the trigger signal specifying the time window inside which the action potentials should be measured may still be generated in embodiments where the paddle lead is used. Likewise, the indifferent electrode 1390 in FIGS. 28-29 may still be used to establish a "quiet" reference in the measurement of action potentials in embodiments where the paddle lead is used. It is also understood that in some further embodiments, once a target nerve site is found, the medical professional may be able to "mark a spot" for future implantation of a lead. For example, a fluorescent dye may be administered along the length of the seeking needle 1350 and at the tip thereof, such that a subsequent surgical approach to expose the nerve is made simple by providing a pathway toward the target nerve site.

It is understood that the foot, the leg, and the sciatic nerve are used herein to merely provide an example to illustrate the various concepts of the present disclosure and are not intended to be limiting. The concepts of the present disclosure may apply to other nerves or other parts of the body, namely, electrical signals (e.g., action potentials) from the painful body area are used as a "beacon" to guide electrode placement. This allows the patient to be fully sedated in many cases, and allows for the electrode to be positioned in "real time", i.e., while the body area needing treatment is continuously being stimulated, so the stop-and-test approach of conventional nerve-finding methods can be avoided.

Figure 31:
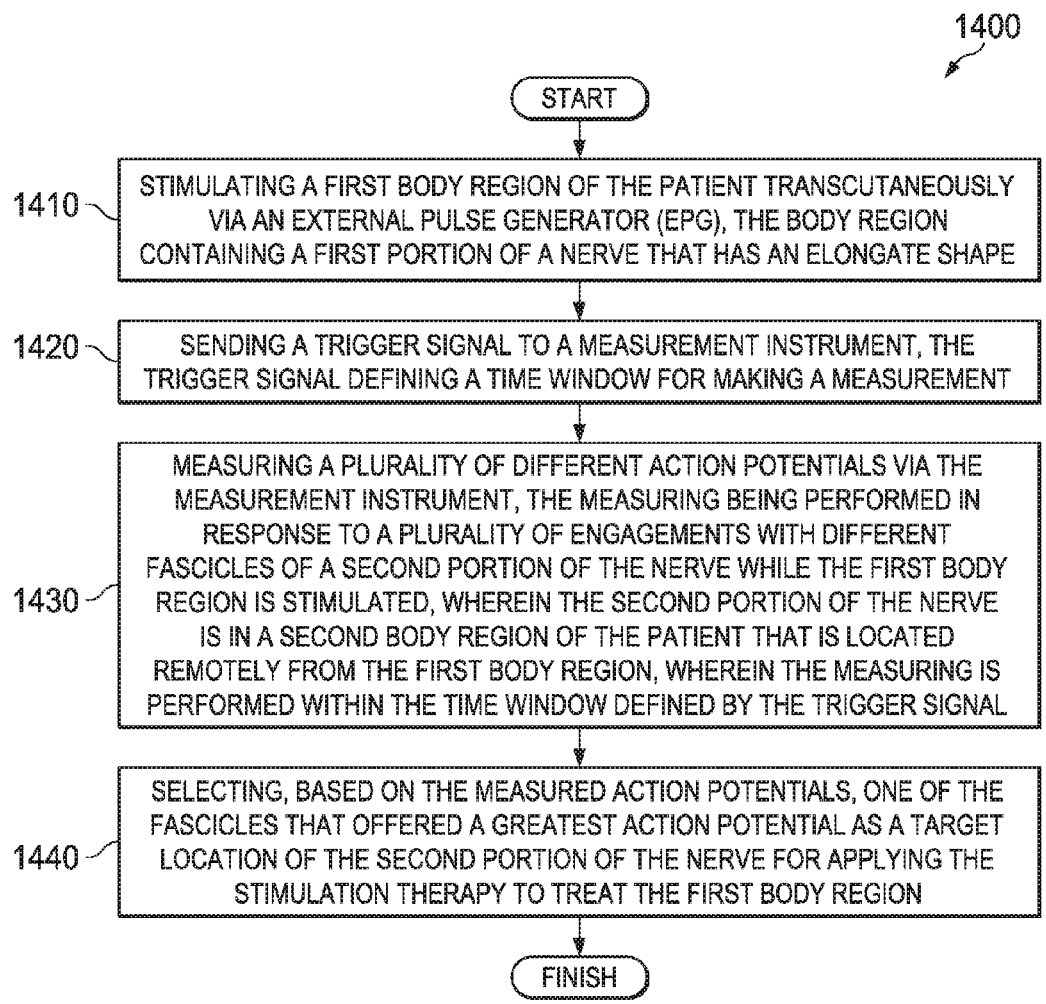
FIG. 31 is a simplified flowchart illustrating a method of identifying a location for applying a stimulation therapy to treat a patient according to an embodiment of the present disclosure.

FIG. 31 is a simplified flowchart of a method 1400 of identifying a location for applying a stimulation therapy to treat a patient according to an embodiment of the present disclosure. The method 1400 includes a step 1410 of stimulating a first body region of the patient transcutaneously via an external pulse generator (EPG). The body region containing a first portion of a nerve that has an elongate shape. The method 1400 includes a step 1420 of sending a trigger signal to a measurement instrument. The trigger signal defines a time window for making a measurement. The method 1400 includes a step 1430 of measuring a plurality of different action potentials via the measurement instrument. The measuring is performed in response to a plurality of engagements with different fascicles of a second portion of the nerve while the first body region is stimulated. The second portion of the nerve is in a second body region of the patient that is located remotely from the first body region. In some embodiments, the measuring is performed within the time window defined by the trigger signal. In some embodiments, the measuring is performed at least in part by using a reference electrode that is placed in a third body region remotely located from the first body region and the second body region. The method 1400 includes a step 1440 of selecting, based on the measured action potentials, one of the fascicles that offered a greatest action potential as a target location of the second portion of the nerve for applying the stimulation therapy to treat the first body region. In some embodiments, the steps 1410-1440 are performed while the patient is sedated.

It is understood that the steps 1410-1440 need not necessarily be performed according to the sequence shown in FIG. 31. In various embodiments, some of these steps may be performed concurrently, or in an order different from what is shown in FIG. 31. It is also understood that additional process steps may be performed before, during, or after the steps 1410-1440. For example, in some embodiments, the method 1400 further includes a step of receiving the different action potentials with one of: a seeking needle or a paddle lead. The method 1400 may also include a step of inserting a percutaneous lead through the needle, and placing the percutaneous lead on the optimized location of the second portion of the nerve. For reasons of simplicity, other additional steps are not discussed herein.

Neurostimulator Configured to Sense Evoked Potentials in Peripheral Nerves

Peripheral nerve stimulation is a technique for medical therapy for different diseases. Depending upon the therapeutic application, peripheral nerve stimulation systems seek to activate only motor nerves (e.g., for functional purposes, such as dorsiflexion for a dropped foot, or a grasp for upper extremity hemiplegia) or only sensory nerves (e.g., for neuropathic pain management). In any particular application, neural selectivity is typically achieved by maximally activating the targeted fascicles while avoiding activation of those fascicles that may lead to side effects (e.g., in pain management, motor stimulation can limit the efficacy of the therapy).

In treating pain, stimulation of innocuous sensory fibers in the periphery nerves ostensibly affects pain transmission to the brain via the Gate Control Theory. Clinically, stimulation of these fibers typically results in a comfortable, moderate 'buzzing' sensation in the area of pain, termed paresthesia. The intensity of these sensations relates generally to the number and breadth of axons stimulated in the nerve, and to a lesser degree the frequency of firing of the axons. While the sensation can be comfortable for the patient, the stimulation also provides the desired physiological effect of pain transmission inhibition.

With implanted electrodes, however, activity by the patient (e.g., limb movement, changes in posture, etc.) can alter the relative orientation and/or position of the electrodes or contacts with respect to the nerves. This can alter the strength of the electrical field along the axons, and either reduce or increase the activation of the nerves. Clinically, this can be manifested as disappearance of the paresthesia or, worse, strongly increased intensity of the paresthesia, possibly to the point of reflexive muscle activation. These variations in the stimulation can cause the patient to use the stimulation less, and thus reduce the overall efficacy of the therapy.

What is needed includes systems, devices, and methods configured to provide electrical nerve stimulation such that the intensity of the paresthesia sensed by a patient remains essentially constant despite body movements or changes in position. According to various embodiments of the present disclosure, systems, devices, and methods are provided that are configured to sense evoked potentials generated through electrical stimulation of a nerve by a microstimulator+leads system, where the microstimulator+leads system is configured to reduce the variation in stimulation sensations perceived by the patient in whom the microstimulator+leads system is implanted and also to sense the resulting evoked potentials as surrogates for neural and physical health. An evoked potential or evoked potential signal is an integrated measure of the conducted action potentials of a collection of nerves in response to stimulation. In some embodiments, the evoked potential signal can reflect the number of neurons activated, the fiber diameter of neurons that have been activated, the conduction velocity of the activated neurons, etc. In some embodiments, an evoked potential signal is captured for each contact or electrode disposed along the target nerve at a variety of stimulation pulse parameter settings. In some embodiments, these evoked potential signals can be stored as waveforms for later retrieval, as well as for analysis of other characteristics. Time and date stamps, as well as information regarding clinical or other conditions in existence at the time such signals were sensed and stored, may also be provided along with the evoked potentials. For the purposes of the present disclosure, the terms "evoked potentials" and "action potentials" or "evoked action potentials" may be used interchangeably.

In some embodiments, the microstimulator includes the PNS device 200 discussed above, and the leads include one or more suitable leads configured for peripheral nerve stimulation, such as a percutaneous lead or a paddle lead. In some embodiments, the paddle lead may be implemented as the paddle lead 600 (discussed above with reference to FIGS. 10-14) with the staggered electrodes arrangement. The PNS device 200 and the leads are implanted inside a patient's body, and the electrodes on the leads are configured to be positioned near a target nerve site.

The PNS device 200 includes measurement circuitry operably coupled to the leads, which receives sensed input signals from the leads. The sensed input signals from the leads may include action potentials, which may be used as a surrogate for indicating paresthesia or other sensations experienced by the patient. In some embodiments, the measurement circuitry may be implemented within, or as a part of, the sense amplifier 490 discussed above with reference to FIG. 7. The measurement circuitry routes its output to a microprocessor or other suitable CPU, processor or controller, such as the microcontroller 400 discussed above with reference to FIG. 7, or to an external processor or controller. The microcontroller 400 digitizes the sensed and detected signals for interpretation/analysis and store them in a memory or other storage device, which may be included in the PNS device 200 in some embodiments or remotely (such as a "cloud" server) in other embodiments.

It is understood that a processor or controller external to the PNS device 200 may also be able to digitize and analyze the signals from the measurement circuitry. For example, an external programmer such as the electronic programmer 250 discussed above with reference to FIGS. 6A-6C may be used to digitize or analyze the signals from the measurement circuitry. In these embodiments, the PNS device 200 may use its telemetry circuitry 310 (discussed above with reference to FIG. 7) to transmit the relevant information to the electronic programmer 250.

In some embodiments, the PNS device 200 monitors (for example with the measurement circuitry) the evoked potentials periodically, for example on a pulse-by-pulse basis. If the PNS device 200 detects that the evoked potentials are starting to deviate from a predefined number, it will automatically adjust stimulation parameters to compensate for the deviation so that the evoked potentials will return to the predefined number. As an example, supposed that a user (e.g., the patient himself or a medical professional) has achieved satisfactory stimulation coverage for the patient by configuring, via a programmer such as the electronic programmer 200, the various stimulation parameters such as amplitude of the pulse, frequency of the pulse, or pulse width, etc. The electronic programmer 200 may offer the user an option to "hold stable" the stimulation, for example via a virtual or physical button on the electronic programmer 200. In response to the user engaging the "hold stable" button, the PNS device 200 records the value of the evoked potential at this time and stores this value in an electronic memory storage, which may be implemented locally inside the PNS device 200 or remotely in the electronic programmer 200 or in a "cloud" server. Thereafter, the PNS device 200 will continuously (or periodically) monitor the evoked potential. If the evoked potential starts to deviate from the recorded value, the PNS device 200 will ramp up or down stimulation parameters such as the pulse amplitude or pulse width to compensate for the deviation, until the measured evoked potential value returns to the recorded value again. In this manner, the patient may experience a constant level of desired sensation (e.g., comfortable paresthesia) without having to manually configure stimulation parameters.

Figure 32A:
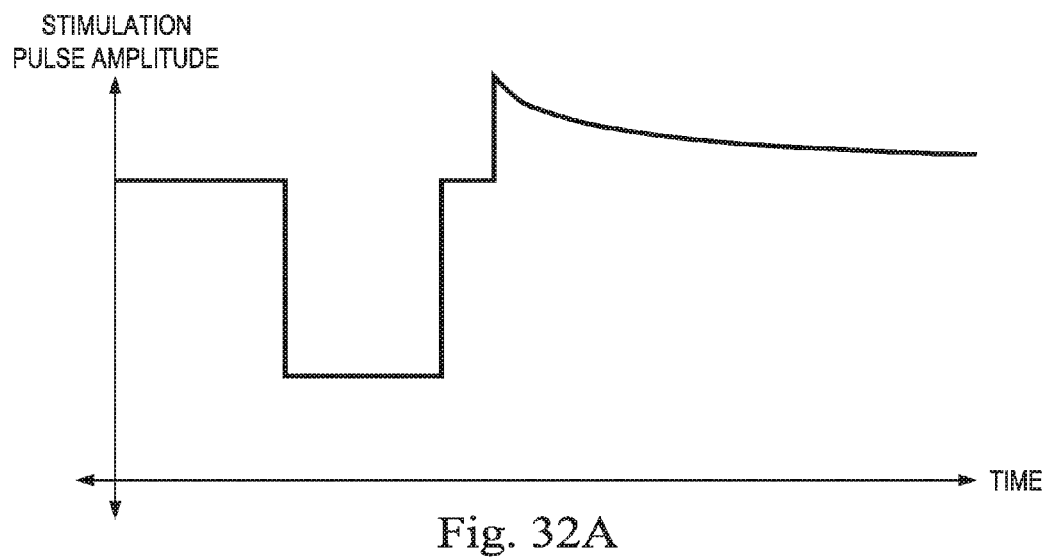
FIGS. 32A-32C are simplified waveforms that provide an example context of one or more calibration processes of the present disclosure.
Figure 32B:
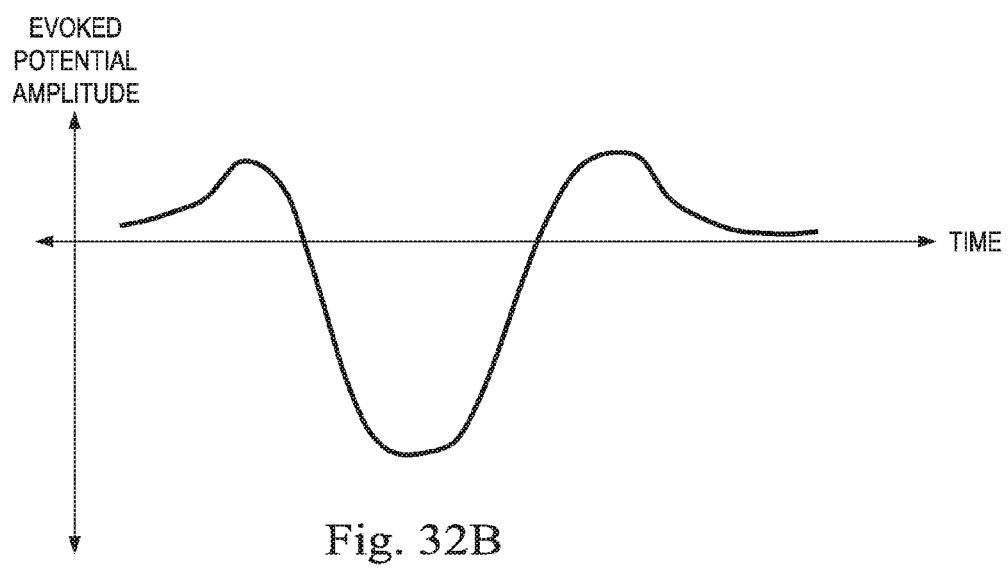

In some embodiments, a plurality of calibration processes may be performed to help the patient experience a constant level of comfortable paresthesia (or another sensation). For example, referring to FIGS. 32A-C, several simplified waveforms are shown to provide an example context of the calibration process of the present disclosure. In more detail, FIG. 32A illustrates a simplified waveform of stimulation pulse amplitude versus time, FIG. 32B illustrates a simplified waveform of evoked potential versus time, and FIG. 32C illustrates a simplified waveform of evoked potential amplitude versus stimulation pulse amplitude.

In each calibration process, test stimulation is delivered to the target nerve site for the patient. As the stimulation is being delivered, a stimulation parameter is being ramped up or down in value. For example, the ramping up or down may include periodically adjusting the value of the stimulation parameter by a small predetermined step size (toward a given direction) each time. In the illustrated embodiment, the stimulation parameter is stimulation pulse amplitude. In other embodiments, the stimulation parameter may include a pulse width. As the value of the stimulation parameter is being ramped up or down, the measurement circuitry (in conjunction with the leads) of the PNS device 200 measures the amount of evoked potential in response to each stimulation pulse that has a different value of the stimulation parameter. The patient is then prompted to indicate a plurality of sensations experienced by the patient in response to the stimulation pulses. These sensations may include, but are not limited to: an initial perception of paresthesia, a comfortable paresthesia, an optimal paresthesia coverage for areas of pain, and an uncomfortable stimulation sensation (i.e., too much stimulation). The respective amount of the measured evoked potential corresponding to each of the plurality of sensations experienced by the patient and the value of the stimulation parameter that resulted in the respective amount of evoked potential is recorded.

Figure 32C:
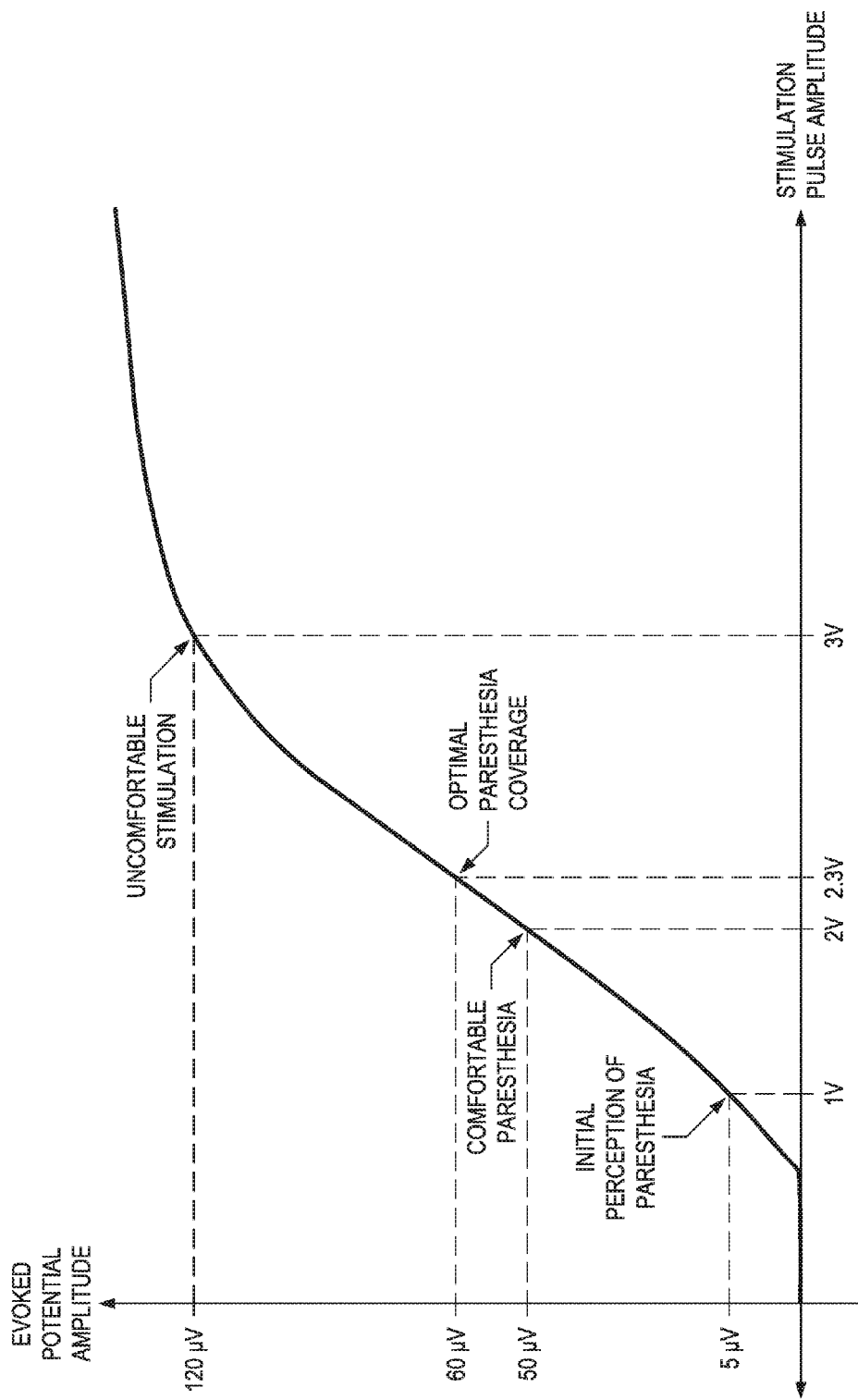

For example, referring to FIG. 32C, at some point during the ramping up of the stimulation pulse amplitude, the patient indicates (either verbally or via the patient feedback tool discussed above) that he/she is now first experiencing paresthesia. At this point, the stimulation pulse amplitude is at 1 volt, and the PNS device 200 measures a voltage of 5 micro-volts for the evoked potential (evoked in response to the 1 volt of stimulation pulse amplitude). The PNS device 200 associates the patient's initial perception of paresthesia with the 1 volt of stimulation pulse amplitude and the 5 micro-volts of evoked potential. This association may be recorded in an electronic storage.

As the ramping up of the stimulation pulse amplitude continues, the patient indicates that he/she is now experiencing comfortable paresthesia. At this point, the stimulation pulse amplitude is at 2 volts, and the PNS device 200 measures a voltage of 50 micro-volts for the evoked potential. The PNS device 200 associates the patient experiencing comfortable paresthesia with the 2 volts of stimulation pulse amplitude and the 50 micro-volts of evoked potential. This association may be recorded in an electronic storage.

As the ramping up of the stimulation pulse amplitude continues, the patient indicates that he/she is now experiencing optimal paresthesia coverage of the pain areas. At this point, the stimulation pulse amplitude is at 2.3 volts, and the PNS device 200 measures a voltage of 60 micro-volts for the evoked potential. The PNS device 200 associates the patient experiencing optical paresthesia coverage of pain areas with the 2.3 volts of stimulation pulse amplitude and the 60 micro-volts of evoked potential. This association may be recorded in an electronic storage.

In some embodiments, the optimal paresthesia coverage of the pain areas may provide the patient with even better pain relief than when the patient first experienced comfortable paresthesia. However, it is understood that the difference between comfortable paresthesia and the optimal paresthesia coverage of the pain areas may not be very significant, and it may be subjective in some cases. Thus, the range between the two may be an area of interest and may be more closely scrutinized. For example, in some embodiments, once the comfortable paresthesia and its corresponding stimulation pulse amplitude and corresponding evoked potential are identified, the calibration process may "slow down," and the ramping up may be performed with smaller step sizes. In other words, the ramping may be performed with finer resolution to reduce the likelihood of missing a stimulation amplitude pulse (and evoked potential) for generating a best case paresthesia. In some embodiments, a plurality of stimulation pulse amplitudes between 2 to 2.3 volts and their corresponding evoked potentials between 50 micro-volts and 60 micro-volts (i.e., between comfortable paresthesia and optical paresthesia coverage) may also be recorded in the electronic storage. These stimulation pulse amplitudes and their associated evoked potentials may be used later as candidates for creating paresthesia.

As the ramping up of the stimulation pulse amplitude continues further, the patient indicates that he/she is now experiencing uncomfortable stimulation (i.e., due to excessive stimulation). At this point, the stimulation pulse amplitude is at 3 volts, and the PNS device 200 measures a voltage of 120 micro-volts for the evoked potential. The PNS device 200 associates the patient experiencing optical paresthesia coverage of pain areas with the 3 volts of stimulation pulse amplitude and the 120 micro-volts of evoked potential. This association may be recorded in an electronic storage.

It is understood that additional patient sensations (and their corresponding stimulation pulse amplitudes and evoked potentials) may be included in other embodiments. It is also understood that all the numerical values used herein are merely for the purposes of providing an example. In real world applications, the values of the stimulation amplitudes and evoked potentials may differ from the ones being shown herein, and they also may vary from patient to patient. It is also understood that while the stimulation pulse amplitude is used herein as an example stimulation parameter that can be calibrated with respect to evoked potential and various sensations experienced by the patient, stimulation pulse width may be used as another suitable stimulation parameter to perform the calibration process discussed above.

The results of the calibration process discussed above may be used to provide fast and automatic treatment. For example, the associations of the various sensations experienced by the patient and their respective stimulation pulse amplitudes and evoked potentials may be stored in the electronic storage onboard the PNS device 200 or on the electronic programmer 250. The electronic programmer 250 may present (via its user interface) the patient (or a medical professional user) one or more stimulation programs that each correspond to one of the sensations experienced by the patient.

For example, the user interface may present a stimulation program (e.g., in the form of a virtual button or icon) indicating that, if executed, will cause "comfortable paresthesia" for the patient. The stimulation program may retrieve the stimulation pulse amplitude (2 volts in this case) that led to comfortable paresthesia for the patient during calibration. Thus, 2 volts is used as an initial value for the pulse amplitude for generating the stimulation pulses. In addition, since 50 micro-volts was recorded as the evoked potential corresponding to the "comfortable paresthesia", the PNS device 200 may monitor the evoked potential after the initial value of 2 volts is used for the stimulation pulse amplitude. If the detected value of the evoked potential is at 50 micro-volts, the PNS device 200 continues applying stimulation with the stimulation amplitude of 2 volts. However, if the detected value of the evoked potential is lower than 50 micro-volts, the PNS device 200 may adjust the stimulation amplitude upwards (e.g., by small step sizes) until 50 micro-volts is detected as the evoked potential again. If the detected value of the evoked potential is higher than 50 micro-volts, the PNS device 200 may adjust the stimulation amplitude downwards (e.g., by small step sizes) until 50 micro-volts is detected as the evoked potential again.

Throughout this entire process, the patient need not manually program or adjust the stimulation parameters. In other words, the application of the stimulation program and any subsequent parameter adjustment thereof are automatic, and the stimulation program is specifically configured to re-create a sensation that the patient wants based on prior calibration results. Similarly, the user interface may also offer other stimulation programs that correspond to "initial perception of paresthesia", "optimal paresthesia coverage", or "uncomfortable paresthesia." These additional stimulation programs may be useful in various scenarios as well. For example, suppose that the patient is generally happy with the "comfortable paresthesia" offered by the stimulation program discussed above but wishes to further optimize it, then the patient may execute the stimulation program corresponding to "optimal paresthesia coverage" to see if that stimulation program will offer even better pain relief. As another example, suppose that due to the passage of time, the patient's pain has evolved to the point where 2 volts of stimulation no longer produces comfortable paresthesia. The patient may execute the stimulation program corresponding to "initial perception of paresthesia", which will automatically provide a starting point or a baseline as the patient may then ramp up the stimulation pulse amplitude to see find a better setting for providing desired pain relief. Similarly, the stimulation program corresponding to "uncomfortable stimulation" may be used to automatically generate an upper limit as the patient ramps down the stimulation amplitude to find a better setting for providing desired pain relief.

In all of these scenarios discussed above, the calibration results allow appropriate stimulation parameters to be automatically and quickly generated for a stimulation program without requiring the patient's (or the medical professional's) input. Such stimulation program may then be executed to quickly re-create a prior condition in which patient experienced a certain type of sensation. This saves time and offers more simplicity and convenience for the patient (or other users). In addition, the evoked potentials are associated with different sensations experienced by the patient and may be used as surrogates or indicators for these sensations. Once any given stimulation program is executed using the stimulation pulse amplitude value associated with the sensation as an initial value, a servo mechanism (e.g., closed loop feedback) may be employed to fine-tune the stimulation pulse amplitude until the desired evoked potential (again, representing the corresponding sensation of the patient) is achieved.

In some embodiments, the user interface may offer the user an option to "lock down" the stimulation parameters. In other embodiments, the user interface may offer the user an option to "hold stable" the evoked potential, whichever value it may be. For example, suppose that the patient executes the stimulation program corresponding to "comfortable paresthesia" using 2 volts as the stimulation pulse amplitude, and the resulting evoked potential is measured as 55 micro-volts instead of the 50-micro-volts recorded by the calibration. The patient may still find the paresthesia generated herein very comfortable, and thus he/she may press a "hold stable" button on the user interface of the electronic programmer 250. The electronic programmer 250 will then instruct the PNS device 200 to stop trying to adjust the stimulation parameters to produce the 50 micro-volt evoked potential and instead maintain (or adjust if necessary) the stimulation parameters to ensure that the 55 micro-volt of evoked potential is achieved.

Figure 33:
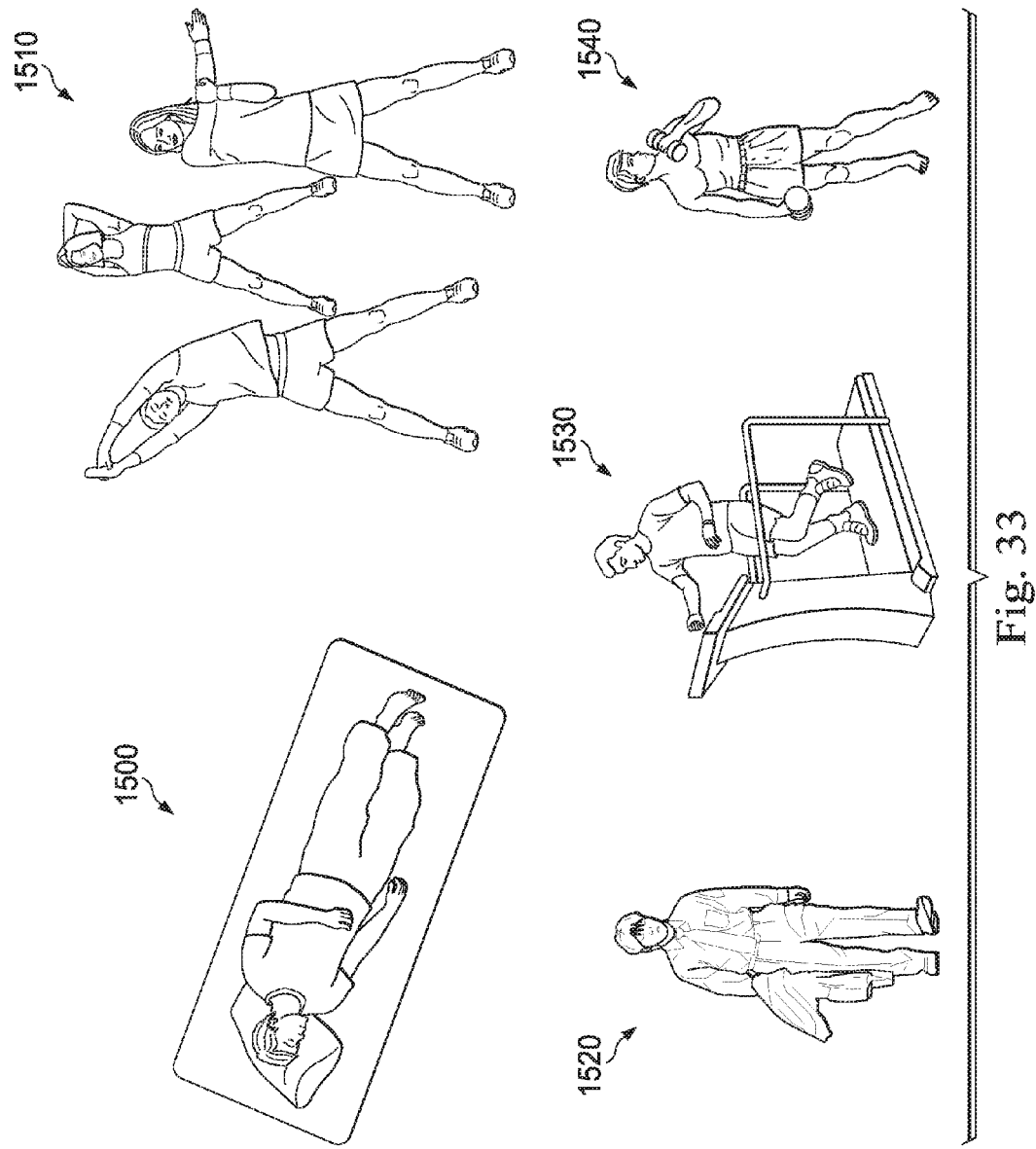
FIG. 33 illustrates a plurality of example patient posture states according to some embodiments of the present disclosure.

The calibration process discussed above may be performed in a given patient posture state. According to the various aspects of the present disclosure, multiple calibration processes similar to the one discussed above may also be performed to take into account of multiple patient posture states. For example, referring now to FIG. 33, a plurality of example patient posture states 1500-1540 is illustrated, though it is understood that these patient posture states 1500-1540 are merely examples and are not intended to constitute an exhaustive list of possible patient posture states.

In the patient posture state 1500, the patient is instruct to lie down, with at least the limb targeted for implantation of the PNS device 200 and/or the leads being in a relaxed position. A first calibration process similar to that discussed above with reference to FIGS. 32A-32C may be performed while the patient is in this patient posture state 1500.

In the patient posture state 1510, the patient is instructed to do various stretching exercises. Specifically, the stretching exercises are designed to stretch the limb targeted for implantation of the PNS device 200 and/or the lead. A second calibration process similar to that discussed above with reference to FIGS. 32A-32C may be performed while the patient is in this patient posture state 1510.

In the patient posture state 1520, the patient is instructed to walk around or otherwise become ambulatory. A third calibration process similar to that discussed above with reference to FIGS. 32A-32C may be performed while the patient is in this patient posture state 1530.

In the patient posture state 1530, the patient is instructed to run. A fourth calibration process similar to that discussed above with reference to FIGS. 32A-32C may be performed while the patient is in this patient posture state 1530. In some embodiments, the patient posture state 1530 may be further sub-divided into a plurality of running speeds, for example a jogging speed and a faster sprinting speed. This could be done in a controlled environment such as on a treadmill. In these embodiments, a calibration process may be performed for each running speed.

In the patient posture state 1540, the patient is instructed to apply pressure on the body region where implantation of the PNS device 200 and/or the leads is targeted. For example, if the patient's left arm is the target location for implantation of the PNS device 200 and/or the leads, the patient may be instructed to flex the muscles on the left arm. A fifth calibration process similar to that discussed above with reference to FIGS. 32A-32C may be performed while the patient is in this patient posture state 1540.

The results for each of the calibration processes corresponding to the different patient posture states are again stored in electronic storage. Thereafter, when stimulation therapy is applied to the target nerve site of the patient, the present patient posture state may be taken into account to determine the optimal stimulation configuration for treating the patient. For example, suppose that based on the calibration processes discussed above, it has been determined that:

while the patient is lying down, he experiences comfortable paresthesia when a 50 micro-volt evoked potential is produced, which according to calibration corresponds to a stimulation pulse amplitude of 2 volts;

while the patient is walking around, he experiences comfortable paresthesia when a 60 micro-volt evoked potential is produced, which according to calibration corresponds to a stimulation pulse amplitude of 2.5 volts; and while the patient is applying pressure to the implantation site, he experiences comfortable paresthesia when a 70 micro-volt evoked potential is produced, which according to calibration corresponds to a stimulation pulse amplitude of 3.0 volts.

Thereafter, in the course of normal stimulation treatment for the patient, the PNS device 200 may detect that the patient has assumed a lying down position (i.e., the patient posture state 1500). Accordingly, the PNS device 200 may generate a stimulation program using 2 volts as the initial value for the stimulation pulse amplitude, with the goal of achieving 50 micro-volts of evoked potential, which corresponds to comfortable paresthesia for the patient according to calibration results. If the 2 volts of stimulation pulse amplitude does not quite result in a 50 micro-volt evoked potential, the PNS device 200 may fine tune the stimulation pulse amplitude up or down (from 2 volts) until 50 micro-volts of evoked potential is achieved.

Suppose that the PNS device 200 has now detected that the patient has begun walking around (i.e., the patient posture state 1520). Accordingly, the PNS device 200 may generate a stimulation program using 2.5 volts as the initial value for the stimulation pulse amplitude, with the goal of achieving 60 micro-volts of evoked potential, which corresponds to comfortable paresthesia for the patient according to calibration results. If the 2.5 volts of stimulation pulse amplitude does not quite result in a 60 micro-volt evoked potential, the PNS device 200 may fine tune the stimulation pulse amplitude up or down (from 2.5 volts) until 60 micro-volts of evoked potential is achieved.

Suppose that the PNS device 200 has now detected that the patient has begun applying pressure to the implantation site (i.e., the patient posture state 1540). Accordingly, the PNS device 200 may generate a stimulation program using 3.0 volts as the initial value for the stimulation pulse amplitude, with the goal of achieving 70 micro-volts of evoked potential, which corresponds to comfortable paresthesia for the patient according to calibration results. If the 3.0 volts of stimulation pulse amplitude does not quite result in a 70 micro-volt evoked potential, the PNS device 200 may fine tune the stimulation pulse amplitude up or down (from 3.0 volts) until 70 micro-volts of evoked potential is achieved.

In some embodiments, the PNS device 200 uses integrated sensors such as the sensors 435-445 to automatically detect the patient posture state (or a change thereof). For example, the accelerometer sensor 445 may be used to detect the movement of the patient, and based on the detected movement, the accelerometer sensor 445 and the microcontroller 400 may collectively determine whether the patient is lying down, or walking, or running. As another example, a pressure sensor may be used (in conjunction with the microcontroller 400) to detect whether the patient is applying pressure to the implantation site. In some embodiments, sensors such as accelerometers, pressure sensors, temperature sensors, etc., may also be implemented on the lead itself. This may allow for more accurate patient posture state detection.

In other embodiments, the patient may manually specify his/her current posture state. As an example, the electronic programmer 250 may display, via its user interface, a plurality of icons or buttons, each of which corresponding to a respective patient posture state. The patient may engage with these icons (such as pressing the button) as necessary to update his/her current posture state. The electronic programmer 250 may then inform the PNS device 200 of the current patient posture state, so that the PNS device 200 can generate a stimulation program tailored to such patient posture state based on the calibration results.

It is understood that the "brains" behind the patient posture detection and the subsequent changing of the stimulation program may be implemented in either the PNS device 200, or in the electronic programmer 250, or both, or in a remote server. For example, in some embodiments, the PNS device 200 itself may be able to determine the patient posture state (via the onboard microcontroller and the sensors) and select a suitable stimulation program customized to the detected patient posture state thereafter. In some other embodiments, the PNS device 200 itself does not make any decisions and may merely report back to the electronic programmer 250 regarding the measurement results of the sensors and regarding the monitored evoked potentials. The electronic programmer 250 may then perform the analysis based on the data sent by the PNS device 200 and devise a treatment plan accordingly.

Based on the discussions above, it can be seen that the multiple calibration processes involve sensing evoked responses of nerves as a surrogate for keeping the intensity of a patient sensation (such as paresthesia) constant. This is better for patients because they may receive a constant amount of pain relief despite changes in position or posture, and despite limb movement, changes in limb position, limb compression, etc. Although not discussed in detail for reasons of simplicity, one of ordinary skill in the art may appreciate that the various concepts discussed above may also apply to the detection of disease state, disease progression, ischemia, and/or nerve integrity or condition.

In addition to detecting patient posture states, the sensors may provide certain other benefits. In some embodiments, the sensors may be used to avoid motor stimulation. For example, assuming that due to whatever reason—such as lead migration over time, or patient posture change, or internal changes within the patient's body—a limb of the patient (in which the PNS device 200 or a lead is implanted) begins to twitch spontaneously in response to electrical stimulation. This is an unintended side effect of the stimulation therapy and is undesirable. The sensors such as the accelerometer sensor 445 may detect the twitch and report it back to the microcontroller 400. The microcontroller 400 may then automatically adjust the stimulation parameters (such as decreasing a stimulation pulse amplitude) in order to stop the twitch. This may be performed without the patient having to manually adjust the stimulation parameters, which would have taken more time (thereby prolonging the patient's discomfort), especially if the twitching is impeding the patient from finding or operating the electronic programmer 250.

In some other embodiments, the sensors may be used to provide cross-checking of the evoked potential. For example, suppose that in any given patient posture state, the desired evoked potential has been achieved, and the stimulation parameters have been fine-tuned to maintain such desired evoked potential. Sometimes, when a part of the patient's body moves—for example the limb in which the PNS device 200 or the leads are implanted—this movement may generate an electrical signal that may be picked up by the measurement or monitoring circuitry of the PNS device 200. This electrical signal may be misinterpreted by the PNS device 200 as (or part of) the evoked potential. Consequently, the PNS device 200 may incorrectly try to adjust the stimulation parameters to try to compensate for this "evoked potential," when it is only temporary and therefore warrants no adjustment of the stimulation therapy.

Here, the sensors such as the accelerometer sensor 445 may detect the movement of the patient that led to the generation of the electrical signal. As the accelerometer sensor 445 reports this detection back to the microcontroller 400, the microcontroller 400 may be able to determine that the extra electrical signal is not really the evoked action potential. The determination may be made based on the correlated time points in which the extra electrical signal is received and in which the patient movement is detected by the accelerometer sensor 445. Accordingly, the microcontroller 400 may correctly determine that the extra electrical signal is really noise and may filter it out from the evoked potential monitoring and analysis.

Figure 34:
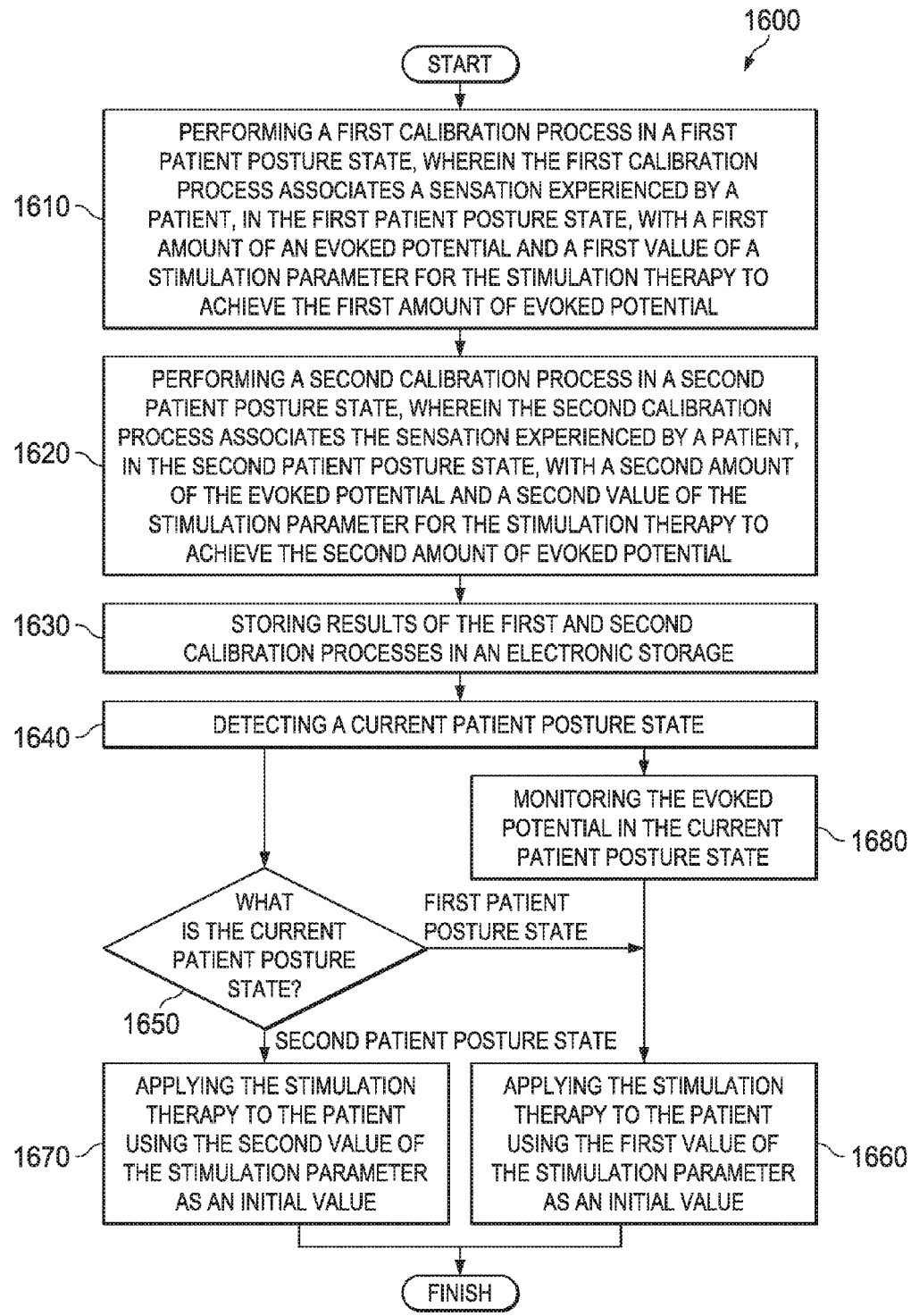
FIG. 34 is a simplified flowchart illustrating a method of providing a stimulation therapy to a patient according to an embodiment of the present disclosure.

FIG. 34 is a simplified flowchart of a method 1600 of providing a stimulation therapy to a patient according to an embodiment of the present disclosure. The method 1600 includes a step 1610 of performing a first calibration process in a first patient posture state. The first calibration process associates a sensation experienced by a patient, in the first patient posture state, with a first amount of an evoked potential and a first value of a stimulation parameter for the stimulation therapy to achieve the first amount of evoked potential. In some embodiments, the stimulation parameter includes one of: stimulation pulse amplitude or stimulation pulse width.

The method 1600 includes a step 1620 of performing a second calibration process in a second patient posture state. The second calibration process associates the sensation experienced by a patient, in the second patient posture state, with a second amount of the evoked potential and a second value of the stimulation parameter for the stimulation therapy to achieve the second amount of evoked potential.

In some embodiments, the first and second calibration processes each include the following steps: delivering stimulation pulses to the patient, wherein the delivering includes ramping up or down a value of the stimulation parameter; measuring a respective amount of evoked potential in response to each stimulation pulse having a different value of the stimulation parameter; prompting the patient to indicate a plurality of sensations experienced by the patient in response to the stimulation pulses, the plurality of sensations experienced including paresthesia; and recording the respective amount of evoked potential corresponding to each of the plurality of sensations experienced by the patient and the value of the stimulation parameter that resulted in the respective amount of evoked potential. In some embodiments, the sensations experienced by the patient comprise: initial perception of paresthesia, comfortable paresthesia, optimal paresthesia coverage for areas of pain, and uncomfortable stimulation.

The method 1600 includes a step 1630 of storing results of the first and second calibration processes in an electronic storage. In some embodiments, the electronic storage resides on a neurostimulator such as the PNS device 200 discussed above. In other embodiments, the electronic storage resides on an electronic programmer such that the electronic programmer 250 discussed above. In yet other embodiments, the electronic storage resides on a remote server (i.e., the "cloud").

The method 1600 includes a step 1640 of detecting a current patient posture state. In some embodiments, the detecting is performed automatically via one or more sensors and without input from the patient. In other embodiments, the detecting is performed in response to a user selection or user input.

The method 1600 includes a decision step 1650 to determine what the current patient posture state is. If it has been determined that the current patient posture state is the first patient posture state, the method 1600 proceeds to a step 1660 of applying the stimulation therapy to the patient using the first value of the stimulation parameter as an initial value. If it has been determined that the current patient posture state is the second patient posture state, the method 1600 proceeds to a step 1670 of applying the stimulation therapy to the patient using the second value of the stimulation parameter as an initial value.

The method 1600 also includes a step 1680 of monitoring the evoked potential in the current patient posture state. Based on the monitoring, the step 1660 of applying the stimulation therapy in the first patient posture state includes adjusting the initial value of the stimulation parameter until the first amount of the evoked potential is reached, and the step 1670 of applying the stimulation therapy in the second patient posture state includes adjusting the initial value of the stimulation parameter until the second amount of the evoked potential is reached.

It is understood that the steps 1610-1680 need not necessarily be performed according to the sequence shown in FIG. 34. In various embodiments, some of these steps may be performed concurrently, or in an order different from what is shown in FIG. 34. It is also understood that additional process steps may be performed before, during, or after the steps 1610-1680. For example, in some embodiments, one or more additional calibration processes are performed in one or more additional patient posture states. The one or more additional calibration processes each associate the sensation experienced by the patient, in the respective one or more additional patient posture states, with a respective amount of the evoked potential and a respective value of the stimulation parameter for the stimulation therapy to achieve the respective amount of evoked potential. If the current patient posture state is detected as one of the one or more additional patient posture states, a stimulation therapy is applied to the patient using the corresponding respective value of the stimulation parameter as the initial value. For reasons of simplicity, other additional steps are not discussed herein.

System and Method for Selective and Maintained Activation of Sensory Peripheral Nerve Fibers In peripheral nerve stimulation, activation of afferent/sensory fibers is believed to be necessary to achieve pain relief, ostensibly via the Gate Control Theory of pain. Most peripheral nerves, however, are mixed nerves, in that they contain both sensory and motor fibers. Motor fibers are efferents, and tend to have a larger diameter and faster conduction velocity than the neighboring sensory afferents. Activation of motor efferents can lead to uncomfortable muscle contractions that can compromise the therapy.

Avoidance of motor efferents can be achieved by careful selection of stimulation parameters, in particular the contact combination to focus the stimulation field within fascicles that carry afferent sensory information. However, finding the appropriate stimulation combination (and other parameters) may be a time-consuming process when the number of stimulation contacts grows beyond four. In addition, the amplitude and pulse width of the stimulation pulses can affect the size of the stimulation field and the locus of activated fibers.

What is needed includes methods, systems, and devices configured to determine stimulation patterns which maximize activation of sensory afferents while minimizing the recruitment of motor efferents. Accordingly, various embodiments of the present disclosure include an algorithm and associated methods, systems, and devices configured to monitor the compound action potential (CAP) resulting from stimulation of a peripheral nerve and select stimulation parameters which minimize the components of the CAP which relate to motor efferent stimulation in favor of those components of the CAP which relate to afferent sensory fiber stimulation.

In some embodiments, a multi-contact array is placed proximal to the targeted nerve to be stimulated. The array can be positioned longitudinally along the axis of the nerve, with at least some contacts distributed along the length of the nerve. In some embodiments, the stimulation is delivered on one contact, and the spatial sum of the resulting conducted action potentials (i.e., the compound action potential, or CAP) from the activated nerves are measured at another contact, at some distance away from the stimulating contact. In some embodiments, the stimulating contact may also be the measurement contact, although this typically requires amplifier blanking and often makes it difficult to see good time separation of the motor efferent and sensory afferent conducted action potentials.

Figure 35:
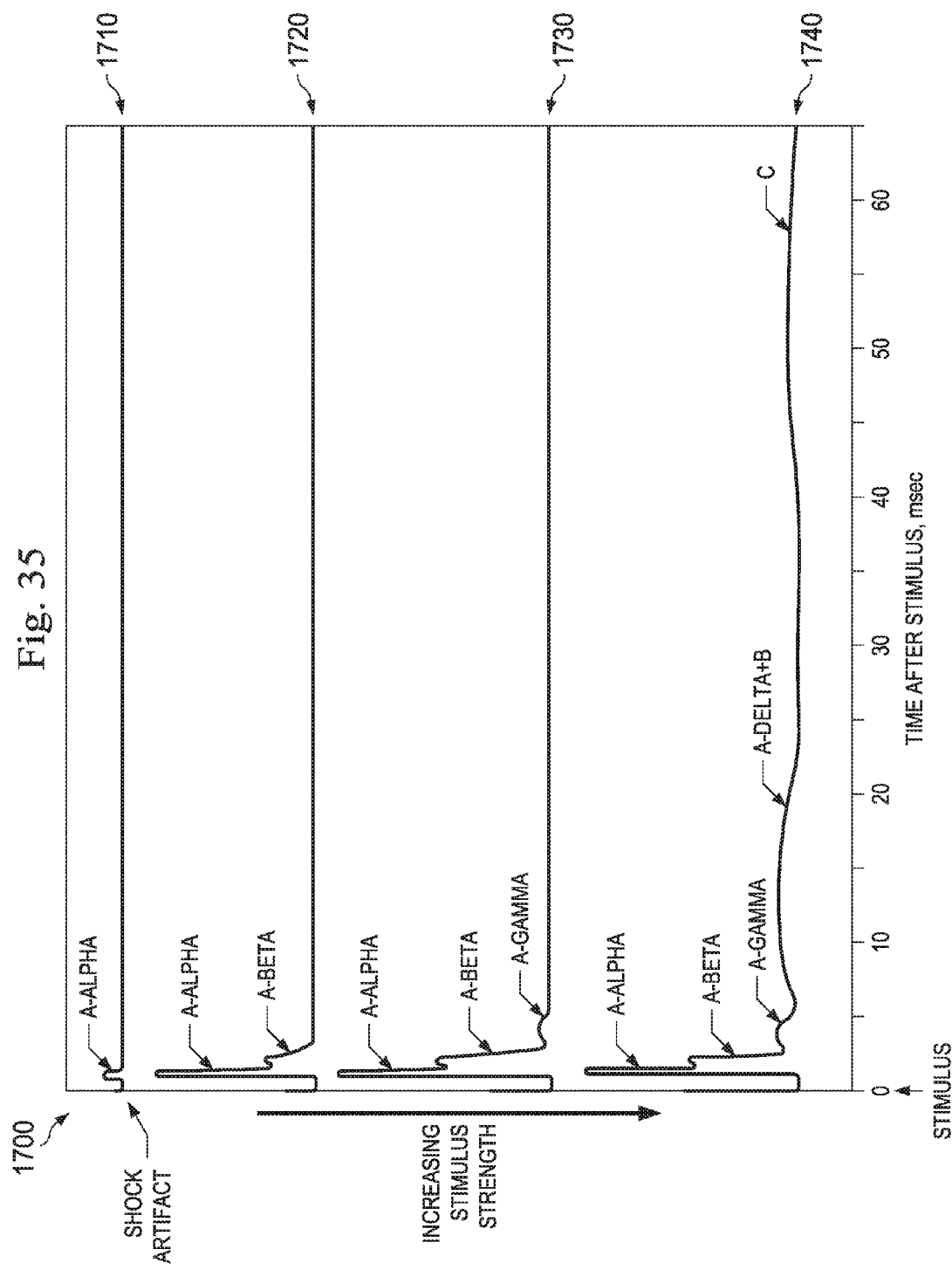
FIG. 35 is a graph illustrating several action potentials according to various aspects of the present disclosure.

FIG. 35 illustrates a graph 1700 that includes the plots of several example action potential signals (e.g., CAP) measured over a period of time after a stimulus is applied. For example, the plots of signals 1710-1740 each represent a respective CAP generated in response to different amounts of stimulation (e.g., greater stimulation pulse amplitude, or greater stimulation pulse width, or both). Generally, the motor efferents, being relatively large, fast-conducting fibers, will primarily contribute to CAP components that are seen very soon following the stimulation artifact (A-alpha), and will have a relatively narrowly-shaped complex. The sensory afferent fibers, on the other hand, are typically smaller in diameter and thus have a slower conduction velocity. This means that their contribution to the CAP will generally appear with greater latency following the stimulation artifact, and the complex will be wider (A-beta, A-gamma, etc).

In the example shown in FIG. 35, the signal 1710 is generated in response to a low amount of stimulation. Consequently, the A-alpha component (representing the motor fiber contribution to the CAP) of the signal 1710 is beginning to show, but the A-beta and A-gamma components (representing the sensory fiber contributions to the CAP) are largely nonexistent in the signal 1710.

The signal 1720 is generated in response to a moderate amount of stimulation that is greater than the stimulation for the signal 1720. Consequently, the A-alpha component of the signal 1720 becomes more significant, and the A-beta component begins to show as well. However, the A-gamma component is still largely nonexistent in the signal 1720. This means that there is some amount of sensory fiber activity in response to the stimulation applied to generate the signal 1720, but not very much yet.

The signal 1730 is generated in response to a larger amount of stimulation that is greater than the stimulation for the signal 1730. As is shown in FIG. 35, the A-alpha component of the signal 1730 may increase a little bit more compared to the A-alpha component of the signal 1720, but not by very much. However, the A-beta component of the signal 1730 increases significantly compared to the A-beta component of the signal 1720. The A-gamma component is beginning to appear as well. This means that, in response to the stimulation applied to generate the signal 1730, the sensory fiber contribution increases much more relative to the motor fiber contribution.

The signal 1740 is generated in response to an even greater amount of stimulation (the largest yet). However, as is shown in FIG. 35, the A-alpha and A-beta components of the signal 1740 remain almost the same compared to the A-alpha and A-beta components of the signal 1730. The A-gamma component increases a little bit, but not by much, and there is a low but detectable A-delta component (also representing the sensory fiber contribution to the CAP). This means that, in response to the stimulation applied to generate the signal 1740, there is not much improvement in terms of maximizing the sensory fiber contribution to the CAP relative to the motor fiber contribution. In other words, even though stimulation strength is increased, it has reached the point of diminishing returns.

Based on the discussions above, it can be seen that it is beneficial to apply test stimulation with a variety of stimulation configurations (i.e., stimulation is applied differently each time), so as to discover the one or more stimulation configurations that offer a sensory fiber contribution to the CAP that is maximized respect to the motor fiber contribution. These stimulation configurations may then be recommended as optimized stimulation configurations to the patient, which should result in improve paresthesia with minimal side effects pertaining to undesirable motor stimulation.

Figure 36:
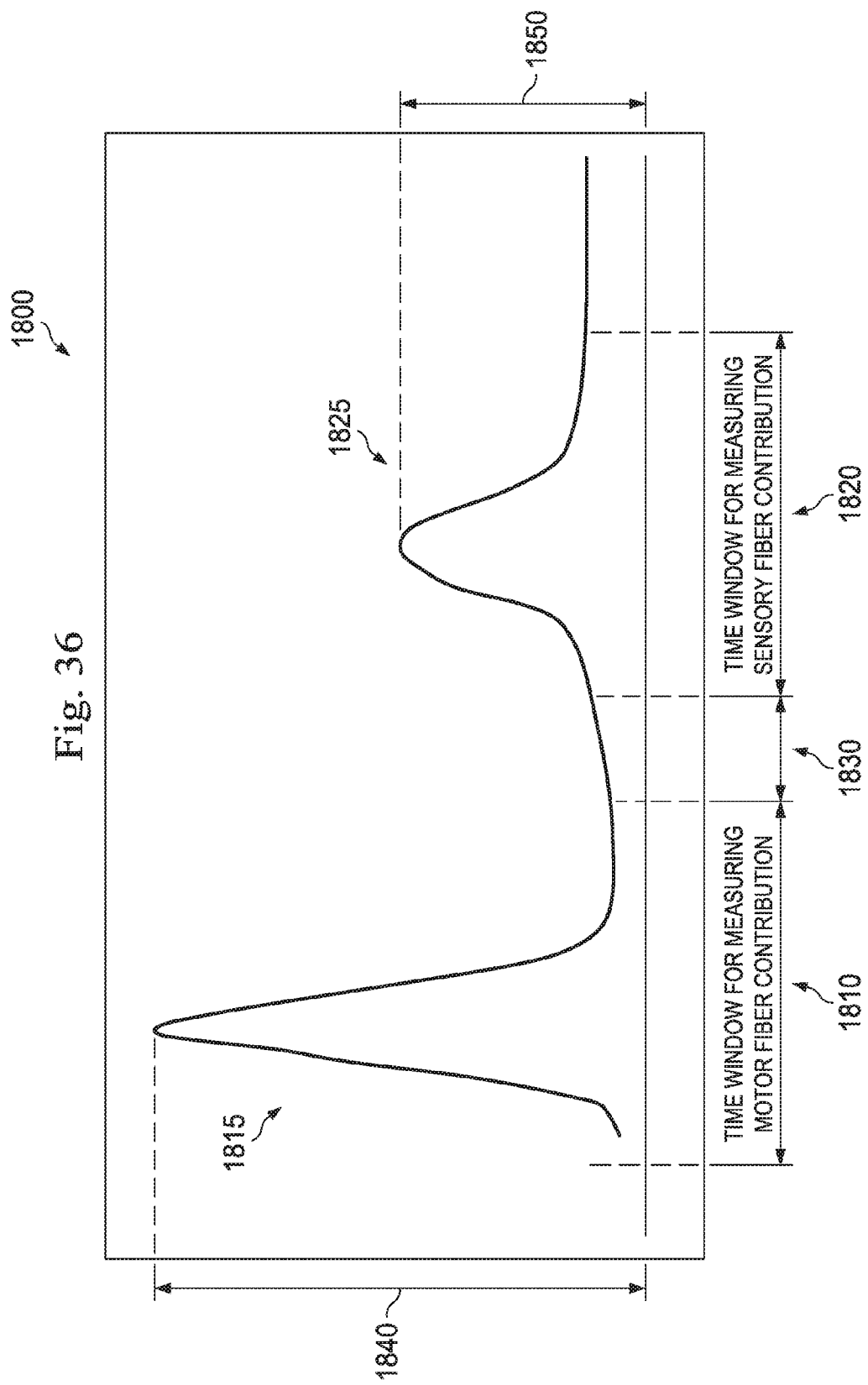
FIG. 36 is a graph illustrating two time windows for measuring a motor fiber contribution and a sensory fiber contribution to an action potential according to an embodiment of the present disclosure.

In order to accurately determine the contributions to the CAP caused by the motor fiber and by the sensory fiber component, the embodiments of the present disclosure establish different time windows to measure these contributions. Referring to FIG. 36, a graph 1800 illustrates a time window 1810 for capturing or measuring a motor fiber contribution 1815 to the CAP, as well as a time window 1820 for capturing or measuring a sensory fiber contribution 1825 to the CAP. In some embodiments, the graph 1800 may be displayed on a measurement instrument, such as an oscilloscope or another suitable instrument.

In some embodiments, the time windows 1810 and 1820 may be established based upon the assumed conduction velocity for large diameter fibers and small diameter fibers, as well as the known distance between the stimulating and measurement electrodes. Since large diameter fibers (i.e., motor fibers) have higher conduction velocity and small diameter fibers (i.e., sensory fibers) have lower conduction velocity, the earlier time window 1810 would capture much of the CAP waveform signal due to large diameter motor fibers and later time windows 1820 would capture CAP signals due to smaller diameter fibers. In other words, the window 1810 is specifically configured for capturing and measuring the motor fiber contribution to the CAP signal, and the window 1820 is specifically configured for capturing and measuring the sensory fiber contribution to the CAP signal. Since the motor fiber contribution signal 1815 is "expected" to be present in the time window 1810, it is easier to identify the motor fiber contribution signal 1815 correctly (especially in situations where significant noise may be present). Likewise, the accurate identification of the sensory fiber contribution signal 1825 is made easier by knowing its expected arrival time (i.e., defined by the time window 1820).

In some embodiments, the time window 1810 starts at microseconds or tens of microseconds after the stimulation pulse is generated, and it has a length of about tens of milliseconds. In some embodiments, the time window 1820 starts at tens of milliseconds after the stimulation pulse is generated, and it has a length of about tens or hundreds of milliseconds. In some embodiments, the time windows 1810 and 1820 are non-overlapping (meaning that the start of the time window 1820 occurs after the end of the time window 1810), and a separation 1830 between the time windows 1810 and 1820 is in a range from about 100 microseconds to about 5 milliseconds. In other embodiments, the time windows 1810 and 1820 may partially overlap, meaning that the start of the time window 1820 occurs before the end of the time window 1810.

As discussed above, in order to better distinguish the motor fiber and sensory fiber contribution signals 1815 and 1825, the measurement electrode is typically placed far away from the stimulation electrode (though it is not necessarily required). This is because the motor fiber contribution signal 1815 travels faster than the sensory fiber contribution signal 1825. A greater distance between the stimulation and measurement effectively lengthens the "lag" between the motor fiber contribution signal 1815 with respect to the sensory fiber contribution signal 1825. The greater the time separation between the signals 1815 and 1825, the better the windows 1810 and 1820 can be defined and used to capture the signals 1815 and 1825.

In the example shown in FIG. 36, the motor fiber contribution signal 1815 has a narrower and taller profile, whereas the sensory fiber contribution signal 1825 has a wider and shorter profile. These signal profiles match up with expected signal profiles for the motor fiber and sensory fiber contributions, respectively. Thus, there is a high confidence level that these signals 1815 and 1825 indeed are the motor fiber and sensory fiber contributions, respectively. In other embodiments, additional techniques may be used to further extract the motor fiber and sensory fiber contribution signals, including but not limited to: template matching, peak detection, zero crossings, or combinations thereof.

After ascertaining that the captured signals 1815 and 1825 indeed are the motor fiber and sensory fiber contribution signals, respectively, the peak amplitudes of the signals 1815 and 1825 are measured, respectively. In this case, the motor fiber contribution signal 1815 has an amplitude of 1840, and the sensory fiber contribution signal 1825 has an amplitude of 1850. A ratio of the amplitude 1850 and the amplitude 1840 is then calculated. For example, suppose that the amplitude 1840 is 50 microvolts, and the amplitude 1850 is 25 microvolts, then a ratio of the amplitude 1850 and the amplitude 1840 is 0.5 (0.5=25/50). As discussed above, the goal herein is to find one or more particular stimulation configuration that maximizes the sensory fiber contribution relative to the motor fiber contribution, as that will typically lead to a more comfortable treatment for the patient.

It is also understood that the approach of measuring the sensory fiber and motor fiber contributions via the different time windows may be just an example of how to effectively measure these contributions. In other embodiments, certain stimulation parameters may be used that are known to be selective to different fiber types to assist in the discrimination of different CAP features. For example, a very narrow, high amplitude pulse width, known to be more selective to activating large diameter (e.g., motor) fibers may first be delivered and the resulting CAP measured at a distant electrode and stored by the system. Next, a wider pulse width may be used for stimulation which is known to recruit a broader spectrum of fiber diameters. The amplitude of the wider pulse is increased until the peak amplitude of the resulting measured CAP matches the peak amplitude of the CAP from the narrower pulse width. This is done since the peak amplitude of the CAP is typically due to activation of the largest diameter fibers, and, generally, a similar number of large diameter motor fibers will be recruited by both pulse widths when the peak amplitude of the CAP is about the same. The waveform difference between the two CAPs is then ostensibly due to activation of smaller diameter afferents. This can also provide an estimate of the size and morphology of the signal that will be due to activation of sensory afferents.

According to the embodiments of the present disclosure, a predefined algorithm may be executed to help determine the optimized stimulation configuration. In some embodiments, a stimulation configuration may include one or more of the following parameters: a subset of electrodes on a lead to be activated, the assigned electrode polarity for each activated electrode, a stimulation pulse width, and a stimulation pulse amplitude. An example algorithm is discussed below with reference to FIG. 37.

Figure 37:
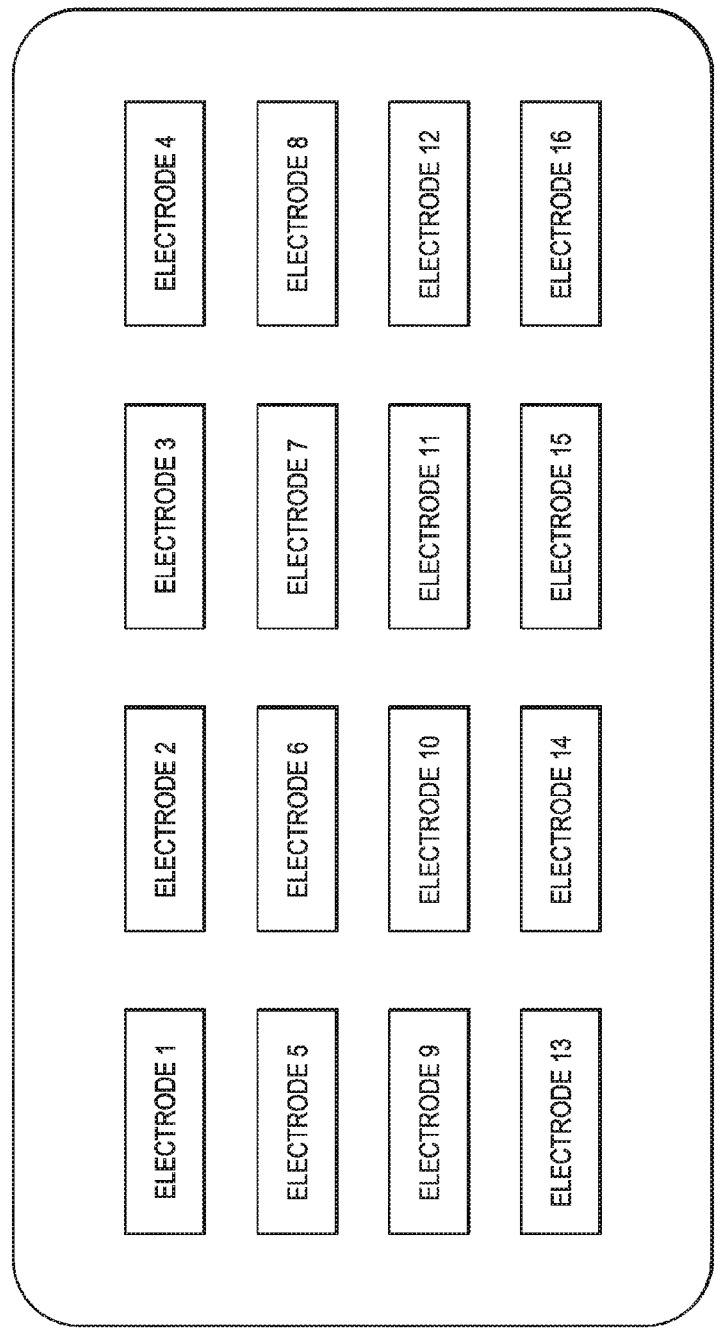
FIG. 37 illustrates an example paddle lead according to an embodiment of the present disclosure.

Referring to FIG. 37, an example paddle lead 1900 is shown. The paddle lead includes 16 electrodes 1-16 herein but may include any other number of electrodes in alternative embodiments. In addition, the various embodiments of the paddle lead 600 with staggered electrodes (shown in FIGS. 10-14) may also be used in various embodiments, as opposed to the neatly-arranged 16 electrodes aligned into 4 rows and 4 columns. Furthermore, percutaneous leads may also be used in some embodiments.

The algorithm here defines a list of electrode combinations to be tested or stepped through. In the first electrode combination, electrode 1 is first selected as a cathode, and its adjacent electrode 2 is selected as an anode. Generally, cathodes are the electrodes that stimulate the axons, because cathodes have a lower activation threshold than anodes. The higher activation thresholds associated with anodes allows it to hyperpolarize a particular neuron. In other words, cathodes offer better sensory fiber activation than anodes. Therefore, the algorithm of the present disclosure prioritizes finding the optimal location for cathodes (as opposed to for anodes).

With the electrode combination of electrode 1 as a cathode and electrode 2 as an anode, stimulation pulse amplitude is ramped up (or down in some alternative embodiments) while pulse width is fixed. The ramping may be done in small user-defined step sizes, and may be performed automatically. In this manner, a plurality of stimulation configurations are tested under this particular electrode combination (electrode 1 being a cathode, and electrode 2 being an anode), where each stimulation configuration has a different stimulation pulse amplitude. Meanwhile, the measurement circuitry of the PNS device 200 in conjunction with the lead 1900 and the measurement instrument (e.g., oscilloscope) monitor the motor fiber contributions and the sensory fiber contributions to the CAP, for example by measuring the motor fiber contribution signal 1815 in the window 1810 and measuring the sensory fiber contribution signal 1825 in the window 1820. For each different stimulation amplitude, a corresponding measurement is made as to the sizes (e.g., amplitudes 1840 and 1850) of the signals 1815 and 1825, and a ratio thereof may be computed and stored in an electronic storage, which could be onboard the PNS device 200, or on the electronic programmer 250, or in a remote server (i.e., the cloud).

When the stimulation pulse amplitude ramping up process is completed (for example after running through 20 different amplitudes) for the electrode combination, the same process is repeated for a new electrode combination. For example, electrode 1 may still be selected as a cathode, but both electrodes 2 and 5 are selected as cathodes. Since the activation of 2 cathodes may provide different activation patterns of the sensory and motor fibers. Again, the stimulation pulse amplitude may be ramped up for this electrode combination while the pulse width is held constant. The sensory fiber and motor fiber contributions are also measured for each different amplitude, and the ratio thereof may be calculated and stored.

Next, the same process may be performed for yet another electrode combination. For example, electrode 2 may be selected as a cathode, while electrodes 1 and 3 may be selected as anodes. Again, the sensory fiber and motor fiber contributions are measured while the amplitude is being ramped up. This process continues until all the electrode combinations in the predetermined list of electrode combinations have been exhausted. Note that the predetermined list of electrode combinations does not include every single possible electrode combination available, as that would have created millions of different combinations, which is unrealistic to try as well as unnecessary. Instead, the algorithm defines a reasonable yet likely effective list of electrode combinations to be stepped through.

Table 2 below lists a very simplified example of a partial list of electrode combinations, along with their respective stimulation amplitudes and stimulation pulse widths according to some embodiments. For reasons of simplicity, suppose that only 3 different stimulation amplitudes are being used in the ramping up process (1 mA, 2 mA, and 3 mA), and that stimulation pulse width is held constant at 0.5 milliseconds (ms). Again, these values are merely examples and do not necessarily represent real world conditions.

TABLE 2

| Cathode | Anode | Stimulation Pulse Amplitude | Stimulation Pulse Width | Ratio of Sensory Fiber Contribution and Motor Fiber Contribution |
|---|---|---|---|---|
| Electrode 1 | Electrode 2 | 1 mA | 0.5 ms | 0.3 |
| Electrode 1 | Electrode 2 | 2 mA | 0.5 ms | 0.32 |
| Electrode 1 | Electrode 2 | 3 mA | 0.5 ms | 0.4 |
| Electrode 1 | Electrodes 2 and 5 | 1 mA | 0.5 ms | 0.42 |
| Electrode 1 | Electrodes 2 and 5 | 2 mA | 0.5 ms | 0.31 |
| Electrode 1 | Electrodes 2 and 5 | 3 mA | 0.5 ms | 0.42 |
| Electrode 2 | Electrodes 1 and 3 | 1 mA | 0.5 ms | 0.5 |
| Electrode 2 | Electrodes 1 and 3 | 2 mA | 0.5 ms | 0.51 |
| Electrode 2 | Electrodes 1 and 3 | 3 mA | 0.5 ms | 0.52 |
| Electrode 2 | Electrodes 1, 3, and 6 | 1 mA | 0.5 ms | 0.53 |
| Electrode 2 | Electrodes 1, 3, and 6 | 2 mA | 0.5 ms | 0.55 |
| Electrode 2 | Electrodes 1, 3, and 6 | 3 mA | 0.5 ms | 0.56 |
| Electrode 3 | Electrodes 2 and 4 | 1 mA | 0.5 ms | 0.72 |
| Electrode 3 | Electrodes 2 and 4 | 2 mA | 0.5 ms | 0.76 |
| Electrode 3 | Electrodes 2 and 4 | 3 mA | 0.5 ms | 0.78 |
| Electrode 3 | Electrodes 2, 4 and 7 | 1 mA | 0.5 ms | 0.71 |
| Electrode 3 | Electrodes 2, 4 and 7 | 2 mA | 0.5 ms | 0.77 |
| Electrode 3 | Electrodes 2, 4 and 7 | 3 mA | 0.5 ms | 0.84 |
| Electrode 4 | Electrodes 3 and 8 | 1 mA | 0.5 ms | 0.64 |
| Electrode 4 | Electrodes 3 and 8 | 2 mA | 0.5 ms | 0.65 |
| Electrode 4 | Electrodes 3 and 8 | 3 mA | 0.5 ms | 0.67 |
| Electrode 5 | Electrodes 1 and 9 | 1 mA | 0.5 ms | 0.43 |
| Electrode 5 | Electrodes 1 and 9 | 2 mA | 0.5 ms | 0.41 |
| Electrode 5 | Electrodes 1 and 9 | 3 mA | 0.5 ms | 0.45 |
| Electrode 5 | Electrodes 1, 9 and 6 | 1 mA | 0.5 ms | 0.51 |
| Electrode 5 | Electrodes 1, 9 and 6 | 2 mA | 0.5 ms | 0.57 |
| Electrode 5 | Electrodes 1, 9 and 6 | 3 mA | 0.5 ms | 0.53 |
| Electrode 6 | Electrodes 5 and 7 | 1 mA | 0.5 ms | 0.44 |
| Electrode 6 | Electrodes 5 and 7 | 2 mA | 0.5 ms | 0.43 |
| Electrode 6 | Electrodes 5 and 7 | 3 mA | 0.5 ms | 0.45 |
| Electrode 6 | Electrodes 5, 7, and 10 | 1 mA | 0.5 ms | 0.47 |
| Electrode 6 | Electrodes 5, 7, and 10 | 2 mA | 0.5 ms | 0.48 |
| Electrode 6 | Electrodes 5, 7, and 10 | 3 mA | 0.5 ms | 0.49 |
| ... | ... | ... | ... | ... |
| Electrode 16 | Electrodes 12 and 15 | 1 mA | 0.5 ms | 0.21 |
| Electrode 16 | Electrodes 12 and 15 | 2 mA | 0.5 ms | 0.23 |
| Electrode 16 | Electrodes 12 and 15 | 3 mA | 0.5 ms | 0.26 |
| Electrode 16 | Electrodes 12, 15, and 11 | 1 mA | 0.5 ms | 0.31 |
| Electrode 16 | Electrodes 12, 15, and 11 | 2 mA | 0.5 ms | 0.32 |
| Electrode 16 | Electrodes 12, 15, and 11 | 3 mA | 0.5 ms | 0.36 |

Essentially, each row of Table 2 constitutes a unique stimulation configuration. It is only partial because not every single electrode combination is shown for reasons of simplicity (i.e., the electrode combinations in which electrodes 7-15 are assigned as cathodes are not shown). It is also simplified since a real world stimulation pulse amplitude ramping process will likely include more than just 3 steps. In addition, the pulse width here is held constant to simplify the algorithm, though a person of ordinary skill in the art would recognize that it is possible for the pulse width to be ramped along with, or separately from the stimulation pulse amplitude herein.

In any case, the ratio of the sensory fiber contribution and the motor fiber contribution is computed and recorded for each stimulation configuration. According to Table 2, a best ratio of 0.84 is obtained under the stimulation configuration in which the electrode combination has the electrode 3 as a cathode, and electrodes 2, 4, and 7 as anodes, with a stimulation pulse amplitude of 3 mA, and a pulse width of 0.5 ms. This particular stimulation configuration may then be automatically recommended (e.g., by the electronic programmer 250) as an optimized stimulation configuration to use in order to maximize the sensory fiber contribution relative to the motor fiber contribution, which facilitates more comfortable stimulation treatment for the patient.

In some embodiments, several stimulation configurations are chosen as possible candidates to be recommended as the optimized stimulation configurations. For example, the stimulation configurations (i.e., rows in Table 2) corresponding to the ratio of 0.77 and 0.78 are also recorded as these possible candidates, since they result in a ratio of sensory fiber contribution relative to the motor fiber contribution that is also pretty high. In some embodiments, after the top 3 or 4 stimulation configurations "candidates" are identified, the algorithm may ramp up or down the stimulation pulse width for these 3 or 4 top stimulation configuration "candidates." At the end of that process, the best candidate may be chosen to be the one that is recommended.

In some embodiments, the algorithm may include two or more stages. In a coarse testing stage, the algorithm steps through the stimulation configurations in a coarse manner, where there is not much resolution between the stimulation pulse amplitudes, or pulse width, or even electrode combination selection. For example, the stimulation pulse amplitude may have just 2 or 3 different values. After the initial coarse testing process is performed, several top stimulation configurations are selected based on their ratios of sensory fiber contribution to the motor fiber contribution. Thereafter, in a fine testing stage, the testing is performed for these candidates with finer resolution, for example by ramping up the stimulation pulse amplitude or pulse width with 20 or 30 different values. This multi-stage approach may save time and may yield the desired result quickly and accurately.

It is understood that the above example illustrate using a ratio (i.e., relative size) of the sensory fiber contribution and the motor fiber contribution to the CAP as a gauge of determining a particular stimulation configuration's effectiveness in maximizing the sensory fiber contribution relative to the motor fiber contribution (or minimizing the motor fiber contribution relative to the sensory fiber contribution). However, in alternative embodiments, the absolute sizes of the sensory fiber and motor fiber contributions may also be used instead of, or in addition to, the relative sizes of the sensory fiber and motor fiber contributions to the CAP.

It is also understood that the above testing process may be performed in an automated manner without requiring the patient's verbal or tactile feedback. For example, after the implantation surgery, the patient goes to the clinic for a follow up visit. The medical professional may attempt to optimize the stimulation parameters in this visit. According to the embodiments of the present disclosure, the algorithm may be loaded onto the PNS device 200 and executed. Once it begins the execution, the patient can sit back and relax. He/she may feel different amounts of paresthesia and in different regions of the body, but he/she understands that it is a result of the various different stimulation configurations being applied. A measurement instrument configured to measure action potentials is coupled to the PNS device (either through a wire or wirelessly). Thus, the sensory fiber and motor fiber contributions are measured and recorded at least partially via the measurement instrument.

As discussed above, the values (either absolute or relative) of the sensory fiber and motor fiber contributions to the CAP as used as surrogates of the patient's paresthesia (or perception of the paresthesia). Since these values can be generated and measured automatically by machines, the verbal and/or tactile feedback from the actual patient is no longer needed. This saves a great deal of time, as conventional methods require the patient's indication of whether a particular stimulation configuration is effective or not, which creates a long time lag between the execution of each possible stimulation configuration. Since the patient's time and the medical professional's time are limited during the patient's visit, the long lag and slow execution of the stimulation configurations under the conventional approach means that often times the best (or at least optimized) stimulation configurations may not be found. In comparison, the automated execution of the algorithm and the feedback obtained from the measurement machines (and without needing patient feedback) means that a much more exhaustive list of stimulation configurations may be tested, thereby increasing the likelihood of discovering one or more optimized stimulation configurations that provide very good treatment for the patient, even if they may or may not be theoretically "the best."

In some embodiments, the transition between the contact combinations is made time-efficient. For example, while one contact combination is being evaluated, the next contact combination in the queue is readied and is activated at a low amplitude (eg, 50% of the paresthesia threshold of the combination under test). When the testing of the present contact combination is complete, the subject is then guided to increase the mA until they feel a nominal paresthesia. Testing of this formerly queued contact combination is then implemented and the next combination in the queue is similarly readied.

It is also understood that the algorithm may be executed when the patient is in actual surgery too. Regardless of the setting or context in which the algorithm is executed, the end result is that one or more optimized stimulation configurations may be automatically recommended, either to the patient or to the medical professional. In some embodiments, the recommendation may be done via the electronic programmer 250, for example in the form of one or more automatically created stimulation programs that each correspond to the one or more optimized stimulation configurations. It is also understood that in various embodiments, the algorithm and the execution results may be stored on the PNS device 200, or on the electronic programmer 250, or in the cloud.

In some embodiments, the algorithm consistently monitors the CAP result of the stimulation pulses, ideally on a pulse-by-pulse basis, but the frequency of electrical CAP measurement can be reduced. If the ratio of sensory afferent CAP component to motor efferent CAP component changes, or the motor efferent CAP becomes too large, then the algorithm can automatically alter the amplitude or pulse width of the stimulation, or gradually transition the present contact combination to another contact combination which was previously among those which maximize sensory CAP and minimize the motor CAP component.

In some embodiments, the algorithm can monitor the amplitude of the sensory CAP component, and, if it decreases, then the stimulation amplitude may be automatically increased to try to maintain it as constant and vice-versa. In this manner, the sensory CAP component can be held fixed by a closed-loop algorithm which does so by titrating the amplitude and/or pulse width, which ostensibly will keep any sensations and therapeutic effect constant in the face of body or limb motion.

In some embodiments, motor activity resulting from reflex activation (i.e., sensory stimulation which, in the spinal cord, triggers motor neuron activity) can also be monitored. In such an algorithm, the window for evaluating the response to intended sensory stimulation is delayed more from the stimulation pulse than in some of the above examples. Fast conducting responses (again, defined by narrow complexes or multiple complexes) that have originated in the spine are looked for in this window. Depending upon the algorithm, if reflex motor efferent activity is observed, this, too, may be used to select 'best' contact combinations, i.e., those that minimize these reflex signals or the ratio of these reflex signals to the sensory afferent components. In some embodiments, if these signals are seen, the amplitude and/or pulse width of the stimulation is adjusted automatically by the algorithm.

Figure 38:
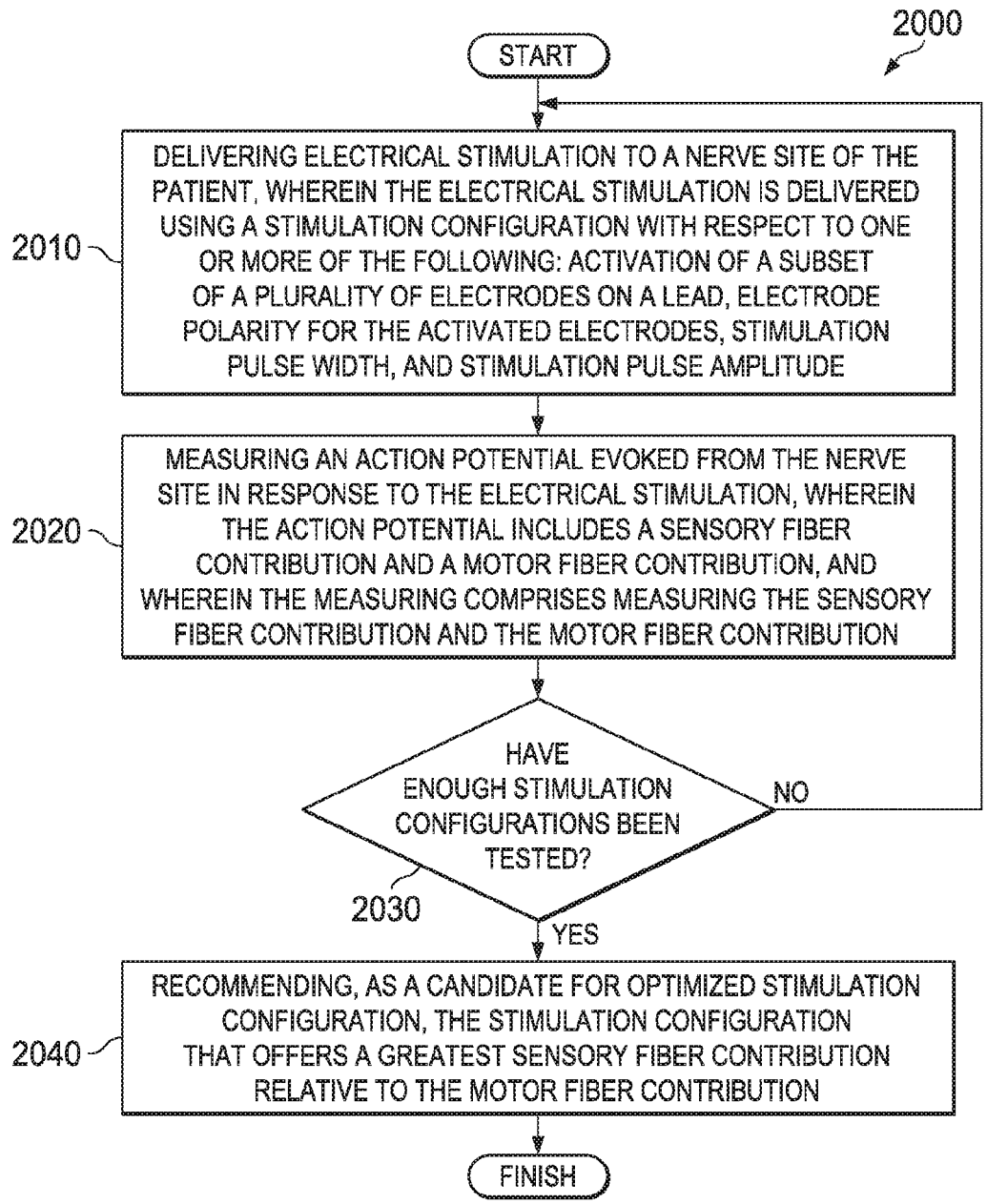
FIG. 38 is a simplified flowchart illustrating a method of establishing a stimulation treatment protocol for a patient according to an embodiment of the present disclosure.

FIG. 38 is a simplified flowchart of a method 2000 of providing a stimulation therapy to a patient according to an embodiment of the present disclosure. The method 2000 includes a step 2010 of delivering electrical stimulation to a nerve site of the patient. The electrical stimulation is delivered using a stimulation configuration with respect to one or more of the following: activation of a subset of a plurality of electrodes on a lead, electrode polarity for the activated electrodes, stimulation pulse width, and stimulation pulse amplitude.

The method 2000 includes a step 2020 of measuring an action potential evoked from the nerve site in response to the electrical stimulation. The action potential includes a sensory fiber contribution and a motor fiber contribution, and wherein the measuring comprises measuring the sensory fiber contribution and the motor fiber contribution. In some embodiments, the step 2020 includes measuring the motor fiber contribution within a first time window, and measuring the sensory fiber contribution within a second time window, the second time window being a later time window than the first time window.

The method 2000 includes a decision step 2030 to determine whether enough stimulation configurations has been tested or stepped through. If the answer from the decision step 2030 is no, then the method 2000 loops back to the step 2010 again. Thus, the steps 2010 and 2020 may be performed a plurality of cycles, where each cycle is performed using a different stimulation configuration. In some embodiments, the repeated execution of steps 2010 and 2020 may be performed according to a predefined algorithm that specifies the activation of electrodes, electrode polarity, the stimulation pulse width, and the stimulation pulse amplitude for each cycle. In some embodiments, the algorithm may include the following steps: selecting an electrode combination that specifies a subset of electrodes to be activated and a respective electrode polarity for each activated electrode; ramping up or down the stimulation pulse amplitude for the selected electrode combination; and repeating the selecting and the ramping a plurality of times until a predetermined list of electrode combinations have been exhausted, wherein a different electrode combination is selected each time. In some embodiments, the selecting, the ramping, and the repeating are performed while holding the stimulation pulse width constant. In these embodiments, the algorithm may further include a step of picking, after the exhaustion of the predetermined list of electrode combinations, one or more electrode combinations with their corresponding stimulation amplitudes that maximized the sensory fiber contribution. The algorithm may also include a step of ramping the stimulation pulse width for the one or more electrode combinations. In some embodiments, the electrode combinations in the predetermined list each include a different cathode. If the answer from the decision step 2030 is yes—meaning that a sufficient number of stimulation configurations has been tested or stepped through—then the method 2000 continues with a step 2040 of recommending, as a candidate for optimized stimulation configuration, the stimulation configuration that offers a greatest sensory fiber contribution relative to the motor fiber contribution. In some embodiments, the various steps of the method 2000 are performed without requiring verbal or tactile feedback from the patient.

It is understood that the steps 2010-2080 need not necessarily be performed according to the sequence shown in FIG. 38. In various embodiments, some of these steps may be performed concurrently, or in an order different from what is shown in FIG. 38. It is also understood that additional process steps may be performed before, during, or after the steps 2010-2040. For reasons of simplicity, these additional steps are not discussed herein.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
    detecting that a patient is in a first posture state;
    applying, via a pulse generator implanted in the patient, a first electrical stimulation therapy to a body region of the patient in response to the detecting that the patient is in the first posture state;
    detecting that the patient is in a second posture state, the second posture state being different from the first posture state; and
    applying, via the pulse generator implanted in the patient, a second electrical stimulation therapy to the body region of the patient in response to the detecting that the patient is in the second posture state, the second electrical stimulation therapy being different from the first electrical stimulation therapy, wherein:
    the applying of the first electrical stimulation therapy comprises:
        generating a first electrical stimulation signal;
        measuring a first evoked potential in response to the first electrical stimulation signal; and
        adjusting the first electrical stimulation signal until the measured first evoked potential reaches a first target evoked potential; and
    the applying of the second electrical stimulation therapy comprises:
        generating a second electrical stimulation signal;
        measuring a second evoked potential in response to the second electrical stimulation signal; and
        adjusting the second electrical stimulation signal until the measured second evoked potential reaches a second target evoked potential.

2. The method of claim 1, wherein:
    the first electrical stimulation signal is generated using a first starting value of an electrical stimulation parameter;
    the adjusting of the first electrical stimulation signal comprises adjusting the first starting value of the electrical stimulation parameter until the measured first evoked potential reaches the first target evoked potential;
    the second electrical stimulation signal is generated using a second starting value of the electrical stimulation parameter; and
    the adjusting of the second electrical stimulation signal comprises adjusting the second starting value of the electrical stimulation parameter until the measured second evoked potential reaches the second target evoked potential.

3. The method of claim 2, further comprising:
    performing a first calibration process to obtain the first starting value of the electrical stimulation parameter and the first target evoked potential, the first calibration process being performed while the patient is in the first posture state; and
    performing a second calibration process to obtain the second starting value of the electrical stimulation parameter and the second target evoked potential, the second calibration process being performed while the patient is in the second posture state.

4. The method of claim 3, wherein:
    the performing of the first calibration process comprises determining the first starting value of the electrical stimulation parameter and the first target evoked potential that cause the patient to experience paresthesia in the first posture state; and
    the performing of the second calibration process comprises determining the second starting value of the electrical stimulation parameter and the second target evoked potential that cause the patient to experience paresthesia in the second posture state.

5. The method of claim 1, wherein the detecting that the patient is in the first posture state or the detecting that the patient is in the second posture state is performed at least in part via one or more sensors implemented on the pulse generator, the one or more sensors including an accelerometer, a pressure sensor, or a temperature sensor.

6. The method of claim 1, wherein the first posture state and the second posture state are selected from the group consisting of: a posture state where the patient is lying down, a posture state where the patient is stretching, a posture state where the patient is ambulatory, a posture state where the patient is running, and a posture state where the patient is applying pressure on the body region of the patient.

7. The method of claim 1, wherein the detecting that the patient is in the first posture state or the detecting that the patient is in the second posture state comprises:
displaying, via a graphical user interface, a plurality of icons that each represent a patient posture state; and
detecting a selection of one of the icons by the patient via the graphical user interface; and
determining that the first posture state or the second posture state is the posture state represented by the selected icon.

8. A medical system, comprising:
a pulse generator configured to be implanted in a patient, the pulse generator being configured to generate electrical stimulation pulses to stimulate a body region of the patient; and
an electronic programmer configured to program the pulse generator to generate the stimulation pulses, wherein the electronic programmer is further configured to perform operations comprising:
receiving a first detection that the patient is in a first posture state;
programming the pulse generator to produce a first electrical stimulation therapy to be applied to a body region of the patient in response to the receiving of the first detection;
receiving a second detection that the patient is in a second posture state, the second posture state being different from the first posture state; and
programming the pulse generator to produce a second electrical stimulation therapy to be applied to the body region of the patient in response to the receiving of the second detection, the second electrical stimulation therapy being different from the first electrical stimulation therapy, wherein:
the programming the pulse generator to produce the first electrical stimulation therapy comprises:
programming the pulse generator to generate a first electrical stimulation signal;
measuring a first evoked potential in response to the first electrical stimulation signal; and
programming the pulse generator to adjust the first electrical stimulation signal until the measured first evoked potential reaches a first target evoked potential; and
the programming the pulse generator to produce the second electrical stimulation therapy comprises:
programming the pulse generator to generate a second electrical stimulation signal;
measuring a second evoked potential in response to the second electrical stimulation signal; and
programming the pulse generator to adjust the second electrical stimulation signal until the measured second evoked potential reaches a second target evoked potential.

9. The medical system of claim 8, wherein:
the first electrical stimulation signal is generated using a first starting value of an electrical stimulation parameter;
the programming the pulse generator to adjust the first electrical stimulation signal comprises adjusting the first starting value of the electrical stimulation parameter until the measured first evoked potential reaches the first target evoked potential;
the second electrical stimulation signal is generated using a second starting value of the electrical stimulation parameter; and
the programming the pulse generator to adjust the second electrical stimulation signal comprises adjusting the second starting value of the electrical stimulation parameter until the measured second evoked potential reaches the second target evoked potential.

10. The medical system of claim 9, wherein the operations further comprise:
performing a first calibration process to obtain the first starting value of the electrical stimulation parameter and the first target evoked potential, the first calibration process being performed while the patient is in the first posture state; and
performing a second calibration process to obtain the second starting value of the electrical stimulation parameter and the second target evoked potential, the second calibration process being performed while the patient is in the second posture state.

11. The medical system of claim 10, wherein:
the performing of the first calibration process comprises determining the first starting value of the electrical stimulation parameter and the first target evoked potential that cause the patient to experience paresthesia in the first posture state; and
the performing of the second calibration process comprises determining the second starting value of the electrical stimulation parameter and the second target evoked potential that cause the patient to experience paresthesia in the second posture state.

12. The medical system of claim 8, wherein:
the pulse generator includes one or more sensors selected from the group consisting of: an accelerometer, a pressure sensor, and a temperature sensor; and
the pulse generator is configured to detect a current posture state of the patient at least in part via the one or more sensors, the current posture state being one of: a posture state where the patient is lying down, a posture state where the patient is stretching, a posture state where the patient is ambulatory, a posture state where the patient is running, or a posture state where the patient is applying pressure on the body region of the patient.

13. The medical system of claim 8, wherein the receiving the first detection that the patient is in the first posture state or the receiving the second detection that the patient is in the second posture state comprises:
displaying, via a graphical user interface of the electronic programmer, a plurality of icons that each represent a patient posture state; and
detecting a selection of one of the icons by the patient via the graphical user interface; and
determining that the first posture state or the second posture state is the posture state represented by the selected icon.

14. The medical system of claim 8, wherein the graphical user interface is a touch-sensitive user interface.

15. A medical apparatus, comprising:

one or more sensors configured to detect a present posture of a patient; and controller circuitry and stimulation circuitry telecommunicatively coupled to the one or more sensors, wherein the controller circuitry and the stimulation circuitry are configured to perform the following operations:

applying a first electrical stimulation therapy to a body region of the patient in response to a detection, by the one or more sensors, that the present posture of the patient is a first posture; and applying a second electrical stimulation therapy to the body region of the patient in response to a detection, by the one or more sensors, that the present posture of the patient is a second posture, wherein the second electrical stimulation therapy is different from the first electrical stimulation therapy, and wherein the second patient posture is different from the first patient posture;

wherein:

the applying of the first electrical stimulation therapy comprises:
  generating a first electrical stimulation signal;
  measuring a first evoked potential in response to the first electrical stimulation signal; and
  adjusting the first electrical stimulation signal until the measured first evoked potential reaches a first target evoked potential; and the applying of the second electrical stimulation therapy comprises:
  generating a second electrical stimulation signal;
  measuring a second evoked potential in response to the second electrical stimulation signal; and
  adjusting the second electrical stimulation signal until the measured second evoked potential reaches a second target evoked potential.

16. The medical apparatus of claim 15, wherein:

the first electrical stimulation signal is generated using a first starting value of an electrical stimulation parameter;

the adjusting of the first electrical stimulation signal comprises adjusting the first starting value of the electrical stimulation parameter until the measured first evoked potential reaches the first target evoked potential;

the second electrical stimulation signal is generated using a second starting value of the electrical stimulation parameter; and the adjusting of the second electrical stimulation signal comprises adjusting the second starting value of the electrical stimulation parameter until the measured second evoked potential reaches the second target evoked potential.

17. The medical apparatus of claim 16, wherein the operations further comprise:

performing a first calibration process to obtain the first starting value of the electrical stimulation parameter and the first target evoked potential, the first calibration process being performed while the patient is in the first posture; and performing a second calibration process to obtain the second starting value of the electrical stimulation parameter and the second target evoked potential, the second calibration process being performed while the patient is in the second posture.

18. The medical apparatus of claim 17, wherein:

the performing of the first calibration process comprises determining the first starting value of the electrical stimulation parameter and the first target evoked potential that cause the patient to experience paresthesia in the first posture; and the performing of the second calibration process comprises determining the second starting value of the electrical stimulation parameter and the second target evoked potential that cause the patient to experience paresthesia in the second posture.

19. The medical apparatus of claim 15, wherein the one or more sensors include one or more of: an accelerometer, a pressure sensor, or a temperature sensor.

20. The medical apparatus of claim 15, wherein the first posture and the second posture are selected from the group consisting of: a posture where the patient is lying down, a posture where the patient is stretching, a posture where the patient is ambulatory, a posture where the patient is running, and a posture where the patient is applying pressure on the body region of the patient.

* * * * *

UNITED STATES PATENT AND TRADEMARK OFFICE
CERTIFICATE OF CORRECTION

PATENT NO. : 9,526,897 B2  
APPLICATION NO. : 15/001327  
DATED : December 27, 2016  
INVENTOR(S) : Joey Chen et al.

Page 1 of 1

It is certified that error appears in the above-identified patent and that said Letters Patent is hereby corrected as shown below:

On the Title Page

Item (73) Column 1, Assignee delete "Greatbach" and insert --Greatbatch--

Signed and Sealed this  
Fourth Day of April, 2017

Michelle K. Lee  
*Director of the United States Patent and Trademark Office*